US012624109B2

(12) United States Patent
Mousa et al.

(10) Patent No.: US 12,624,109 B2
(45) Date of Patent: May 12, 2026

(54) αV-INTEGRIN TARGETED SMALL MOLECULE DRUG CONJUGATES

(71) Applicant: TargetThera LLC, Troy, NY (US)

(72) Inventors: Shaker A. Mousa, Wynantskill, NY (US); Bruce A. Hay, Niskayuna, NY (US)

(73) Assignee: TargetThera LLC, Troy, NY (US)

( * ) Notice: Subject to any disclaimer, the term of this patent is extended or adjusted under 35 U.S.C. 154(b) by 502 days.

(21) Appl. No.: 18/138,935

(22) Filed: Apr. 25, 2023

(65) Prior Publication Data

US 2024/0376212 A1 Nov. 14, 2024

(51) Int. Cl.

| | |
|---|---|
| ***C07K 16/28*** | (2006.01) |
| ***A61K 47/60*** | (2017.01) |
| ***A61K 47/68*** | (2017.01) |
| ***A61P 35/00*** | (2006.01) |

(52) U.S. Cl.

CPC .......... *C07K 16/2848* (2013.01); *A61K 47/60* (2017.08); *A61K 47/6849* (2017.08); *A61P 35/00* (2018.01)

(58) Field of Classification Search

CPC ....................... C07K 16/2848; C07K 2317/77; A61K 47/60; A61K 47/6849; A61K 47/542; A61P 35/00

See application file for complete search history.

(56) References Cited

U.S. PATENT DOCUMENTS

| | | | |
|---|---|---|---|
| 6,245,809 | B1 | 6/2001 | Scarborough et al. |
| 11,186,551 | B2 | 11/2021 | Mousa et al. |
| 2017/0355769 | A1 | 12/2017 | Benatuil et al. |

FOREIGN PATENT DOCUMENTS

| | | | | |
|---|---|---|---|---|
| EP | 1219305 A1 | 3/2002 | | |
| WO | 2003043583 A2 | 5/2003 | | |
| WO | 2014096551 A1 | 6/2014 | | |
| WO | 2014177771 A1 | 11/2014 | | |
| WO | WO-2020094471 A1 * | 5/2020 | ............. | A61K 47/54 |
| WO | 2021221836 A1 | 11/2021 | | |

OTHER PUBLICATIONS

BroadPharm, 2017 Product BP-21610; URL = https://broadpharm.com/product/bp-21610; First available: Mar. 13, 2017; Accessed Oct. 17, 2025 (Year: 2017).*

Ahmad, et al., Adv Med, Den and Health Sci, 2021 4(4):37 (Year: 2021).*

Slack et al., Emerging therapeutic opportunities for integrin inhibitors, Jan. 2022 | vol. 21, www.nature.com/nrd, 19 pages.

Godugu et al., Nano Diaminopropane tetrac and integrin αvβ3 expression in different cancer types: Anti-cancer efficacy and Safety, Cancer Treatment and Research Communications 28 (2021) 100395, 8 pages.

Nair et al., A simple practice guide for dose conversion between animals and human, 2016 Journal of Basic and Clinical Pharmacy, Published by Wolters Kluwer—Medknow, J Basic Clin Pharma 2016; 7:27-31, 5 pages.

Jacob et al., Dose Conversion Between Animals and Humans: A Practical Solution, Indian Journal of Pharmaceutical Education and Research, vol. 56, Issue 3, Jul.-Sep. 2022, 8 pages.

Alsibai et al., Fluorescent Non-peptidic RGD Mimetics with High Selectivity for αVβ3 vs αIIbβ3 Integrin Receptor: Novel Probes for in Vivo Optical Imaging, Journal of Medicinal Chemistry, Downloaded via Univ Albany State Univ New York on Feb. 15, 2022 at 22:11:46 (UTC), https://pubs.acs.org/sharingguidelines for options on how to legitimately share published articles, dx.doi.org/10.1021/jm501197c | J. Med. Chem. 2014, 57, 9971-9982 Downloaded via, 12 pages.

Battistini et al, RGD Peptide-Drug Conjugates as Effective Dual Targeting Platforms: European Journal of Organic Chemistry, Recent Advances, Minireviews doi.org/10.1002/ejoc.202100240, Eur. J. Org. Chem. 2021, 2506-2528, 23 pages.

Carlson et al., Selective Tumor Cell Targeting Using Low-Affinity, Multivalent Interactions, Downloaded via Univ Albany State Univ New York on Feb. 15, 2022 at 22:17:17 (UTC). https://pubs.acs.org/sharingguidelines for options on how to legitimately share published articles, ACS Chemical Biology, vol. 2 No. 2, 119-127, 2007, www. acschemicalbiology.org, 9 pages.

Cirillo et al., Molecular Delivery of Cytotoxic Agents via Integrin Activation, Cancers 2021, 13, 299, https://doi.org/10.3390/cancers13020299, https://www.mdpi.com/journal/cancers, 25 pages.

Anselmi et al., Linker Hydrophilicity Modulates the Anticancer Activity of RGD-Cryptophycin Conjugates, Chemistry—A European Journal, doi.org/10.1002/chem.202003471, Chem. Eur. J. 2021, 27, 1015-1022, 8 pages.

Currier et al., Targeted Drug Delivery with an Integrin-Binding Knottin-Fc-MMAF Conjugate Produced by Cell-Free Protein Synthesis, Molecular Cancer Therapeutics, www.aacrjournals.org, Downloaded from http://aacrjournals.org/mct/article-pdf/15/6/1291/1850826/1291.pdf by guest on Feb. 16, 2022, 10 pages.

Dal Corso et al., Fast Cyclization of a Proline-Derived Self-Immolative Spacer Improves the Efficacy of Carbamate Prodrugs, GDCh, Research Articles, Downloaded from https://onlinelibrary.wiley.com/doi/10.1002/anie.201916394 by Suny University At Albany, Wiley Online Library on [Sep. 1, 2023]. Angew. Chem. Int. Ed. 2020, 59, 4176-4181, See the Terms and Conditions (https://onlinelibrary.wiley.com/terms-and-conditions) on Wiley Online Library for rules of use; OA articles are governed by the applicable Creative Commons License, 6 pages.

(Continued)

*Primary Examiner* — Julie Wu

*Assistant Examiner* — Sydney Van Druff

(74) *Attorney, Agent, or Firm* — Schmeiser, Olsen & Watts, LLP

(57) ABSTRACT

A chemical compound and a method for treating cancer in a mammal. The chemical compound is a first Markusch structure of A-$L_1$-$PEG_1$-$L_2$-$PEG_2$-CL-X, a second Markusch structure of A-$L_1$-$PEG_1$-$N_3$, or a third Markusch structure of A-$L_1$-$PEG_1$-OMethyl. A-$L_1$-PEG is a targeting structure configured for targeting av integrins in cancer cells and does not include a standard multivalent nitrogen moiety. A is a structure that includes a standard carboxylic acid moiety. $L_1$ and $L_2$ are linking structures. $PEG_1$ and $PEG_2$ are polyethylene glycol structures having $n_2$ and $n_4$ monomer units, respectively, where $n_2$ is in range of 5-72, $n_4$ is in range of 0-67, and $n_2$+$n_4$ is in range of 20-72. CL is a cleavage linker linked to $PEG_2$. X is a chemotherapy linked to CL. $N_3$ is —N=N=N. In one embodiment, the method uses the first Markusch structure to treat the cancer.

27 Claims, 11 Drawing Sheets

(56) References Cited

OTHER PUBLICATIONS

Dal Corso et al., αvβ3 Integrin-Targeted Peptide/Peptidomimetic-Drug Conjugates: In-Depth Analysis of the Linker Technology, Bentham Science, Current Topics in Medicinal Chemistry, 2016, 16, 314-329, 16 pages.
Dayam et al., Discovery of Small Molecule Integrin αvβ3 Antagonists as Novel Anticancer Agents, J. Med. Chem. 2006, 49, 4526-4534, Downloaded via Albany Colg Pharmacy & Health Sci on Feb. 17, 2022 at 19:42:20 (UTC), https://pubs.acs.org/sharingguidelines for options on how to legitimately share published articles, 9 pages.
Dias et al., Synthesis and Biological Evaluation of RGD and isoDGR-Monomethyl Auristatin Conjugates Targeting Integrin αvβ3, ChemPubSoc Europe, DOI: 10.1002/cmdc.201900049, ChemMedChem 2019, 14, 938-942, Wiley Online Library, 5 pages.
Doronina et al., Development of potent monoclonal antibody auristatin conjugates for cancer therapy, 2003 Nature Publishing Group, http://www.nature.com/naturebiotechnology, Nature BioTechnology, vol. 21 No. 7 Jul. 2003, 8 pages.
Elliot et al., Novel inhibitors of the αvβ3 integrin-lead identification strategy, Bioorganic & Medicinal Chemistry Letters, 19 (2009) 4832-4835, 4 pages.
Fu et al., Antibody drug conjugate: the "biological missile" for targeted cancer therapy, Signal Transduction and Targeted Therapy, Revised: Feb. 26, 2022 Accepted: Mar. 3, 2022, Published online: Mar. 22, 2022, 25 pages.
Hammood et al., pharmaceuticals, MDPI, Impact of Endocytosis Mechanisms for the Receptors Targeted by the Currently Approved Antibody-Drug Conjugates (ADCs)—A Necessity for Future ADC Research and Development, Pharmaceuticals 2021, 14, 674. Retrieved from Internet: https://doi.org/10.3390/ph14070674, 33 pages.
Hatley et al., An αv-RGD Integrin Inhibitor Toolbox: Drug Discovery Insight, Challenges and Opportunities, www.angewandte.org, Angew. Chem. Int. Ed. 2018, 57, 3298-3321, 24 pages.
Hersey et al., A Randomized Phase 2 Study of Etaracizumab, a Monoclonal Antibody Against Integrin αvβ3, + Dacarbazine in Patients With Stage IV Metastatic Melanoma, DOI: 10.1002/cncr.24821, Revised: Jun. 9, 2009; Accepted: Jun. 10, 2009, Published online Jan. 27, 2010 in Wiley InterScience (www.interscience.wiley.com), Cancer Mar. 15, 2010, 9 pages.
Integrin alpha(v)beta(3), Retrieved from Internet: https://www.creative-biolabs.com/adc/target-integrin-alpha-v-beta-3-211.htm, © 2023 Creative Biolabs, 6 pages.
Tbone_Chop, Converting mouse dosages to human equivalent dosages (HED) retrieved on Apr. 2, 2023 from the Internet: https://www.reddit.com/r/NicotinamideRiboside/comments/4jf3gz/converting_mouse_dosages_to_human_equivalent, 3 pages.
Kemker et al., Size-Dependent Cellular Uptake of RGD Peptides, ChemPubSoc Europe, DOI: 10.1002/cbic.201900512, Downloaded from https://chemistry-europe.onlinelibrary.wiley.com/doi/10.1002/cbic.201900512 by Test, Wiley Online Library on [Jun. 1, 2023]. See the Terms and Conditions (https://onlinelibrary.wiley.com/terms-and-conditions) on Wiley Online Library for rules of use; OA articles are governed by the applicable Creative Commons License, ChemBioChem 2020, 21, 496-499, 4 pages.
Lerchen et al., A Small Molecule-Drug Conjugate (SMDC) Consisting of a Modified Camptothecin Payload Linked to an αVβ3 Binder for the Treatment of Multiple Cancer Types, cancers, MDPI, Cancers 2022, 14, 391. https://doi.org/10.3390/cancers14020391, https://www.mdpi.com/journal/cancers, 19 pages.
Liu et al., Chemically Programmed Bispecific Antibody Targeting Legumain Protease and αvβ3 Integrin Mediates Strong Antitumor Effects, Downloaded via Univ Albany State Univ New York on Feb. 15, 2022 at 22:28:51 (UTC), https://pubs.acs.org/sharingguidelines for options on how to legitimately share published articles, 7 pages.
Liu et al. Targeting Cell Surface Alpha(v)beta(3) Integrins Increases Therapeutic Efficacies of a Legumain Protease-Activated Auristatin Prodrug, Published in final edited form as: Mol Pharm. Jan. 1, 2012; 9(1): 168-175. doi: 10.1021/mp200434n, 17 pages.
Miller et al., Emergence of Small-Molecule Non-RGD-Mimetic Inhibitors for RGD Integrins, Miniperspective, Downloaded via Albany Colg Pharmacy & Health Sci on Feb. 17, 2022 at 19:58:05 (UTC). J. Med. Chem. 2017, 60, 3241-3251, See https://pubs.acs.org/sharingguidelines for options on how to legitimately share published articles, 11 pages.
Patnaik et al., A phase 1 study of SGN-B6A, an antibody-drug conjugate targeting integrin beta-6, in patients with advanced solid tumors (SGNB6A-110, Trial in Progress), , a phase 1 study of SGN-B6A, J. Clin. Oncol. 39, 2021, Abstract, 1 page.
Paulus et al., Synthesis and Evaluation of a Non-Peptide Small-Molecule Drug Conjugate Targeting Integrin αvβ3, Frontiers in Chemistry | www.frontiersin.org, Apr. 2022 | vol. 10 | Article 869639, 18 pages.
Pina et al., Targeting Integrin αvβ3 with Theranostic RGD-Camptothecin Conjugates Bearing a Disulfide Linker: Biological Evaluation Reveals a Complex Scenario, ChemistrySelect 2017, 2, 4759-4766, DOI: 10.1002/slct.201701052, 8 pages.
Piras et al., Design and synthesis of an RGD peptidomimetic-paclitaxel conjugate targeting αvβ3 integrin for tumour-directed drug delivery, DOI: 10.1055/s-0036-1590898; Art ID: st-2017-r0479-1, Georg Thieme Verlag Stuttgart • New York—Synlett 2017, 28, 2769-2776, 8 pages.
Pourcelle et al., Clickable PEG conjugate obtained by "clip" photochemistry: Synthesis and characterization by quantitative 19F NMR, Published in: Journal of Fluorine Chemistry (2012), vol. 140, pp. 62-69, Status: Postprint (Author's version), 12 pages.
Rerat et al., αvβ3 Integrin-Targeting Arg-Gly-Asp (RGD) Peptidomimetics Containing Oligoethylene Glycol (OEG) Spacers, J. Med. Chem. 2009, 52, 7029-7043, DOI: 10.1021/jm901133z, Downloaded via Univ Albany State Univ New York on Feb. 15, 2022 at 22:10:18 (UTC), https://pubs.acs.org/sharingguidelines for options on how to legitimately share published articles, J. Med. Chem. 2009, 52, 7029-7043, DOI: pubs.acs.org/jmc, 15 pages.
Tong et al., An Insight into FDA Approved Antibody-Drug Conjugates for Cancer Therapy, Molecules 2021, 26, 5847. https://doi.org/10.3390/molecules26195847, https://www.mdpi.com/journal/molecules, 23 pages.
Zanella et al., Tumor Targeting with an isoDGR-Drug Conjugate, DOI : 10.1002/chem.201701844, Chem. Eur. J. 2017, 23, 7910-7914, 5 pages.
Zhou et al., Discovery of small molecule inhibitors of integrin αvβ3 through structure-based virtual screening, ScienceDirect, Bioorganic & Medicinal Chemistry Letters 16 (2006) 5878-5882, 5 pages.
Coleman et al., Nonpeptide αvβ3 Antagonists. Part 11: Discovery and Preclinical Evaluation of Potent αvβ3 Antagonists for the Prevention and Treatment of Osteoporosis, J. Med. Chem. 2004, 47, 4829-4837, Downloaded via Univ Albany State Univ New York on Jan. 9, 2023 at 14:29:35 (UTC), https://pubs.acs.org/sharingguidelines for options on how to legitimately share published articles, 9 pages.
Hutchinson et al., Nonpeptide αvβ3 Antagonists. 8. In Vitro and in Vivo Evaluation of a Potent αvβ3 Antagonist for the Prevention and Treatment of Osteoporosis, Downloaded via Univ Albany State Univ New York on Jan. 9, 2023 at 14:35:19 (UTC), J. Med. Chem. 2003, 46, 4790-4798, https://pubs.acs.org/sharingguidelines for options on how to legitimately share published articles, 9 pages.
Ito et al., Drug Discovery: Recent Progress and the Future, A Stable and Cleavable O-Linked Spacer for Drug Delivery Systems, Chem. Pharm. Bull. 68, 212-215 (2020), vol. 68, No. 3, 4 pages.
Viswanathan, CL et al., Synthesis and Evaluation of L-Glutamic acid Analogs as Potential Anticancer Agents, Indian Journal of Pharmaceutical Sciences, vol. 70, No. 2, Mar.-Apr. 2008, doi: 10.4103/0250-474X.41467, pp. 245-249; entire publication.
ISR—Written Opinion, Aug. 28, 2024, International application No. PCT/US2024/024874, International filing date Apr. 17, 2024, 16 pages.

* cited by examiner

αV-INTEGRIN TARGETED SMALL MOLECULE DRUG CONJUGATES

BACKGROUND

Antibody-drug-conjugates (ADCs) are an important new class of anti-cancer drugs, with at least 12 approved by the FDA, and many more undergoing clinical trials (recently reviewed in Fu, *Signal Transduct Target Ther* 7, 2022). These ADC molecules target cancer cells, where most of these molecules release a chemotherapy inside tumor cells, which can result in a big improvement in therapeutic index for the chemotherapy, since systemic toxicity is reduced because of less systemic exposure to the chemotherapy. ADCs typically have high selectivity for tumor cells with good in vivo stability. The mechanism for release of chemotherapy for most ADCs requires the ADC to be internalized into the cell, eventually ending up in a cell organelle called the late endosome, or in a cell organelle called the lysosome. After being internalized inside the tumor cell, the chemotherapy is cleaved from the ADC via a specific enzyme (cathepsin B) that is active in these organelles (i.e., late endosome and/or lysosome).

One issue with ADCs is that typically only a very small fraction (<1%) of the dosed ADC enters the tumor, some of which is believed to be due at least partially to ineffective transport of the macromolecular ADC to the tumor site (Tong, *Molecules* 2021, 26, 5847). Another issue with ADCs is the internalization efficiency varies with different ADCs, and is usually suboptimal (Hammood, *Pharmaceuticals* 2021, 14, 674). In addition, ADCs are an expensive therapy that needs to be dosed via IV infusion, with each infusion requiring a visit to the doctor's office.

There are a number of reports on Small Molecule Drug Conjugates (SMDCs) using integrin αvβ3 targeting. The vast majority of these SMDCs use Arginylglycylaspartic acid (RGD) peptide or related peptides as the targeting agent, but there are a few SMDCs that use peptidomimetics. A peptidomimetic is a small protein-like chain designed to mimic a peptide. The reported peptidomimetics mimic the RGD peptide by using the standard formula of an acidic functionality and a standard multivalent nitrogen moiety spaced 12-14 angstroms apart.

The standard multivalent nitrogen (hereinafter, "multivalent nitrogen"), whose scope includes multivalent nitrogen moieties illustrated infra, is defined as a chemical substructure with at least 2 nitrogen atoms connected by a single atom, that mimics the guanidine in the arginine of the Arginylglycylaspartic acid (RGD) peptide, where guanidine has the following chemical structure:

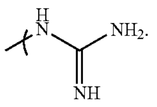

Guanidine

The multivalent nitrogen moiety is illustrated by the following Guanidine, Amidine, 2-aminopyridine, Urea, 1,2,3-triazole type structures:

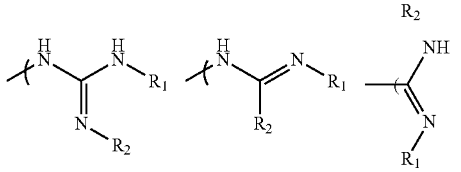

Guanidines

Amidines

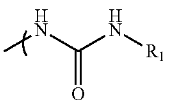

Ureas

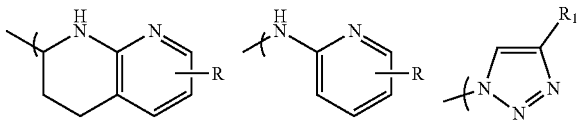

Aminopyridines 1,2,3-Triazoles

Attached chemotherapies include Doxorubicin, paclitaxel, camptothecins, monomethylauristatin, cisplatin, etc. There are several recent literature reviews on SMDCs (Cirillo et al, *cancers* 2021, 13, 299 and Battistini et al, *Eur. J. Org. Chem.* 2021, 2506-2528) as well as some earlier reviews (Dal Corso et al, *current topics in medicinal chemistry,* 2016, 16, 314-329). The abstract of the 2016 Dal Corso et al review recites "Despite the significant efforts made in this field, integrin αvβ3 integrin-targeted SMDCs are still far from the clinic."

Huthchinson, *J. Med Chem* 2003, 46, 4790 discloses MK-0429 (shown infra) which has the basic multivalent nitrogen 12-14 angstroms from carboxylic acid. Carboxylic acid has the following chemical structure: —C(═O)OH.

Some specific references of interest on RGD targeted SMDCs include (Dias et al *ChemMedChem* 2019, 14, 938-942), with RGD peptide targeting the chemotherapy of monomethylauristatin, that use cleavable linker Val-Cit-PAB (VCP), connected to a small polyethylene glycol (PEG) (i.e., PEG3). PEG3 is PEG having 3 monomer units. This VCP linker is also used in an RGD peptide targeted paclitaxel (Zanella et al, *Chem. Eur. J.* 2017 23 7910-14).

Val-Cit-PAB (VCP) and similar cathepsin B cleavable linkers, as well as chemotherapy monomethylauristatin E (MMAE), have been used extensively in ADCs for the last 20 years. For early references, see Doronina 2003 *Nature Biotechnology* 2003, 21, 778-784 and the patent WO 03/043583 with a filing date of 20 Nov. 2002. The Val-Cit-PAB and related cleavable linkers need a chemotherapy with a primary or preferably a secondary amine functionality to attach the cleavable linker to the chemotherapy.

There are also a few references for integrin αvβ3 peptidomimetic targeting of SMDCs, which use the "standard" integrin αvβ3 peptidomimetic that has the acidic group and the multivalent nitrogen group 12-14 angstroms apart, including the following compound from WO2022094471 which has a PEG3 linker. There are no PEG linkers in integrin avb3 targeted small molecule drug conjugates longer than PEG15 disclosed or claimed in the literature or patents.

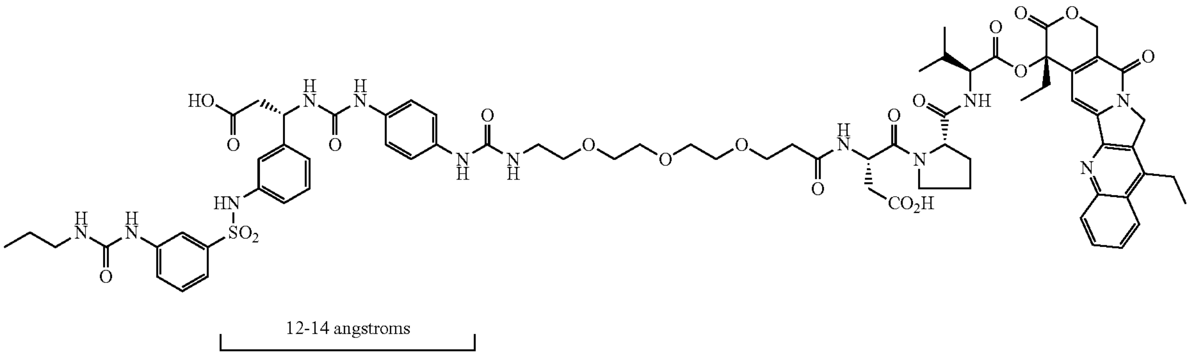 [SMILES: CCCNC(=O)Nc1cccc(S(=O)(=O)Nc2cccc([C@H](CC(=O)O)NC(=O)Nc3ccc(NC(=O)NCCOCCOCCOCCC(=O)N[C@@H](CC(=O)O)C(=O)N4CCC[C@H]4C(=O)N[C@H](C(=O)O[C@]4(CC)C(=O)OCc5c4cc4n(c5=O)Cc5c-4nc4ccccc4c5CC)C(C)C)cc3)c2)c1]

The preceding compound has a peptidomimetic integrin αvβ3 targeting piece that contains a multivalent nitrogen of about 12-14 angstroms from the carboxylic acid functionality, as in the RGD peptide. There are actually two of these multivalent nitrogens the proper distance from the carboxylic acid. The molecule in the preceding compound is not reported to internalize in tumor cells, but instead cleaves via neutrophil elastase outside the tumor. The molecule in the preceding compound is a complicated molecule, which could potentially result in some issues when scaling up the synthesis. The preceding compound is synthesized in more than 20 steps.

One of the big issues with ADCs is the high cost, which is a result of the difficulties running bioconjugations with large biomolecules on a large scale. The SMDCs, while much smaller than the ADC biomolecules, still need to have the targeting piece, the chemotherapy, and a method of linking the targeting piece and the chemotherapy that is stable in the blood stream but cleaves at the tumor site. Thus, SMDCs are likely to be bigger than traditional small molecule therapeutics, which can make scale-up more challenging for SMDCs, making SMDCs potentially more costly than the traditional small molecule therapies, but still cheaper than ADCs.

There are other integrin αvβ3 peptidomimetic targeted SMDCs, including one that has a paclitaxel chemotherapy attached via a linker to a spot in the peptidomimetic that is roughly halfway between the carboxylic acid and multivalent nitrogen group in a "standard" integrin αvβ3 peptidomimetic (Piras et al. *Synlett* 28 2917 2769-2776). The attached linker and chemotherapy results in a significant decrease in the integrin αvβ3 potency of the molecule, and the overall cytotoxicity of the conjugate was less than the chemotherapy alone in these conjugates.

Paulus and Sewald (*Frontiers in Chemistry,* 2022, 10, 869639) report an integrin αvβ3 peptidomimetic targeted conjugate with monomethylauristatin E linked via a cathepsin B cleavable linker, resulting in conjugates with significantly less integrin αvβ3 potency than standard RGD molecules. See also (Carlson et al, *acschemicalbiology,* 2007, 2, 119-127), and (Liu et al., *Mol. Pharm.* 2012, 9, 168-175) who report SMDCs with a "traditional" integrin αvβ3 peptidomimetic with the requisite acidic and multivalent nitrogen functionalities, with a chemotherapy linked to the aryl sulfonamide portion of the molecule. Scale-up of these complex molecules, which are zwitterionic and also contain a multivalent nitrogen moiety, would be challenging.

Similar peptidomimetics have also been used for targeted imaging; see for example (Alsibai et al, *J. Med. Chem* 2014, 57, 9971-9982). Rerat et al. (Rerat, *J. Med. Chem.* 2009, 52, 7029-7043) have attached small PEGs (PEG3-PEG5) to a tyrosine based integrin αvβ3 scaffold, with the goal of functionalizing biosurfaces with integrin αvβ3 ligands. There are other examples of small (less than 5 monomer units) PEGs used to connect a traditional integrin αvβ3 peptidomimetic to different biological moieties. A large PEG conjugated to a traditional integrin αvβ3 peptidomimetic is disclosed in Pourcelle at al (Poucelle, J. Fluorine Chem 2012, 140, 62-69), namely a nonspecific attachment of the integrin αvβ3 piece to a polydisperse PEG1000, where the PEG has a molecular weight of approximately 1000 Daltons.

Previously disclosed integrin avb3 targeted SMDCs are usually zwitterionic, as they typically have both a carboxylic acid and a multivalent nitrogen, and are also larger than typical small molecule therapeutics, as they by necessity have a targeting piece, a chemotherapy, and a linker that releases the chemotherapy. Thus the vast majority of integrin αvβ3 targeted SMDCs in the literature require a very inefficient reverse phase chromatography purification, making scale-up of these SMDC compounds in the literature problematic.

Integrin αvβ3 targeted antibodies have been used as ADCs to deliver chemotherapy, including commercially available integrin αvβ3 targeted antibodies; see website "www.creative-biolabs.com/adc/target-integrin-alpha-v-beta-3-211.htm". An integrin αvβ3 antibody on its own made it to phase 2 in clinical trials (Hersey, *Cancer* 2010, A Randomized Phase 2 Study of Etaracizumab . . . ), and an αvβ6 targeted ADC with MMAE as the payload entered phase 1 (Patnaik, a phase 1 study of SGN-B6A, *J. Clin. Oncol.* 39, 2021).

There are some reports of less potent integrin avb3 binding compounds that do not have the multivalent nitrogen and carboxylic acid moieties 12-14 angstroms apart. Elliot et al. (*BMCL* 2009, 19, 4832-4835) discloses structures (see below), the most potent of which for integrin αvβ3 is 11 nM.

Other structures include the compounds of Dayam et al (Dayam, *J. Med Chem* 2006, 49, 4526-4534) (see below) which appear to be pan assay interference compounds (PAINS), which are compounds that falsely show up as potent compounds in biological screens. Others have dismissed these compounds disclosed by Dayam et al. disclosing that that these leads "may be unsuitable for development". See the review by Miller et al (Miller, J. Med. Chem. 2017, 60, 3241-3251). There are other relevant compounds from Zhou et al (Zhou, *Bioorg med chem lett* 2006, 16, 5878-5882) (see below) which appear to have the multivalent nitrogen piece, but not the carboxylic acid. Note that while the three structure types below do not have the carboxylic acid and multivalent nitrogen 12-14 angstroms apart, they are also significantly less potent for integrin αvβ3 (at least 1-2 orders of magnitude) than peptidomimetics that do have the carboxylic acid and multivalent nitrogen 12-14 angstroms apart.

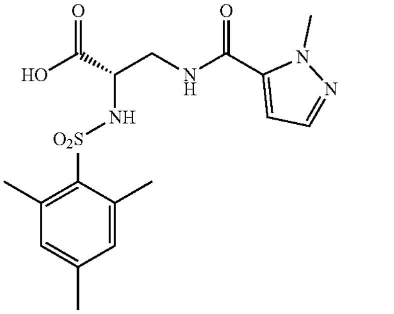

Elliot et al, BMCL 2009, 19, 4832-4835

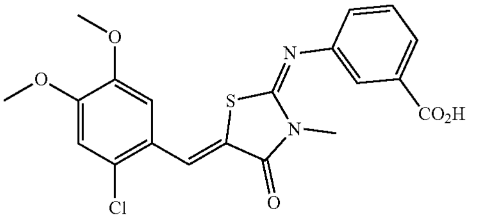

Dayam et al, J. Med Chem. 2006, 49, 4526-4534

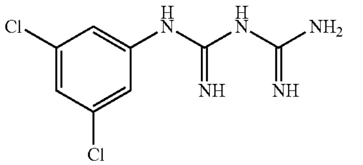

Zhou et al., Bioog. Med. Chem. Lett. 2006, 16, 5878-5882

For most ADCs, after binding to receptors on the exterior of the tumor cell, the ADC is internalized, ending up in the cell late endosome or lysosome. It is important to have a cleavable linker that releases the chemotherapy inside the cancer cell, but not systemically in the blood stream. Most ADCs use a cathepsin B cleavable linker, such as Val-Cit-PAB or Val-Ala-PAB for this purpose.

Active cathepsin B enzyme is present in high concentration in cell lysosomes and late endosomes, but not elsewhere in vivo, making this a very efficient way to release chemotherapy inside the tumor cell when small molecule drug conjugates (SMDCs) are used, provided that the SMDCs are internalized effectively into the cancer cell lysosomes. However, getting this type of effective internalization of simple integrin αvβ3 targeted small molecule drug conjugates, using single integrin αvβ3 ligands, has been problematic in the past, since the simple integrin αvβ3 targeted conjugates do not internalize effectively in cells (Pina, *chemistry select,* 2017, 2, 4759; Dal Corso, Curr. *Topics in medicinal chemistry,* 2016, 16, 314-329). The targeted integrin αvβ3 piece in these SMDCs requires multiple integrin αvβ3 ligands in order to get the combination of integrin αvβ3 targeting and effective transport to the lysosome. However, multiple targeting ligands on a SMDC presents major obstacles for the synthesis of the conjugate.

RGD peptide internalization can change when the peptide is bound to a very large PEG, see Kemper and Sewald et. Al, (*ChemBio Chem* 2020, 21, 496-499). The Sewald group's structure has a large polydisperse PEG with a molecular weight of 5000, with no chemotherapy attached. No integrin avb3 peptidomimetics with a PEG greater than 10 monomer units have been reported, and there are no reports demonstrating that PEG size has any effect on integrin αvβ3 peptidomimetic internalization.

SUMMARY

First embodiments of the present invention include a chemical compound, comprising the following Markusch structure:

$A\text{-}L_1\text{-}PEG_1\text{-}L_2\text{-}PEG_2\text{-}CL\text{-}X$ wherein $A\text{-}L_1\text{-}PEG_1$ is a targeting structure configured for targeting av integrins in cancer cells and does not include a standard multivalent nitrogen moiety;

wherein A is a structure that includes a standard carboxylic acid moiety;

wherein $L_1$ is a first linking structure selected from the group consisting of

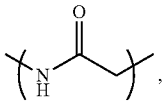, 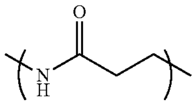,

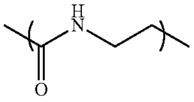, and NULL;

wherein $PEG_1$ is the following structure, wherein $n_2$ is in a range of 5-72;

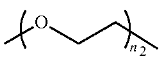;

wherein $L_2$ is the following second linker structure, wherein $n_3$ is in a range of 0-4:

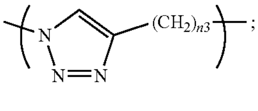;

wherein $PEG_2$ is the following repeating structure, wherein $n_4$ is in a range of 0-67 and $n_2$+$n_4$ is in a range of 20-72;

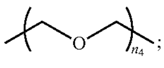;

wherein CL is the following cleavable linker:

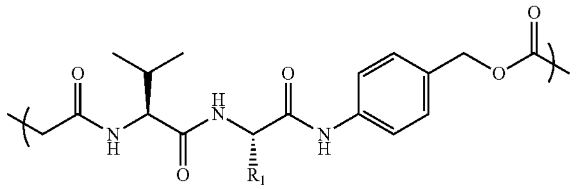

wherein $R_1$ is selected from the group consisting of methyl,

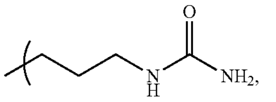

and

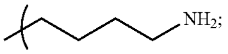

wherein X is either Chemo1 or $L_3$-Chemo2, wherein Chemo1 denotes a first chemotherapy, wherein Chemo2 denotes a second chemotherapy, and wherein $L_3$ is the following linker that links Chemo2 to CL:

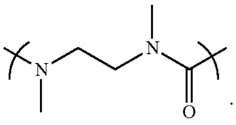

Second embodiments of the present invention include a chemical compound, comprising the following Markusch structure:

$A-L_1-PEG_1-N_3$ wherein $A-L_1-PEG_1$ is structure that does not include a standard multivalent nitrogen moiety;

wherein A is a structure that includes a standard carboxylic acid moiety;

wherein

A= 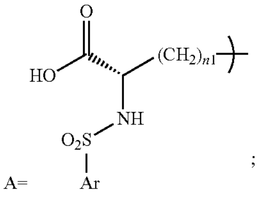 ;

wherein $n_1$ is in a range of 1-6;

wherein Ar is selected from the group consisting of

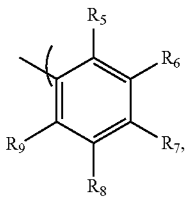

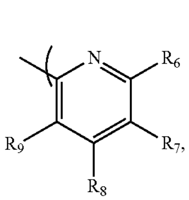

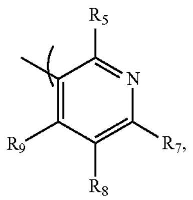

-continued

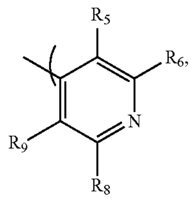

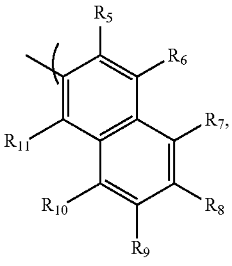

and

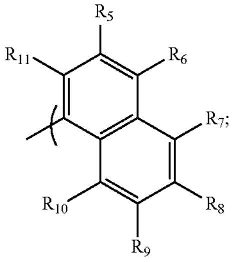

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2$Me, —O-Alkyl, and -3,5-dimethyl-1-pyrazolyl;

wherein Alkyl is selected from the group consisting of: Me, Et, iPr, nPr, nBu, iBu, secBu, tBu, $C_5$-$C_{12}$ n-alkyl, cyclopentyl, and cyclohexyl;

wherein $L_1$ is a first linking structure selected from the group consisting of

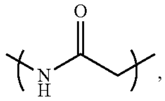

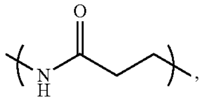

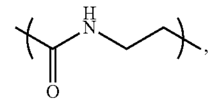

and NULL;

wherein $PEG_1$ is the following structure, wherein $n_2$ is in a range of 5-72;

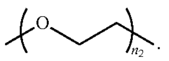

Third embodiments of the present invention include a chemical compound, comprising the following Markusch structure:

$A-L_1-PEG_1$-OMethyl wherein $A-L_1-PEG_1$ is a targeting structure configured for targeting av integrins in cancer cells and does not include a standard multivalent nitrogen moiety;

wherein A is a structure that includes a standard carboxylic acid moiety;

wherein $L_1$ is a first linking structure selected from the group consisting of

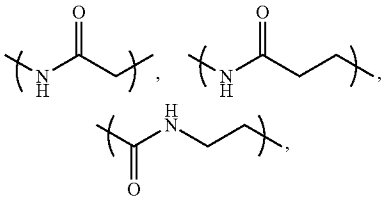

and NULL;

wherein $PEG_1$ is the following structure, wherein $n_2$ is in a range of 20-72;

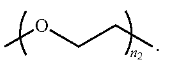

Fourth embodiments of the present invention include a method for treating cancer in a mammal.

The method includes administering a therapeutically effective amount of a chemical compound to the mammal;

wherein αv integrins are overexpressed in tumors comprising cancer cells of the cancer in the mammal;

wherein the chemical compound comprises the following Markusch structure:

$A-L_1-PEG_1-L_2-PEG_2-CL-X$ wherein $A-L_1-PEG_1$ is a targeting structure configured for targeting the αv integrins in cancer cells and does not include a standard multivalent nitrogen moiety;

wherein A is a structure that includes a standard carboxylic acid moiety;

wherein

A= 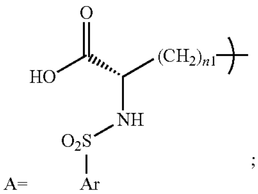 ;

wherein $n_1$ is in a range of 1-6;

wherein Ar is selected from the group consisting of

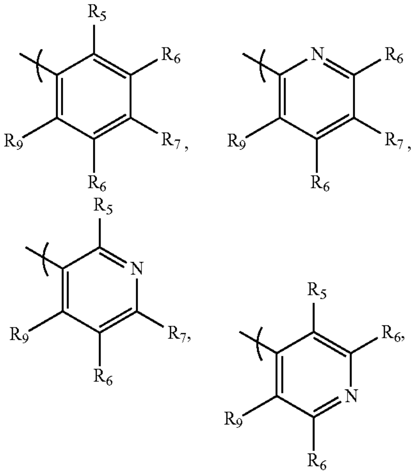

-continued

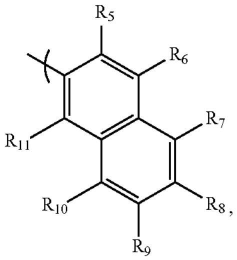 and 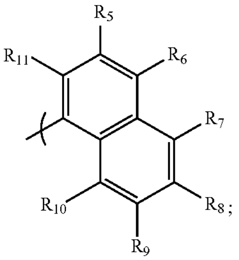

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2Me$, —O-Alkyl, and -3,5-dimethyl-1-pyrazolyl;

wherein Alkyl is selected from the group consisting of: Me, Et, iPr, nPr, nBu, iBu, secBu, tBu, $C_5$-$C_{12}$ n-alkyl, cyclopentyl, and cyclohexyl;

wherein Me denotes Methyl, Et denotes Ethyl, Pr denotes Propyl, and Bu denotes Butyl;

wherein $L_1$ is a first linking structure selected from the group consisting of

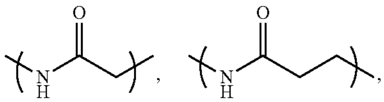 and

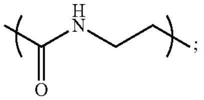

wherein $PEG_1$ is the following structure, wherein $n_2$ is in a range of 5-48;

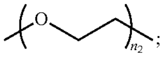

wherein $L_2$ is the following second linker structure, wherein $n_3$ is in a range of 0-4:

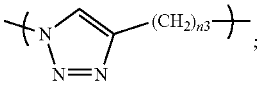

wherein $PEG_2$ is the following repeating structure, wherein $n_4$ is in a range of 0-43 and $n_2$+$n_4$ is in a range of 20-72:

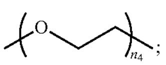

wherein CL is the following cleavable linker:

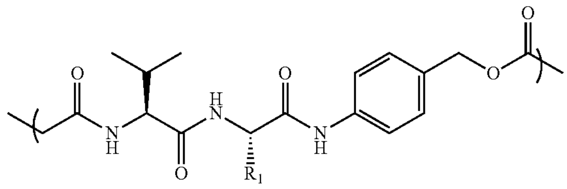

wherein $R_1$ is selected from the group consisting of methyl,

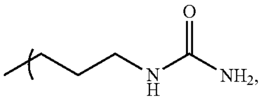
and
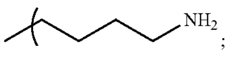
;

wherein X is either Chemo1 or $L_3$-Chemo2, wherein Chemo1 denotes a first chemotherapy, wherein Chemo2 denotes a second chemotherapy, and wherein $L_3$ is the following linker that links Chemo2 to CL:

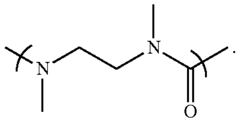
.

DETAILED DESCRIPTION

Figure 1A:
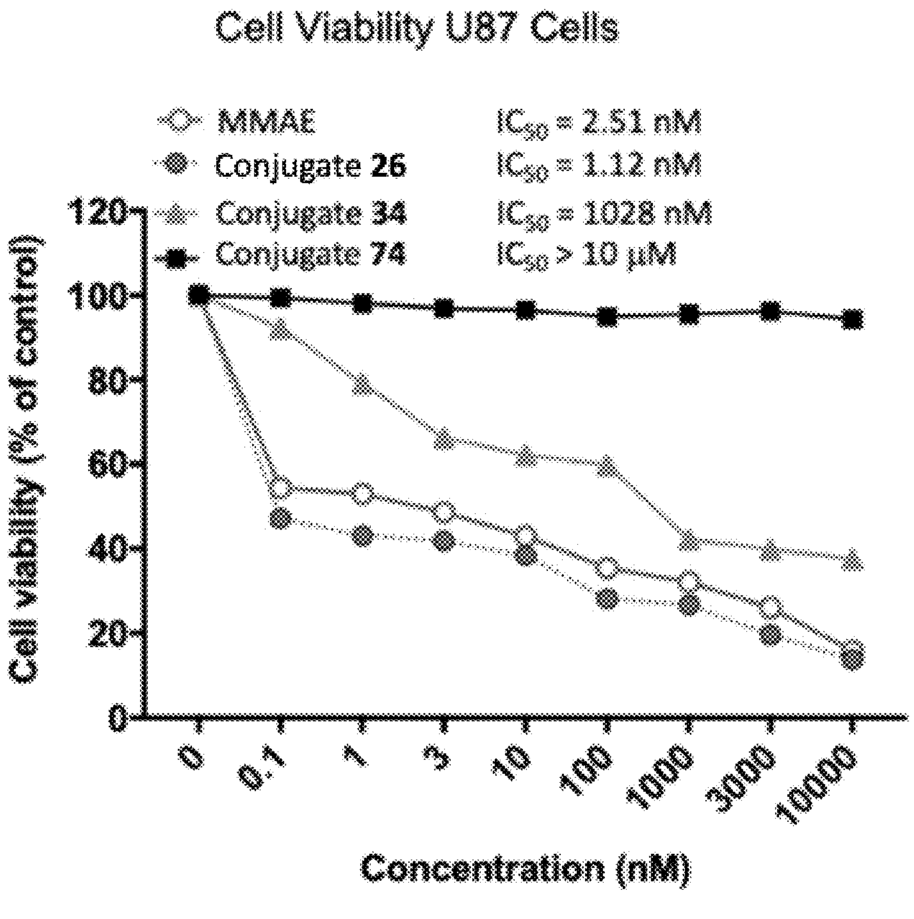
FIGS. 1A and 1B are graphs of cell viability versus compound concentration of conjugates 26, 34 and 74 for human glioblastoma U87 cells and human breast cancer MCF7 cells, respectively, in accordance with embodiments of the present invention.

The detailed description of the invention is divided into the following sections.

1. Introduction
2. Markusch Structures
3. Conjugates
   3.1 Conjugates Having Integrin av Targeting Piece With Chemotherapy
   3.2 Conjugates Having Integrin av Targeting Piece Without Chemotherapy
4. Synthesis Schemes With Implementation of Synthesis Steps
   4.1 General Synthesis Schemes
   4.2 Synthesis Schemes For Conjugates
   4.3 Implementation of Synthesis Steps
5. Testing Effectiveness of Conjugates
   5.1 In vitro integrin αvβ3 binding biological assay
   5.2 In vitro cell adhesion biological assay
   5.3 In vitro cell viability biological assay
   5.4 In vivo biological efficacy
   5.5 Application of Test Results To Treatment of Cancer 1. Introduction The present invention identifies conjugates. A conjugate is a chemical compound formed by the joining of two or more chemical compounds. Each conjugate has a unique chemical structure and is assigned a unique conjugate number for identification purposes. Conjugates and associated conjugate numbers may also be identified as structures and associated structure numbers (e.g., conjugate 26 and structure 26 refer to the same chemical compound).

The description of the present invention identifies embodiments of polyethylene glycol (PEG) as PEGn denoting PEG having n monomer unites. For example, PEG36 denotes PEG having 36 monomer units.

Small molecule-drug-conjugates (SMDCs), utilizing a small molecule instead of the large antibody to target the chemotherapy to the tumor, could potentially avoid some of the antibody-drug-conjugate (ADC) issues. An ideal SMDC would satisfy the following criteria:

(i) strong and selective binding to a protein highly expressed at the tumor site with minimal systemic expression;

(ii) an efficient internalization into tumor cells, allowing for effective chemotherapy release via the same selective cathepsin B mediated cleavage that occurs with many ADCs;

(iii) good stability in the blood stream, with minimal release of chemo prior to tumor internalization;

(iv) a simple, scalable synthesis, allowing for a much more cost effective treatment than ADCs; and (v) subcutaneous dosing, so that the therapy can be self-administered.

To date, there have been no SMDCs that meet all of the preceding criteria, resulting in no SMDCs being clinically approved.

The present invention presents SMDCs that:

(i) target cancer cells with a high affinity (0.1-0.2 nanomolar binding) for the integrin αvβ3 receptor, which is highly expressed in cancer cells relative to normal cells;

(ii) internalize efficiently in cancer cells, which is especially apparent in cell viability assays, where the targeted conjugates of the present invention releases chemotherapy which results in cell death levels similar to cell death levels observed with the chemotherapy alone;

(iii) have in vivo subcutaneous dosing in mice that shows equal or better tumor shrinkage relative to chemotherapy alone, with a better safety profile than the chemotherapy alone; and (iv) are synthesized by a 5-13 step route with high yields at all steps and no difficult purification steps.

The following structural configuration of the present invention includes, inter alia: (i) a simple integrin αvβ3 peptidomimetic targeting piece connected to a large monodisperse polyethylene glycol (PEG, 20-72 ethylene glycol units long); (ii) cleavable linkers that are used in many ADCs connected to the PEG; and (iii) the same chemotherapies used in ADCs connected to the cleavable linkers, although new subsequently developed chemotherapies and additional cleavable linkers can likewise be used effectively in the following structural configuration of the present invention.

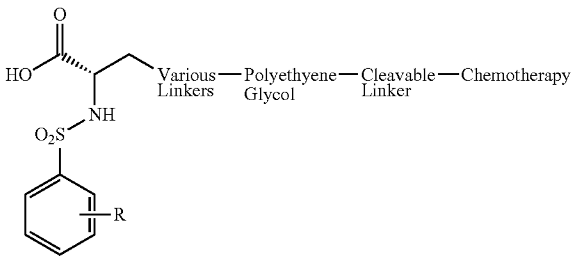

The preceding structural configuration includes either one PEG structure or two PEG structures connected via a linker such as, inter alia, a 1,2,3-triazole. Thus, the PEG length of 20-72 in the preceding structural configuration is a total PEG length, namely either the PEG length of the one PEG structure or the sum of the PEG lengths in the two PEG structures.

The preceding structural configuration broadly defines SMDC conjugates of the present invention. More specific Markusch structures of the present invention are presented infra.

The polyethylene glycol (PEG) replaces the basic or multivalent nitrogen moiety that was believed to be required for activity in essentially all potent integrin αvβ3 peptidomimetics. The simple integrin αvβ3 peptidomimetic targeting piece has very potent integrin αvβ3 binders even though the basic or multivalent nitrogen moiety has been replaced. The preceding structural configuration is a simple integrin αvβ3 targeting piece, connected to a relatively large monodisperse PEG, connected to the cleavable linker, which is connected to the chemotherapy, via the simplest chemistry possible. This simpler design results in a less expensive synthesis, resulting in lower costs. The integrin αvβ3 targeting piece is structured as A-$L_1$-$PEG_1$, wherein structure A is linked to a first PEG ($PEG_1$) by linking structure $L_1$, and wherein A, $L_1$ and $PEG_1$ collectively facilitate the integrin αvβ3 binding.

The relatively large polyethylene glycol (20-72 monomer units) facilitates proper internalization of the conjugates after binding to integrin αvβ3. Conjugates need to be internalized and transported to the late endosomes/lysosomes so that the Cathepsin B enzyme can release the chemotherapy. Data obtained by inventors of the present invention demonstrates that conjugates with smaller PEGs (e.g., 15 monomer units) are much less effective than conjugates with larger PEGs (e.g., 36 monomer units).

The conjugates can be made via a straightforward, scalable, convergent synthesis. There are no low yield steps or difficult purifications, unlike all other SMDCs disclosed to date. The simpler synthesis results in a less expensive therapy than ADCs and other SMDCs.

Targeting portions of the inventive conjugates are similar to previously disclosed integrin αvβ3 binders, with an exception of not having the multivalent nitrogen moiety that was believed to be required for activity (see Coleman, *JmedChem* 2004, 47, 4829 and references therein). The conjugates of the present invention are equally potent compounds by replacing the multivalent nitrogen function with a simple polyethylene glycol. The known potent, exemplary integrin αvβ3 antagonist and clinical candidate MK-0429 (below) (Huthchinson, *J. Med Chem* 2003, 46, 4790) has the multivalent nitrogen group spaced 12-14 angstroms from the required carboxylic acid. In contrast, conjugates 61 and 26 (below) of the present invention do not include a multivalent nitrogen group 12-14 angstroms from the carboxylic acid group.

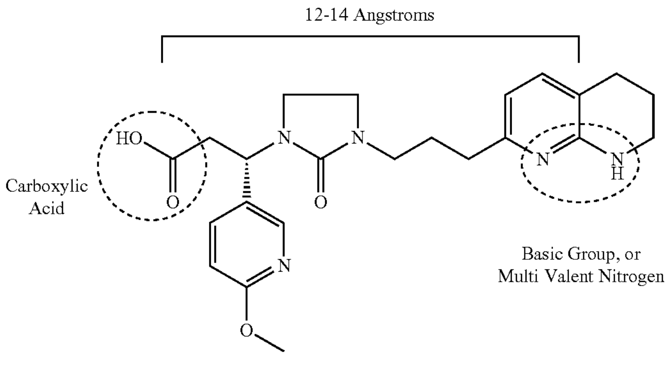

MK-0429

-continued

Conjugate 61

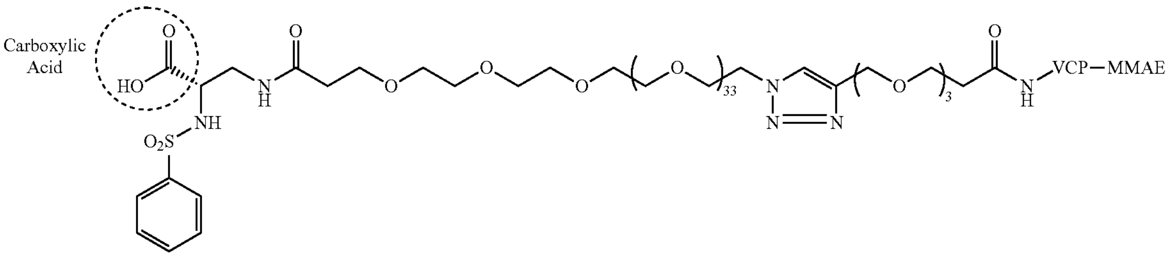

Conjugate 26

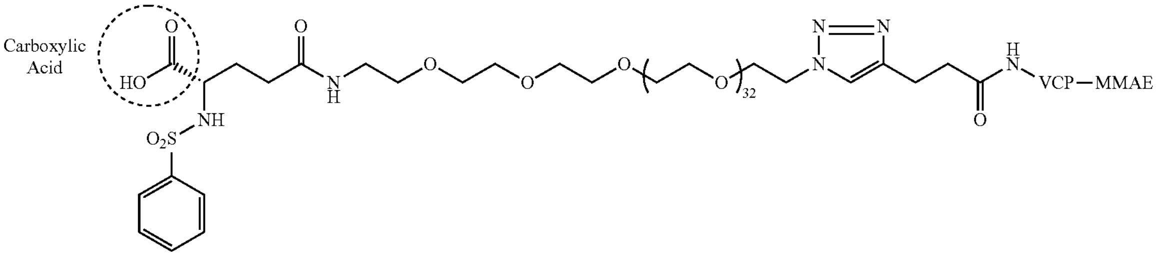

Research by inventors of the present invention has surprisingly and unexpectedly revealed that a large PEG within a specified range of monomer units is critical for proper cell internalization after binding to the integrin αvβ3 receptor, based on in vitro and in vivo data obtained by inventors of the present invention (presented infra in Section 5), which includes cell viability studies, where conjugates with smaller PEGs have 3 orders of magnitude lower potency than larger PEG conjugates. In vivo data shows both efficacy and safety advantages for PEG39 conjugates (i.e., PEG with 39 monomer units) versus PEG15 conjugates (i.e., PEG with 15 monomer units). Note that there are 2 different neighboring PEG groups in some conjugates such as conjugate 61. For conjugate 61, with 2 PEGs with lengths of 36 and 3, respectively, we designate a total PEG length of 39. These biology results with large PEGs require release of the chemotherapy from the SMDC via internalization into the late endosomes/lysozomes. The present invention provides integrin αvβ3 peptidomimetics designed to internalize by use of the PEG conjugates in a specified range on monomer units.

There is some literature that indicates that a RGD peptide internalization method can change when the peptide is bound to a very large PEG; e.g., see Kemper and Sewald et. al, (*ChemBio Chem* 2020, 21, 496-499). However, there are no reports stating that larger PEGs can change the internalization of integrin αvβ3 peptidomimetics, let alone a pegylated integrin αvβ3 peptidomimetic that does not have a multivalent nitrogen moiety. The Sewald group's structure is significantly more complex than the conjugates of the present invention, with no chemotherapy attached, and has a large polydisperse PEG with a molecular weight of 5000 daltons. In contrast, compounds of the present invention include a mondisperse PEG20-PEG72, which corresponds to a molecular weight of 880-2112 daltons. Conjugates with smaller PEGs than the PEGs used in conjugates of the present invention do not work as well. Larger polydisperse PEGs, up to the 5000 Dalton MW used in the Kemper/Sewald ChemBioChem paper, would be difficult to synthesize and thus not reasonably viable in practice, since synthesis of such large PEG compounds is progressively more difficult as the PEGs get larger. Thus, PEG20-PEG72 is the "sweet spot" for the inventive structures of the present invention, since smaller PEGs don't work as well and larger PEGs are significantly more difficult to synthesize. Note that the PEGs used in the present invention are monodisperse (i.e., single length PEGs), and the PEG used in the Kemper/Sewald paper is polydisperse (i.e., a mixture of different PEG lengths with an average molecular weight of 5000 Daltons). Monodisperse PEG containing conjugates are much more desirable in SMDCs than polydisperse PEG containing conjugates, as monodisperse PEG containing conjugates are easier to synthesize and purify than polydisperse PEG containing conjugates, and it is much easier to do bioanalytical work, such as quantification of compound levels in vivo, with monodisperse PEG containing conjugates than with polydisperse PEG containing conjugates, as the polydisperse PEG conjugates are in effect mixtures of multiple compounds with different molecular weights.

The conjugate molecules of the present invention use cleavable linkers and chemotherapies similar to those cleavable linkers and chemotherapies used in ADCs, and the inventive conjugates 61 and 26 use the exact same Val-Cit-PAB linked to monomethylauristatin E (MMAE) that is used in clinically approved ADCs, including Brenuximab Vedotin, Polatuzamab Vedotin, and Enforetunab Vedotin. Val-Cit-PAB and similar cathepsin B cleavable linkers, as well as the chemotherapy monomethylauristatin E (MMAE) have been used extensively in ADCs for the last 20 years; see Doronina 2003 *Nature Biotechnology* and the patent WO 03/043583 with a filing date of 20 Nov. 2002. The Val-Cit-PAB and related cleavable linkers need a chemotherapy with a primary or preferably a secondary amine functionality to attach the cleavable linker to the chemotherapy.

Inventive conjugates of the present invention have a few chemotherapies listed as Markusch structures that do not have the required amine, including chemotherapies SN38 and PNU-159682. These inventive conjugates have an additional linker, $L_3$, between the Val-Cit-PAB and the chemotherapy that will also be released after cathepsin B cleavage of the Val-Cit-PAB, thus releasing the free chemotherapy. These additional $L_3$ linkers have been described elsewhere, including Dal Corso (Angew *Chem Int Ed.* 2020, 59, 4176-418) and Ito et al. (*Chem Pharm. Bull.* 68, 2020, 212-215). There are quite a few different chemotherapies that have been used in ADCs that have entered clinical trials that could be included in inventive conjugates of the present invention.

All of the pieces of inventive SMDCs of the present invention can be readily synthesized on their own, but there are issues with putting the entire molecule together. Large PEGylated molecules are typically not crystalline; thus some type of chromatography is probably required at the end of the scheme, and normal phase chromatography of these types of molecules is not as simple as it is with traditional small molecules. The key to synthesis of the inventive molecules is efficient connection of both the integrin αvβ3 targeting piece as well as the chemotherapy/cleavable linker piece to the PEG, which requires a differentially substituted (i.e., different reactive functional groups on the two ends of the PEG), large, monodisperse PEG. A synthesis strategy that is utilized for the present invention is using techniques in which one end of the PEG is selectively connected to either the integrin αvβ3 targeting piece or the cleavable linker/chemotherapy piece; then the other end of the PEG is connected to the targeting piece or linker/chemotherapy piece, whichever is still needed, so that there are as few as possible steps run on large PEG substrates. Fortunately, a few of these large, differentially substituted PEGs are now commercially available, with terminal functionalities like amine, protected amine, carboxylic acid, activated carboxylic acid, terminal alkyne, and azide. The large PEG in Conjugate 61, for instance, is not added until the very end of the synthesis, so only the last 2 steps are run with large PEG substrates, and these are a very simple amide coupling, and a copper-catalyzed alkyne-azide cycloaddition (CuAAC, also known as click chemistry), respectively. These 2 steps are shown in the synthesis schemes below for inventive Conjugate 61 and inventive Conjugate 26.

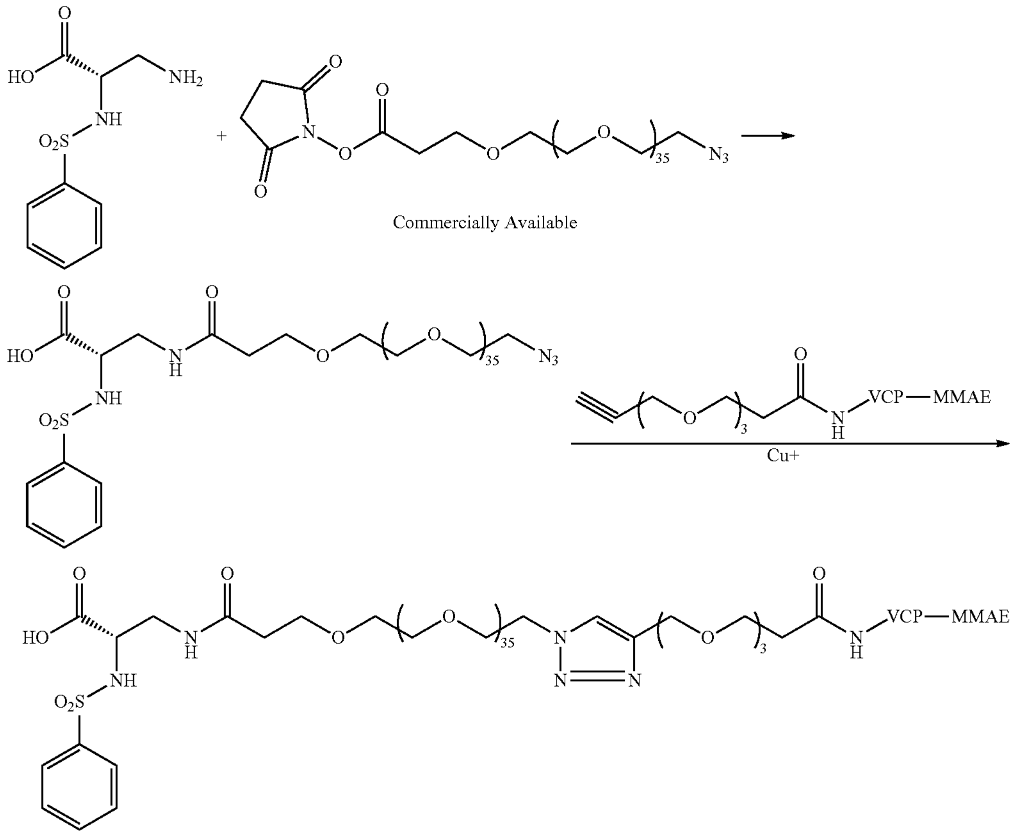

Conjugate 61

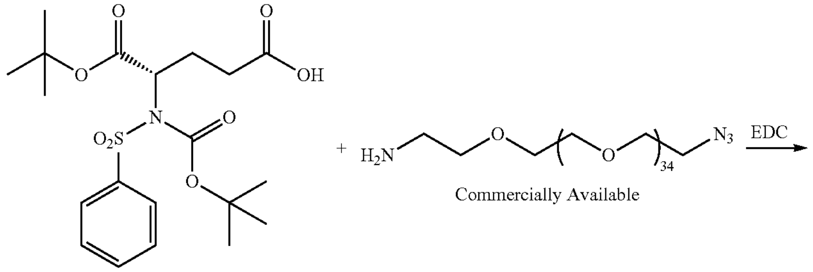

-continued

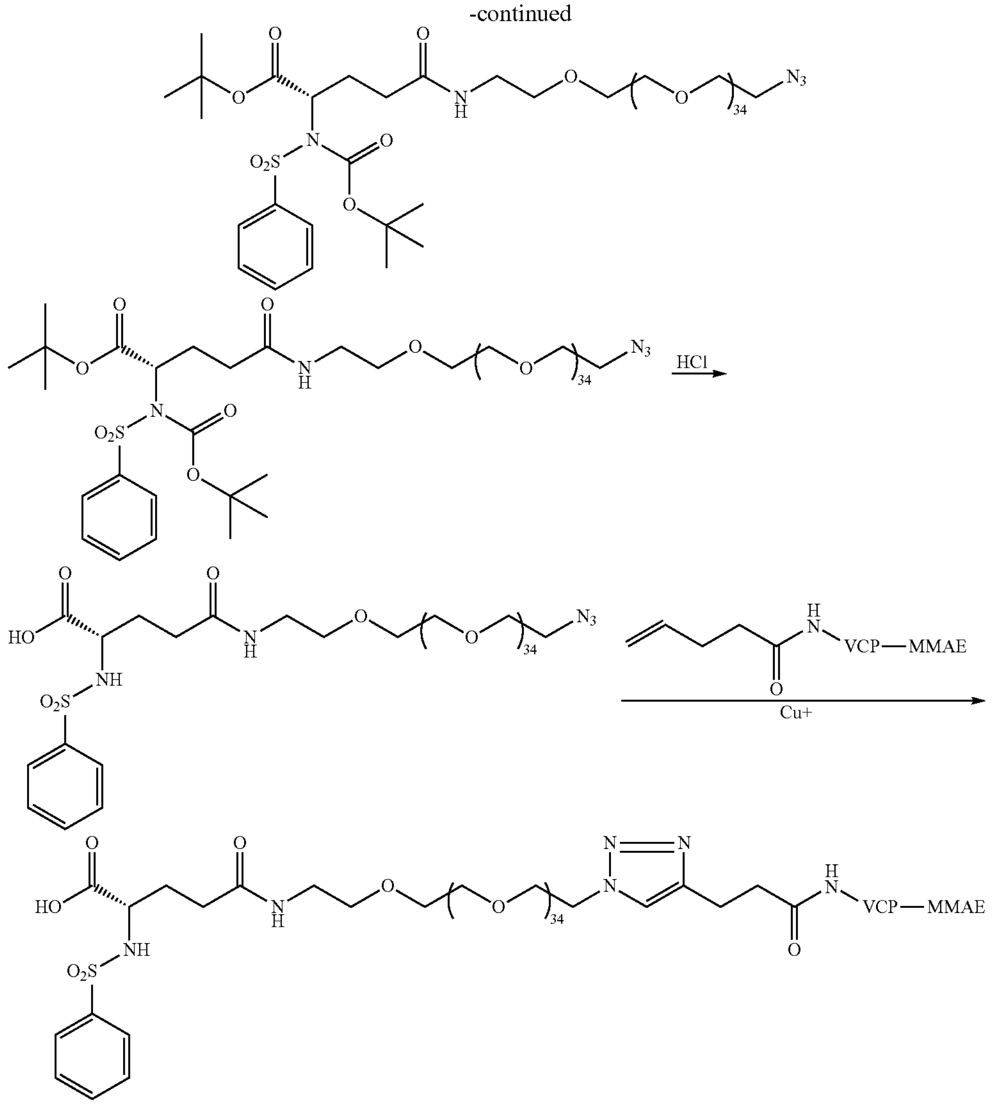

Conjugate 26

Conjugate 26 requires only 3 steps to be run on large PEG substrates, an amide coupling, a simple acid deprotection step, and a CuAAC click reaction, as shown in the preceding synthesis scheme. Note that the syntheses of the various conjugates are between 5 and 13 steps from commercially available materials, although synthesis of the conjugates is not limited to between 5 and 13 steps. The synthesis schemes are also designed to be as simple as possible, using simple reactions and convergent syntheses. The syntheses of all of the conjugates are readily scalable, with no reverse phase chromatography purification required. In contrast, the vast majority of integrin αvβ3 targeted SMDCs in the literature require a very inefficient reverse phase chromatography purification, making scale-up of these literature compounds much more difficult.

Inventive conjugates of the present invention provide anti-cancer efficacy from both the integrin αvβ3 targeting piece and the chemotherapy, with synergy between the integrin αvβ3 targeting piece and the chemotherapy. In contrast, the anti-cancer efficacy of SMDCs of the prior art is typically exclusively from the chemotherapy.

The targeted chemotherapy of the present invention uses; inter alia, integrin αvβ3 as the targeting piece and employs small molecule drug conjugates (SMDCs) that have some similarities to antibody drug conjugates (ADCs) but are much cheaper to make and easier to dose, with potential safety advantages as well.

Conjugates that bind to integrin αvβ6 or integrin pan-av instead of binding to integrin αvβ3 may be alternatively used in structures of the present invention.

The novel and unobvious structures of the present invention are characterized, in embodiments, by: (i) larger PEG than conventionally used which unexpectedly improves in vivo potency and in vivo safety; and (ii) an integrin αvβ3 targeting piece that includes the standard carboxylic acid but does not include the standard multivalent nitrogen moieties, and thus does not include the standard carboxylic acid and the standard multivalent nitrogen moieties 12-14 angstroms apart.

Not having the multivalent nitrogen group results in a much easier synthesis of the inventive conjugates.

Thousands of potent integrin αvβ3 antagonists with a carboxylic acid and multivalent nitrogen moiety 12-14 angstroms apart are known. The lipophilic aryl group in the proper orientation is widely assumed to be a requirement for potent integrin αvβ3 antagonists. The lipophilic aryl group is exemplified by the methoxypyridine in MK-0429 and by the Ar group in conjugates of the present invention.

There are a very small number of known less potent integrin αvβ3 inhibitors that do not have a multivalent nitrogen functionality 12-14 angstroms from the carboxylic acid. The AZ compounds exemplified by the structure below (Elliot et al, *BMCL* 2009, 19, 4832-4835) are an example. Note that this AZ compound, the most potent in their series, is 1-2 orders of magnitude less potent than the inventive compounds tested in vitro of the present invention.

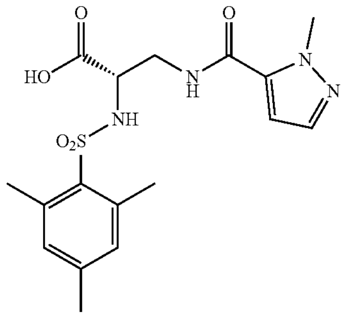

Elliot et al, BMCL 2009, 19, 4832-4835
Integrin avb3 bindng IC50 = 11 nM

An example of a known integrin αvβ3 targeted small molecule drug conjugate is the following structure from WO 2020 094471:

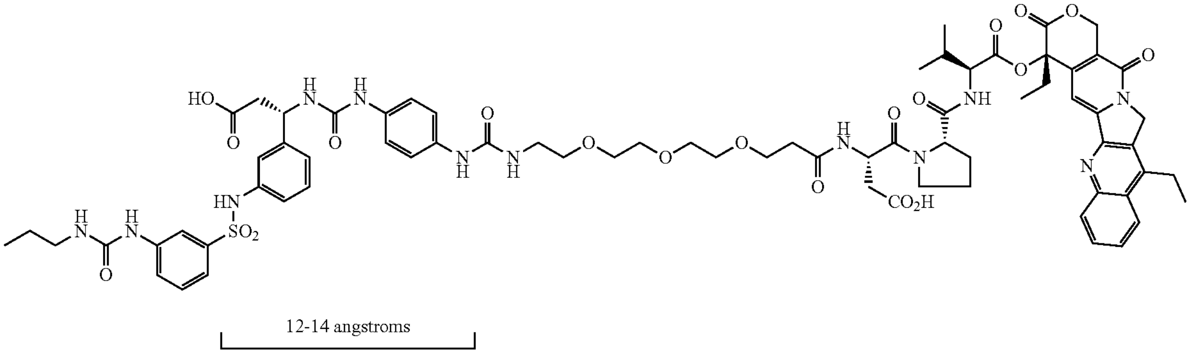 [SMILES: CCCNC(=O)Nc1cccc(S(=O)(=O)Nc2cccc([C@H](CC(=O)O)NC(=O)Nc3ccc(NC(=O)NCCOCCOCCOCCC(=O)N[C@@H](CC(=O)O)C(=O)N4CCC[C@H]4C(=O)N[C@H](C(=O)O[C@]4(CC)C(=O)OCc5c4cc4n(c5=O)Cc5c-4nc4ccccc4c5CC)C(C)C)cc3)c2)c1]

This structure has an integrin αvβ3 ligand with carboxylic acid and multivalent nitrogen 12-14 angstroms apart as well as a small PEG (i.e., PEG3) linker, in contrast with inventive PEG linker of the present invention in a range of PEG20-PEG72.

Inventors of the present invention present infra in vitro and in vivo data that supports the superiority of larger PEGs of the inventive conjugates in comparison with the conventional smaller PEGs.

Although the preceding discussion was specific to integrin αvβ3 integrin targeting, the scope of the therapeutic conjugates of the present invention also includes αvβ6 integrin targeting and pan-av integrin targeting.

2. Markusch Structures

Markusch structures of the present invention are configured as follows.

$A-L_1-PEG_1-L_2-PEG_2-CL-X$ (Full Markusch With Chemo)

$A-L_1-PEG_1-N_3$ (Intermediates in synthesis of Full Markusch)

$A-L_1-PEG_1$-Omethyl $PEG_1$ and $PEG_2$ are polyethylene glycol structures.

Chemo stands for Chemotherapy.

$N_3$ is the following chemical structure: —N═N═N.

Omethyl is the following chemical structure: —O—$CH_3$.

Structure $A-L_1-PEG_1$ is a targeting structure configured for integrin targeting such as, inter alia, integrin αvβ3 targeting, αvβ6 integrin targeting, etc.

For each of the three preceding Markusch structures, A is a structure that includes the standard carboxylic acid moiety, and $A-L_1-PEG_1$ does not include the standard multivalent nitrogen moiety. Thus, $A-L_1-PEG_1$ targeting structure does not include the standard carboxylic acid and the standard multivalent nitrogen moieties 12-14 angstroms apart. The standard carboxylic acid moiety and the standard multivalent nitrogen moiety are defined as depicted supra in the chemical structure of MK-0429.

In embodiments, $A-L_1-PEG_1-N_3$ is an intermediate structure in a process for synthesizing the Full Markusch.

In embodiments, $A-L_1-PEG_1$-Omethyl is configured to be used therapeutically on its own without added chemotherapy to treat cancer in mammals.

$L_1$ is a first linking structure selected from the group consisting of

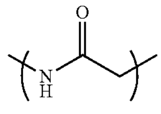,
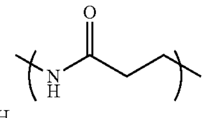,
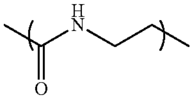, and NULL.

The first linking structure $L_1$ links $PEG_1$ to A unless $L_1$ is NULL such that $PEG_1$ is directly linked to A.

In embodiments, structure $A-L_1$ is within any one of three classes denoted as a first $A-L_1$ class, a second $A-L_1$ class, and a third $A-L_1$ class.

The first A-$L_1$ class is characterized by:

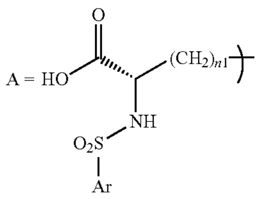

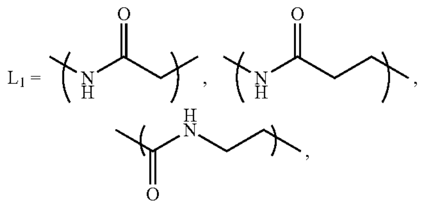

or NULL, wherein $n_1$ is in a range of 1-6.

The embodiment of $L_1$ being NULL is characterized by $L_1$ being absent such that A is directly connected to $PEG_1$ without the intervening linking structure $L_1$.

The second A-$L_1$ class is characterized by:

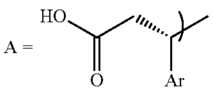

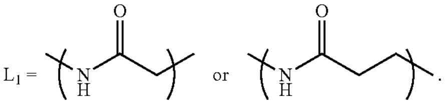

The third A-$L_1$ class is characterized by:

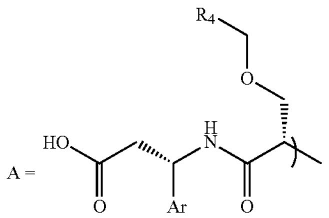

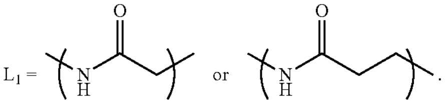

R4 is selected from the group consisting of hydrogen, Alkyl, and Ar.

Ar is selected from the group consisting of

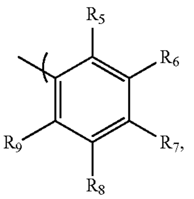

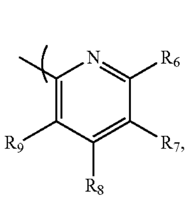

-continued

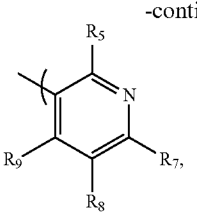

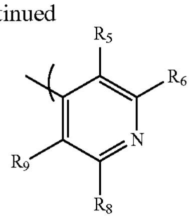

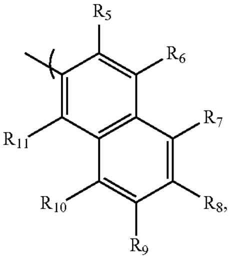

and

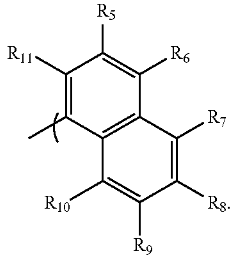

$R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2Me$, —O-Alkyl, and -3,5-dimethyl-1-pyrazolyl.

Alkyl is selected from the group consisting of: Me, Et, iPr, nPr, nBu, iBu, secBu, tBu, $C_5$-$C_{12}$ n-alkyl, cyclopentyl, and cyclohexyl.

Me denotes Methyl, Et denotes Ethyl, Pr denotes Propyl, and Bu denotes Butyl.

$PEG_1$ is the following polyethylene glycol structure wherein $n_2$ is in a range of 5-72 generally and is in a range of 5-48 in one embodiment:

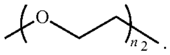

$L_2$ is a linker that is the following structure, wherein $n_3$ is in a range of 0-4:

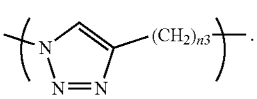

$PEG_2$ is the following polyethylene glycol repeating structure:

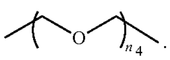

In one embodiment, $n_4$ is in a range of 0-67 and $n_2$+$n_4$ is in a range of 20-72.

In one embodiment, $n_4$ is in a range of 0-43 and $n_2$+$n_4$ is in a range of 20-48.

The embodiment of $n_4$=0 is characterized by $L_2$ being directly connected to CL with $PEG_2$ being absent.

CL is the following cleavable linker.

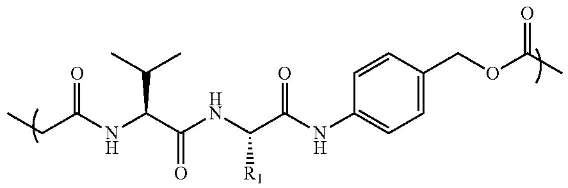

wherein $R_1$ is one of the following structures:

methyl or

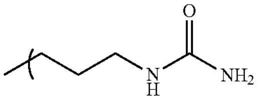 or 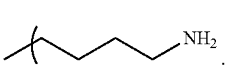

X is either Chemo1 or $L_3$-Chemo2. Chemo1 denotes a first chemotherapy within a first group of chemotherapies. Chemo2 denotes a second chemotherapy within a second group of chemotherapies. $L_3$ is the following linker that links Chemo2 to CL.

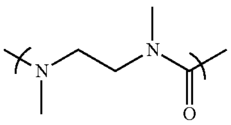

Chemo1 representing X in the Full Markusch is, inter alia, within a first class of chemotherapies used in ADCs, within a second class of chemotherapies used as kinase and Poly (ADP-ribose) polymerase (PARP) inhibitors, or within a third class of chemotherapies of nucleosides.

The following chemotherapies, which are embodiments of Chemo1 representing X in the Full Markusch, are within the first class of chemotherapies used in ADCs, though other chemotherapies used in ADCs may be used as well for Chemo1.

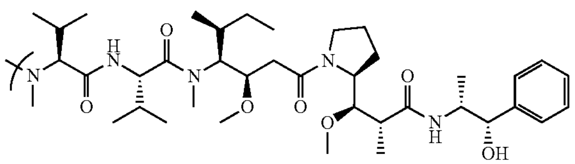

Monomethylauristatin E (MMAE)

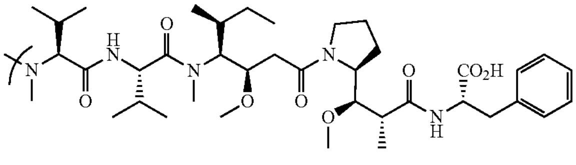

monomethylauristatin F (MMAF)

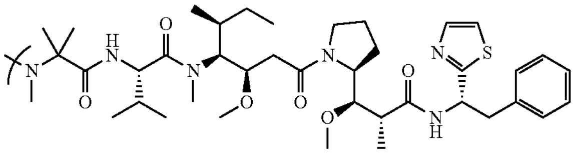

AUR0101

-continued

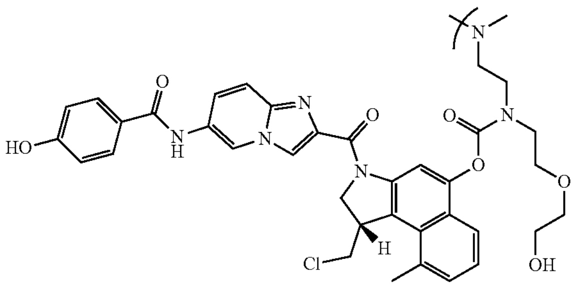

seco-DUBA

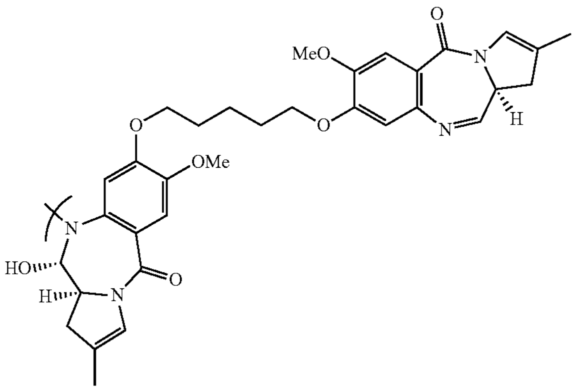

Pyrrolobenzodiazepine dimer

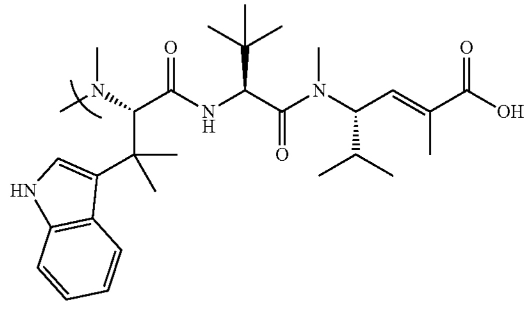

Hemiasterlin A

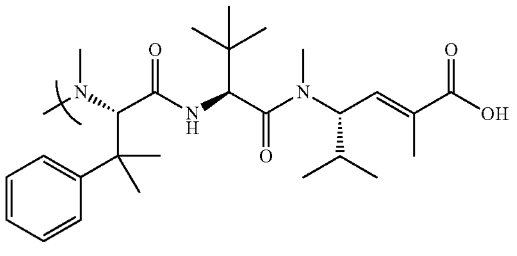

Taltobulin

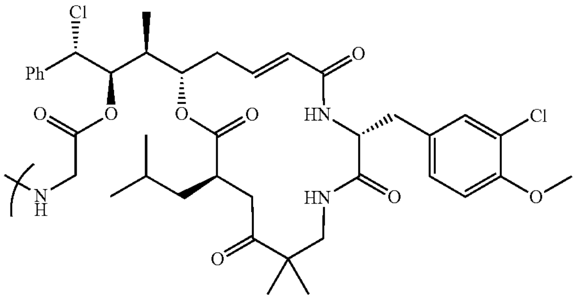

Cryptophycin

-continued

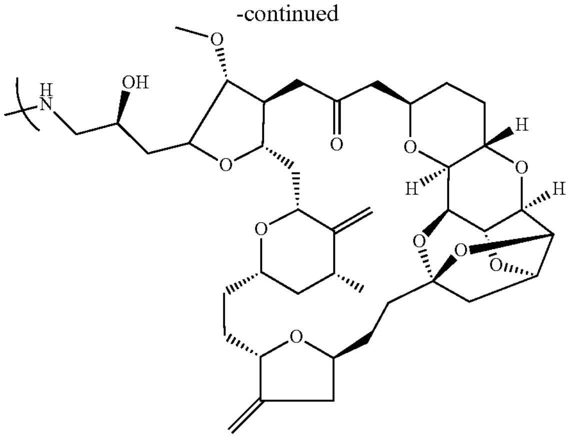

Eribulin

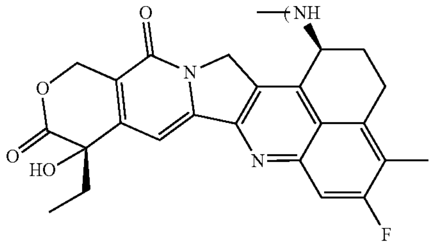

Exatecan

The following chemotherapies, which are embodiments of Chemo1 representing X in the Full Markusch, are within the second class of chemotherapies used as kinase and PARP inhibitors, though other chemotherapies used as kinase and PARP inhibitors may be used as well for Chemo1.

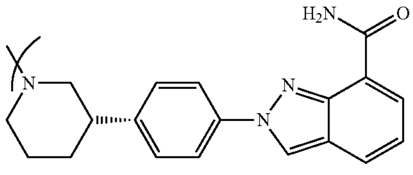

Niparib (PARP inhibitor)

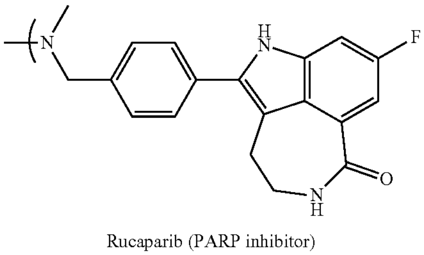

Rucaparib (PARP inhibitor)

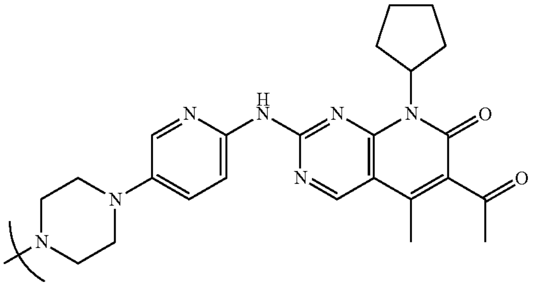

Palbociclib

-continued

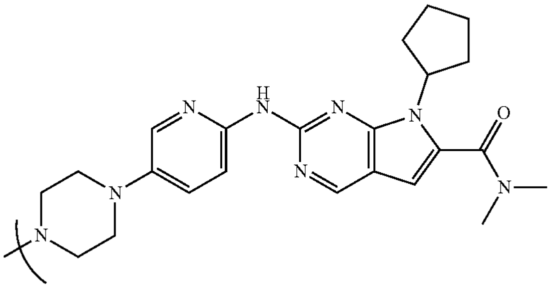

Ribociclib

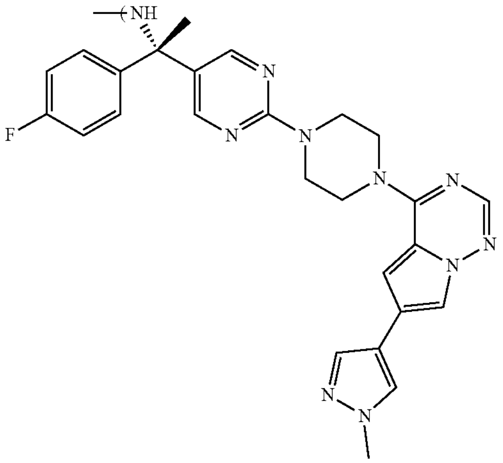

Avapritinib

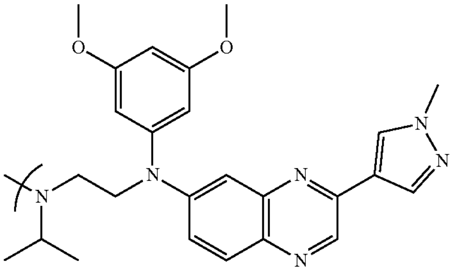

Erdafitinib

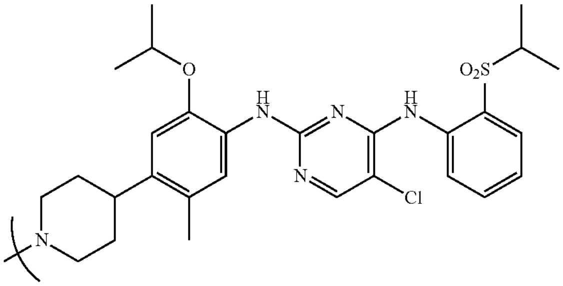

Ceritinib

-continued

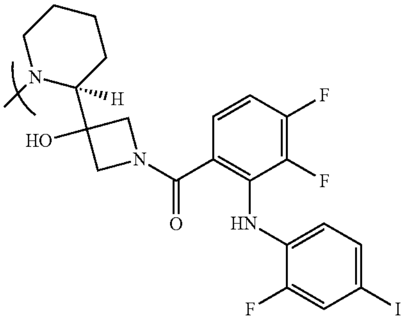

Cobimetinib

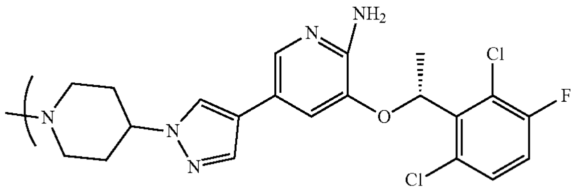

Crizotinib

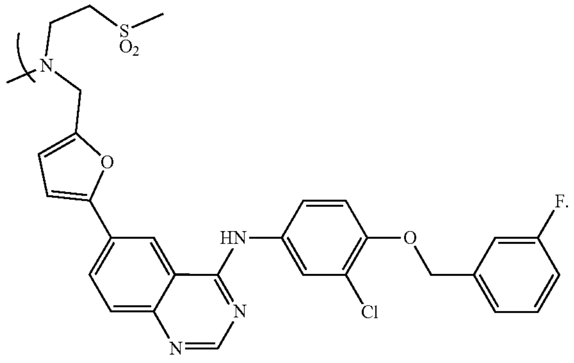

Lapatinib

The following chemotherapies, which are embodiments of Chemo1 representing X in the Full Markusch, are within the third class of chemotherapies of nucleosides, though other chemotherapies of nucleosides may be used as well for Chemo1.

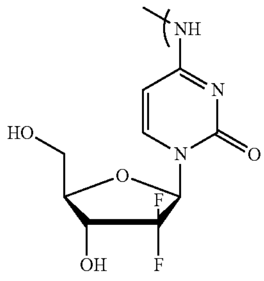

Gemcitabine

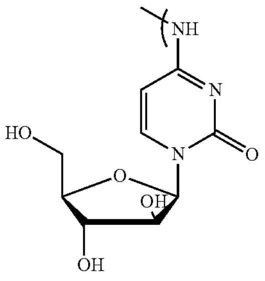

Cytarabine

-continued

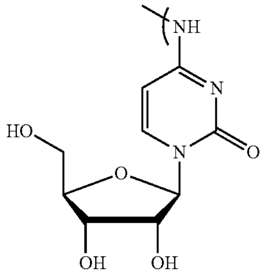

Azacytidine

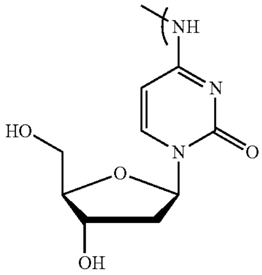

Decitabine

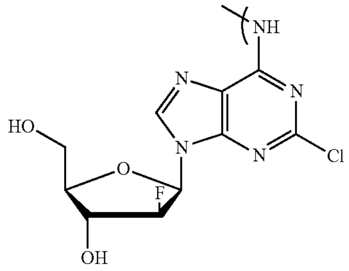

Clofarabine

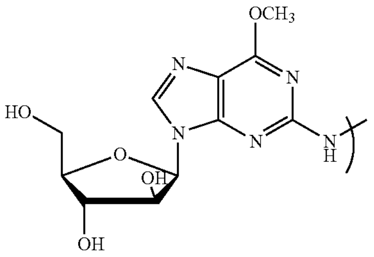

Nelarabine

Chemo2 within $L_3$-Chemo2 representing X in the Full Markusch is, inter alia, within the following chemotherapies linked to the linker $L_3$, though other chemotherapies linked to the linker $L_3$ may be used as well for Chemo2.

SN38 and derivatives

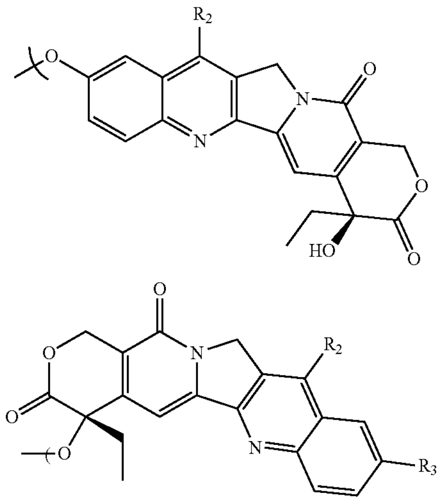

$R_2$=H or ethyl and $R_3$=H or OH.

PNU-159682 Doxorubicin derivative

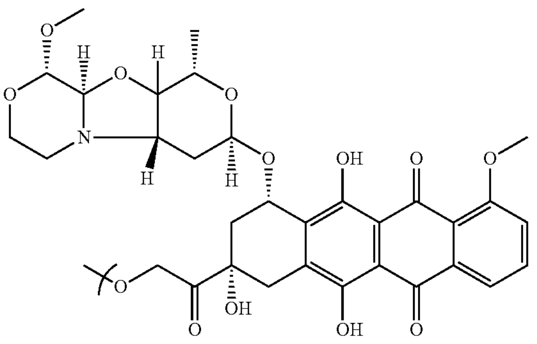 [SMILES: COCC(=O)[C@]1(O)Cc2c(O)c3c(c(O)c2[C@@H](O[C@H]2C[C@H]4C(O[C@@H]5[C@@H](OC)OCCN54)[C@H](C)O2)C1)C(=O)c1c(OC)cccc1C3=O]

As mentioned previously, $L_3$ =

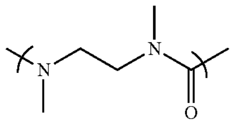

3. Conjugates

Each identified conjugate has an assigned conjugate number, a chemical structure, and a shorthand written description of the conjugate structure which may include some or all of the following information:

(i) identification of a chemotherapy ("chemo") that is a specific embodiment of X in the full Markusch;

(ii) a list of the biological tests (if any) that were performed for each conjugate (selected from: in vitro integrin αvβ3 binding, in vitro cell adhesion, in vitro cell viability, in vivo efficacy);

(iii) "Targeted A" or "Targeted B" referring to whether the conjugate has the conjugate 26 series targeting moiety or the conjugate 61 series targeting moiety, respectively (26 and 61 series conjugates have different $L_1$ linkers); "Targeted C" denoting that the conjugate does not include an $L_1$ linker;

(iv) PEG length (in monomer units) which is a single number if there is just one PEG (i.e., $PEG_1$), and two numbers if there are 2 PEGs (i.e., $PEG_1$ and $PEG_2$), the PEG length (e.g., "PEG39 (36+3)") identifies the total PEG length (i.e., 39) and the PEG length of each PEG (i.e. 36 and 3);

(v) "active" indicates significant activity of the conjugate in at least one of the biological tests;

(vi) "not synthesized" indicates that the conjugate has not yet been actually synthesized, and absence of "not synthesized" indicates that the conjugate has been actually synthesized.

Syntheses schemes for synthesizing the conjugates are described infra in Section 4.

3.1 Conjugates Having Integrin Av Targeting Piece with Chemotherapy

This section identifies conjugates with integrin av targeting (i.e., conjugates 22, 23, 26, 34, 35, 40, 45, 57, 58, 59, 61, 62, 64, 69, 72, 73, 74, 92, 97, 104, 82, 108, 85) and chemotherapies (14, 24, 37, 41, 70) that are used, inter alia, in these conjugates.

Conjugate 22

22

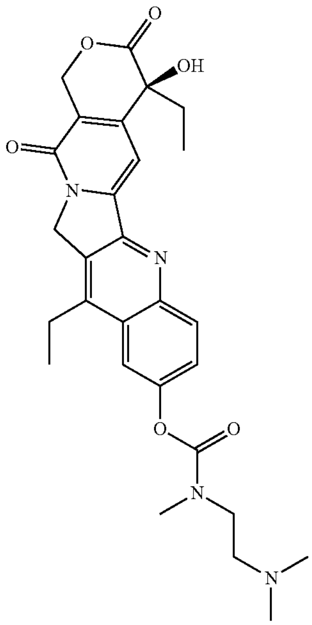

-continued
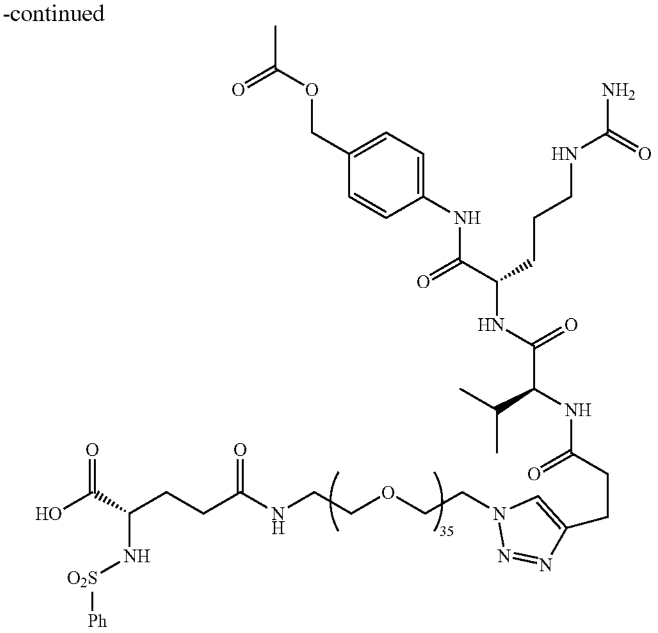
Targeted A, PEG35, SN38 chemo; phenol linked
Conjugate 23
Targeted A, PEG35, SN38 chemo; active; in vitro integrin αvβ3 binding assay; in vitro cell viability assay.
23
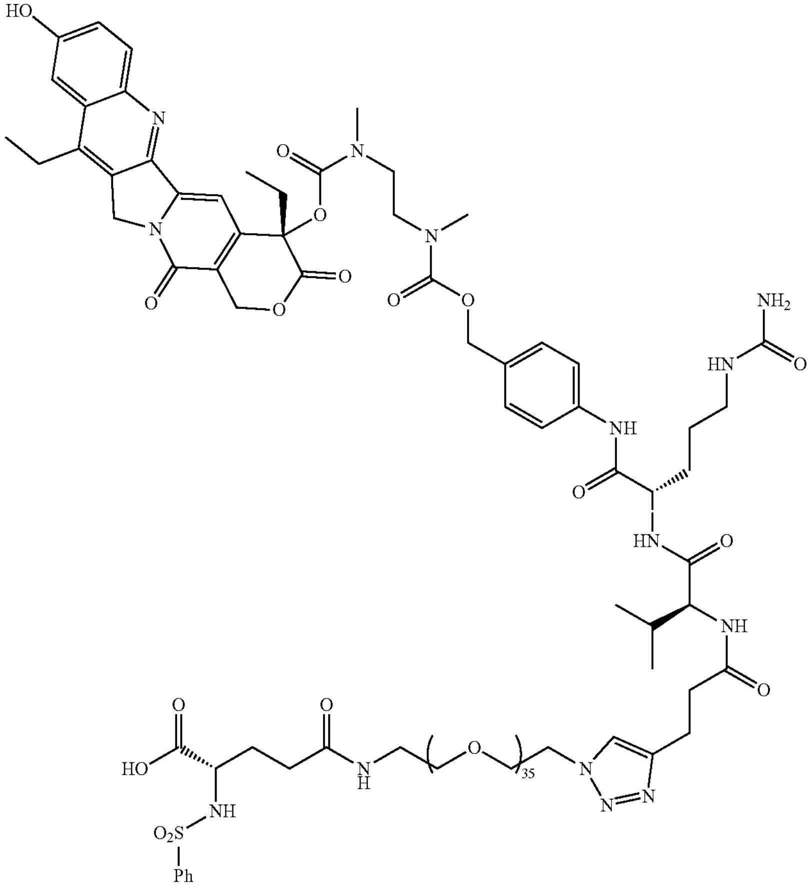

Conjugate 26
26
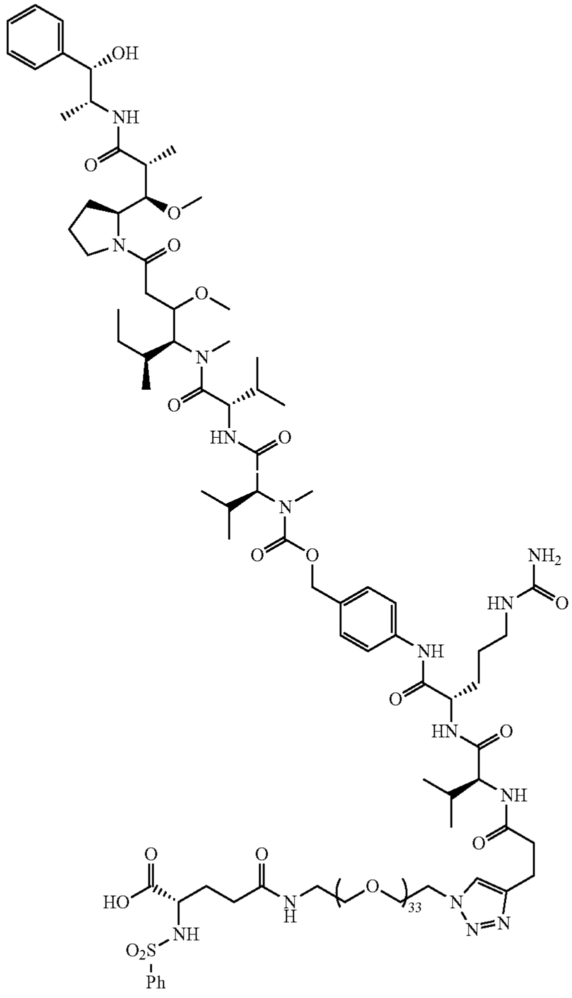
Targeted A, PEG35, MMAE chemo; active; in vitro cell viability assay
Conjugate 34
34
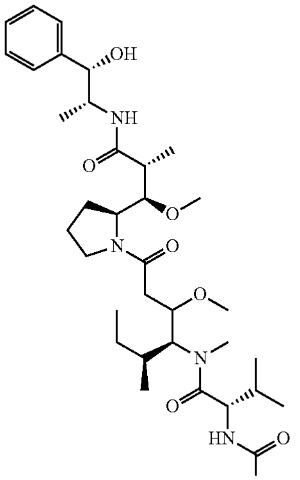
-continued
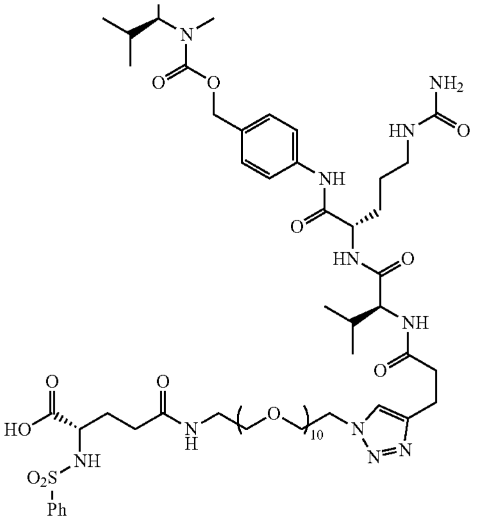
Targeted A, PEG10, MMAE Chemo; in vitro cell viability assay
Conjugate 35
35
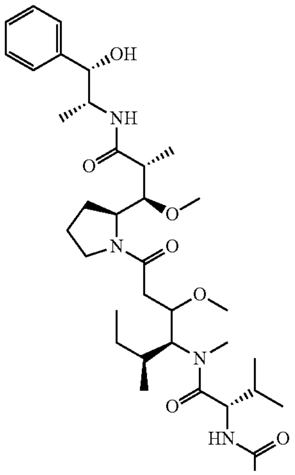

-continued
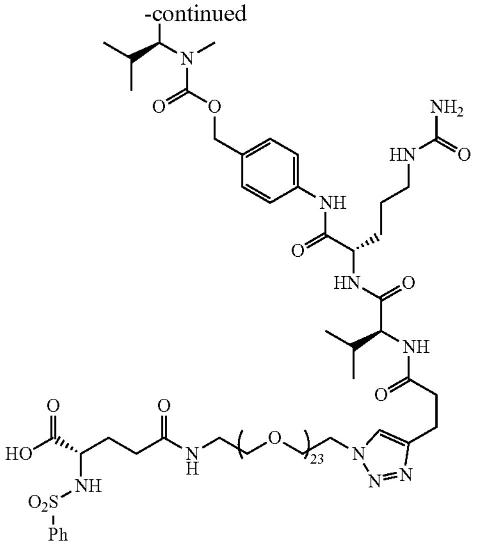
Targeted A, PEG23, MMAE chemo
Conjugate 40
40
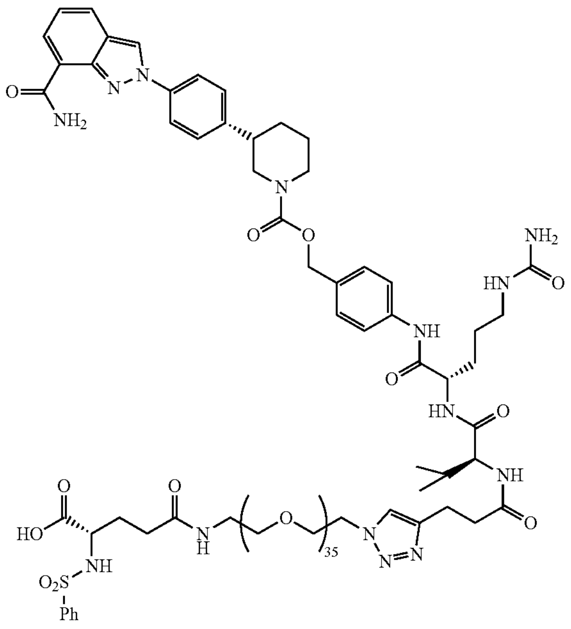
Targeted A, PEG35, Niraparib chemo; active; in vitro integrin αvβ3 binding assay; in vitro cell viability assay.
Conjugate 45
45
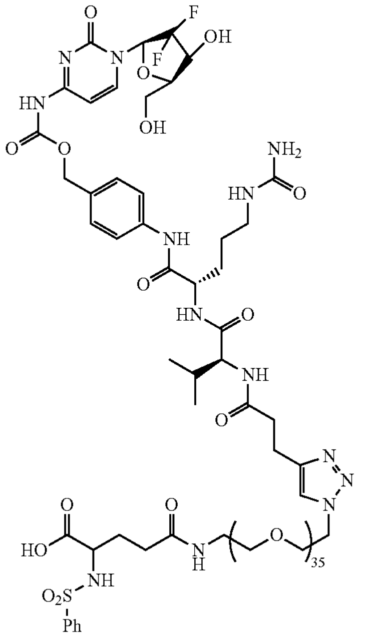
Targeted A, PEG35, Gemcitabine chemo; active; in vitro integrin αvβ3 binding assay, in vitro cell viability assay
Conjugate 57
57
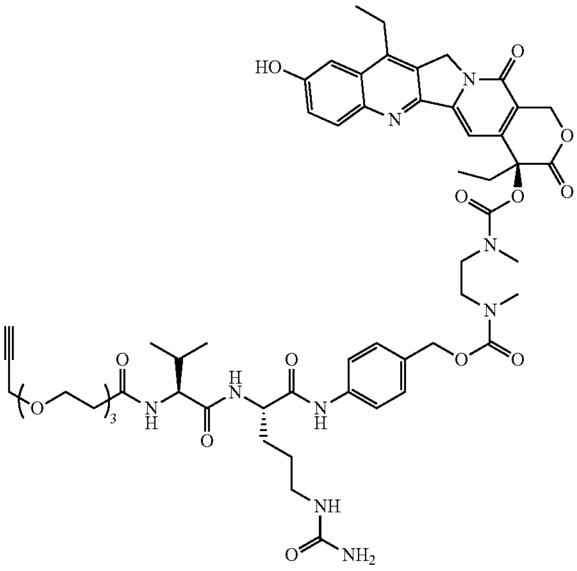
Non-targeted, PEG3, SN38 chemo; in vitro cell viability assay Conjugate 58
58
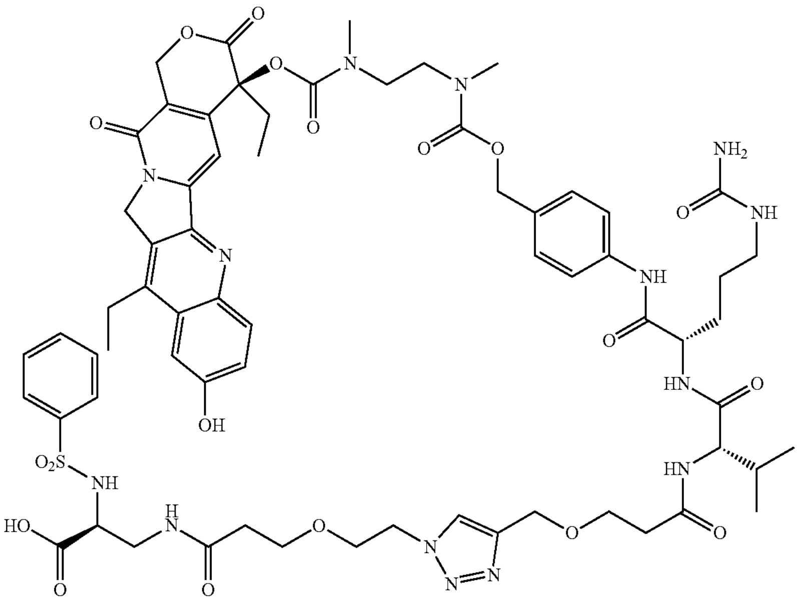
Targeted B, PEG39 (36+3), SN38 chemo
Conjugate 61
61
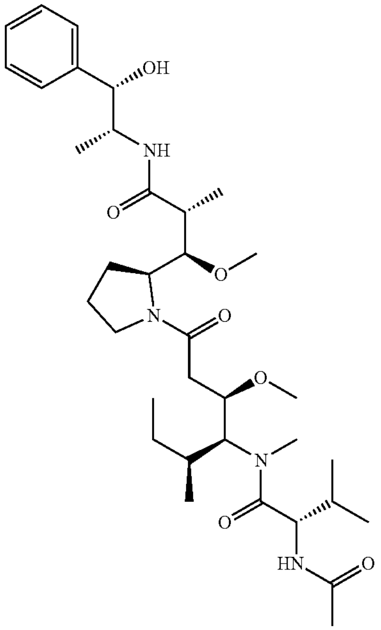

-continued
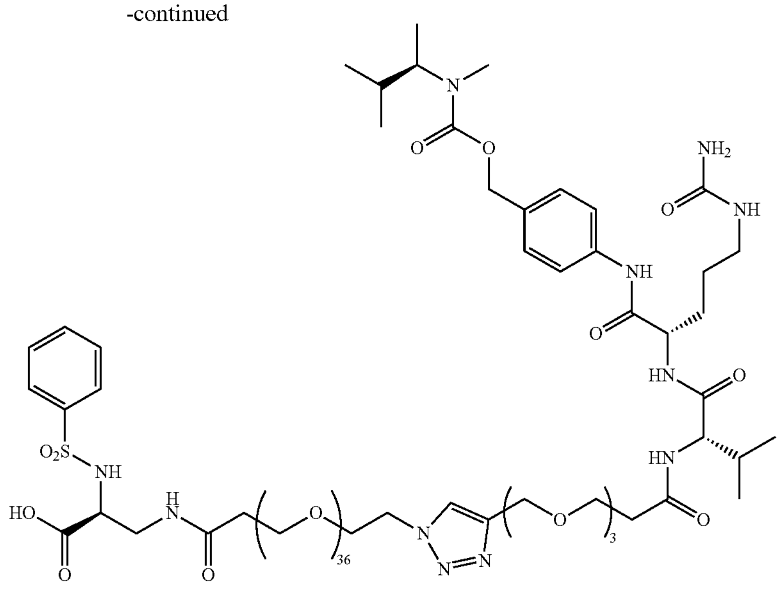
Targeted B, PEG39 (36+3), MMAE chemo; active; in vivo efficacy
Conjugate 62
62
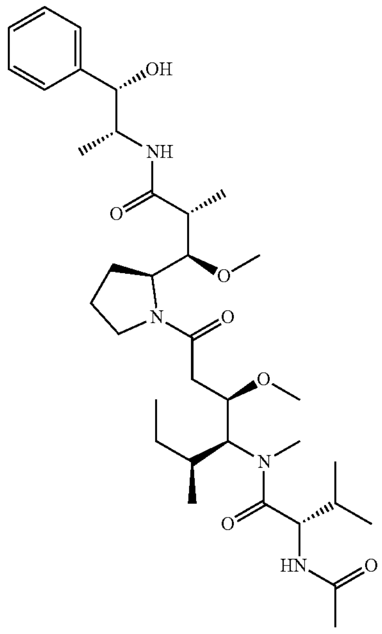

-continued
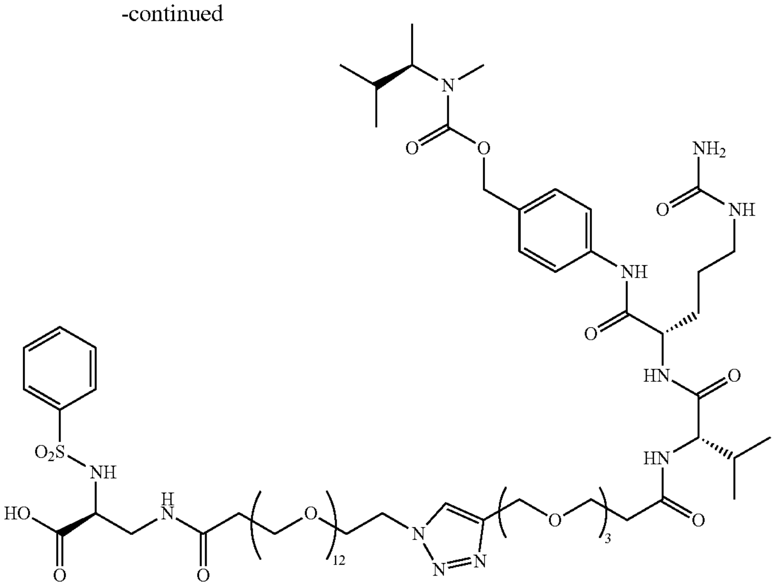
Targeted B, PEG15 (12+3), MMAE chemo; in vivo efficac
Conjugate 64
64
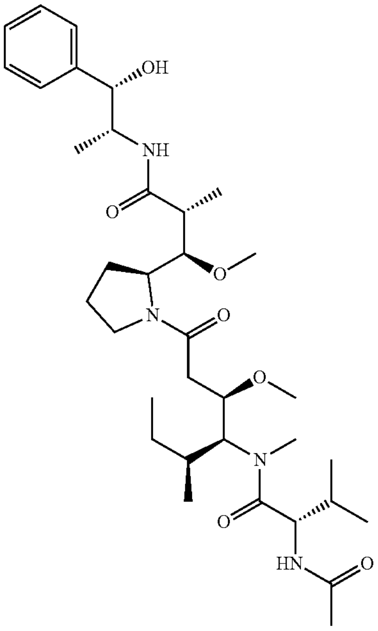

-continued
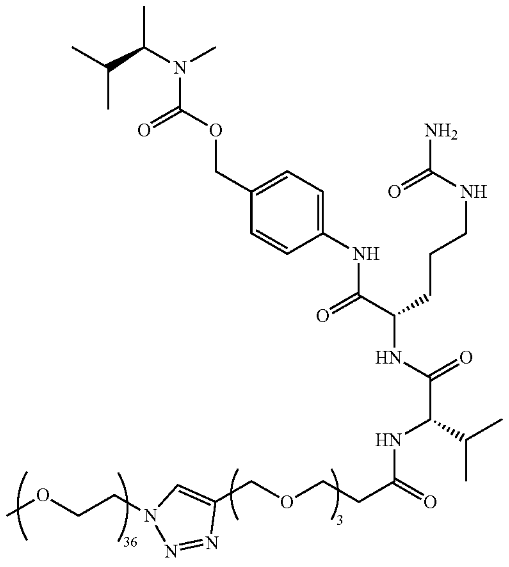
Non-targeted, PEG39 (36+3), MMAE chemo
Conjugate 69
69
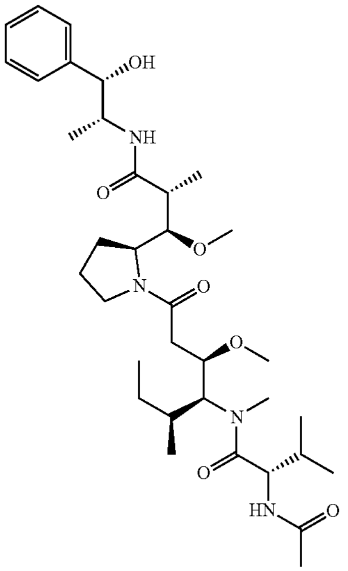

-continued
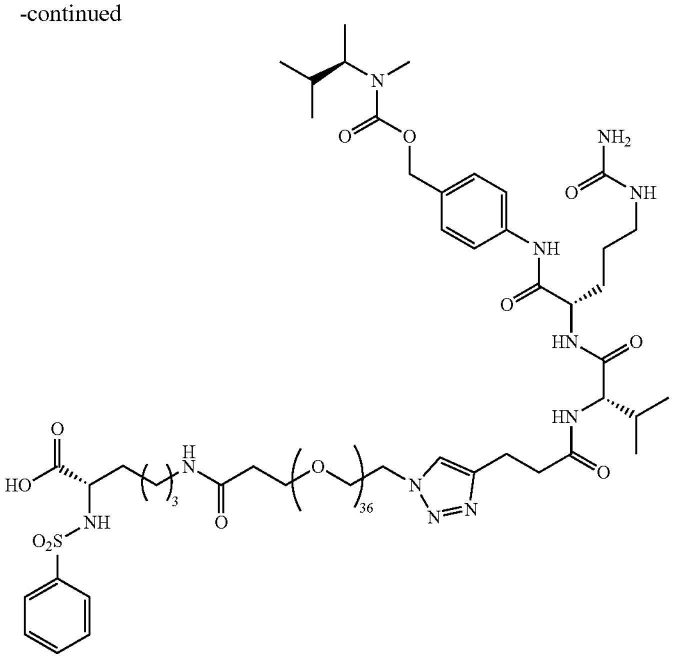
Targeted B, PEG36, MMAE chemo; longer $n_1$ carbon chain
Conjugate 72
72
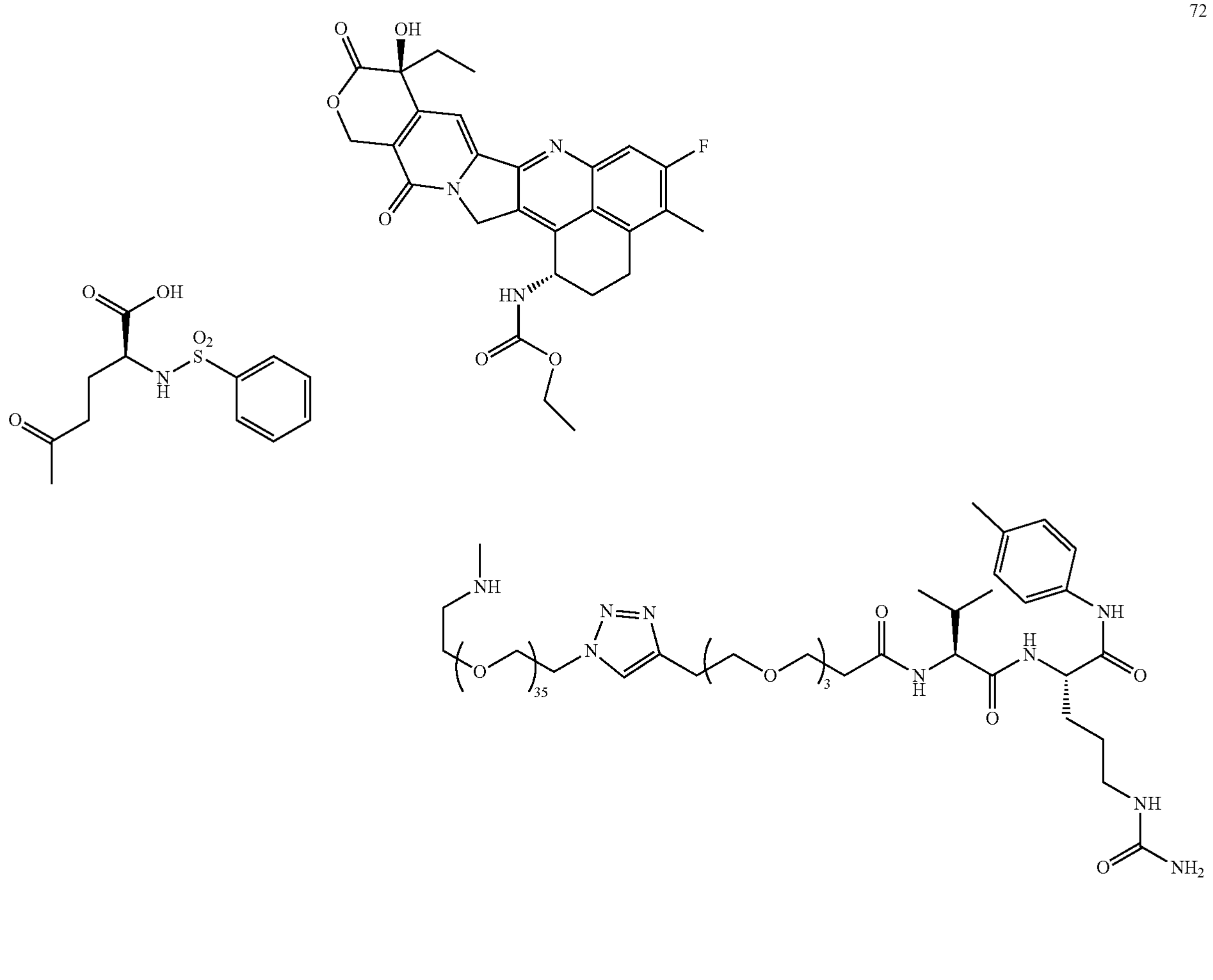

Targeted A, PEG38 (35+3), Exatecan chemo
Conjugate 73
73
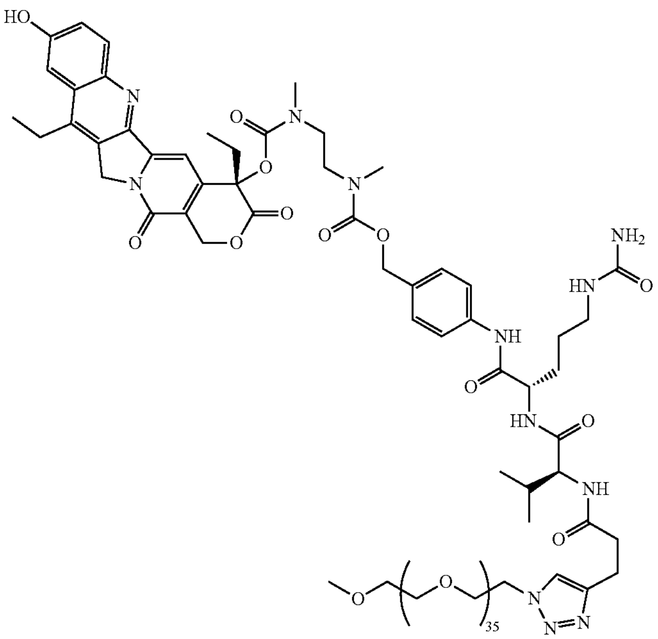
Non-targeted, PEG36, SN38 chemo; in vitro cell viability assay
Conjugate 92
92
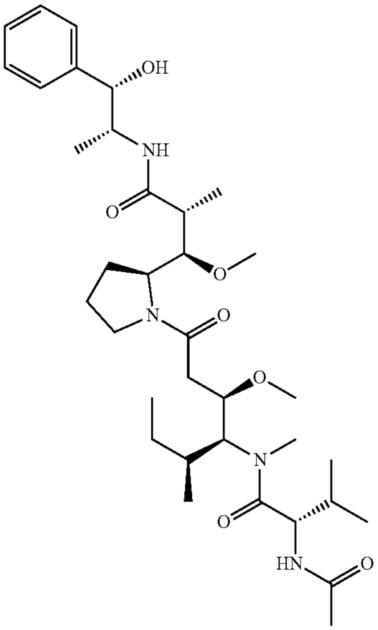

-continued
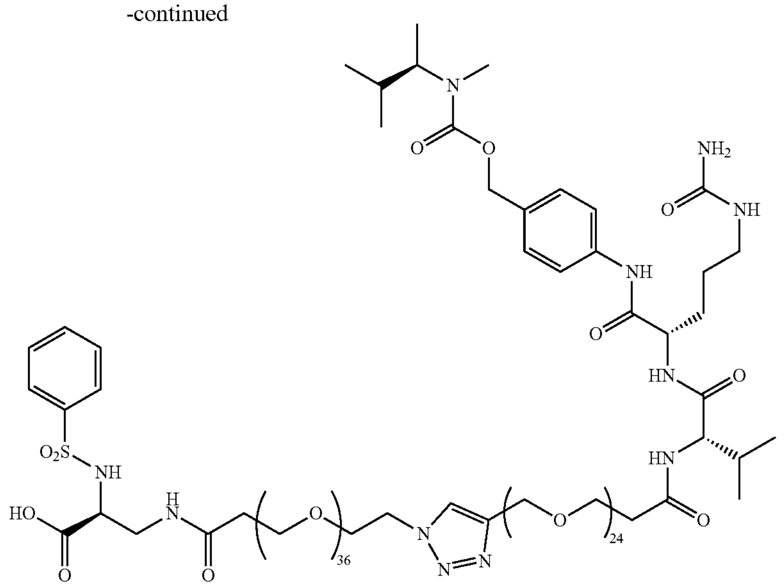
Targeted B, PEG60 (36+24), MMAE chemo
Conjugate 97
97
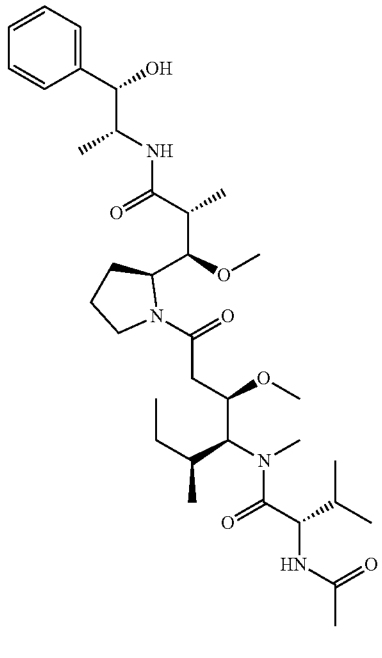

-continued
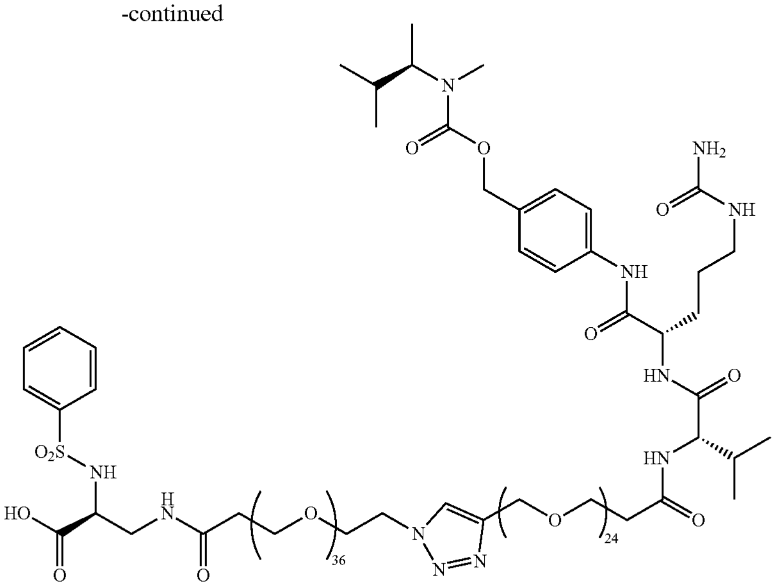
Targeted B, PEG72 (36+36), MMAE chemo
Conjugate 104
104
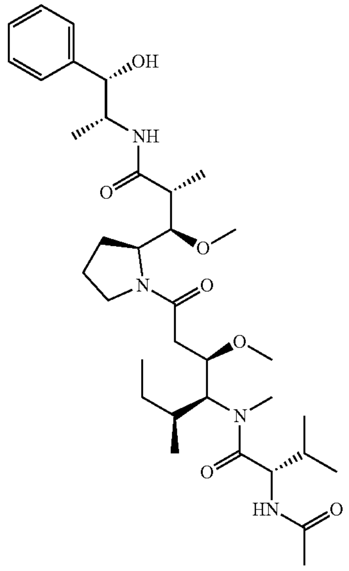

-continued

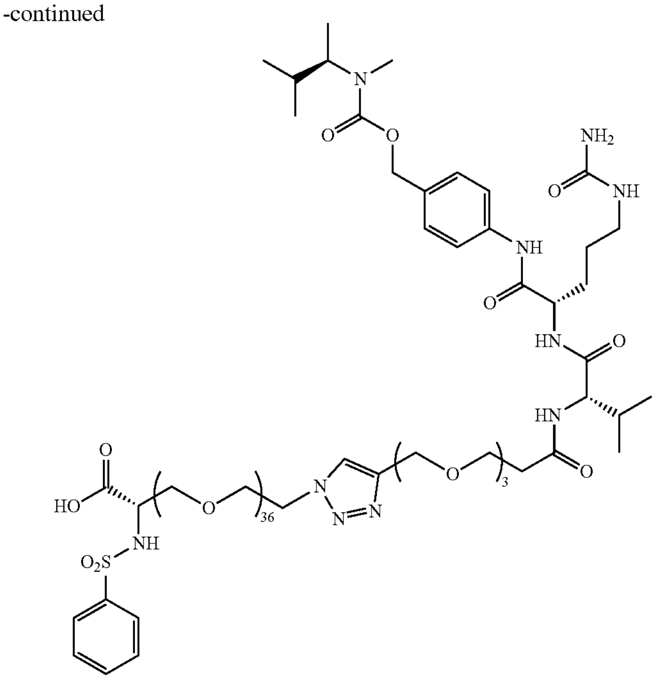

Targeted C (no $L_1$ linker), PEG35 (35+3), MMAE Chemo; conjugate 104 is essentially the same conjugate as conjugate 61, except that conjugate 61 does not include the $L_1$ linker that is included in conjugate 61.

Chemo 14

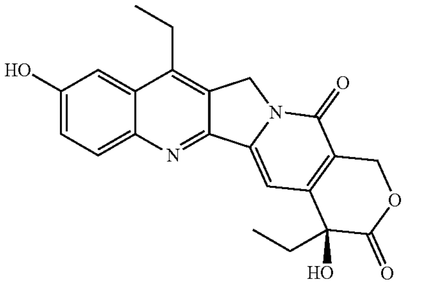 [SMILES: CCc1c2c(nc3ccc(O)cc13)-c1cc3c(c(=O)n1C2)COC(=O)[C@]3(O)CC]

SN38 (chemo only); in vitro cell viability assay

Chemo 24

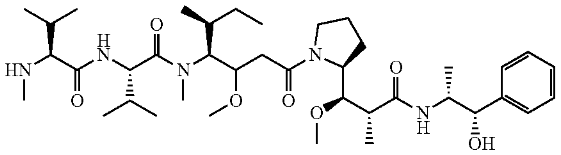 [SMILES: CC[C@H](C)[C@@H](C(CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

MMAE (monomethylauristatin E) (chemo only); in vitro cell viability assay

Chemo 37

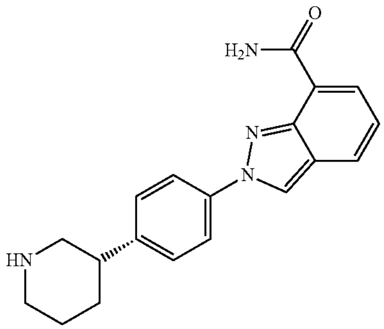

Niraparib (chemo only); in vitro cell viability assay

Chemo 41

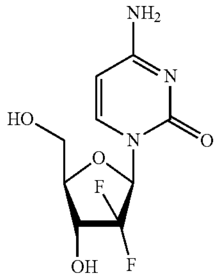

Gemcitabine (chemo only; in vitro cell viability

Chemo 70
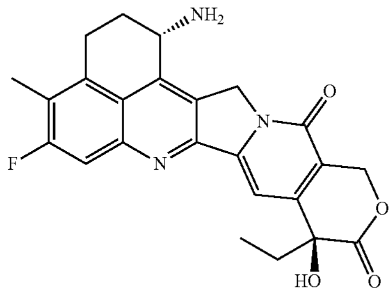 [SMILES: CC[C@@]1(O)C(=O)OCc2c1cc1n(c2=O)Cc2c-1nc1cc(F)c(C)c3c1c2[C@@H](N)CC3]
exatecan (chemo only)
Conjugate 82
82
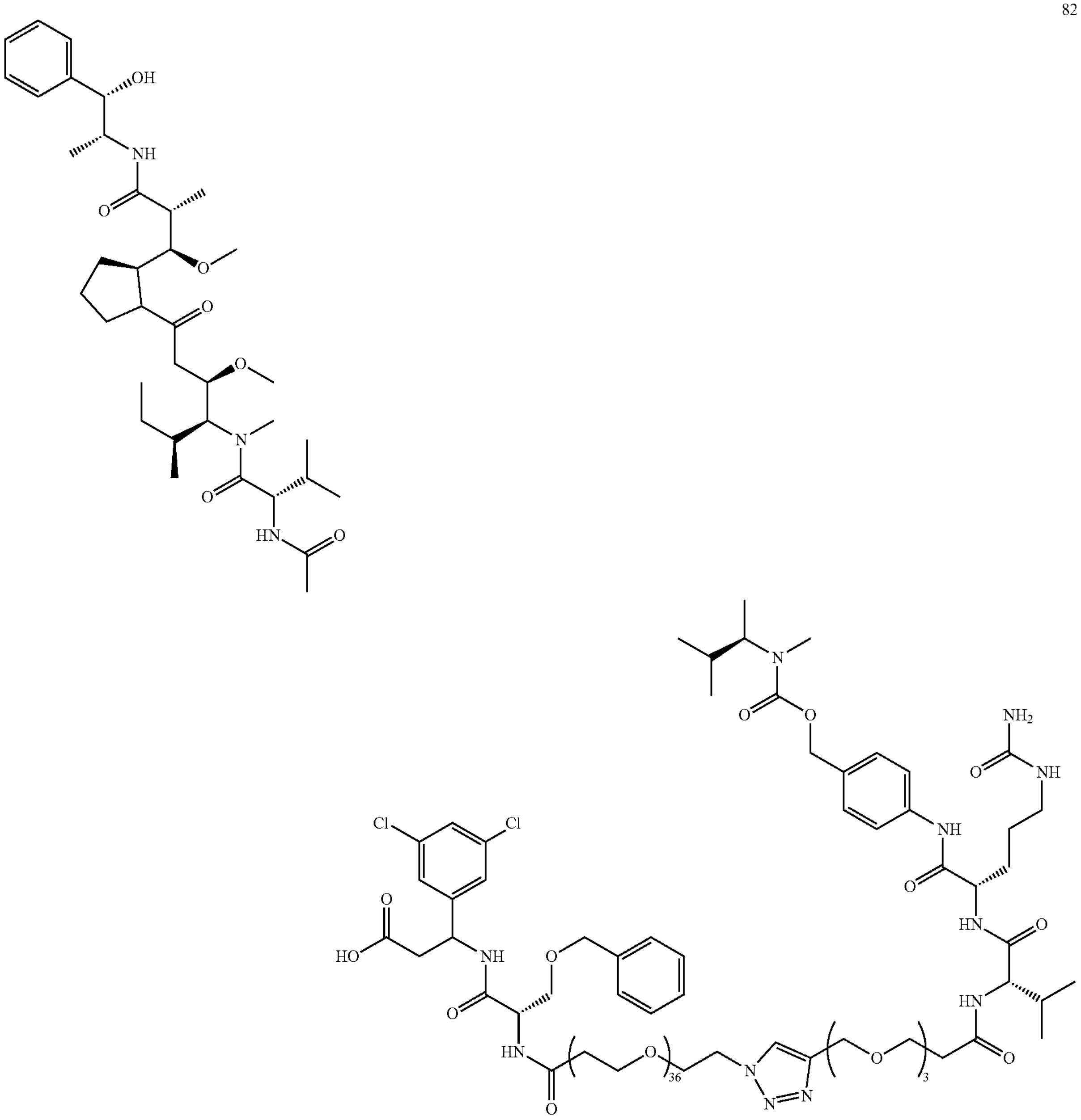

PEG39 (36+3); MMAE chemo; not synthesized.

The αv targeting piece is:

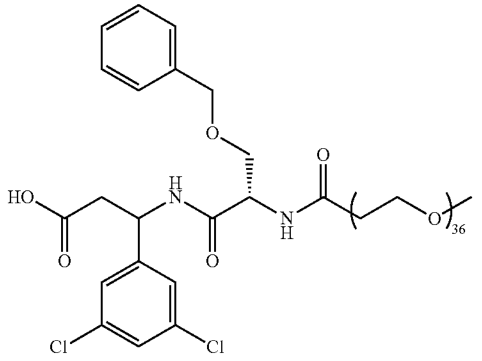

The following scheme provides a rationale as to why use of conjugate 82 would be therapeutically effective.

EMD527040 Potent and Selective Av Antagonist

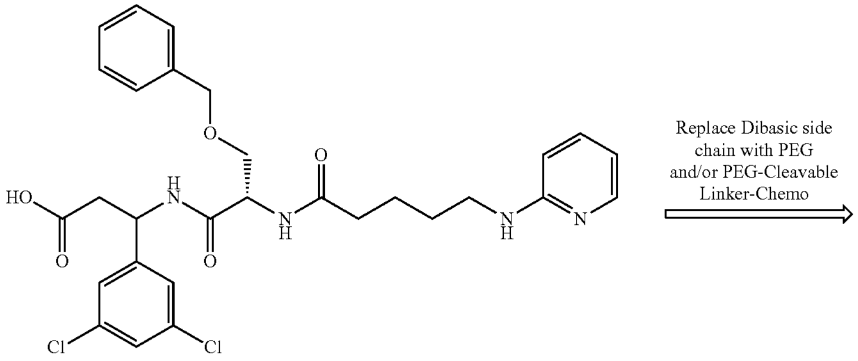

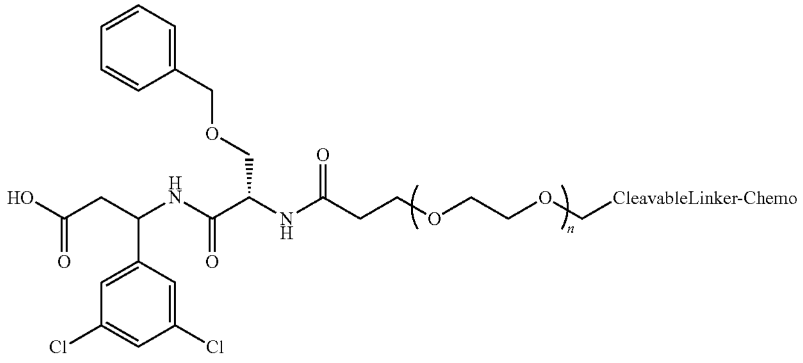

An embodiment of the preceding conjugate, resulting from the replacement of the dibasic side chain, is Conjugate 82 whose synthesis scheme is presented infra in Section 4.2 using the following αv targeting piece.

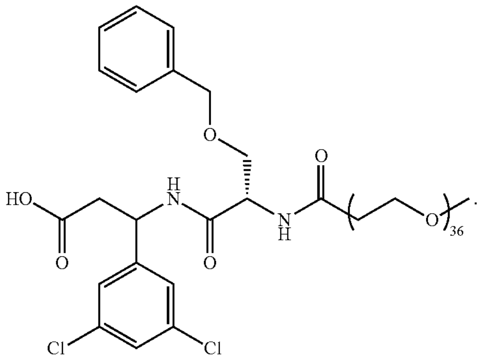
Conjugate 108
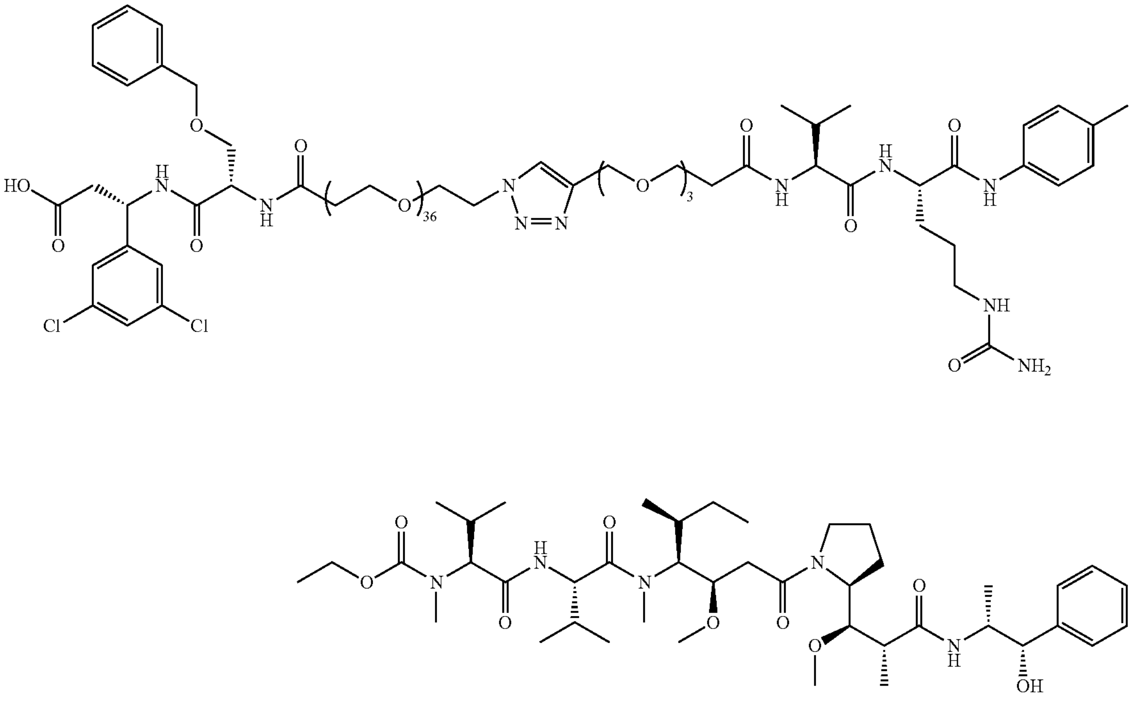
PEG39 (36+3); MMAE chemo; not synthesized.
The αv targeting piece is:
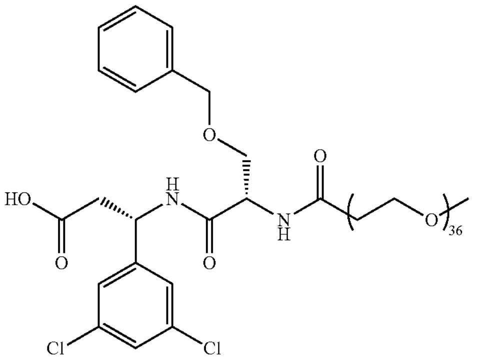

Conjugates 108 and 82 differ only in their respective targeting αv pieces. The targeting piece of both conjugates 108 and 82 have a stereocenter at the carbon next to the dichloroaryl ring as well as a stereocenter in the neighboring O-benzylserine. Conjugate 82 is 2 different diastereomers (i.e., one chiral center with a single enantiomer and one racemic center that has two different enantiomers that are mirror images of each other and are not superimposable). Conjugate 108 is a single diastereomer with single enantiomers at both stereocenters.

The scheme presented supra that provides a rationale as to why use of conjugate 82 would be therapeutically effective applies likewise to conjugate 108.

Conjugate 85

85

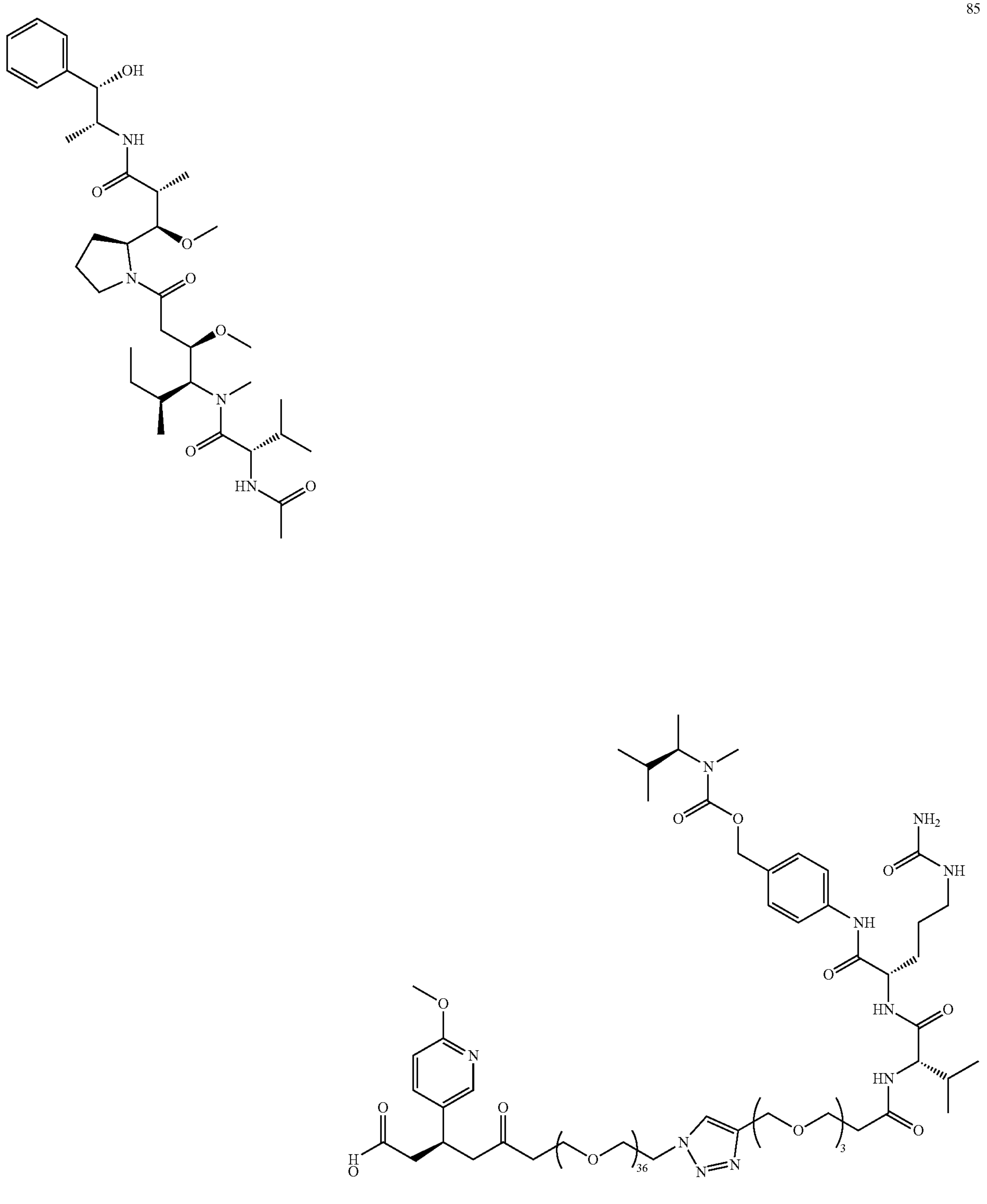

PEG39 (36+3); MMAE chemo; not synthesized.

The αv targeting piece is:

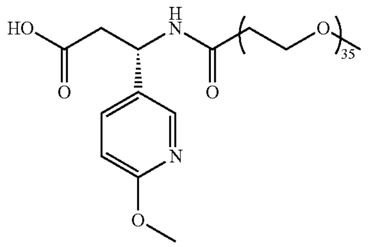

The following scheme provides a rationale as to why use of conjugate 85 would be therapeutically effective.

MK0429 αv Antagonist

3.2 Conjugates Having Integrin αv Targeting Piece without Chemotherapy

Conjugate 76

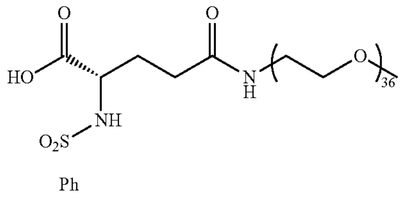

Targeted A, PEG36, no chemo; no cleavable linker; not active; viable therapeutic on its own; in vitro cell viability assay.

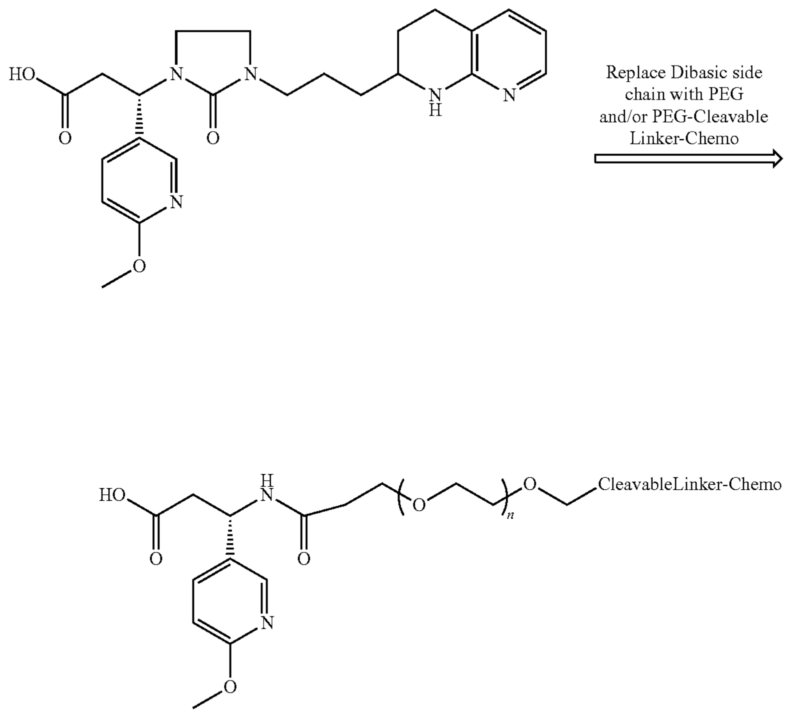

An embodiment of the preceding conjugate, resulting from the replacement of the dibasic side chain, is Conjugate 85 whose synthesis scheme is presented infra in Section 4.2 using the following αv targeting piece.

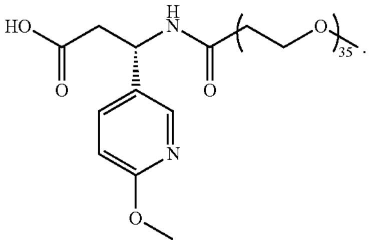

Conjugate 87

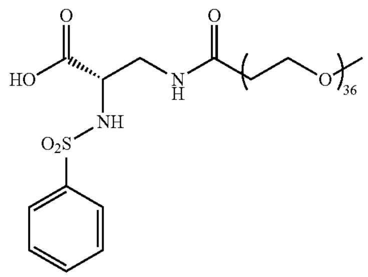

Targeting B, PEG36, no chemo; viable therapeutic on its own; not synthesized.

Conjugate 59

59

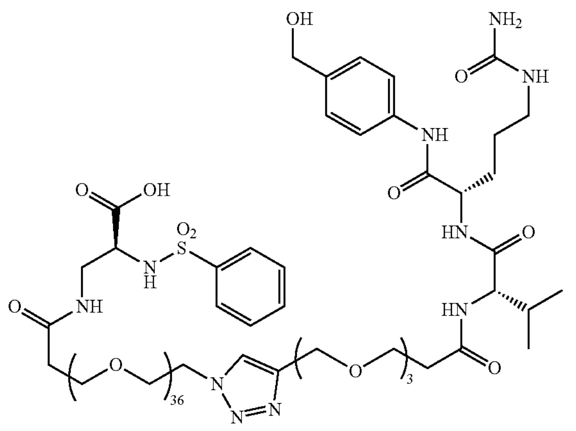

Targeted B, PEG39 (36+3), no chemo; in vitro cell adhesion assay; in vivo efficacy.

Conjugate 74

74

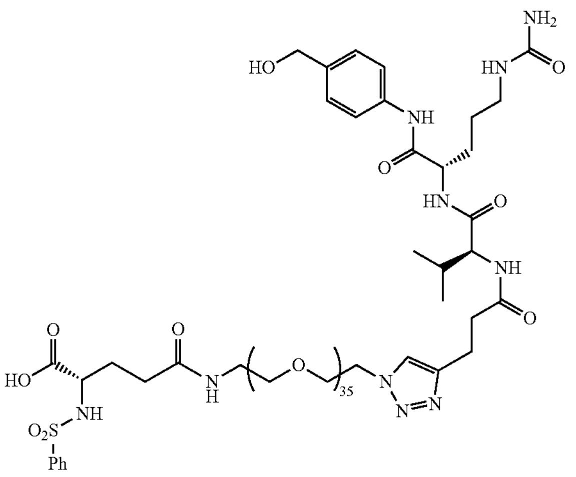

Targeted A, PEG36, no chemo; in vitro cell adhesion assay; in vitro cell viability assay.

4. Synthesis Schemes With Implementation of Synthesis Steps

4.1 General Synthesis Schemes

This section presents 6 general synthesis schemes, namely Schemes 1-6 pertaining to synthesis of conjugates characterized by integrin αvβ3 targeting.

Scheme 1

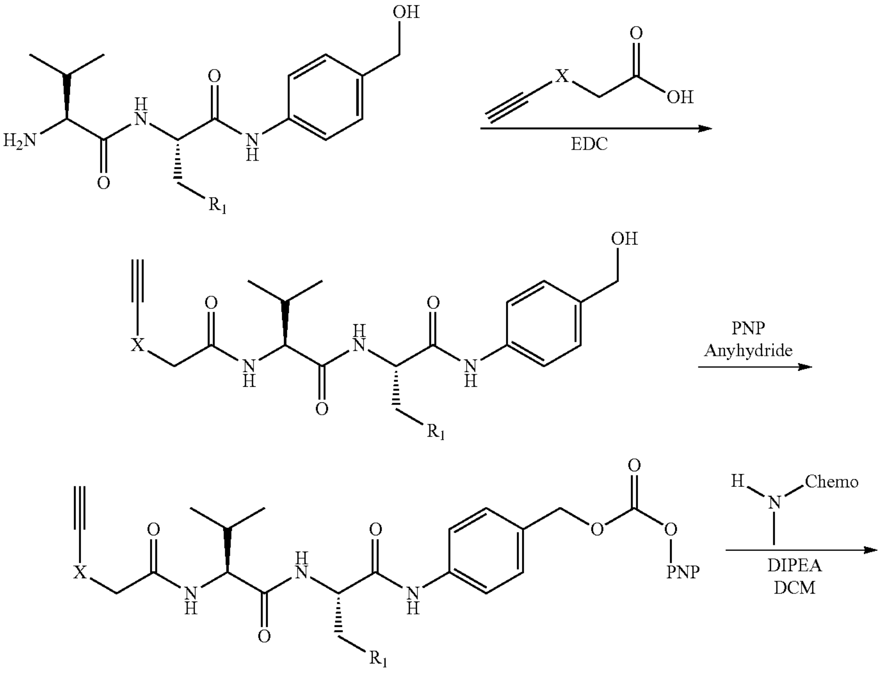

-continued

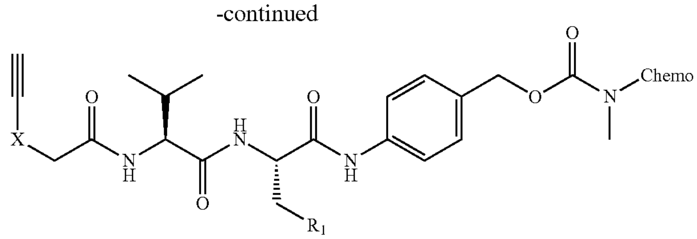

X = $(CH_2)_n$, $(CH_2—O—CH_2)_n$ $R_1$ = $—(CH_2)_2—NH(CO)NH_2$ n = 1-3

In Scheme 1, commercially available alkynyl acids undergo an amide coupling with the amine function of commercially available Val-Cit-PAB (VCP, $R_1$=—$(CH_2)_2$—$NH(CO)NH_2$) or Val-Ala-PAB ($R_1$=H), which generates a compound that is activated with PNP anhydride to generate another compound that reacts with various chemotherapies that have a primary or secondary amine functionality, forming a carbamate linkage. Compounds with the structure on the top right of scheme 1 are now available commercially, which makes Scheme 1 shorter by 2 steps.

Scheme 2

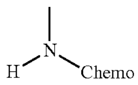

= Chemo-Amine =

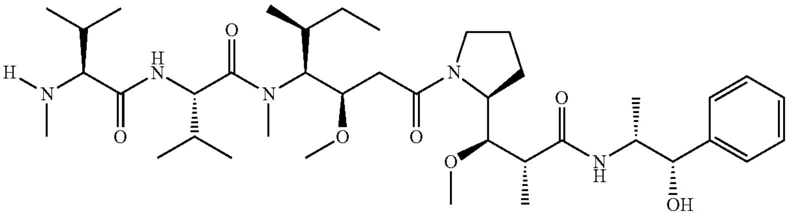

MMAE

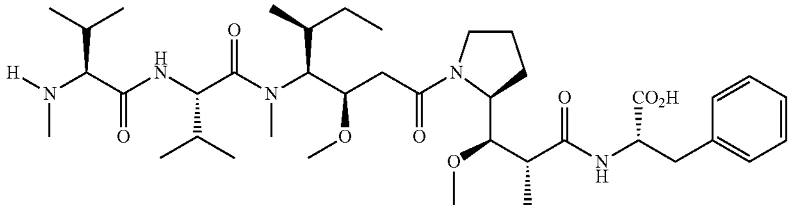

MMAF

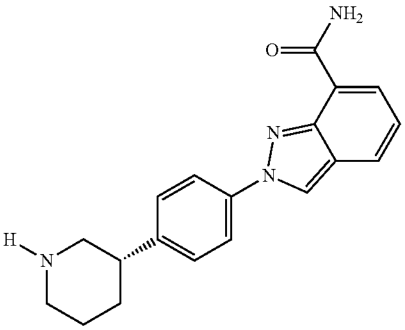

Niraparib

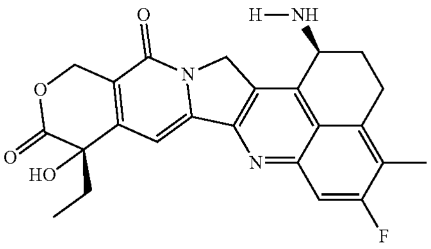

Exatecan

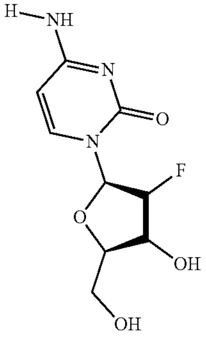

Gemcitabine

-continued
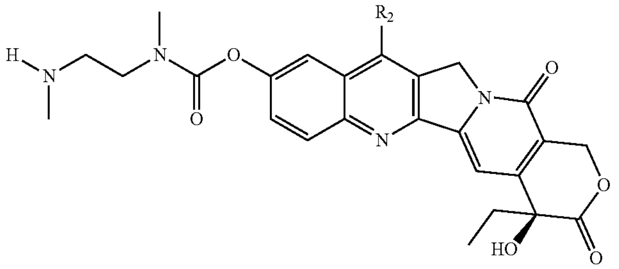
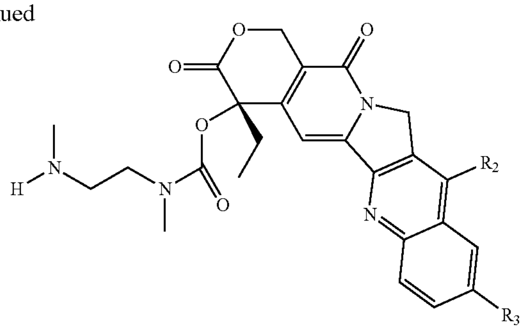
DimethylaminoSN38 and derivatives
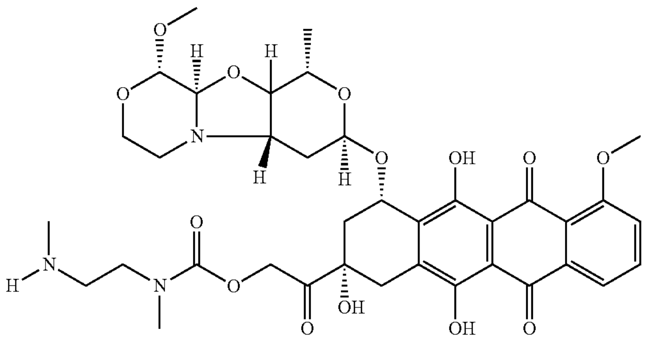
Dimethylaminomethyl
Doxorubicin derivative
$R_2$ = H, Et
$R_3$ = H, OH
In Scheme 2, chemotherapies with a primary or secondary amine attach to alkynyl VCP as in Scheme 1.
Scheme 3
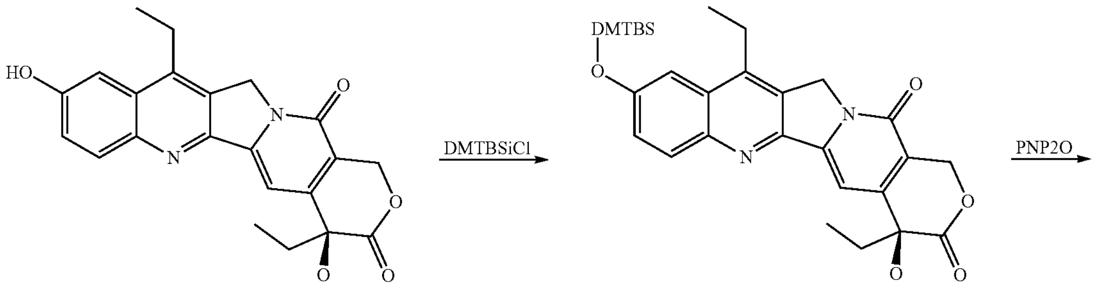

-continued
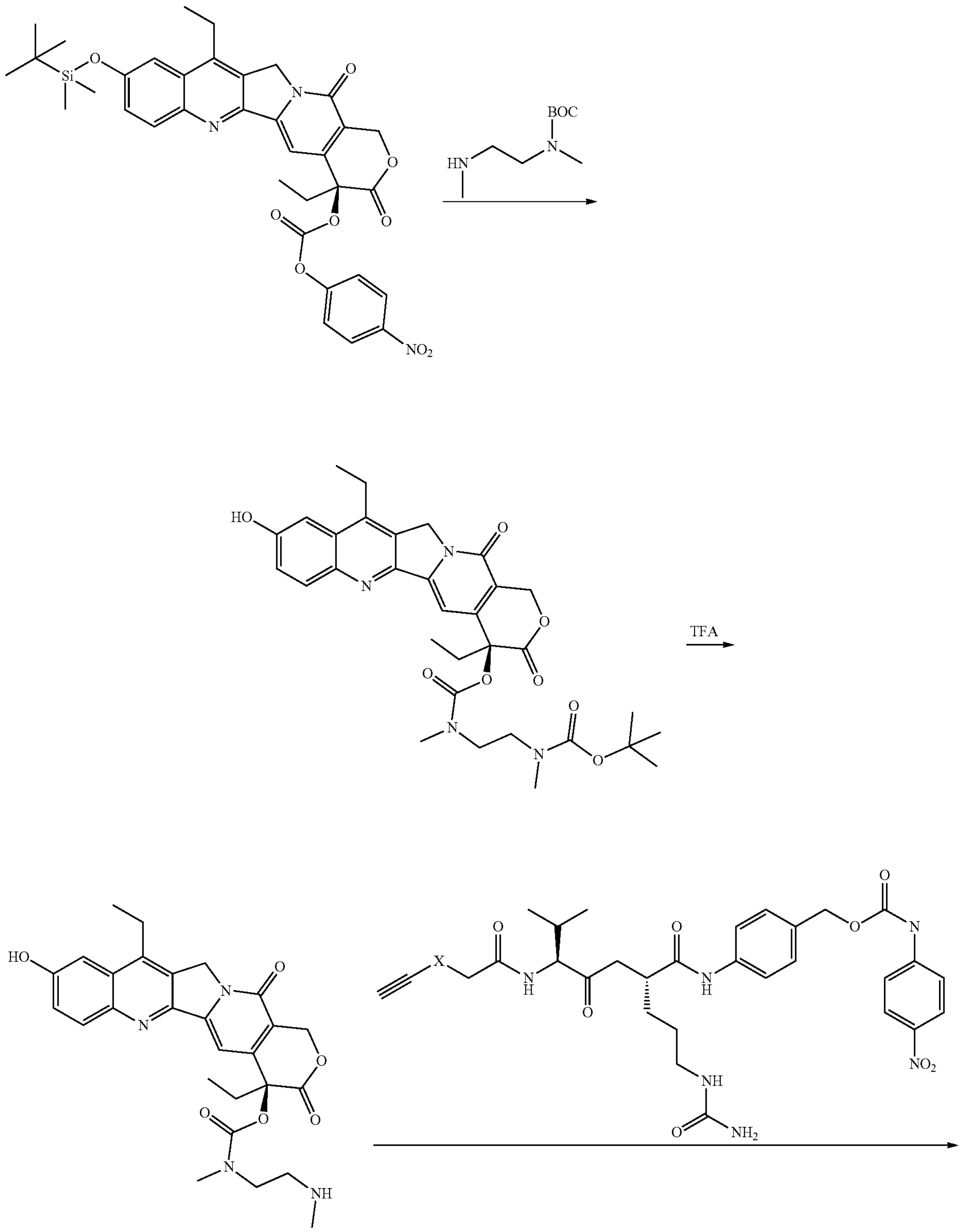

-continued
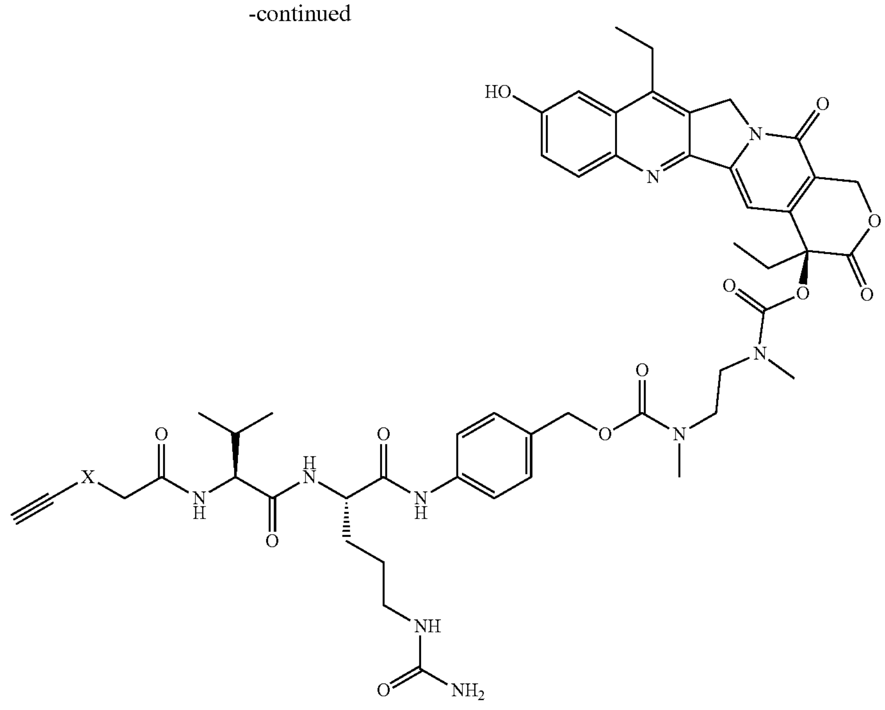
In Scheme 3, some chemotherapies, such as SN38, do not have the required primary or secondary amine to attach the chemotherapies to the cleavable linker VCP, so that an additional linker (1,2dimethylethyenediamine) is inserted. This linker will fall off after the VCP cleaves when the conjugate is internalized in the lysosome/late endosome.
Scheme 4
Scheme 4
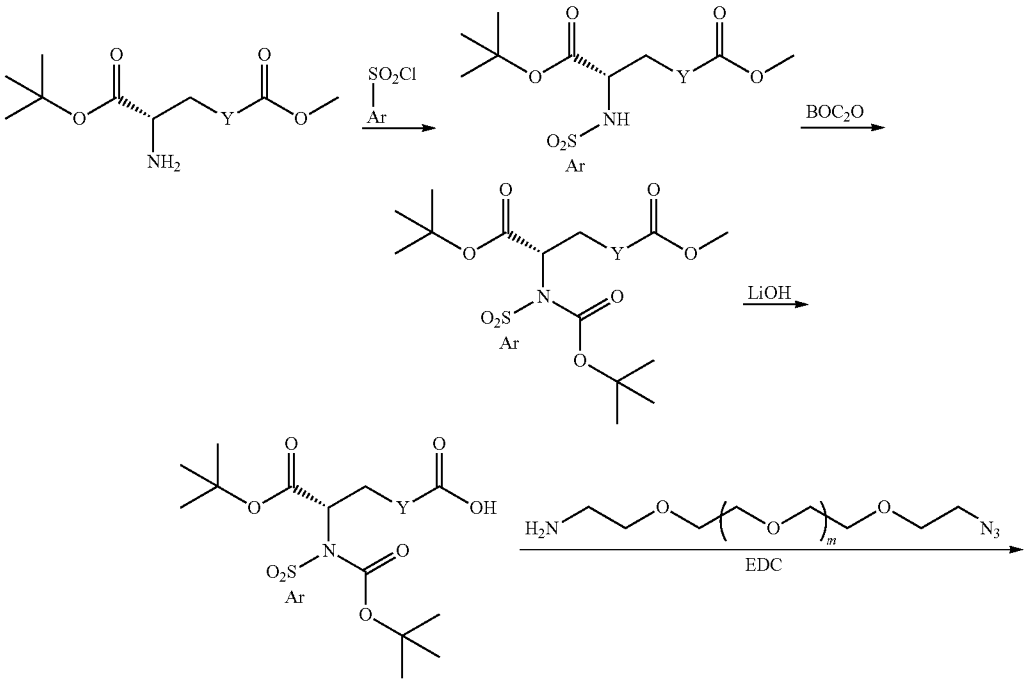

-continued

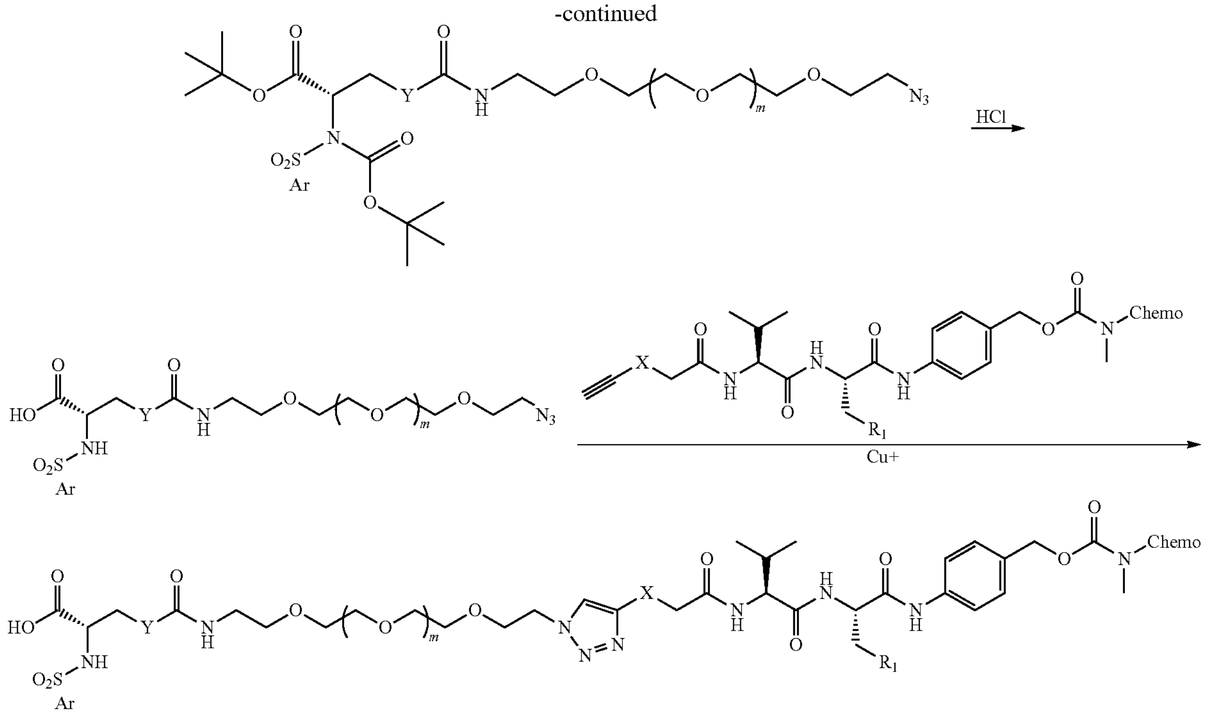

X = —(CH$_2$)$_n$)—, —(CH$_2$—O—(CH$_2$)$_n$
Y = (CH$_2$)$_n$
R$_1$ = H, —(CH$_2$)$_2$—NH(CO)NH$_2$
m = 18-46
n = 0-4

In Scheme 4, sulfonyl chlorides react with the amine function in protected aspartic, glutaric, and related amino acids to yield a sulfonamide. Additional BOC protection of the sulfonamide followed by LiOH hydrolysis of the methyl ester yields a free carboxylic acid which undergoes an amide coupling with commercially available monodisperse polyethylene glycol differentially substituted with both amine and azide functionality. Acid catalyzed removal of the protecting groups followed by click reaction with the alkynyl VCP conjugated chemotherapy yields the desired final conjugates.

Scheme 5

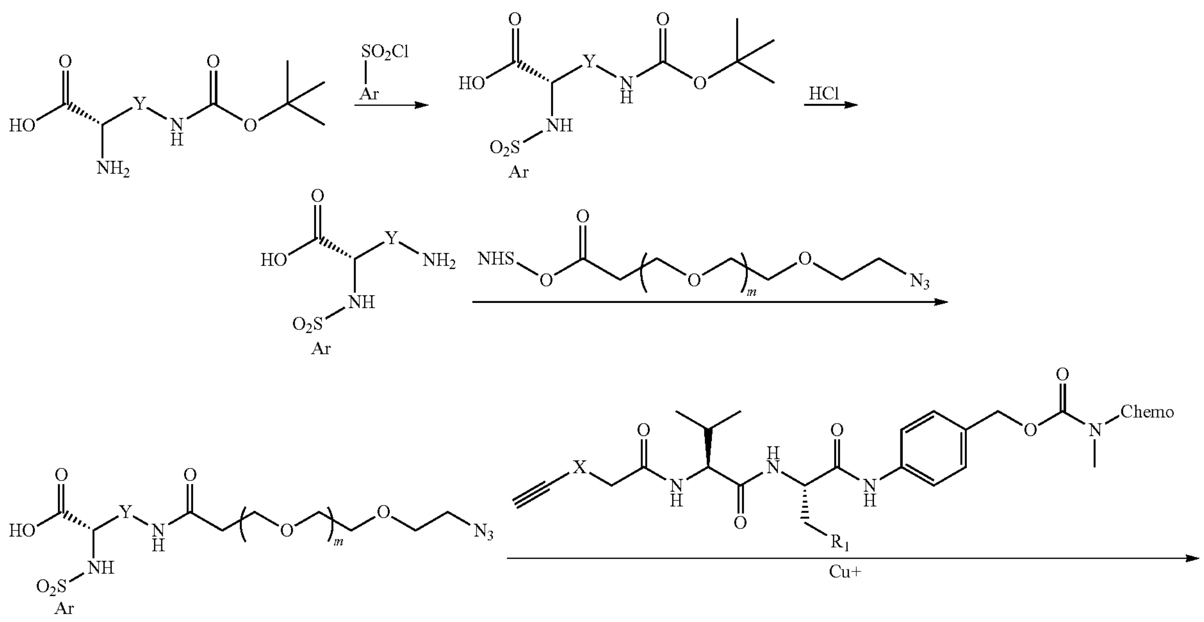

-continued

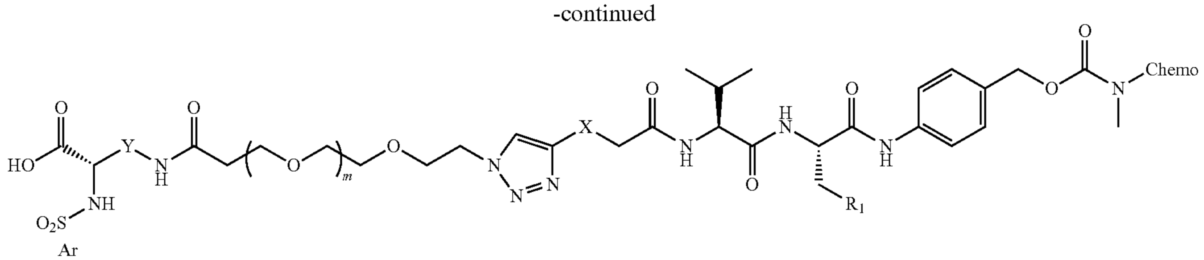

X = $-(CH_2)_n)-$, $-(CH_2-O-(CH_2)_n-$
Y = $(CH_2)_n$
$R_1$ = H, $-(CH_2)_2-NH(CO)NH_2-$
n = 1-4
m = 19-47

In Scheme 5, for a different set of commercially available protected DAP, ORN, LYS, and related derivatives, sulfonyl chlorides are reacted with the amine function to yield sulfonamides which undergo an amide coupling with a commercially available monodisperse polyethylene glycol differentially substituted with both an NHS activated carboxylic acid and an azide functionality. Copper catalyzed click reaction with the alkynyl VCP conjugated chemotherapy yields the desired final conjugates.

Scheme 6

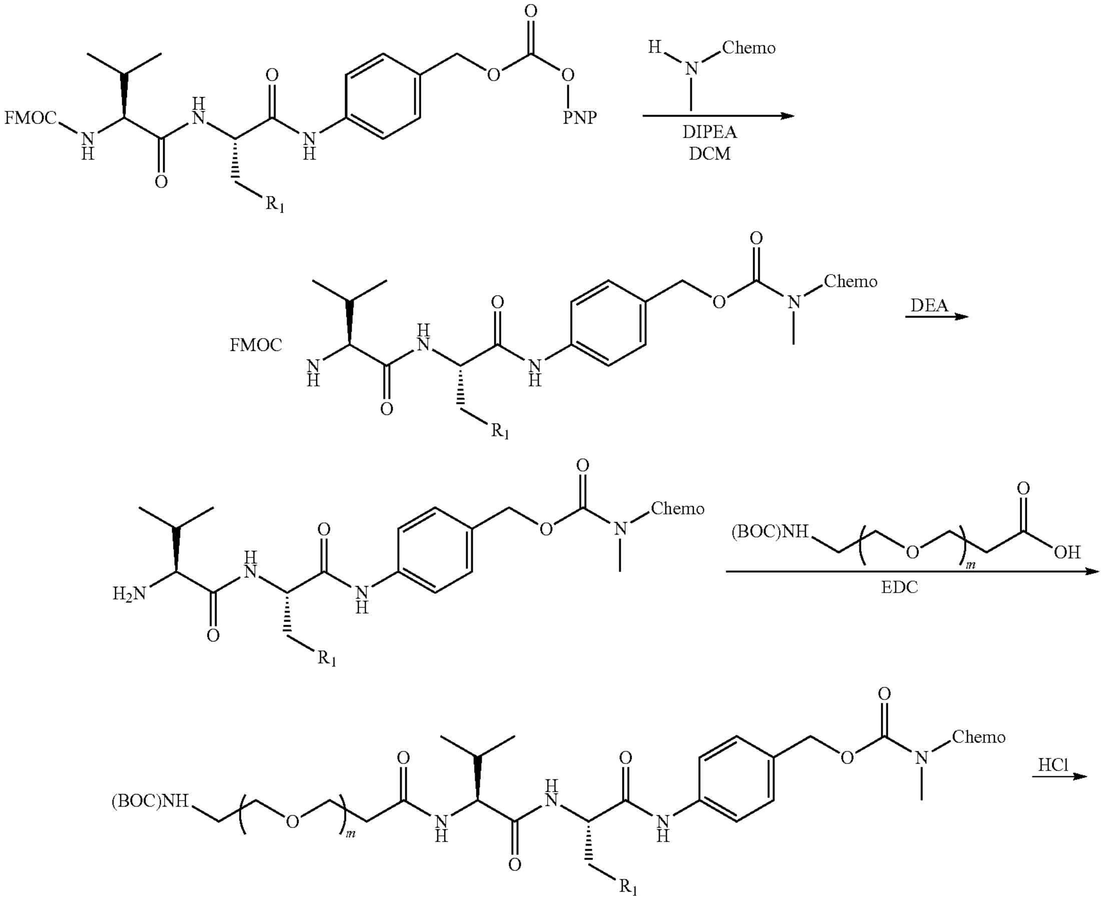

-continued

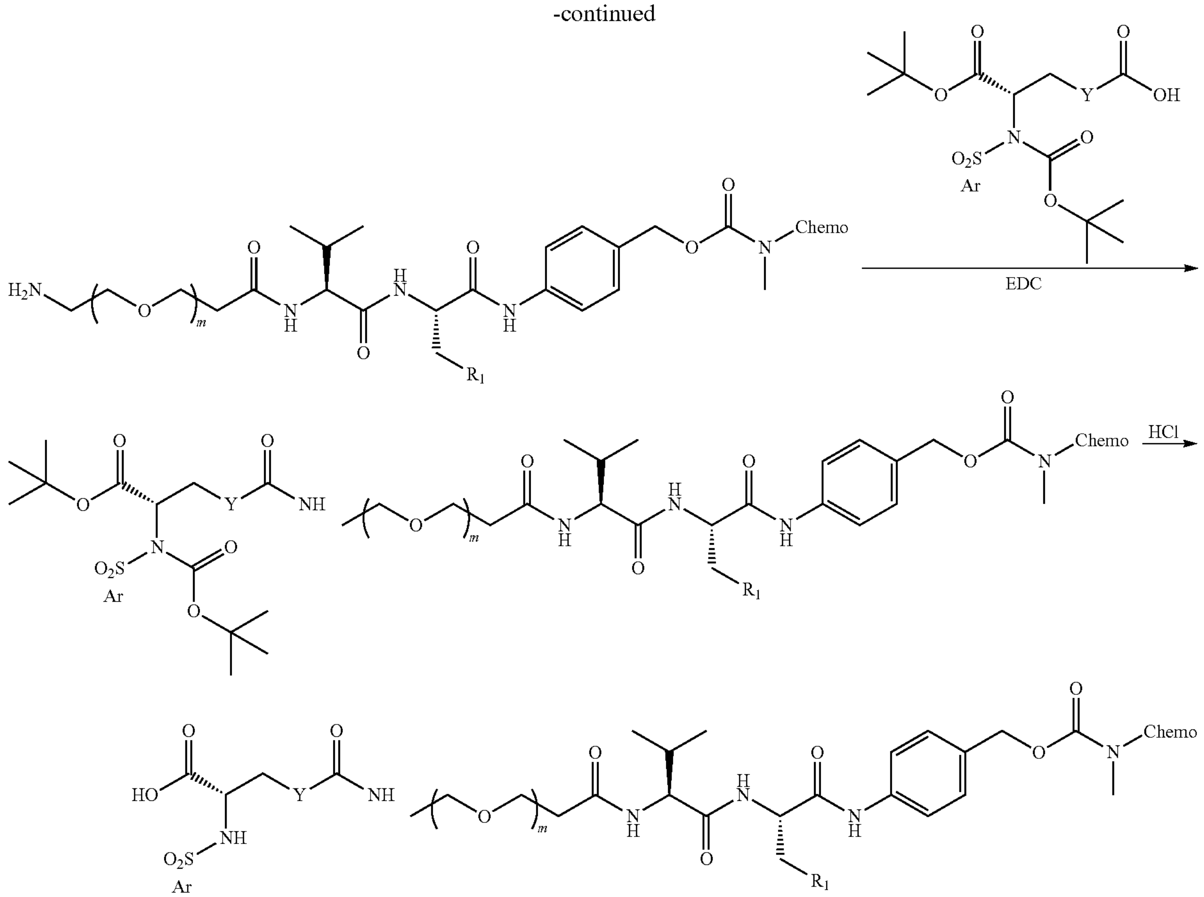

$R_1 = -(CH_2)_2-NH(CO)NH_2-$
m = 20-48

In Scheme 6, an alternate route to conjugates starts with a commercially available, FMOC protected, PNP activated VCP reacting with the amine substituted chemotherapy. The FMOC protecting group comes off in the reaction workup resulting in a compound that is reacted with a commercially available monodisperse polyethylene glycol differentially substituted with carboxylic acid and BOC-amine functionality. The BOC is removed under acidic conditions, and the product undergoes an amide coupling with the protected Glu/Asp sulfonamide. Acidic deprotection of the BOC and tbutyl ester groups yields the final conjugate.

4.2 Synthesis Schemes For Conjugates

This section presents schemes for synthesizing the conjugates/structures identified in Section 3. All conjugates/structures are identified by a conjugate/structure number.

Conjugate 26 is synthesized in the following 9 steps.

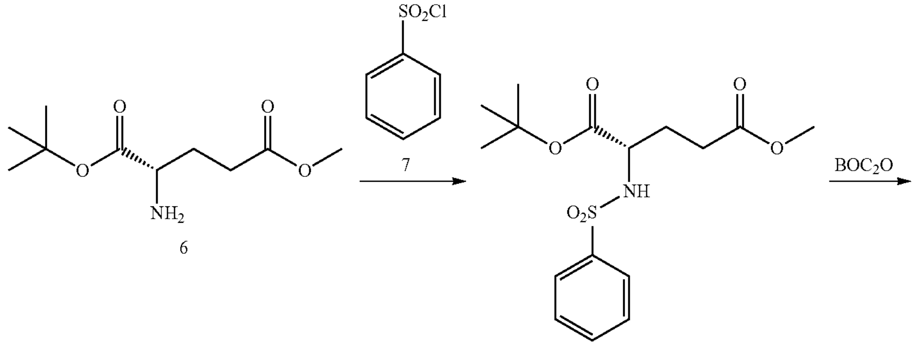

6

8

-continued
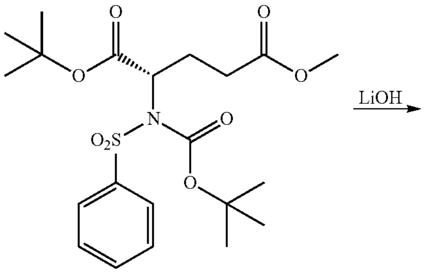
9
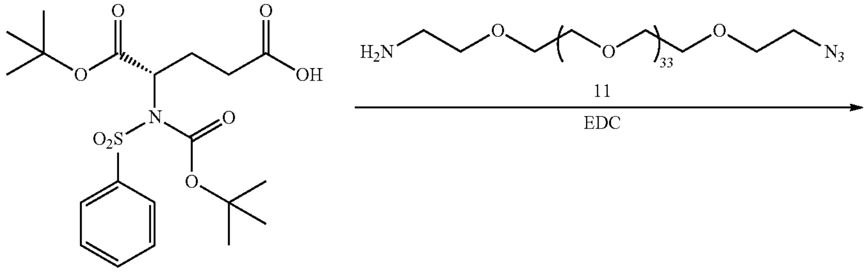
10
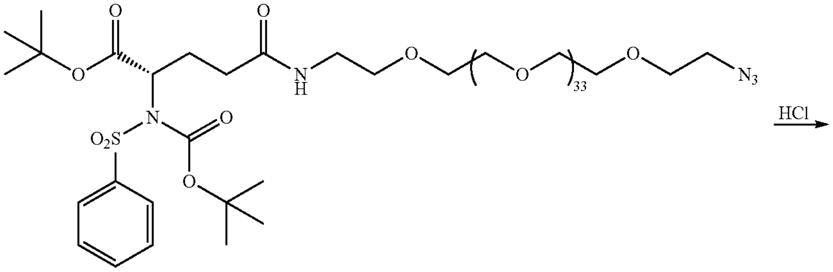
12
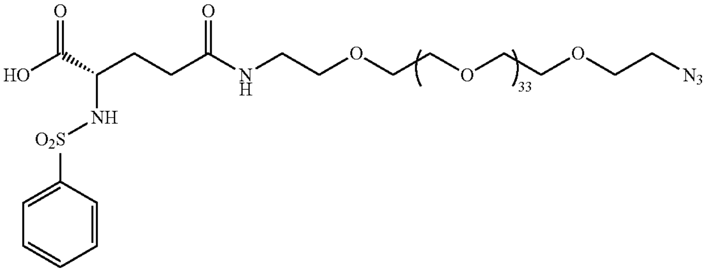
13
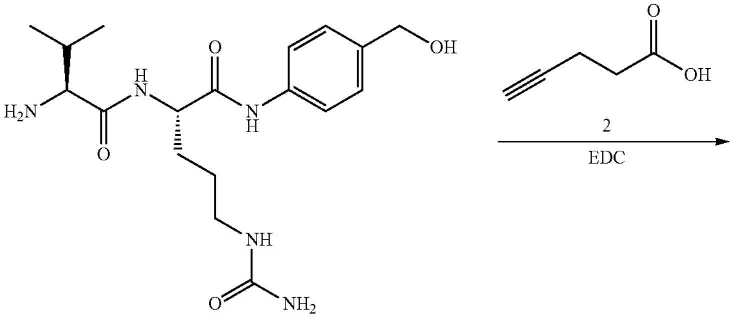
1

-continued
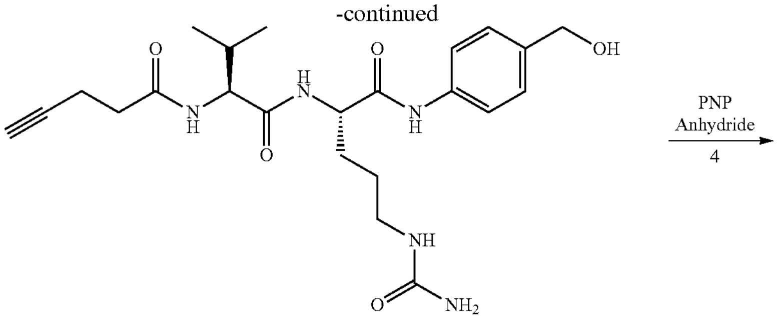
3
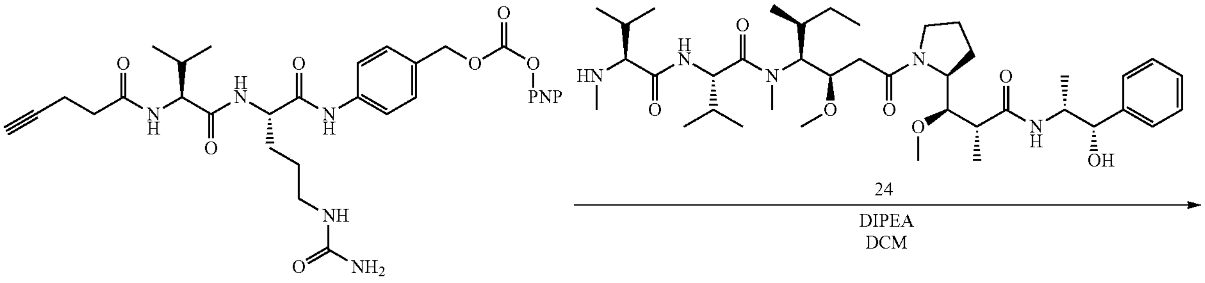
5
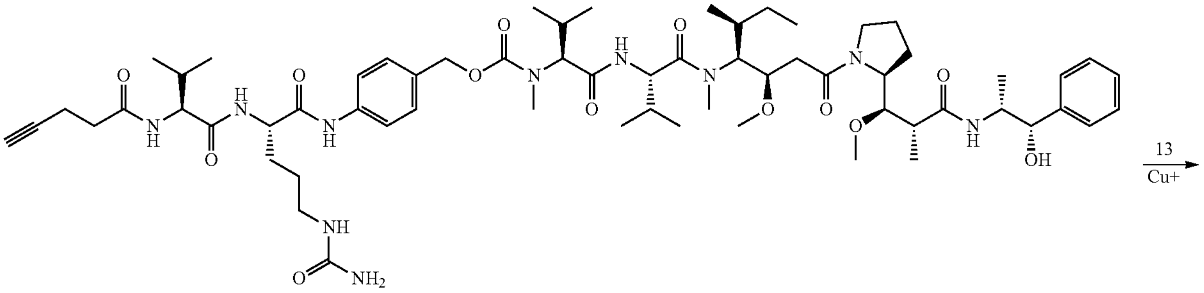
25
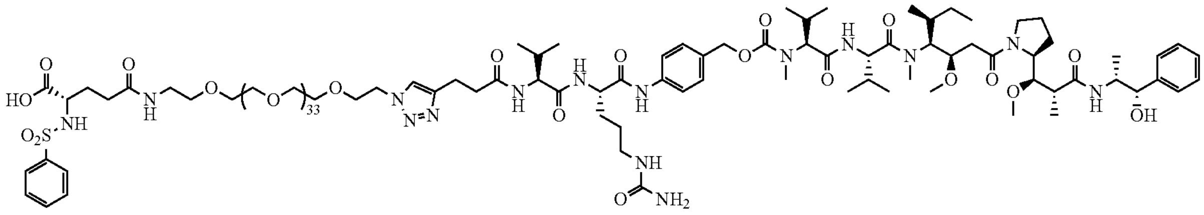
26
Conjugate 61 was synthesized in the following 7 steps. Compound 55 is now commercially available (AxisPharm, San Diego) and does not have to be synthesized in the manner shown below. Thus, the synthesis of Conjugate 61 can alternatively be run in 5 steps, using commercially available Conjugate 55, instead of the 7 steps shown below.
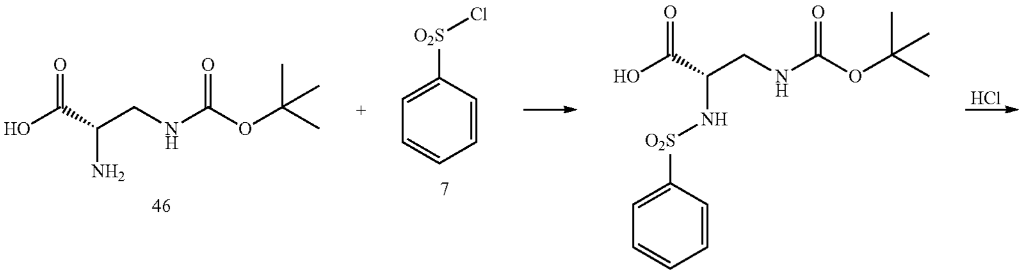
46
7
47

-continued
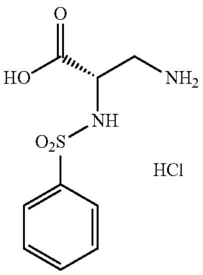
48
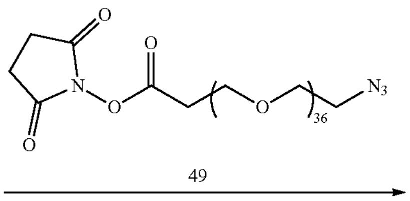
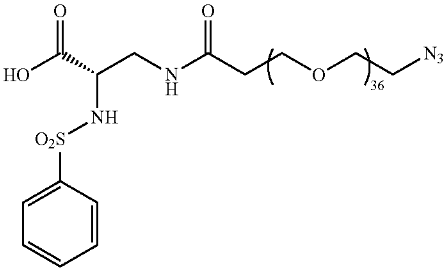
51
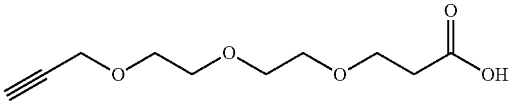
53
+
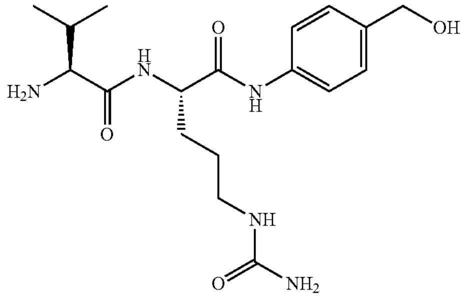
1
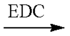
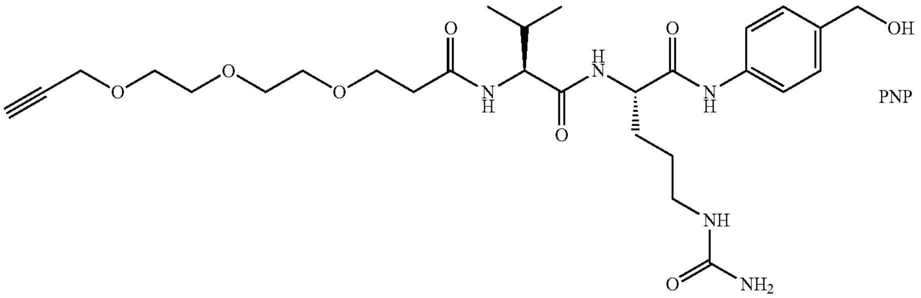
PNP
+
54
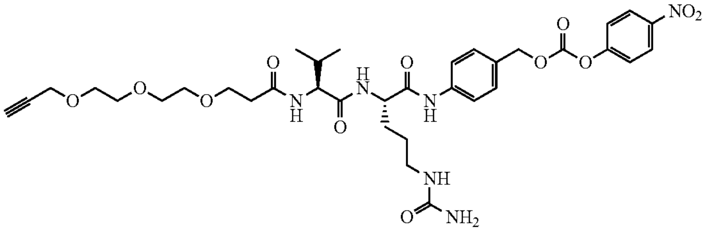
55
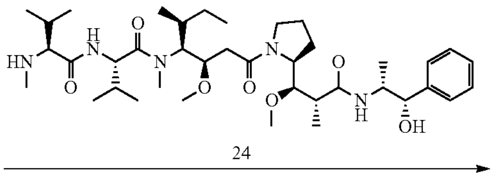
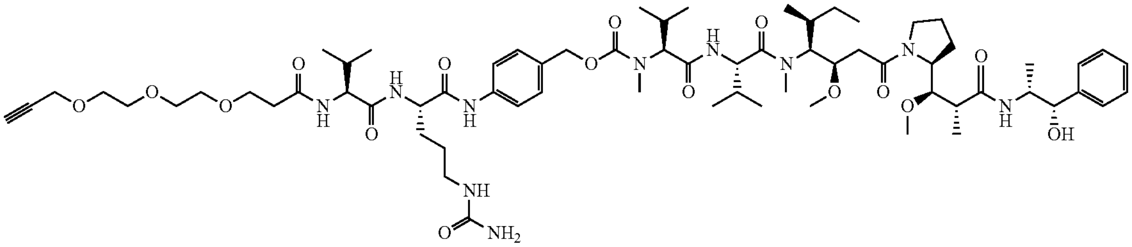
60
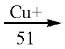

-continued
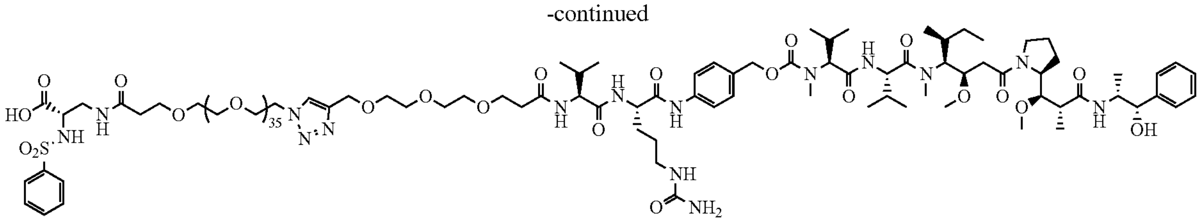
61
Conjugate 23 is synthesized in the following 12 steps, wherein synthesis schemes for structure 5 (2 steps) and structure 13 (5 steps) are shown in the synthesis scheme for conjugate 26.
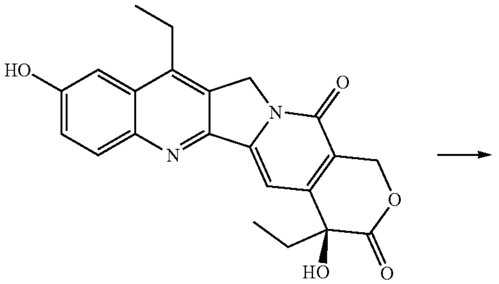
14
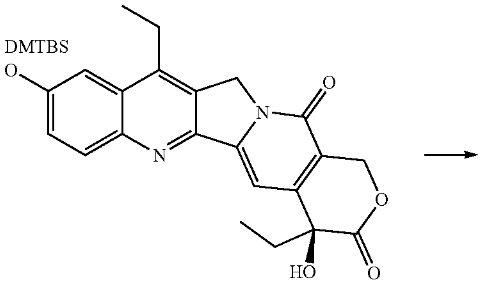
18
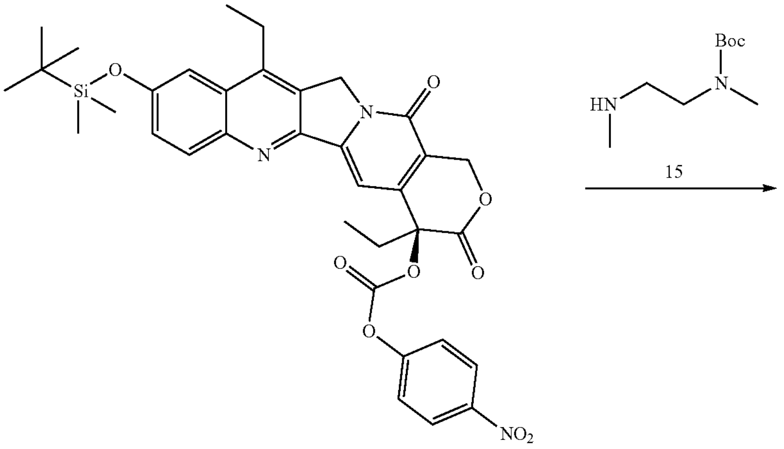
15
19
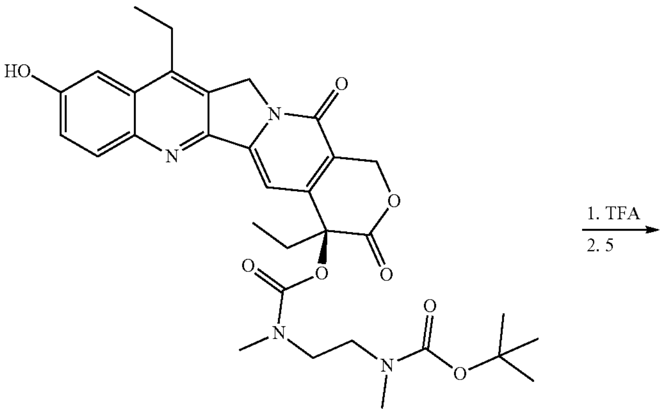
20

-continued
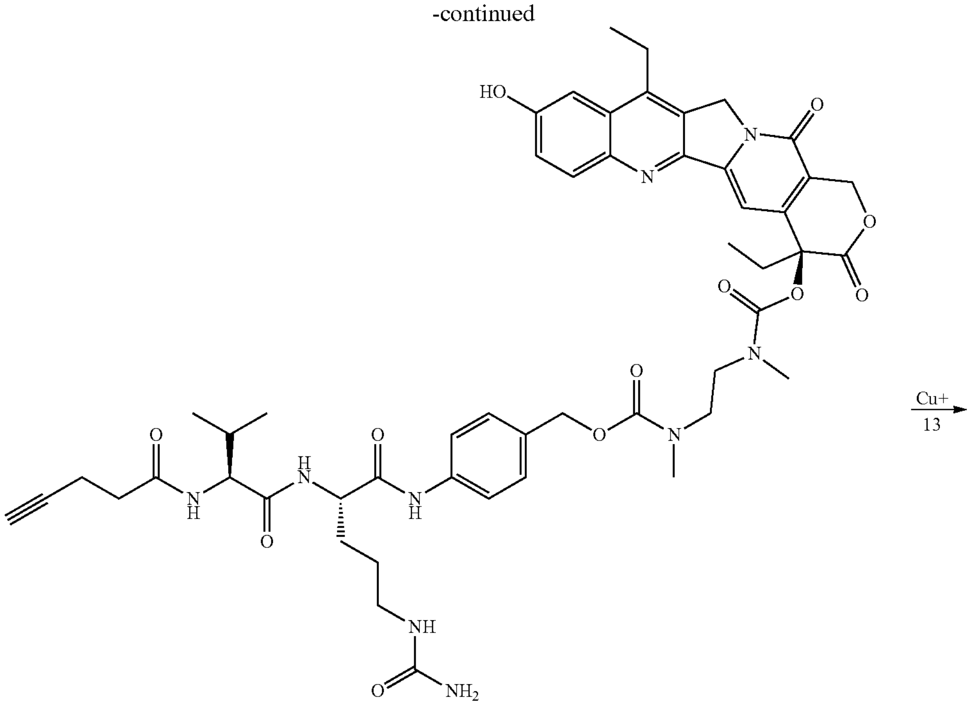
21
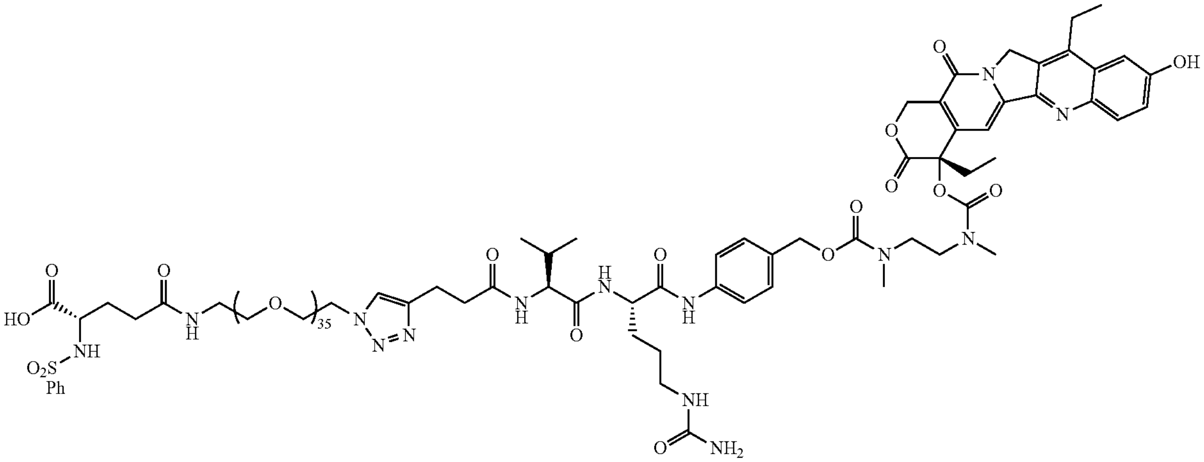
23
Conjugates 57 and 58 are synthesized in the following 6 steps and 10 steps, respectively, wherein synthesis schemes for structure 51 (3 steps) and structure 55 (2 steps), or in fewer steps if commercially available. Conjugate 55 is used, are shown in the synthesis scheme for conjugate 61.
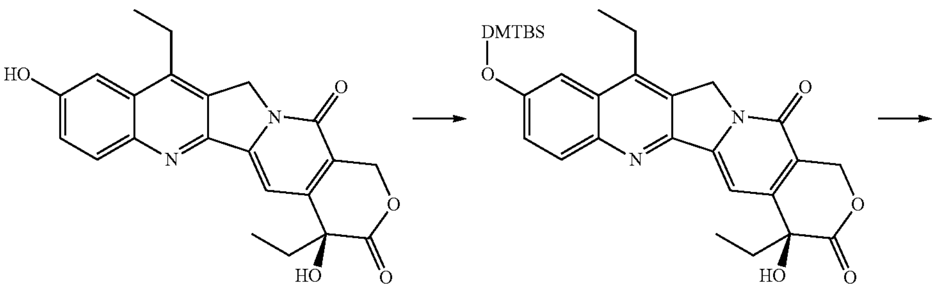
14 18

-continued
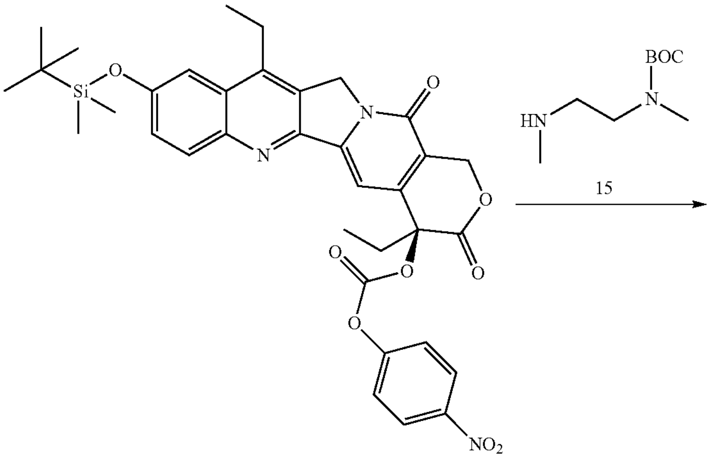
19
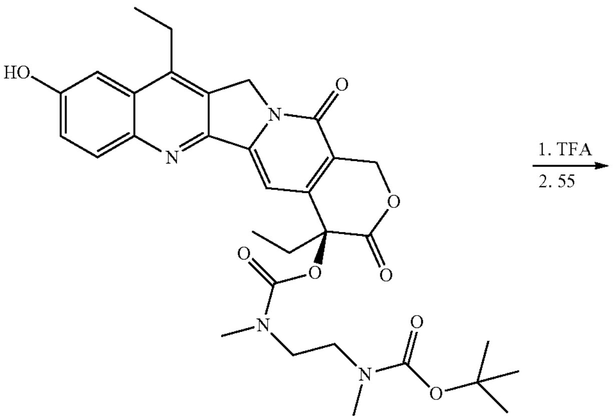
20
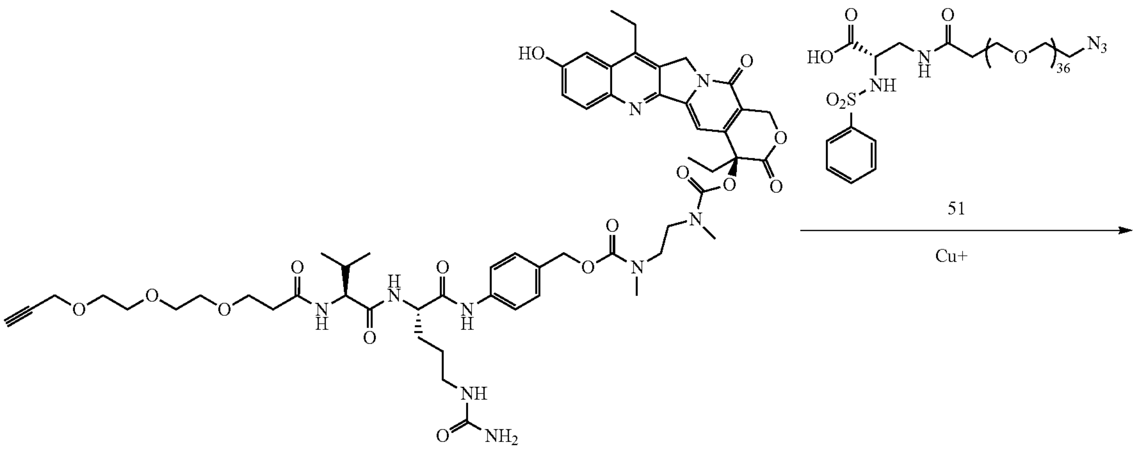
57

-continued
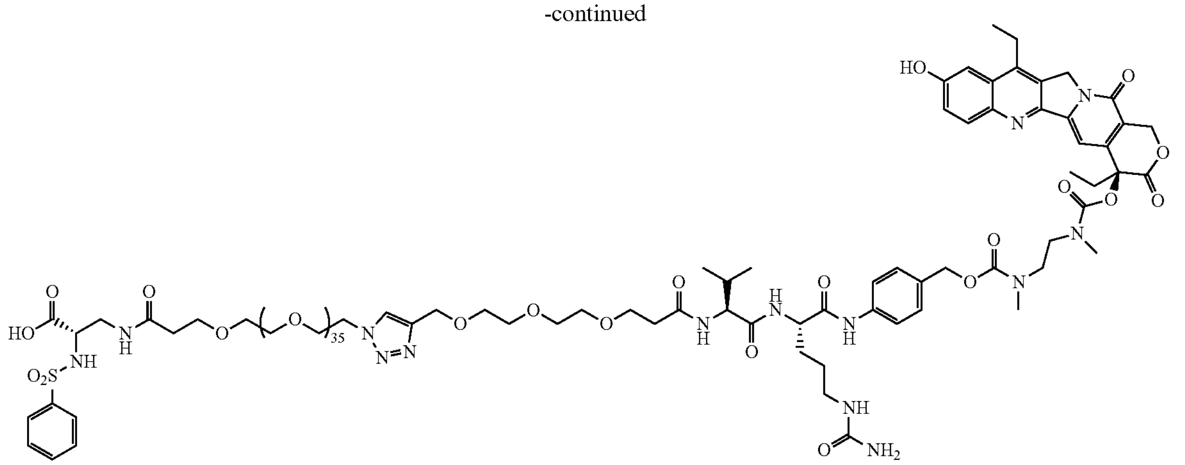
58
Conjugate 22 is synthesized in the following 10 steps, wherein synthesis schemes for structure 5 (2 steps) and structure 13 (5 steps) are shown in the synthesis scheme for conjugate 26.
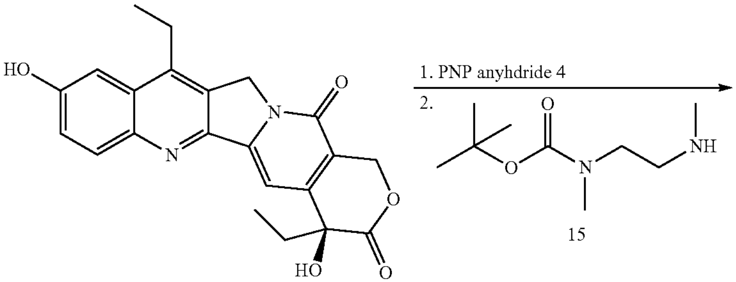
15
14
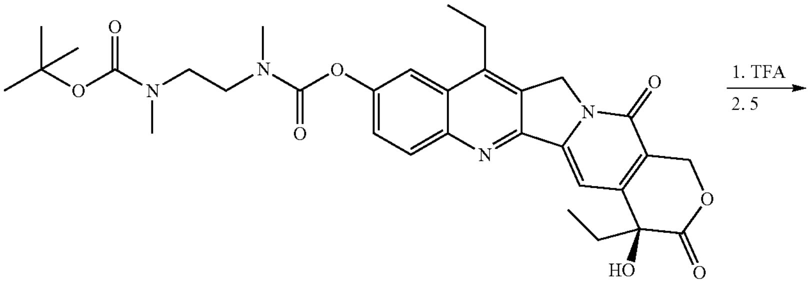
16
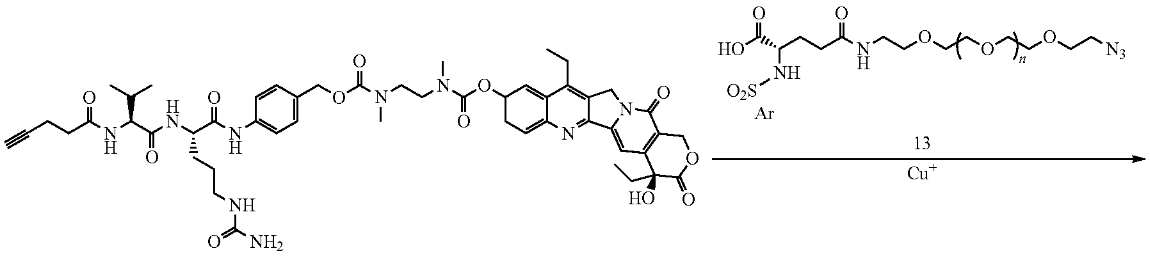
17

-continued
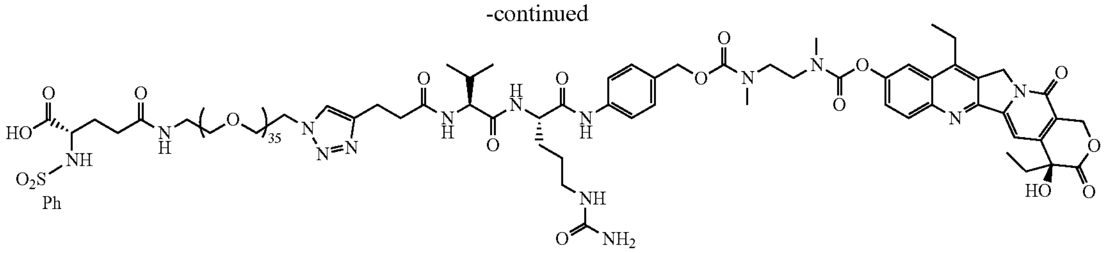
22
Conjugates 34 and 35 are synthesized in the following 9 steps, wherein synthesis schemes for structure 10 (3 steps) and structure 25 (3 steps) are shown in the synthesis scheme for conjugate 26.
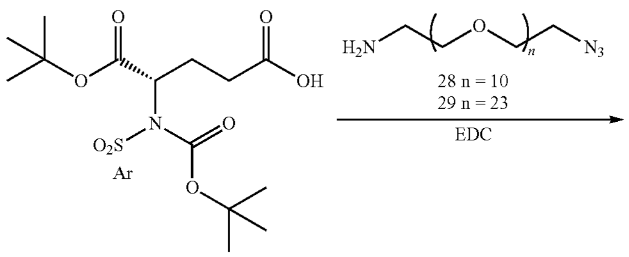
10
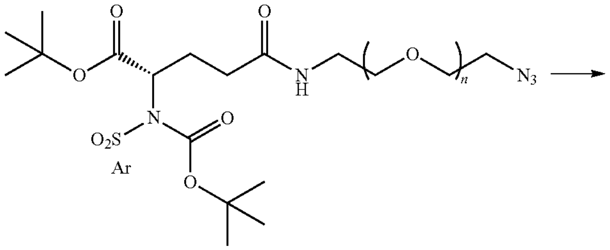
30 n = 10
31 n = 23
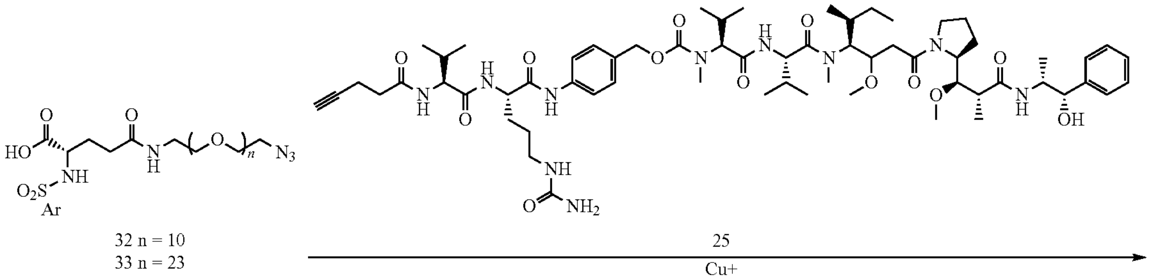
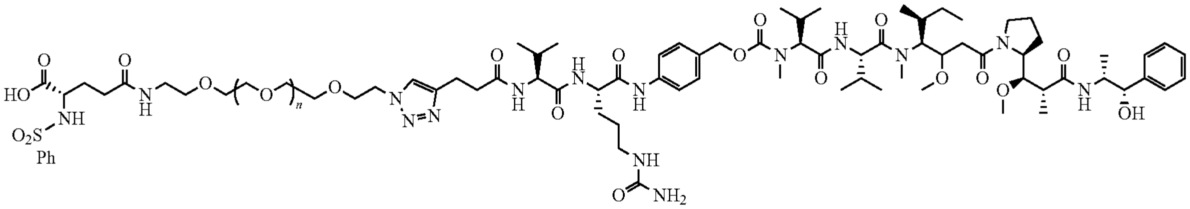
34 n = 8
35 n = 21

Conjugate 40 is synthesized in the following 8 steps, wherein a synthesis scheme for structure 13 (5 steps) is shown in the synthesis scheme for conjugate 26.
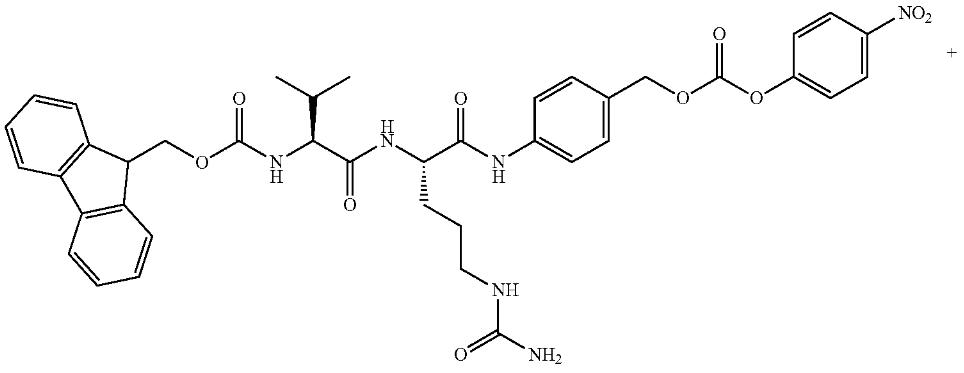
36
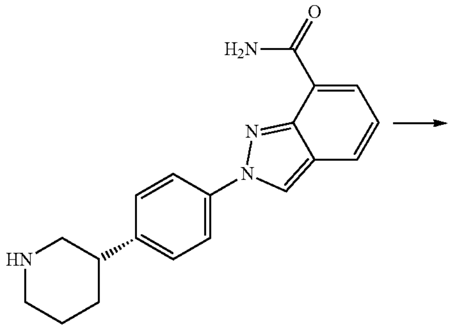
37
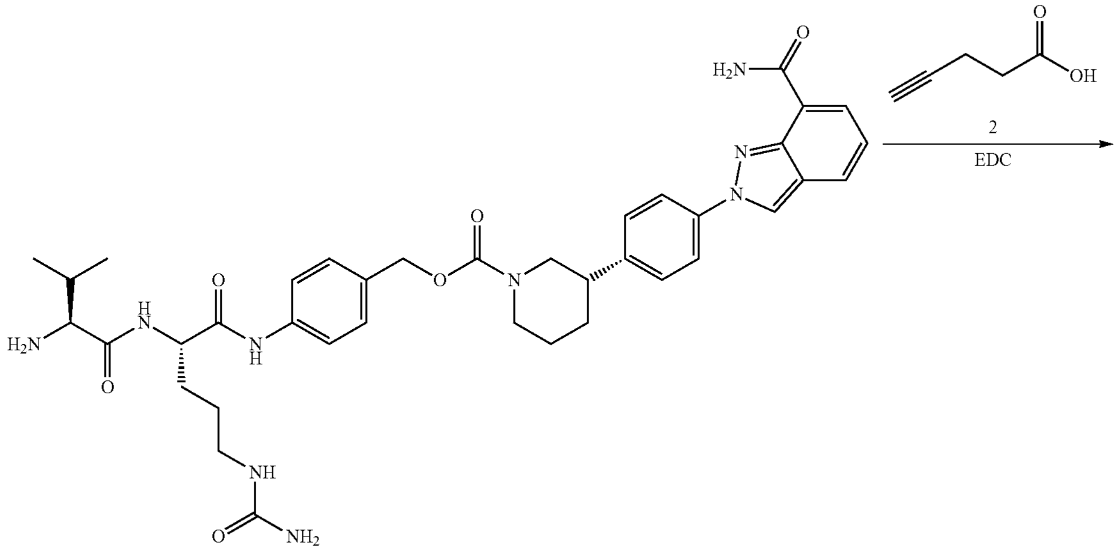
38

-continued
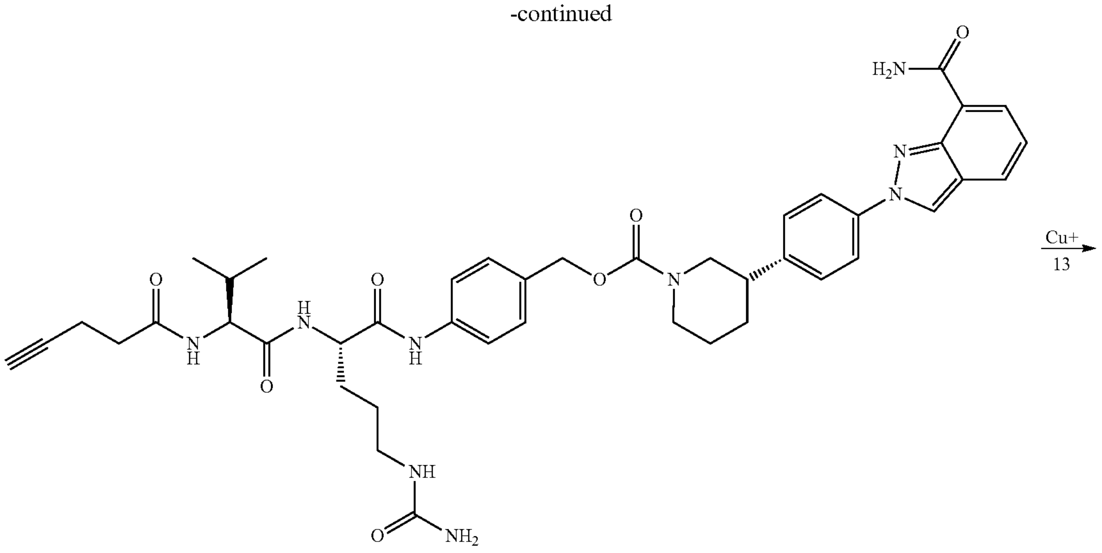
39
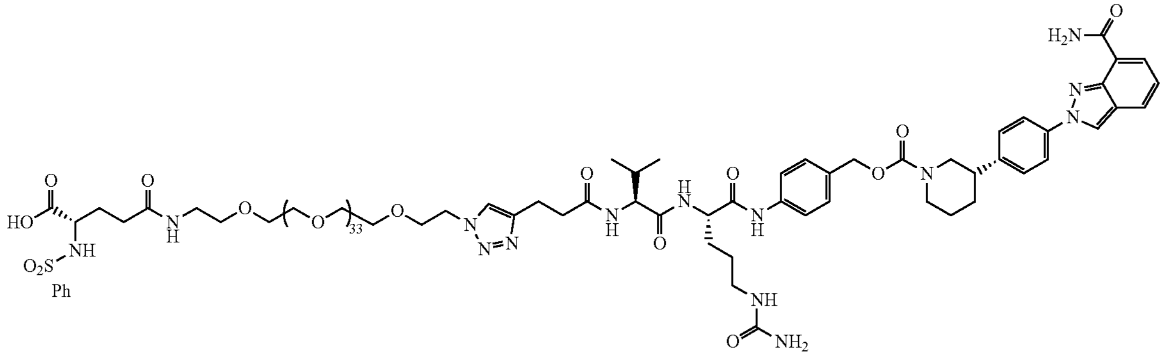
40
Conjugate 45 is synthesized in the following 11 steps, wherein synthesis schemes for structure 5 (2 steps) and structure 13 (5 steps) are shown in the synthesis scheme for conjugate 26.
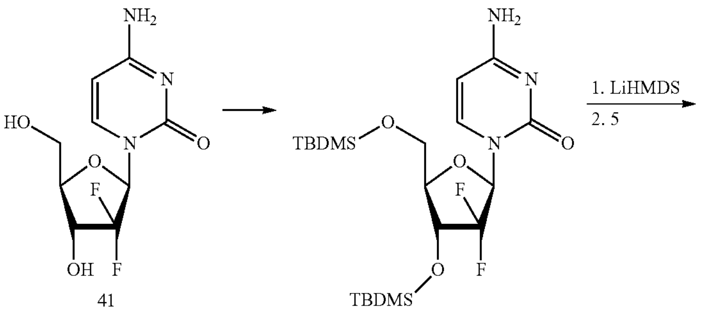
41
42

-continued
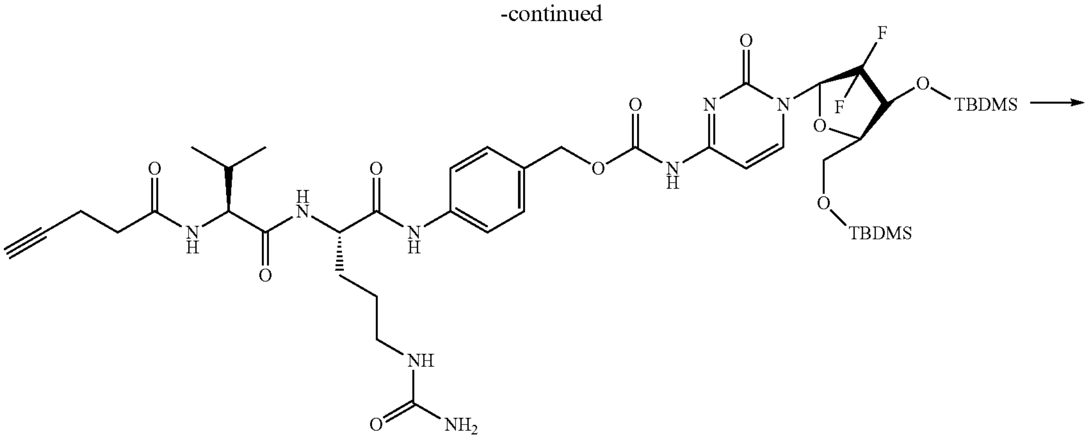
43
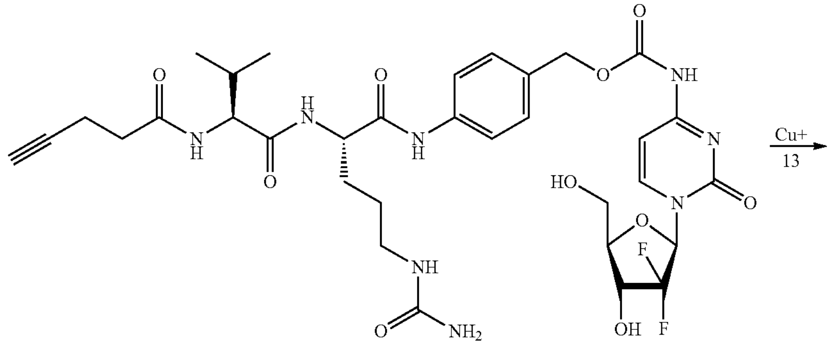
44
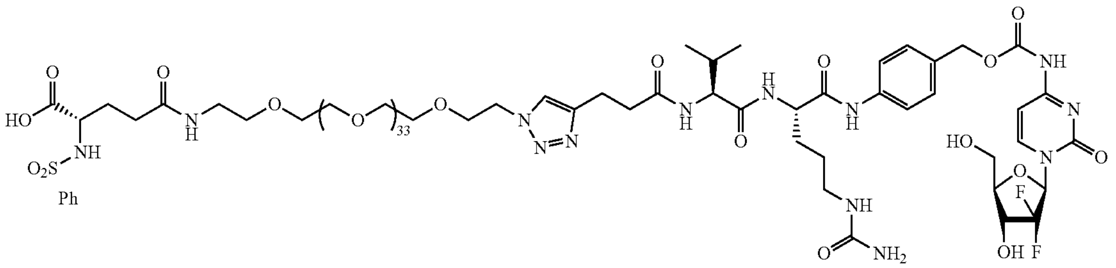
45
Conjugate 59 is synthesized in the following 5 steps, wherein synthesis schemes for structure 51 (3 steps) and structure 54 (1 step) are shown in the synthesis scheme for conjugate 61.
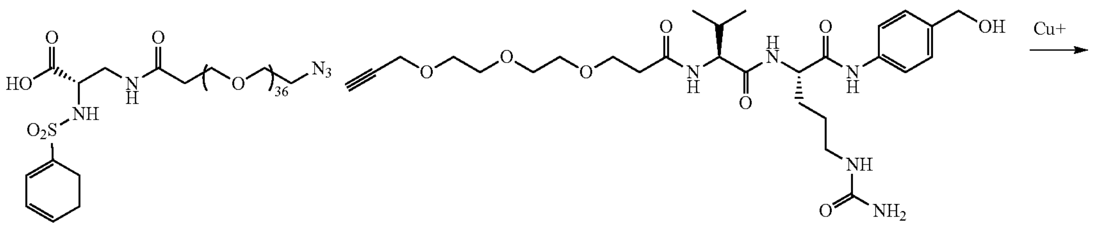
51 54

-continued
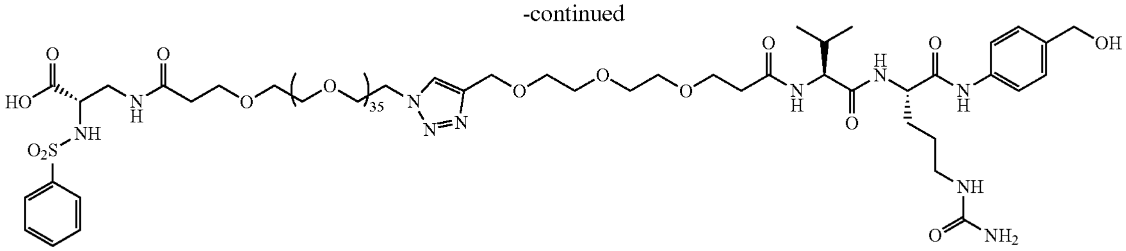
59
Conjugate 62 is synthesized in the following 7 steps, wherein synthesis schemes for structure 48 (2 steps) and structure 60 (3 steps) are shown in the synthesis scheme for conjugate 61.

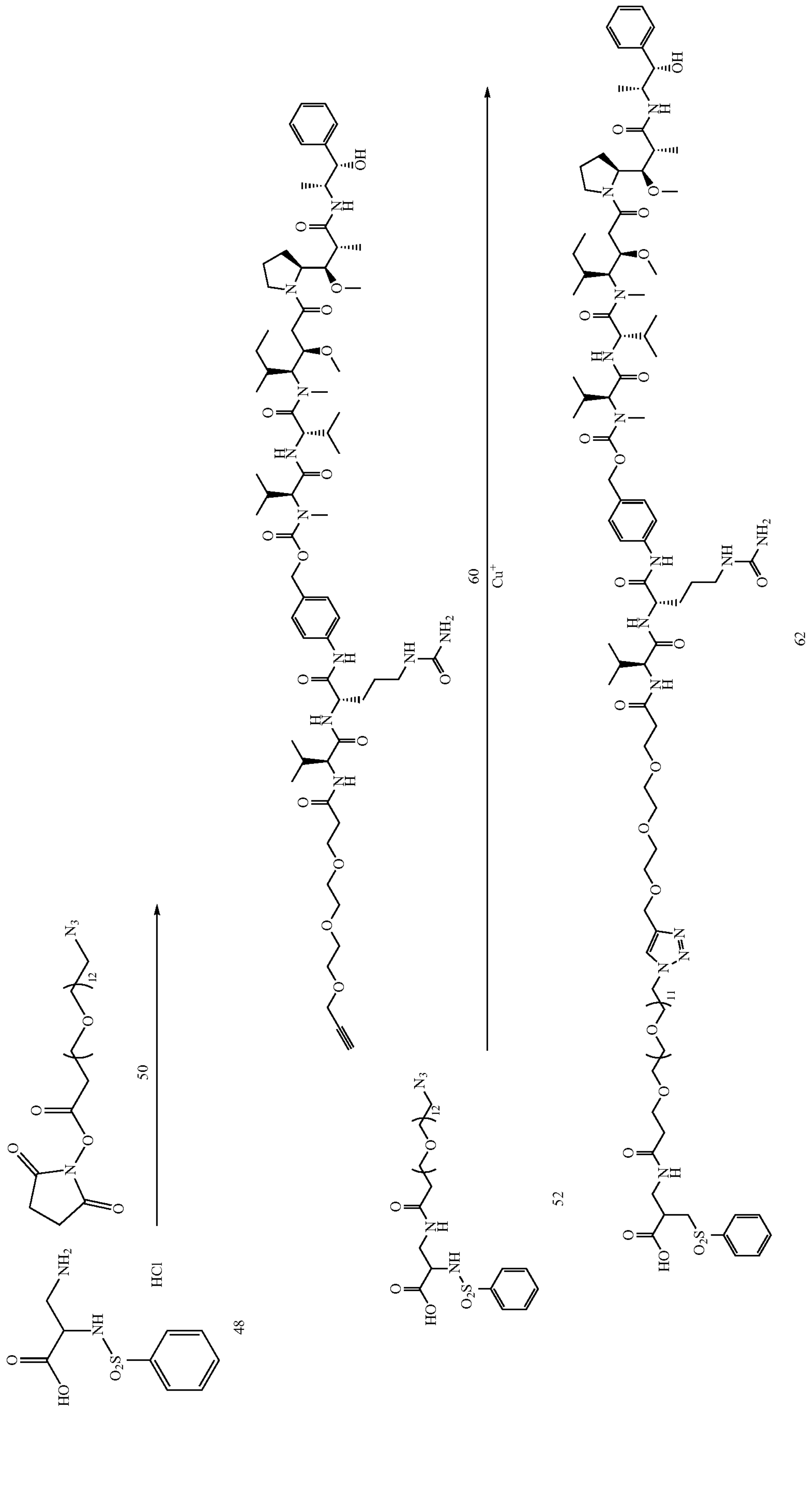
48
52
62

Conjugate 64 is synthesized in the following 4 steps, wherein a synthesis scheme for structure 60 (3 steps) is shown in the synthesis scheme for conjugate 61.
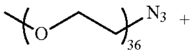
63
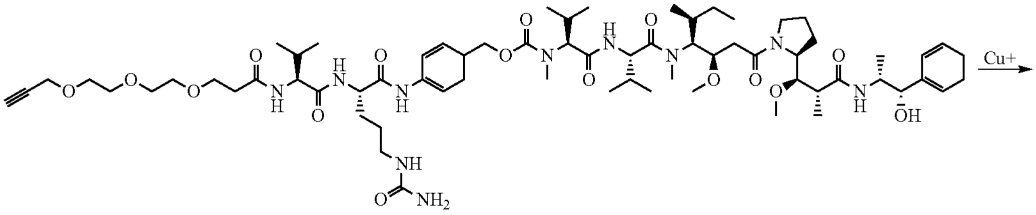
60
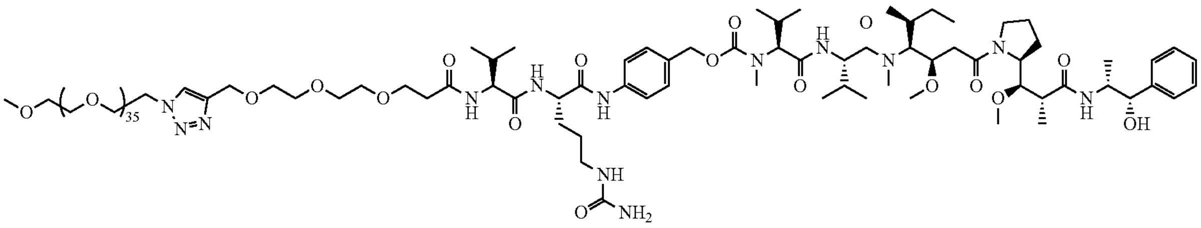
64
Conjugate 69 is synthesized in the following 7 steps, wherein synthesis a scheme for structure 25 (3 steps) is shown in the synthesis scheme for conjugate 26.
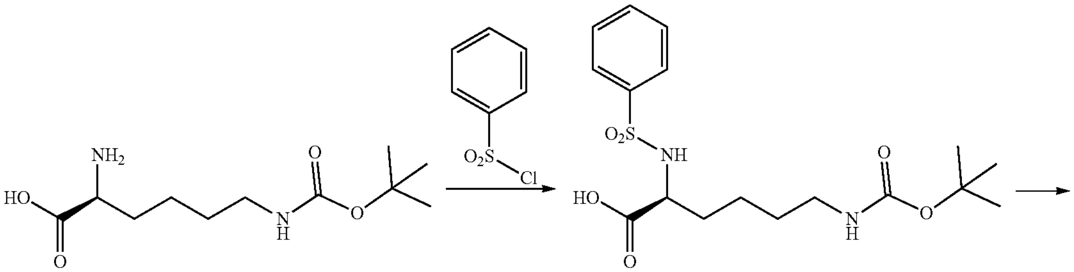
65 66
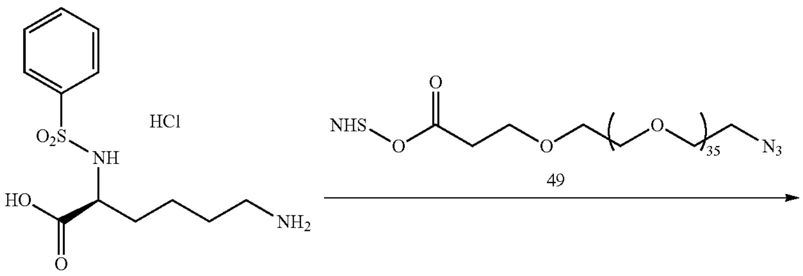
49
67

-continued
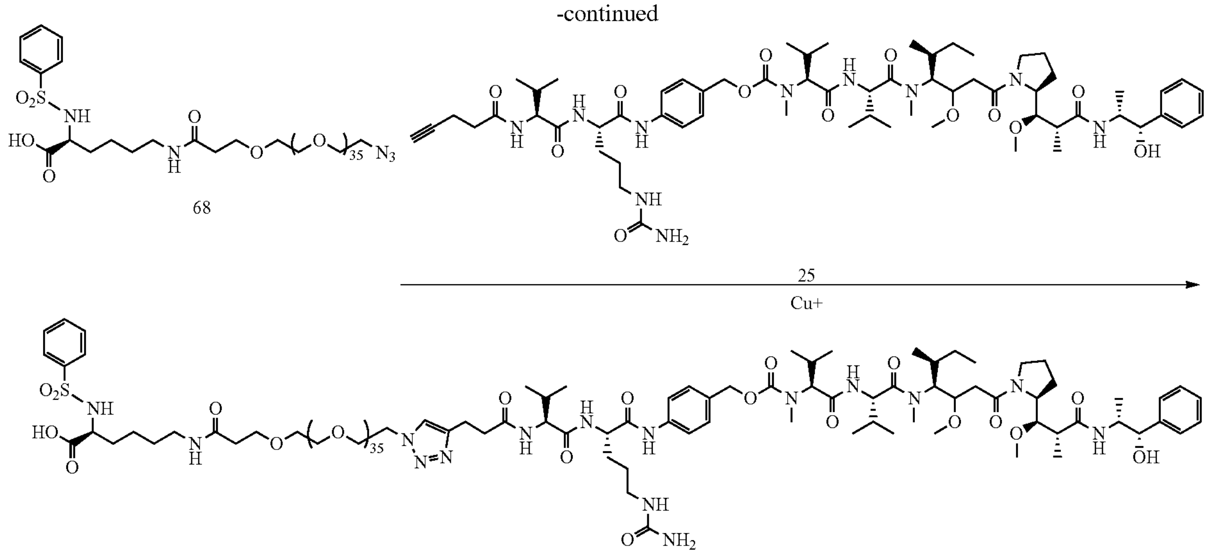
Conjugate 72 is synthesized in the following 9 steps, wherein a synthesis scheme for structure 55 (2 steps) is shown in the synthesis schemes for conjugate 61, and a synthesis scheme for structure 13 (5 steps) is shown in the synthesis schemes for conjugate 26.
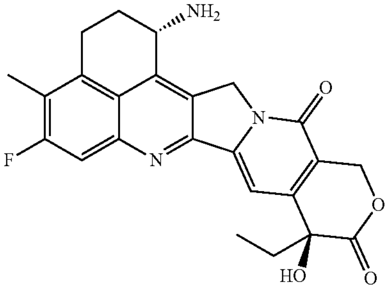
70
+
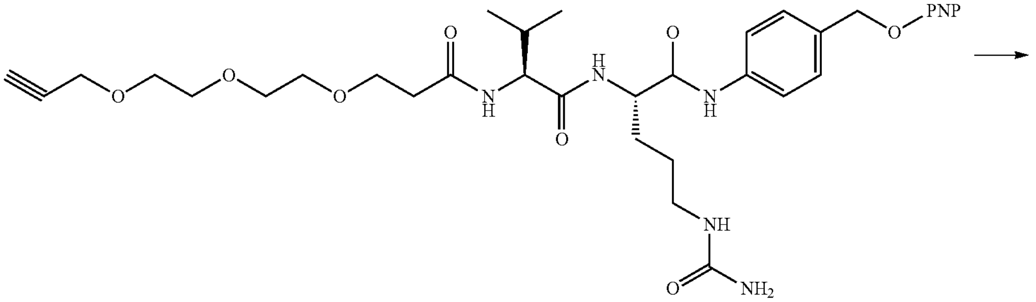
55

-continued
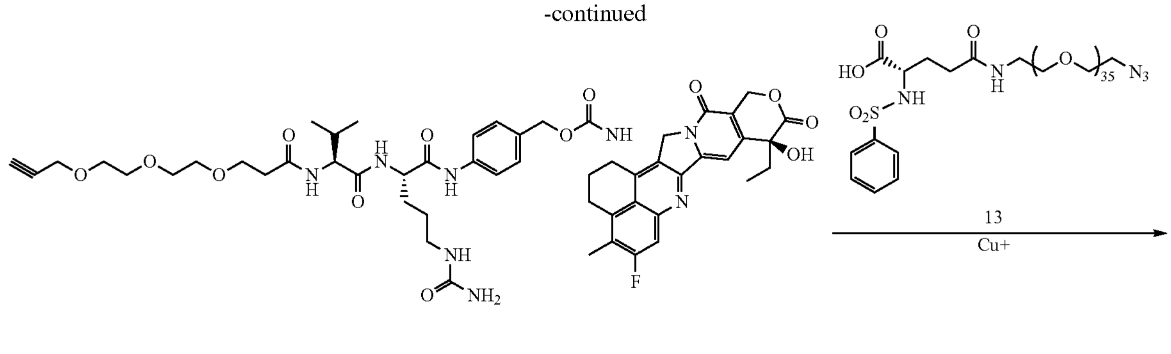
71
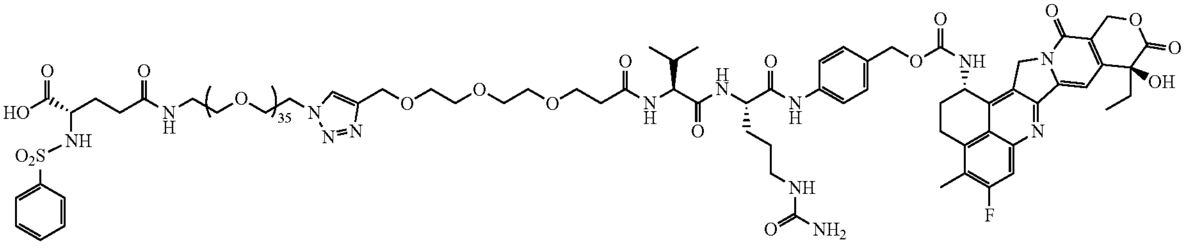
72
Conjugate 73 is synthesized in the following 6 steps, wherein a synthesis scheme for structure 21 (5 steps) is shown in the synthesis schemes for conjugate 23.
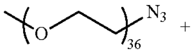
63
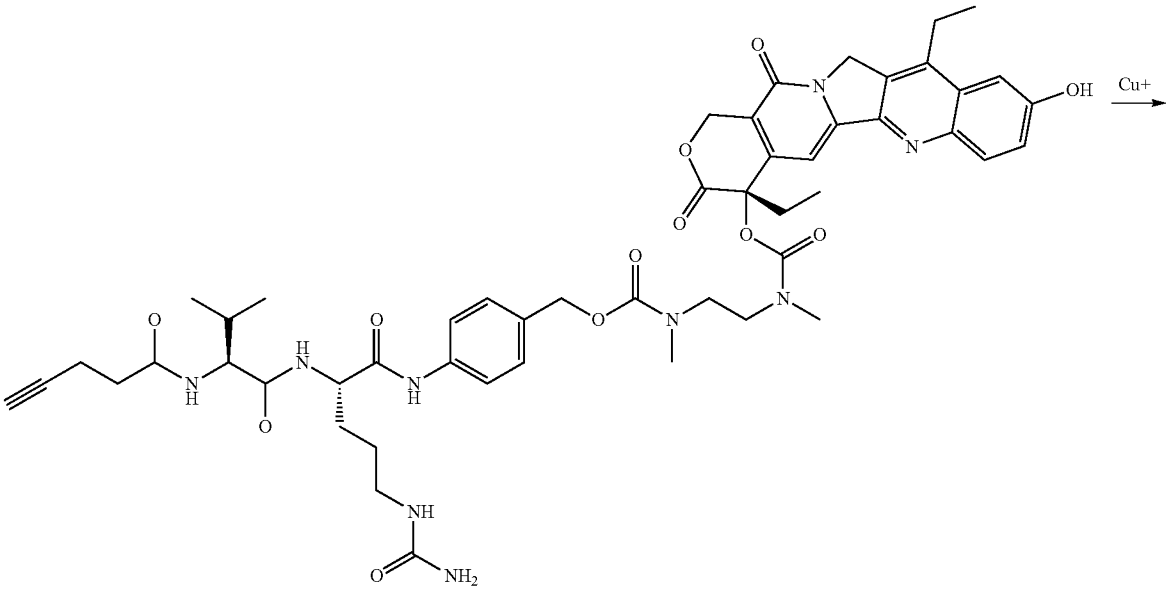
21

-continued
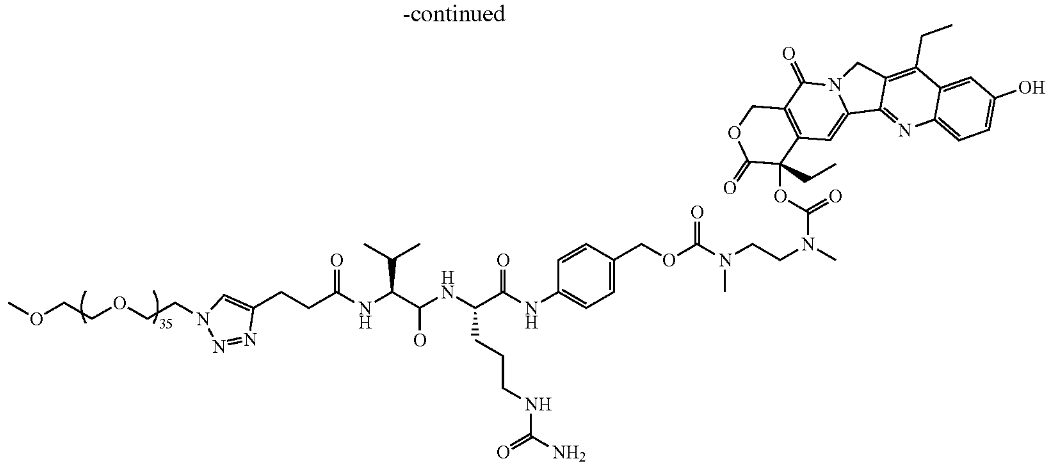
73
Conjugate 74 is synthesized in the following 7 steps, wherein synthesis schemes for structures 13 (5 steps) and 3 (1 step) are shown in the synthesis schemes for conjugate 26.
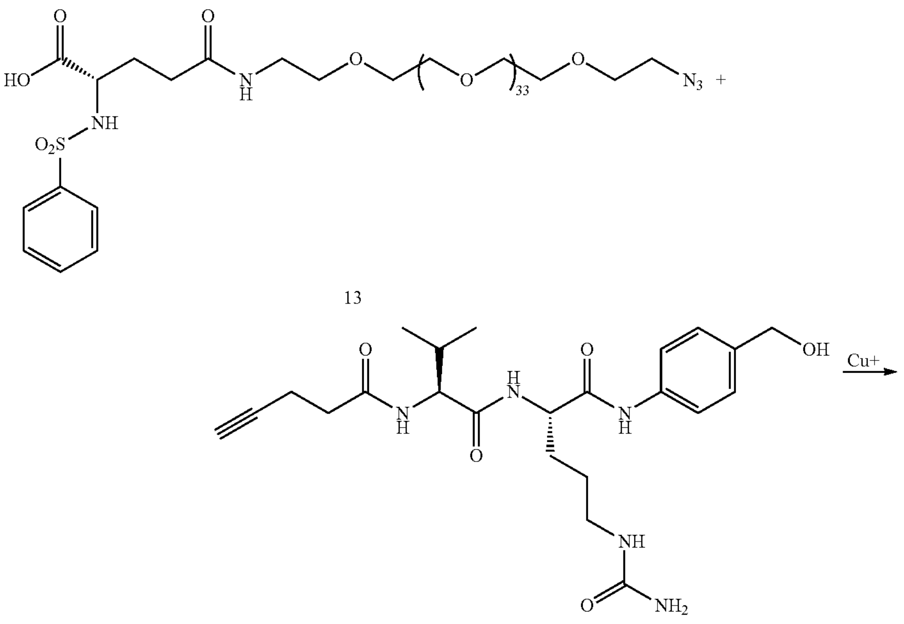
13
3
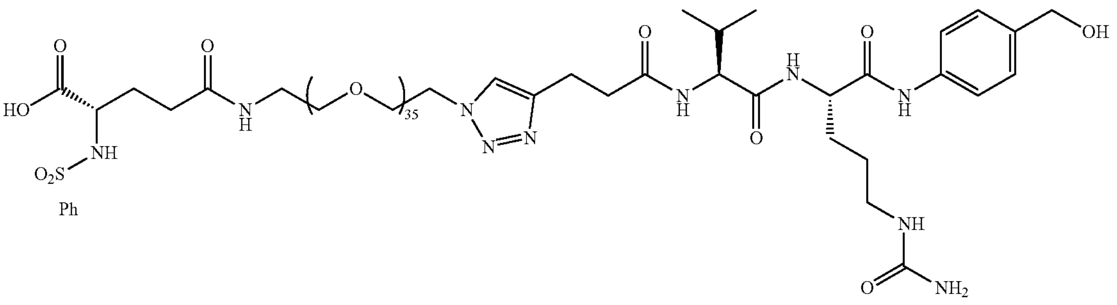
74

Conjugate 76 is synthesized in the following 5 steps, wherein a synthesis scheme for structure 10 (3 steps) is shown in the synthesis schemes for conjugate 26.
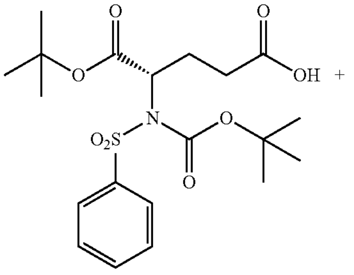
10
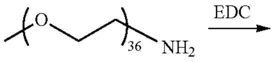
-continued
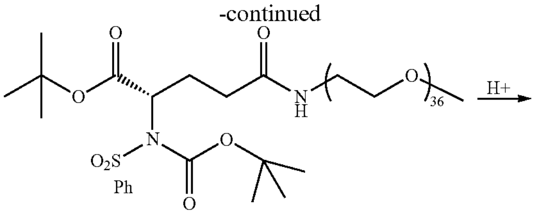
75
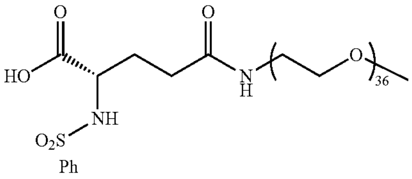
76
Conjugate 82 is synthesized in the following 7 steps, wherein a synthesis scheme for structure 60 (3 steps) is shown in the synthesis scheme for conjugate 61.

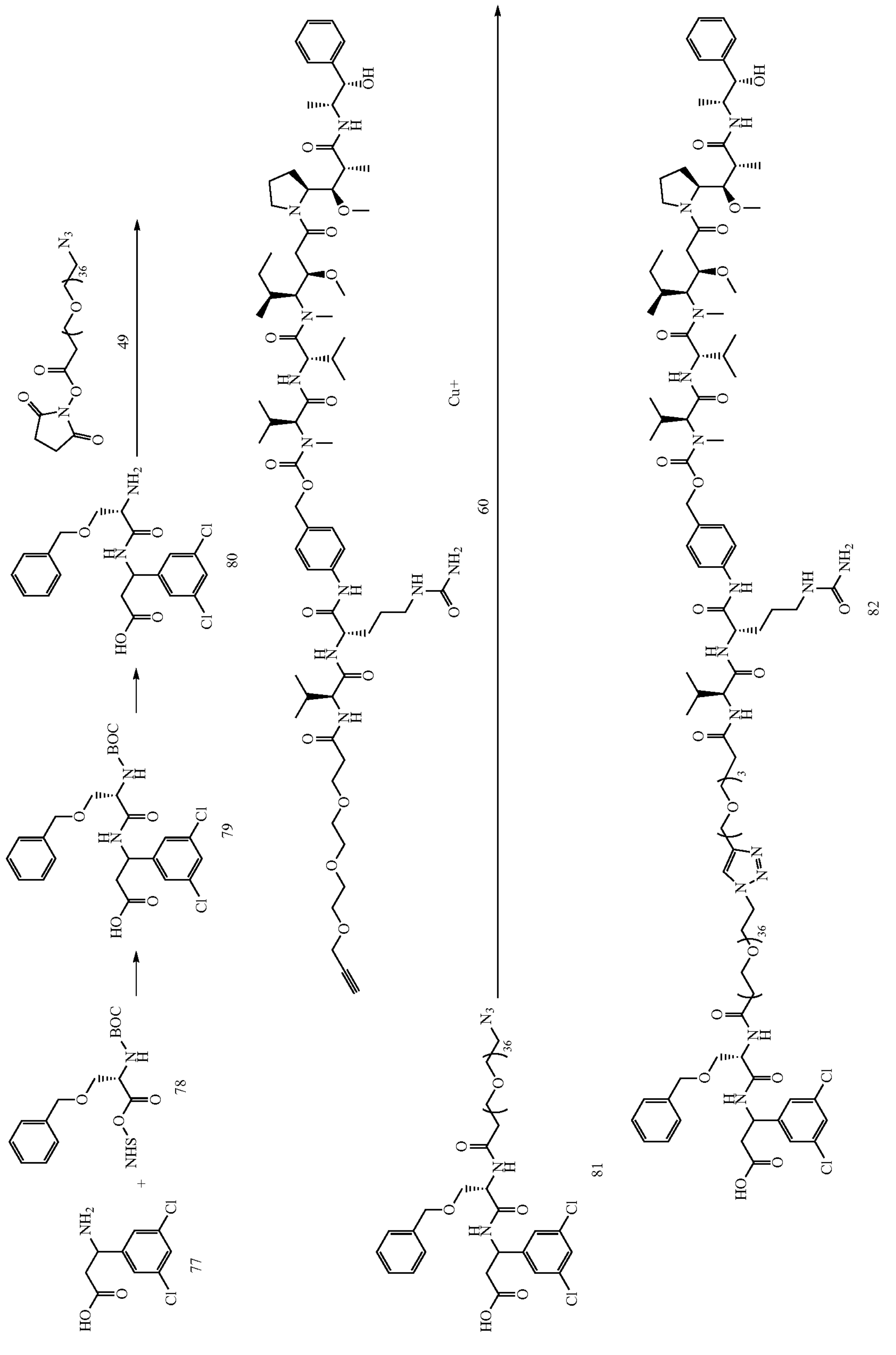
77 78 79 80 81 82

Conjugate 108 is synthesized in the following 8 steps, wherein a synthesis scheme for structure 60 (3 steps) is shown in the synthesis scheme for conjugate 61.

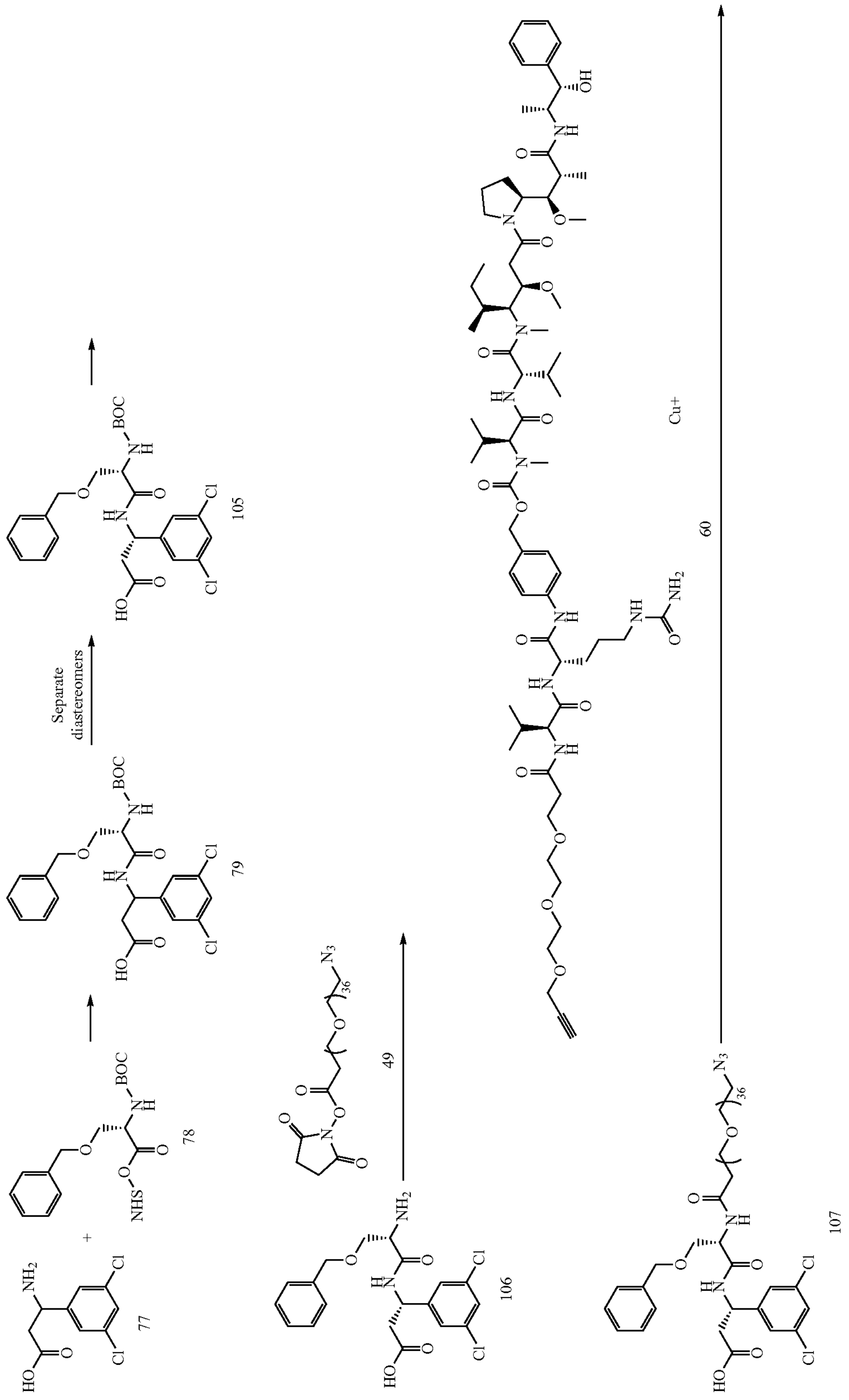
77 78 79 105 106 49 107 60

-continued
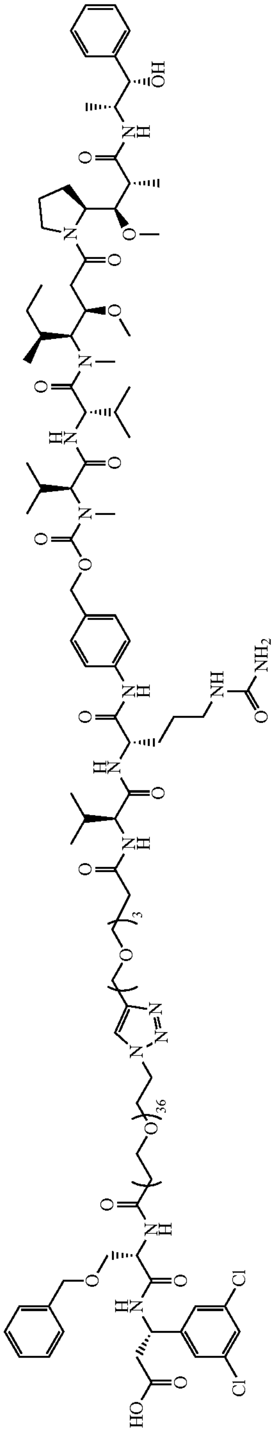
108

Conjugate 85 is synthesized in the following 5 steps, wherein a synthesis scheme for structure 60 (3 steps) is shown in the synthesis scheme for conjugate 61.
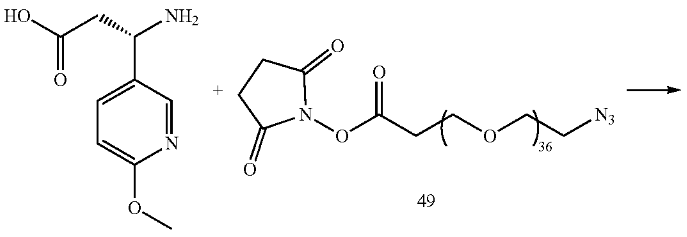
49
83
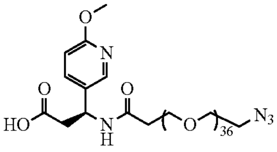
84
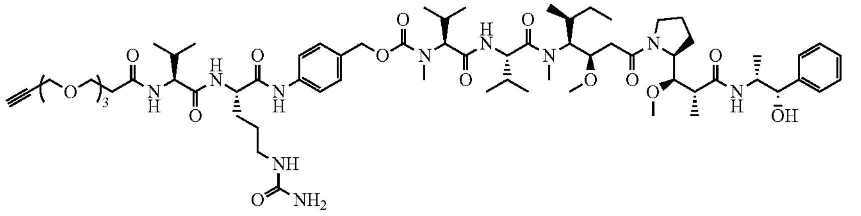
60
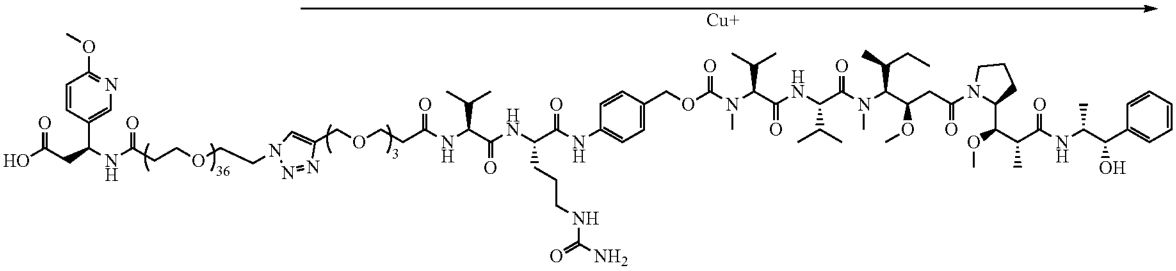
85
Conjugate 87 is synthesized in the following 3 steps, wherein a synthesis scheme for structure 48 (2 steps) is shown in the synthesis scheme for conjugate 61.
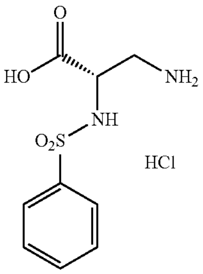
48
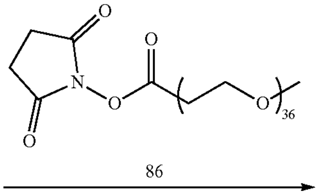
86
-continued
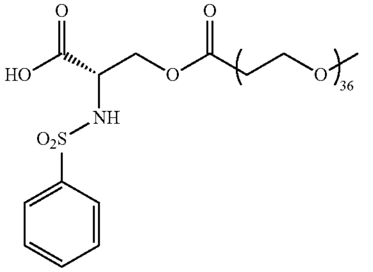
87
Conjugate 92 is synthesized in the following 7 steps.

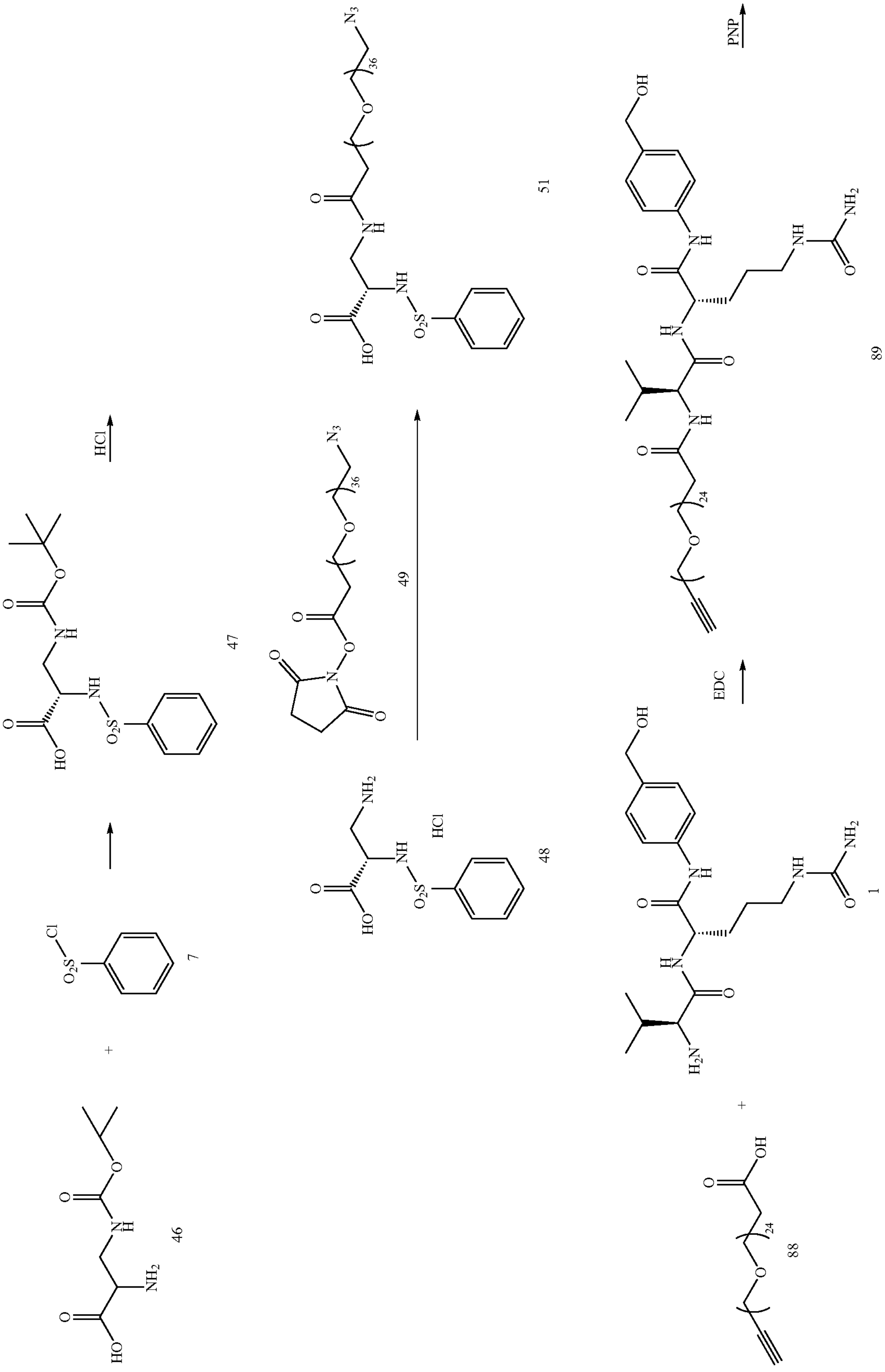
46 + 7 → 47
48 (HCl) → 51
88 + 1 → 89

-continued
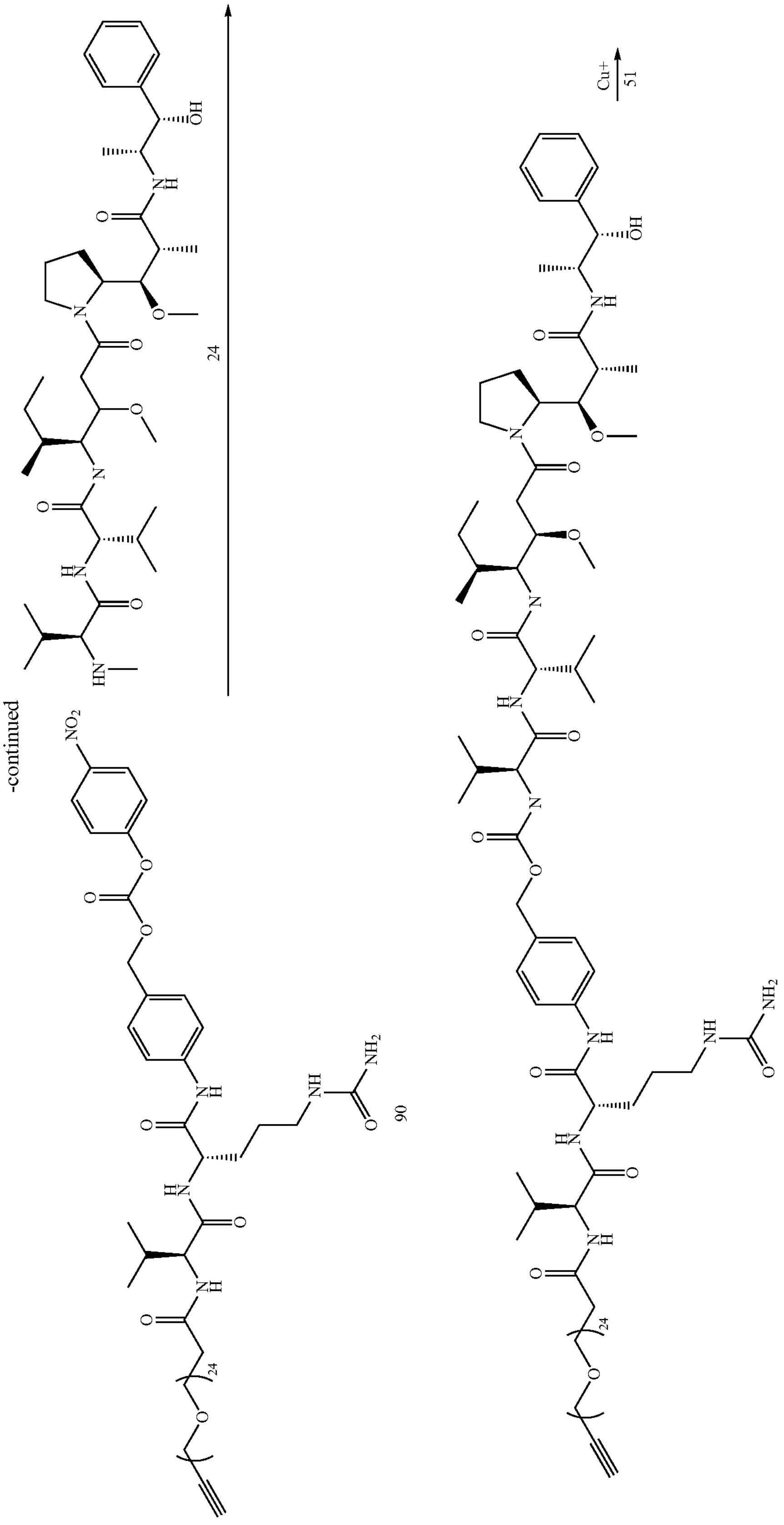
90
91

-continued
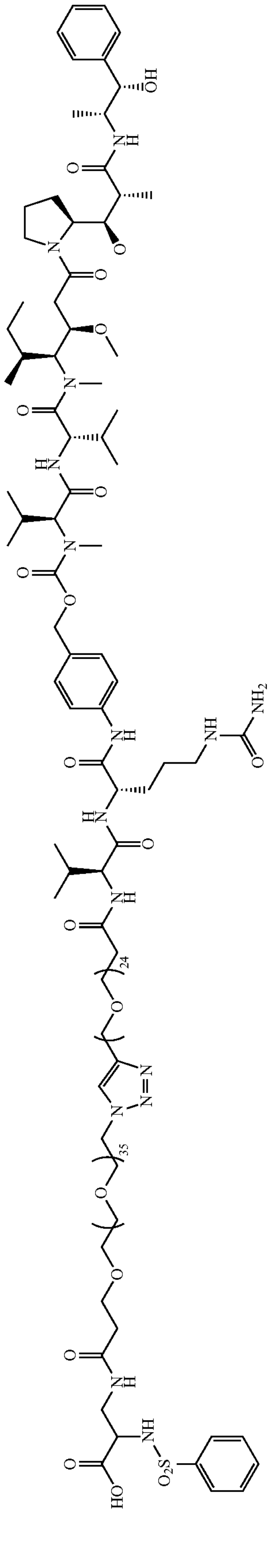
92

Conjugate 97 is synthesized in the following 7 steps. IDC-133

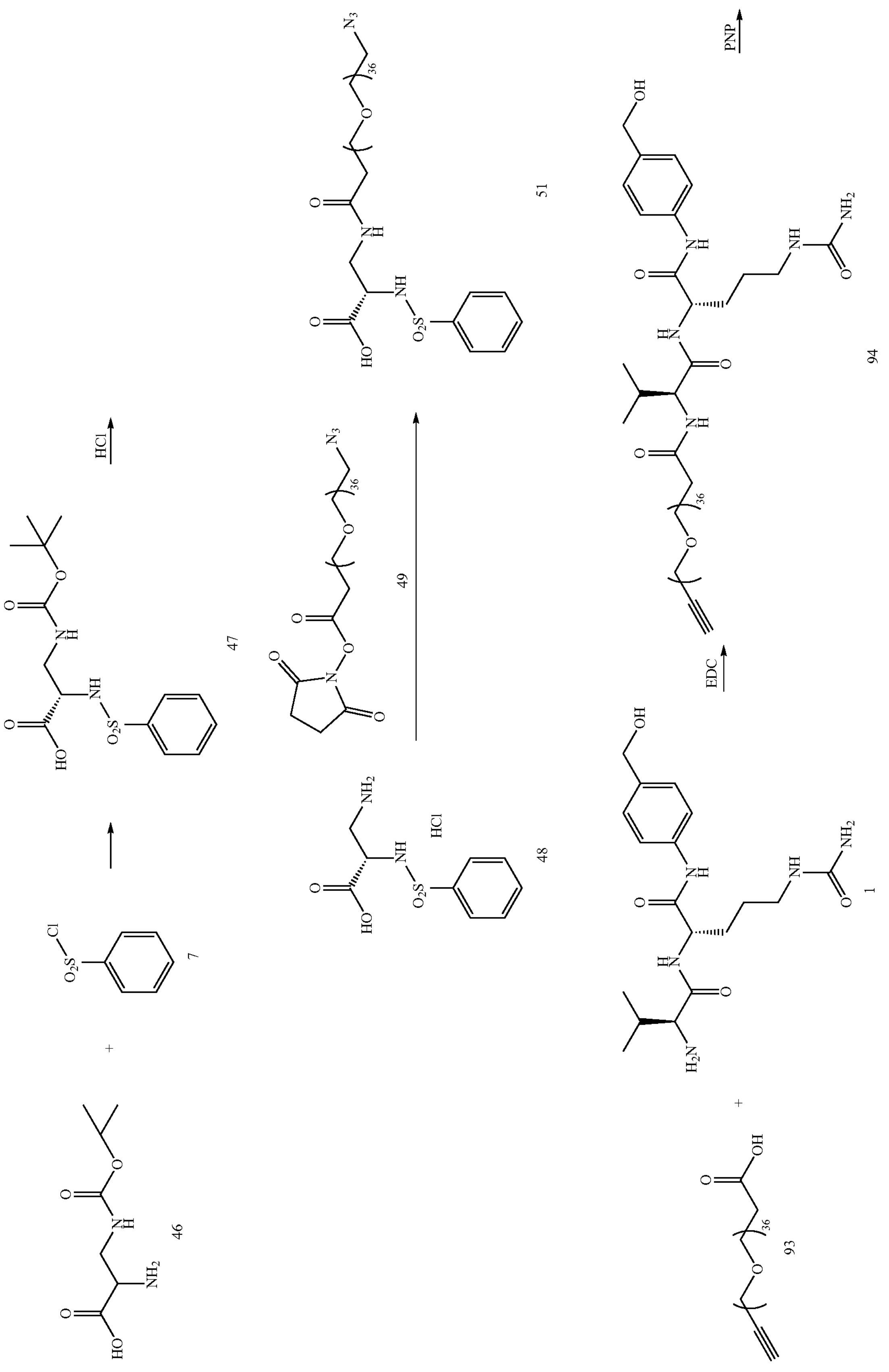
46 7 47 48 51 93 1 94

-continued
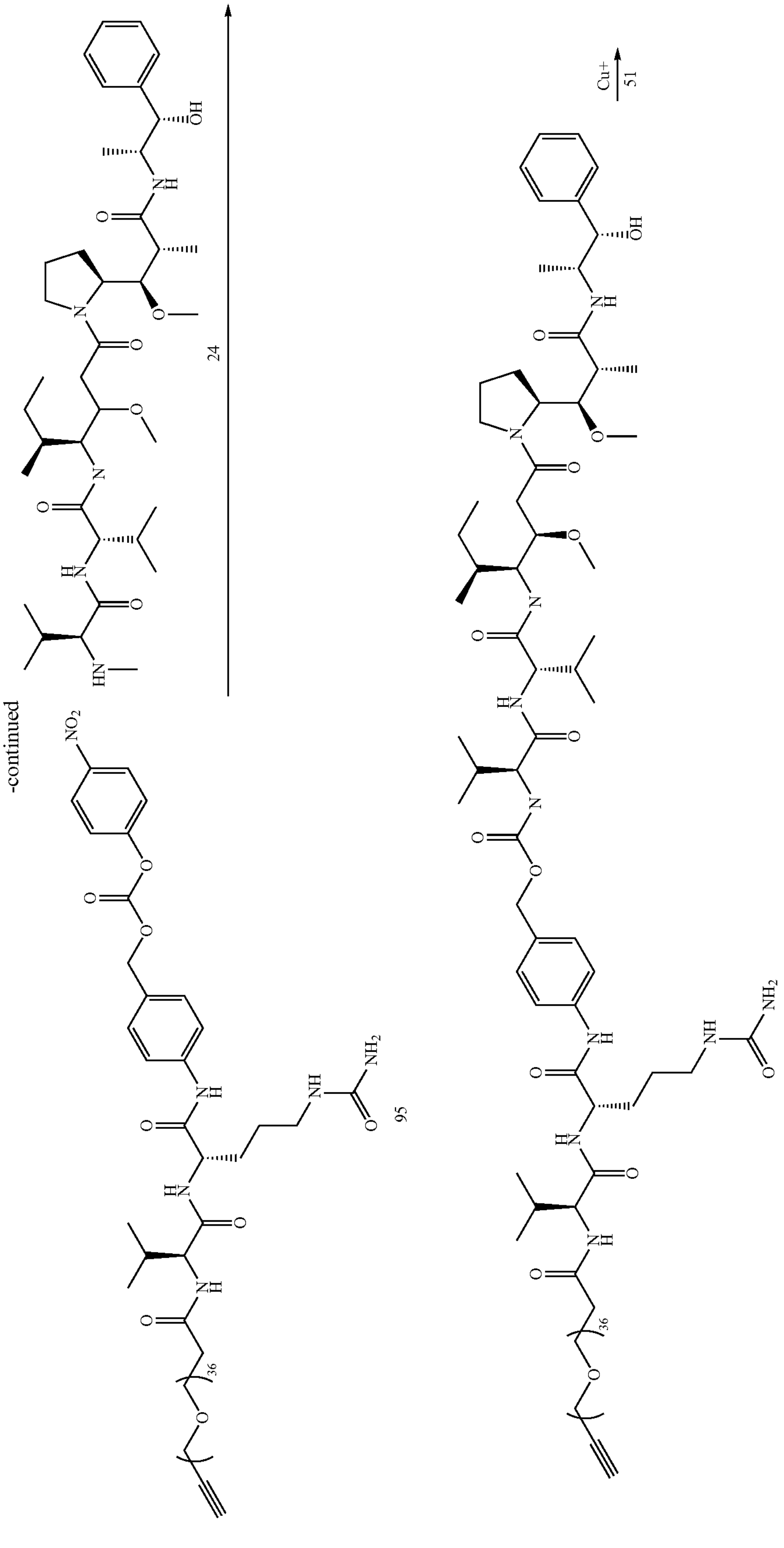
95
96

-continued
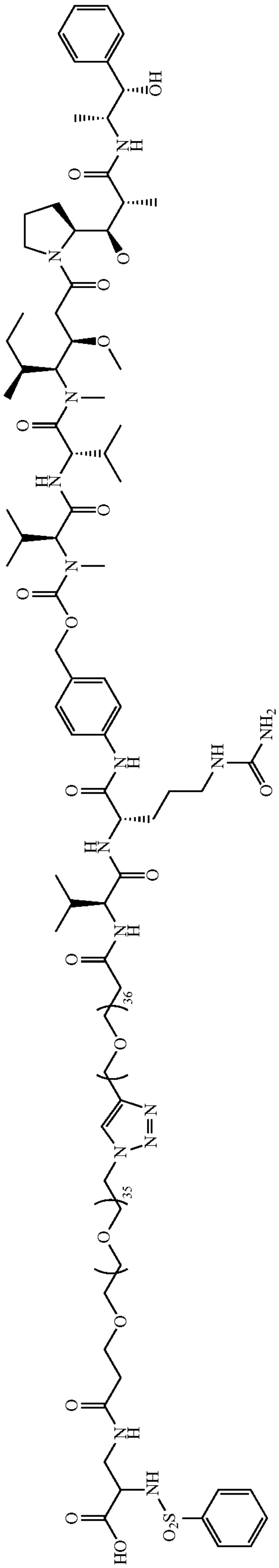
97

Conjugate 104 is synthesized in the following 5 steps.

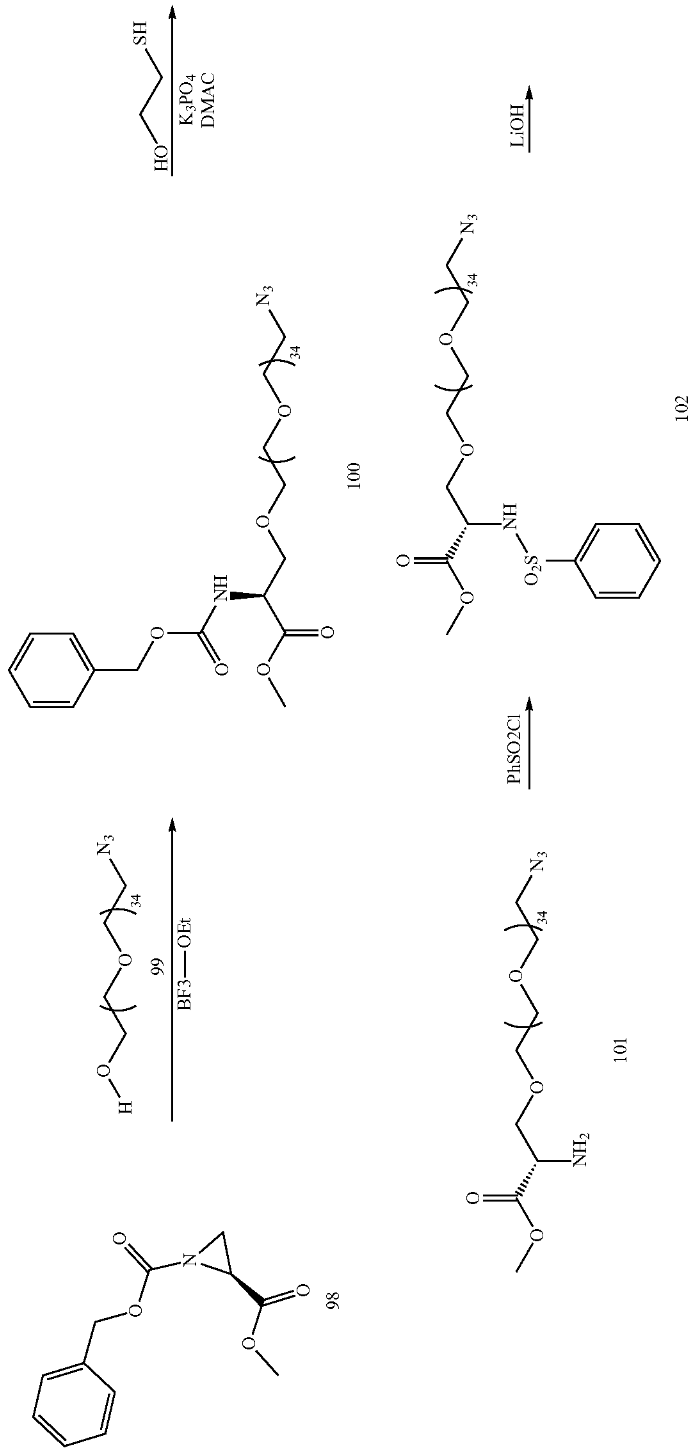
98
99
100
101
102

-continued
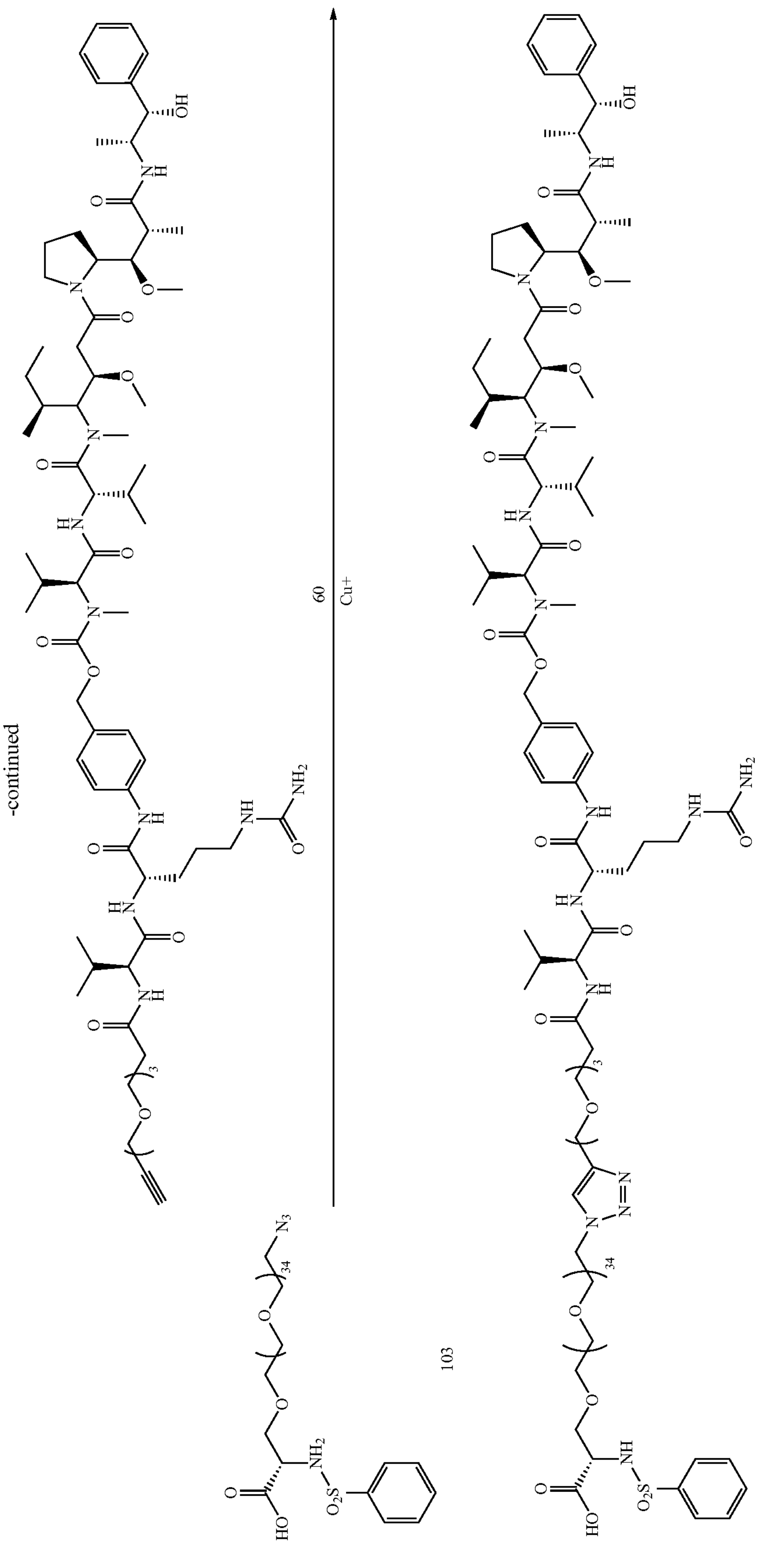
103
104

The preceding synthesis of desired conjugate 104 includes: (i) a first set of reactions starting with compound 98 and ending with intermediate conjugate 103; and (ii) and a second set of reactions starting with conjugate 103 and ending with the desired conjugate 104 and involving intermediate conjugate 60 which determines the desired Chemo (MMAE) that is in the generated desired conjugate 104.

Conjugate 104 is essentially the same conjugate as conjugate 61, except that conjugate 104 does not include the $L_1$ linker that is included in conjugate 61. The synthesis of conjugate 61 similarly concludes with a reaction involving intermediate conjugate 60 that determines the desired Chemo MMAE.

To similarly synthesize other desired conjugates 104A lacking the $L_1$ linker, a person of ordinary skill in the art would recognize, using the chemistry described herein for other desired conjugates of the present invention having the $L_1$ linker, how to: (i) perform the first set of reactions with different PEG lengths and different aryl groups to generate an intermediate conjugate 103A that is analogous to the intermediate conjugate 103; and (ii) perform the second set of reactions, starting with conjugate 103A and ending with the desired conjugate 104A and involving a different intermediate conjugate 60A which determines the desired Chemo (which may differ from MMAE) in the desired conjugate 104A.

4.3 Implementation of Synthesis Steps

This section describes embodiments of how procedures for the synthesis schemes shown in Section 4.2 may be performed.

High-Performance Liquid Chromatography (HPLC) Analysis

HPLC-UV-CAD Analysis was run on a Waters 2695 Separations Module (Waters, Milford, MA) equipped with a Waters 2996 Photo Diode Array Detector (PAD) and a Thermo Scientific Charged Aerosol Detector (CAD). A Pursuit XRs 3 C18 column (150×4.6 mm, Agilent, Santa Clara, CA) was used for separation in reversed phase. The software used for operating the HPLC and analyzing data was Empower 3 Software (Waters). Mobile phases were Millipore purified water containing 0.1% formic acid and 5% HPLC grade acetonitrile (A) and HPLC grade methanol (B). The flow rate was 1.0 mL/min. The gradient was linear from 50% B at 0 min to 95% B at 40-45 min. The column temperature was room temperature and the injection volume was 10 μL. Nitrogen was used for a drying gas for CAD. Default instrument parameters were used for other operation parameters. UV spectra were obtained from 210-400 nm and used for qualification and integration of peaks. Quantification of was carried out using peak areas at a wavelength of 227 nm of UV chromatograms and peak areas of CAD chromatograms. Compounds for injection were prepared in 50% ACN/H2O at 1 mg/mL.

Performance of Synthesis Steps

The following procedures have been actually performed except for procedures pertaining to structures 82, 85, 87, 92 and 97.

A procedure for generating Structure 3 is as follows:

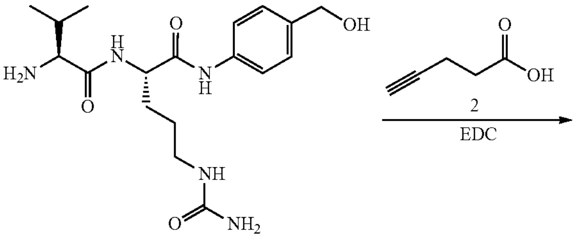

1

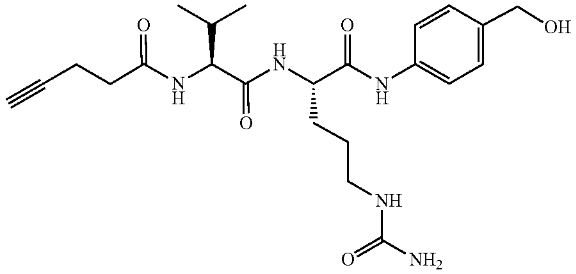

3

200 mg (0.5277 mmol) 1, 51.7 mg (1 eq) 2, 380 uL DIEA (4 eq) were dissolved in 4 mL of anhydrous DMF. 84 mg (1.2 eq) HOBt and 13 mg (0.2 eq) DMAP added, then 200 mg (2 eq) EDC added. The reaction was stirred overnight, then precipitated in 40 mL of diethyl ether. The mixture was centrifuged, the liquid decanted off, and the excess ether was removed under vacuum. The remaining solid was dissolved in 20 mL of 15% MeOH in DCM and chromatographed on silica in 85:15 DCM/MeOH to yield 200 mg 3 (91%). MS (ESI+)=482.3, M+Na.

A procedure for generating Structure 5 is as follows:

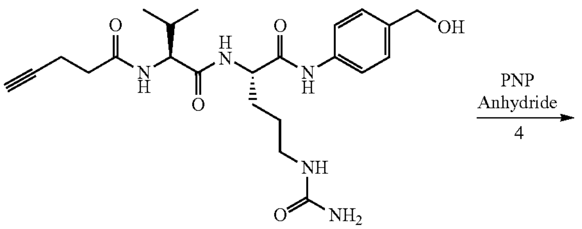

3

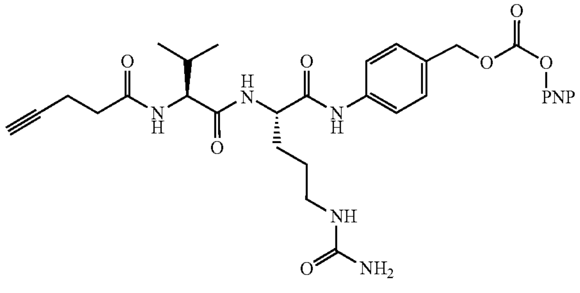

5

50 mg (0.109 mmol) 3 was dissolved in 1 mL of ice cold anhydrous DMF. 38 μL of DIEA (2 eq) added, then 99 mg (3 eq) PNP anhydride 4 was added with stirring. The mixture was stirred for 3 h, then added to 20 ml of diethyl ether. The mixture was centrifuged, the liquid decanted, off, and the remaining solid was dried under vacuum, then dissolved in 10 mL of 9:1 DCM:MeOH and chromatographed on silica gel in the same solvent. 57 mg (84%) of the product 5 was isolated, MS (ESI+) 647.3, M+Na.

A procedure for generating Structure 8 is as follows:

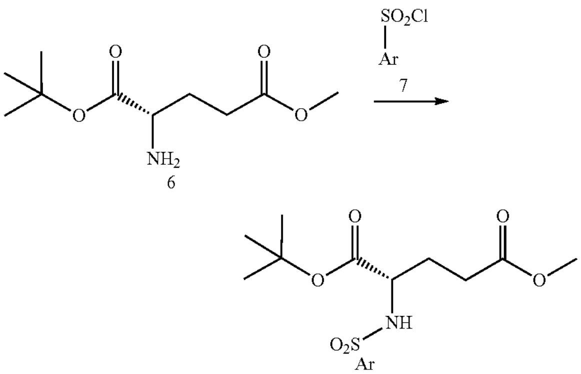

6

8

100 mg of the HCl salt of 6 (0.39 mmol) was dissolved in 3 mL of acetone, then 180 mg of sodium bicarbonate in 3 mL of water was added. The mixture was chilled, with stirring, to OC, and 100 uL (1.2 eq) phenylsulfonyl chloride 7 in 3 ml of acetone was added slowly. The reaction was allowed to warm to room temp and stirred for 16 hour, at which time the acetone was removed under reduced pressure. The remaining material was extracted 3×5 mL with DCM, the solvent was removed under reduced pressure, and the material was chromatographed on silica in 0-50% ethyl acetate/hexane, yielding 113 mg (81%) 8, Ar=Ph. MS (ESI+) 380.2, M+Na.

A procedure for generating Structure 9 is as follows:

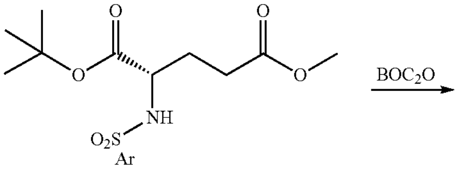

8

-continued

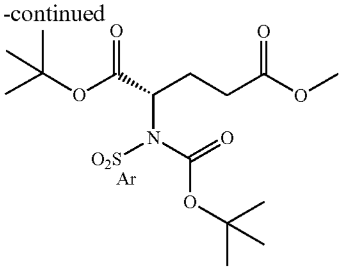

9

572 mg (1.60 mmol) 8, 275 uL (1 eq) DIPEA, and 39 mg DMAP (0.2 eq) were dissolved in 10 mL of DCM. 700 mg of BOC anhydride (2 eq) was added slowly, the reaction was stirred for 3 hr, and chromatographed directly on silica gel with 0-30% hexane/ethyl acetate, yielding 643 mg (88%) of 9 (Ar=Ph) after drying under vacuum overnight to remove all traces of ethyl acetate. MS (ESI+) 480.3 (M+Na).

A procedure for generating Structure 10 is as follows:

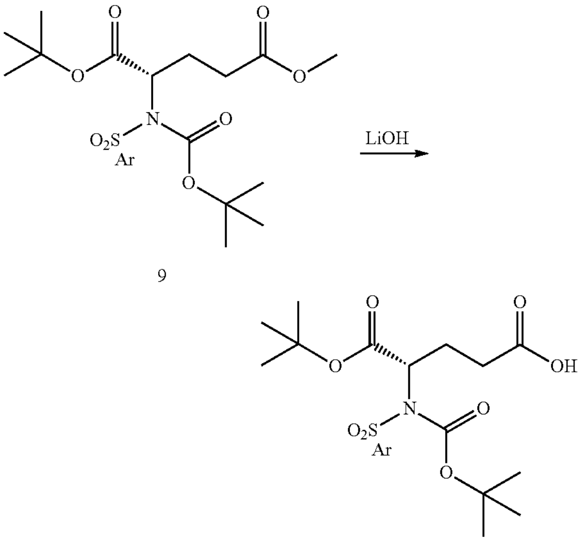

9

10

133 mg (0.29 mmol) 9 was dissolved in 5 mL of THF. The reaction was cooled to OC, and a solution of 96 mg LiOH in 5 mL water was added with stirring. The reaction was stirred for 6 hours, then the reaction was brought to pH 3.0 with citric acid, and the THF was removed under reduced pressure. An equal volume of saturated brine was added, the reaction was extracted 5×5 mL with DCM, and chromatographed on 0-15% MeOH in DCM, yielding 92 mg (72%) 10 (Ar=Ph). MS (ESI+) 466.4 (M+Na).

A procedure for generating Structure 12 is as follows:

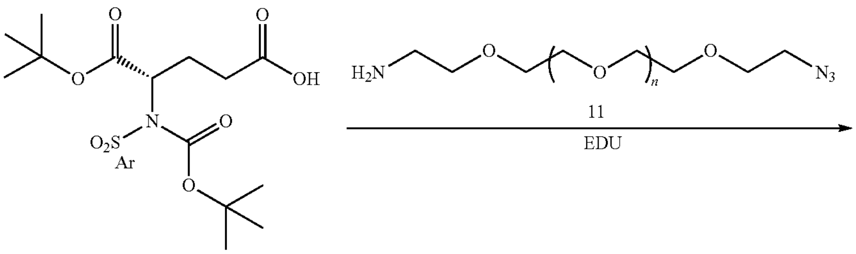

10

-continued

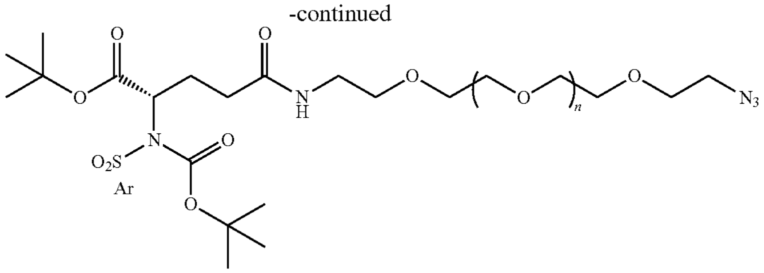

12

100 mg of NH2-PEG36-N3 11 (0.0614 mmol, n=33), 33 mg 10 (1.2 eq), 43 uL TEA, and catalytic HOBt and DMAP (1 mg of each) was dissolved in 2 mL of DCM, and 23 mg (2 eq) EDC was added. The reaction was stirred overnight and was chromatographed directly on silica gel in 0-15% MeOH in DCM, yielding 104 mg (81%) of 12 (Ar=Ph, n=33). MS (ESI+)=1049.6 (M+2Na)/2.

A procedure for generating Structure 13 is as follows:

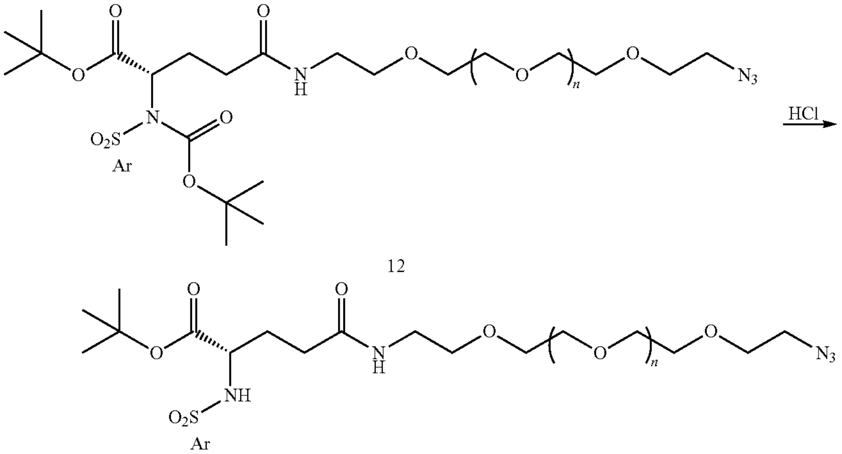

12

13

65 mg (0.0317 mmol) 12 (Ar=Ph, n=33) was dissolved in 6.5 mL of DCM and cooled in an ice bath. 3.25 mL of 4M HCl in dioxane was added, the reaction was stirred for 4 h at room temperature, then the solvents were removed under reduced pressure. The product was triturated with diethyl ether and dried overnight under vacuum to yield 57 mg (95%) of product 13 (Ar=Ph, n=33). MS (ESI+)=971.6 ((M+2Na)/2. HPLC ret. Time=16.448 min.

A procedure for generating Structure 16 is as follows:

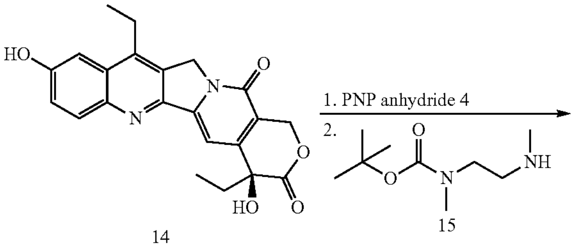

14

15

-continued

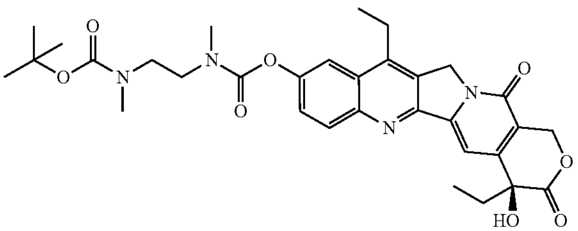

16

100 mg SN38 (14) (0.255 mmol) dissolved in 2 mL of anhydrous DMF, then 171 mg PNP anhydride 4 (2.2 eq) added followed by 44 uL (2 eq) DIEA. Stir 3 h, then add 120 mg (2.5 eq) monobocdiamine 15. Stir 2 h, precipitate with diethyl ether, and chromatograph 0-20% methanol in DCM, yielding 95 mg (66%) 16. MS (ESI+) 629.1, M+Na.

A procedure for generating Structure 17 is as follows:

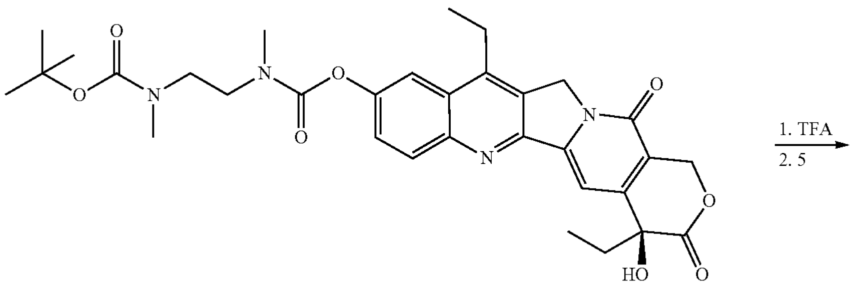

16

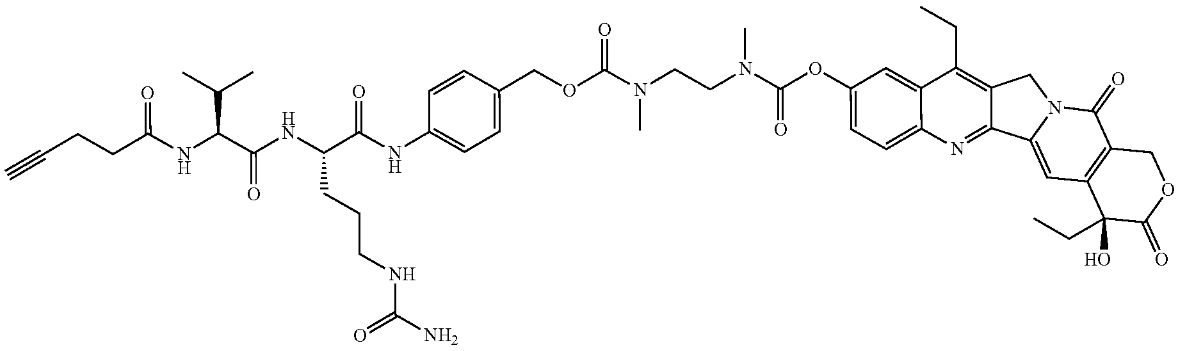

17

30 mg 16 (0.05 mmol) dissolved in 1 ml of DCM, and 0.25 mL of TFA added with stirring. Stir 90 minutes, then remove all solvents under educed pressure. Chase 2× with 5 ml DCM. Dissolve the residue in 1 ml of anhydrous DMF, add 20 μL of pyridine and 0.6 mg (10 mol %) HOBt, then 34 mg of 5 (1.1 eq). Stir overnight, then precipitate with diethyl ether and chromatograph on silica gel with 0-15% MeOH in DCM to yield 30 mg (61%) 17. MS (ESI+) 507.1 (M+Na)/2. HPLC ret time=16.988 min.

A procedure for generating Structure 18 is as follows:

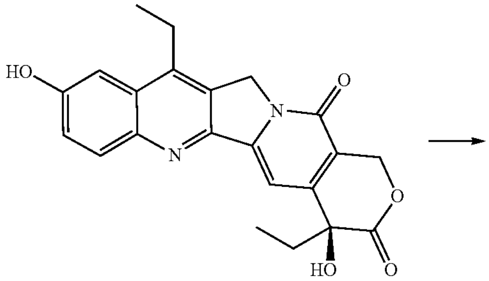

17

-continued

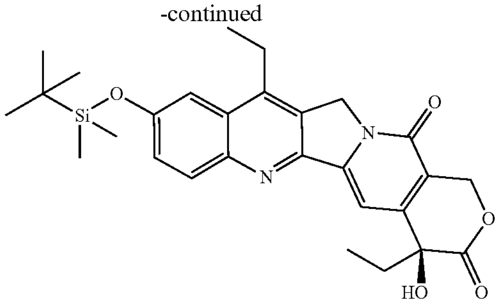

18

100 mg SN38 (14) (0.255 mmol) dissolved in 1 mL of DCM, and 150 μL of DIEA was added with stirring and ice bath cooling. 100 mg of TBDMSiCl in 1 mL of DCM was added to the suspension, the mixture was stirred for 4 hr at room temp, then the solution was chromatographed on silica gel with DCM/MeOH as eluent yielding 18 in 18% yield. MS (ESI+) 1034.7 (2M+Na).

A procedure for generating Structure 19 is as follows:

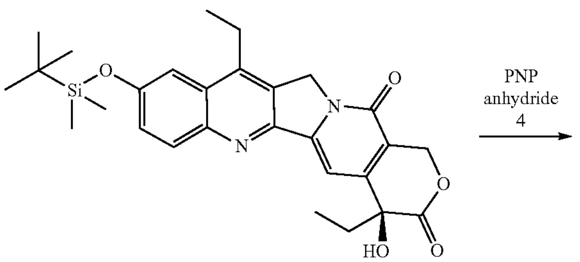

18

-continued

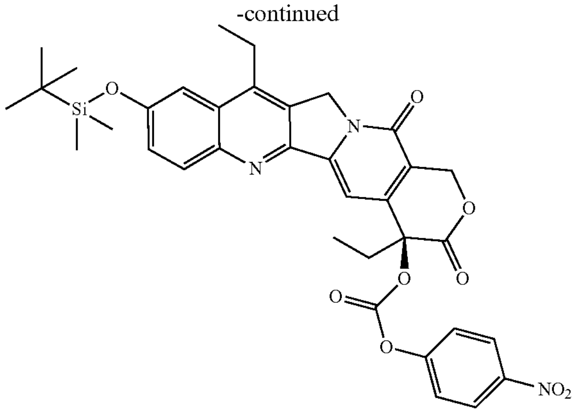

19

341 mg TBDMS SN38 (18) (0.672 mmol) and 245 mg DMAP (3 eq) were dissolved in 18 mL of DCM, then 258 mg (1.2 eq) PNP anhydride 4 was added, and the mixture was stirred overnight, then chromatographed on silica gel with 0-5% MeOH in DCM, yielding 365 mg of product 19 (81%). MS (ESI+) 1364.2 (2M+Na).

A procedure for generating Structure 20 is as follows:

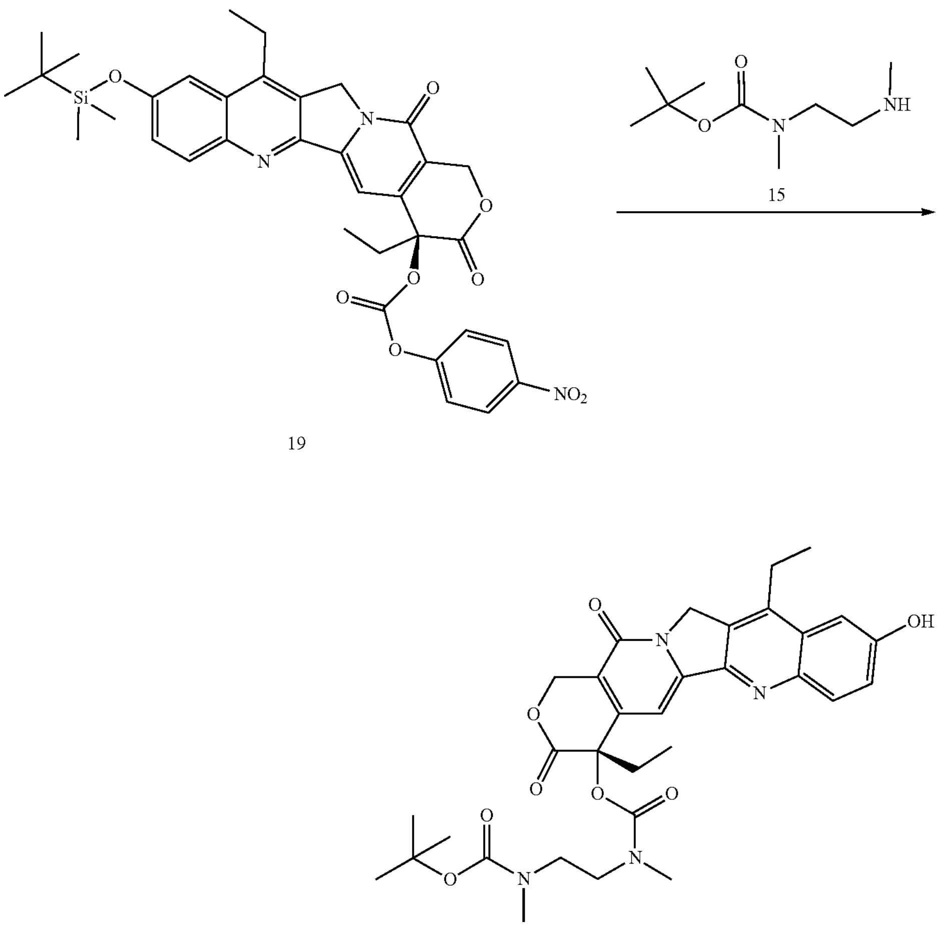

19

15

20

475 mg DMTBS-SN38-PNP 19 (0.78 mmol), 399 mg monoBOC-1,2-dimethylethylene diamine 15 (3 eq), 47 mg HOBt were dissolved in 12 ml of 8:2 DMF/pyridine. The mixture was stirred overnight, precipitated with diethyl ether, and chromatographed on silica gel with DCM/MeOH eluent to yield 354 mg (75%) of the desired product 20. MS(ESI+) 629.0 (M+Na), 1234.7 (2M+Na). The silyl protecting group appears to come off during this step.

A procedure for generating Structure 21 is as follows:

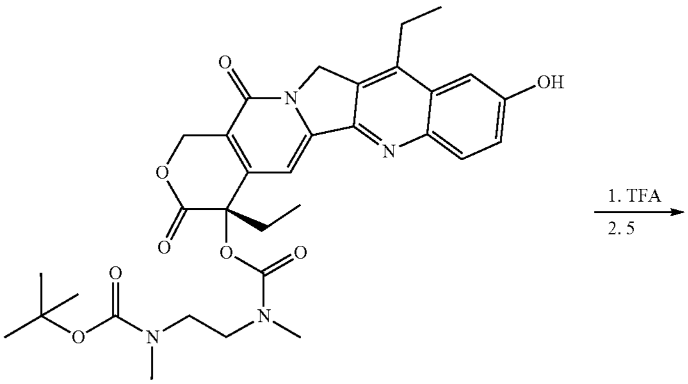

20

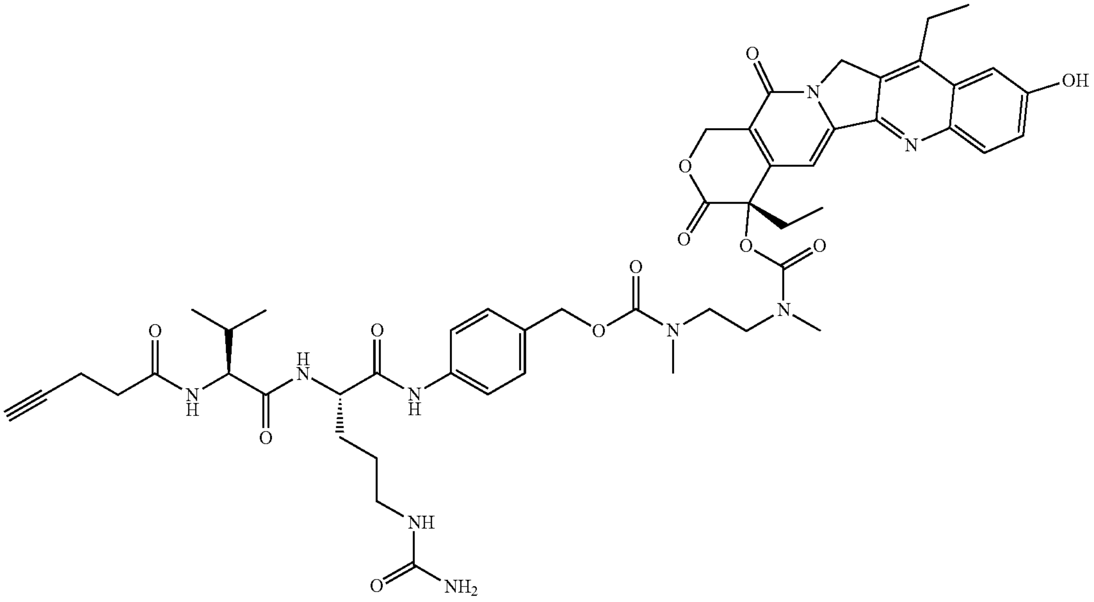

21

30 mg 20 (0.05 mmol) is dissolved in 1 ml of DCM, and 0.25 mL of TFA is added with stirring. Stir 90 minutes, then remove all solvents under reduced pressure. Chase 2× with 5 ml DCM. Intermediate MS (ESI+) 507.3 (M+Na), 1035.5 (2M+Na). Dissolve the residue in 1 ml of anhydrous DMF, add 20 μL of pyridine and 0.6 mg (10 mol %) HOBt, then 34 mg of 5 (1.1 eq). Stir overnight, then precipitate with diethyl ether and chromatograph on silica gel with 0-15% MeOH in DCM to yield 38 mg (7%) 21. MS (ESI+) 507.1 (M+Na)/2. HPLC ret. Time=16.951 min.

A procedure for generating Structure 22 is as follows:

22

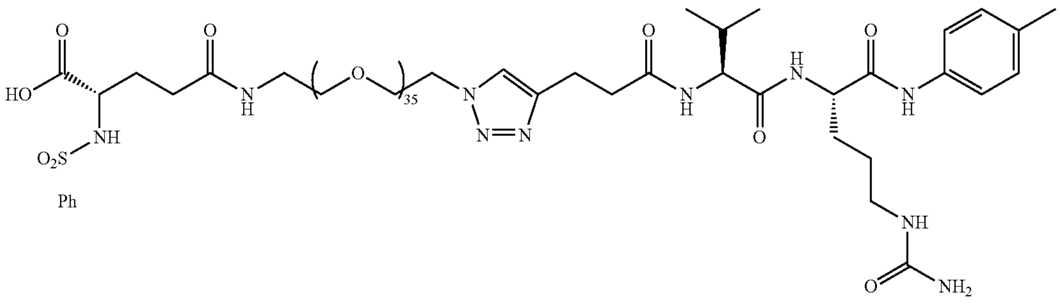

-continued

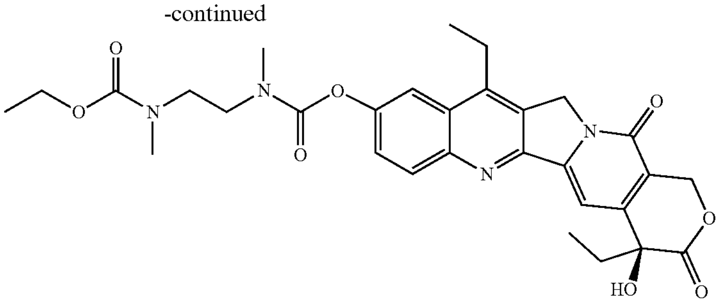

Dissolve 30 mg of 17 (0.0303 mmol), 51.8 mg of 13 (0.9 eq), and 0.7 mg TBTA in 1.75 ml of tBuOH. Dissolve 0.7 mg CuSO4 and 7 mg of sodium ascorbate in 2.6 mL of water. Sparge both solutions with nitrogen, combine, and stir under $N_2$ for 3 hr. Bring pH to ~3.0 with citric acid, add an equal volume of saturated brine, and extract 5×2 mL with DCM. Wash the combine extracts 2×2 mL with a 1:1 mix of saturated brine and 1M disodium EDTA, 1× w/2 mL of brine, and dry with anhydrous sodium sulfate. Strip solvents, and chromatograph on silica with 0-20% MeOH in 0.5% formic acid in DCM. 31 mg 41% of 22 recovered. MS (ESI+)=1465.8 (M/2+Na), 985.1 (M/3=1.5 Na). HPLC r.t.=21.601 min.

A procedure for generating Structure 23 is as follows:

23

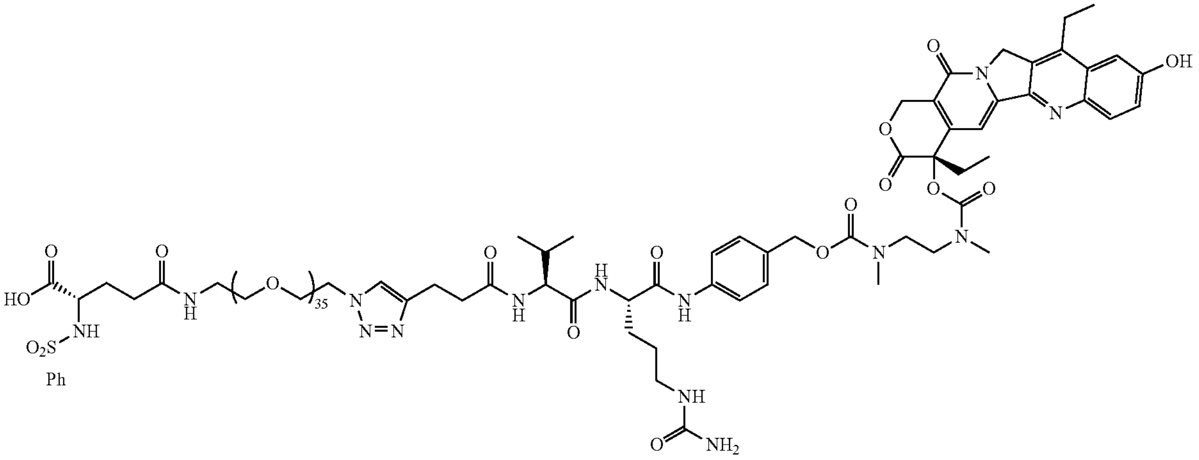

Dissolve 30 mg of 21 (0.0303 mmol), 51.8 mg of 13 (0.9 eq), and 0.7 mg TBTA in 1.75 ml of tBuOH. Dissolve 0.7 mg CuSO4 and 7 mg of sodium ascorbate in 2.6 mL of water. Sparge both solutions with nitrogen, combine, and stir under $N_2$ for 3 hr. Bring pH to ~3.0 with citric acid, add an equal volume of saturated brine, and extract 5×2 mL with DCM. Wash the combine extracts 2×2 mL with a 1:1 mix of saturated brine and 1M disodium EDTA, 1× w/2 mL of brine, and dry with anhydrous sodium sulfate. Strip solvents, and chromatograph on silica with 0-20% MeOH in 0.5% formic acid in DCM. 37 mg 49%. Of 23. MS (ESI+)=1466.0 (M/2+Na), MS (ESI−)=1442.0 ((M−H)/2. HPLC=21.804 min.

A procedure for generating Structure 25 is as follows:
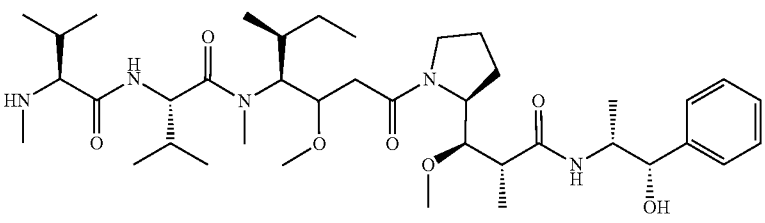
24
+
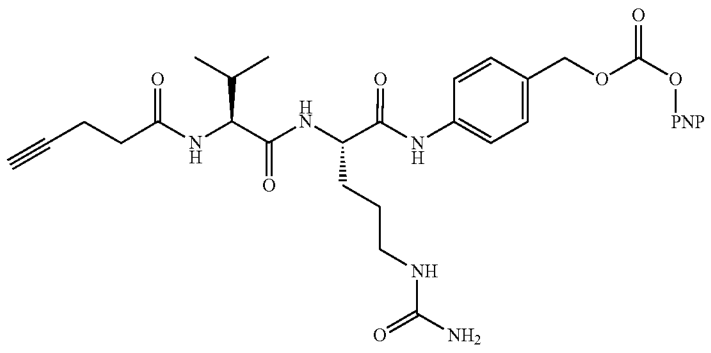
5
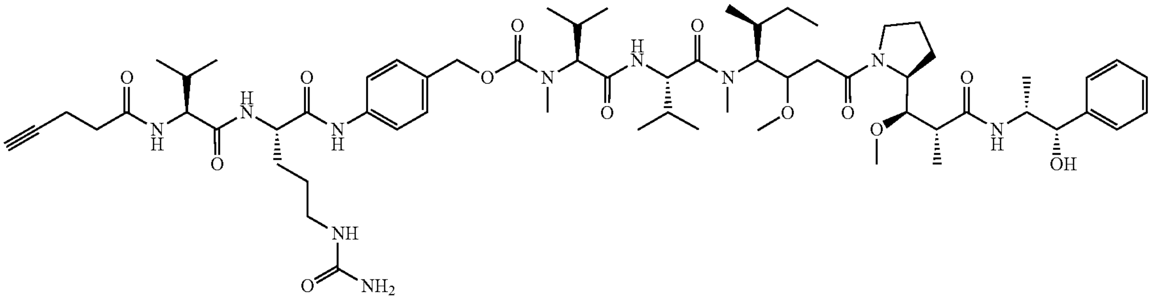
25
25 mg (0.0348 mmol) MMAE (24) added to 1.75 mL of DMF. 24 mg 5 (1.1 eq) added, then 18.2 uL of DIEA (3 eq). Stir 3 h, add 20 ml diethyl ether, centrifuge, decant, remove residual ether under vacuum, and chromatograph 0-20% MeOH in DCM to yield 23 mg (55%) 25. MS (ESI M+) 1225.6 (M+Na), MS (ESI M−) 1237.4 (M+Cl). HPLC ret. Time=26.032 min.
A procedure for generating Structure 26 is as follows:

26
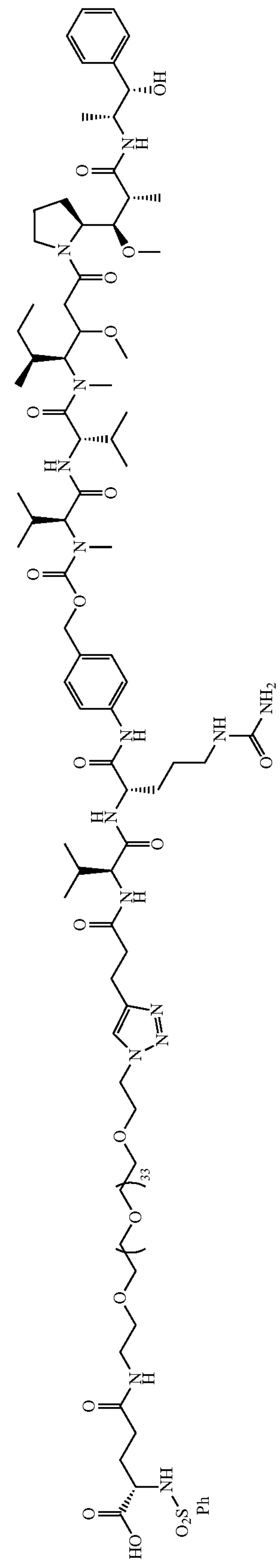

10.4 mg 25 (0.00864 mmol), 14.8 mg 13 (0.9 eq), 0.2 mg TBTA, dissolved in 0.5 mL tBuOH. 0.2 mg CuSO4 and 3 mg sodium ascorbate dissolved in 0.75 mL H2O. Both solutions are sparged with nitrogen, combined, and stirred under $N_2$ for 3 h. Solution acidified to ~pH 3.0 with 1 drop of dilute HCl, and most of the tBuOH removed under reduced pressure. Partition between DCM and saturated brine, extract 4×1 mL with DCM, combine organic layers and wash 2× with a 1:1 mix of saturated brine and 1 M disodium EDTA, dry over sodium sulfate, and strip the solvents under vacuum. Add methanol, strip, then toluene, strip. Chromatograph on silica 0-20% MeOH in 0.5% formic acid in DCM. 4.0 mg compound 26. MS (ESI+)=1551.8 (M+2H), 1034.9 (M+3H). HPLC r.t.=27.844 min.

A procedure for generating Structures 30 and 31 is as follows:

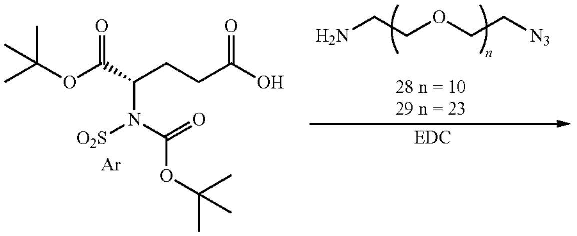

10

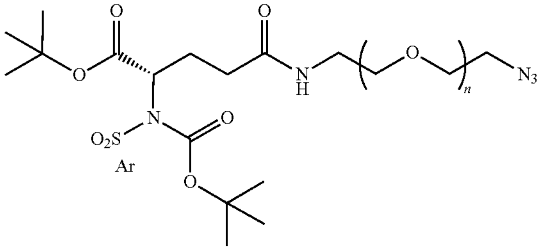

30 n = 10
31 n = 23

50 mg of NH2-PEG10-$N_3$ (28, n=10, 0.094 mmol), 45.8 mg BOC-tBu-PhSO2Glu-OH (10, 1.1 eq), 43 uL TEA, and catalytic HOBt and DMAP (1 mg of each) was dissolved in 2 mL of DCM, and 36 mg (2 eq) EDC was added. The reaction was stirred overnight and was chromatographed directly on silica gel in 0-15% MeOH in DCM, yielding 70 mg (78%) of the desired product 30. MS (ESI+)=974.5 (M+Na). A similar reaction substituting 104.5 mg (0.094 mmol) NH2-PEG23-N3 (29, n=23) for the PEG 10 derivative yielded 110 mg (77%) of the desired PEG23 derivative 31, MS (ESI+)=1546.3 (M+Na), 785.2 (M+2Na)/2.

Steps for generating Structures 32 and 33 is as follows:

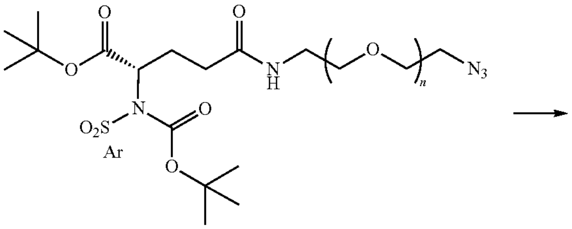

30 n = 10
31 n = 23

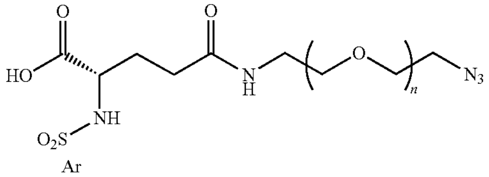

32 n = 10
33 n = 23

60 mg (0.063 mmol) of the PEG10 derivative 30 was dissolved in 6.5 mL of DCM and cooled in an ice bath. 3.25 mL of 4M HCl in dioxane was added, the reaction was stirred for 4 h at room temperature, then the solvents were removed under reduced pressure. The product was triturated with diethyl ether and dried overnight under vacuum to yield 49 mg (98%) of the desired PEG10 derivative 32. MS (ESI+)=817.4 (M+Na). HPLC ret. Time=9.137 min. A similar reaction was run with 100 mg of the corresponding PEG23 derivative 31, yielding 83 mg (96%) of the desired product 33. MS (ESI+)=1389.8 (M+Na), 706.3 (M+2Na)/2, 479.1 (M+3Na)/3. HPLC ret. Time=13.492 min.

A procedure for generating Structures 34 and 35 is as follows:

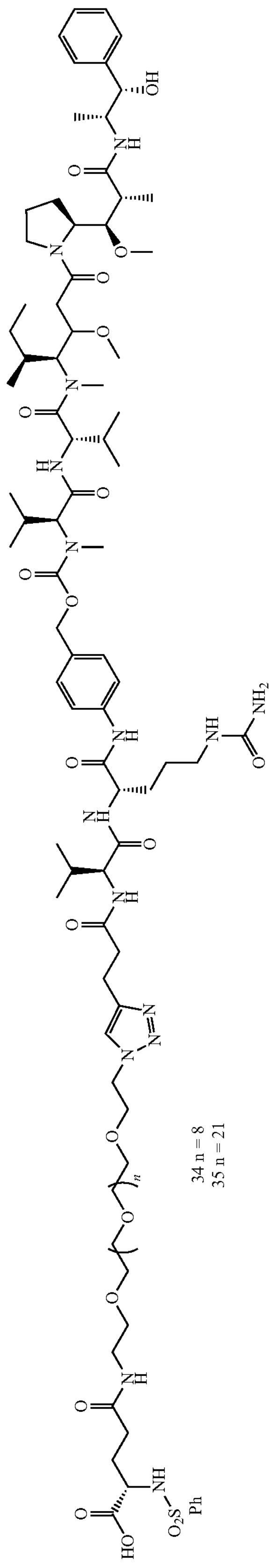
34 n = 8
35 n = 21

10.5 mg (0.01238 mmol) of the Glu-PEG10 derivative 32, 17 mg of the VCP-MMAE derivative 25 (1.1 eq), 0.2 mg TBTA, dissolved in 0.5 mL tBuOH. 0.2 mg CuSO4 and 3 mg sodium ascorbate dissolved in 0.75 mL H2O. Both solutions is sparged with nitrogen, combined, and stirred under N2 for 3 h. Solution acidified to ~pH 3.0 with 1 drop of dilute HCl, and most of the tBuOH removed under reduced pressure. Partition between DCM and saturated brine, extract 4×1 mL with DCM, combine organic layers and wash 2× with a 1:1 mix of saturated brine and 1 M disodium EDTA, dry over sodium sulfate, and strip the solvents under vacuum. Add methanol, strip, then toluene, strip. Chromatograph on silica 0-20% MeOH in 0.5% formic acid in DCM. 6.0 mg (24%) 34 (n=8) recovered. MS (ESI+)=1010.0 (M+2H)/2. HPLC r.t.=27.174 min. A similar reaction with 18 mg of the Glu-PEG23 derivative 33 (n=21) yielded 9 mg (18%) of the desired product 35 (n=21). MS (ESI+)=1307.8 (M+3Na)/2.

A procedure for generating Structure 38 is as follows:

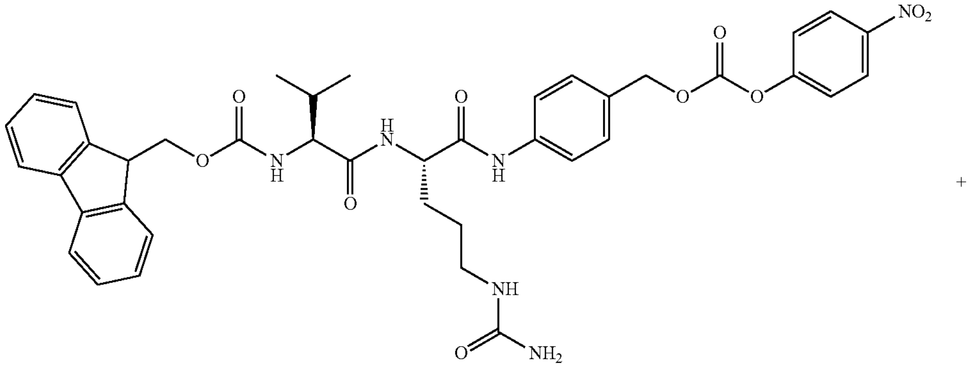

36

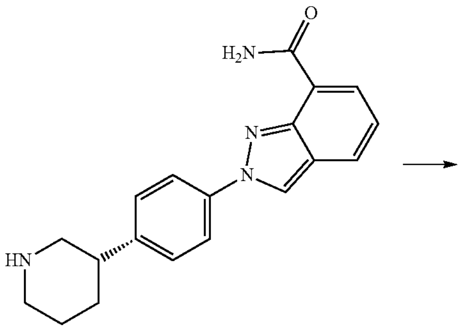

37

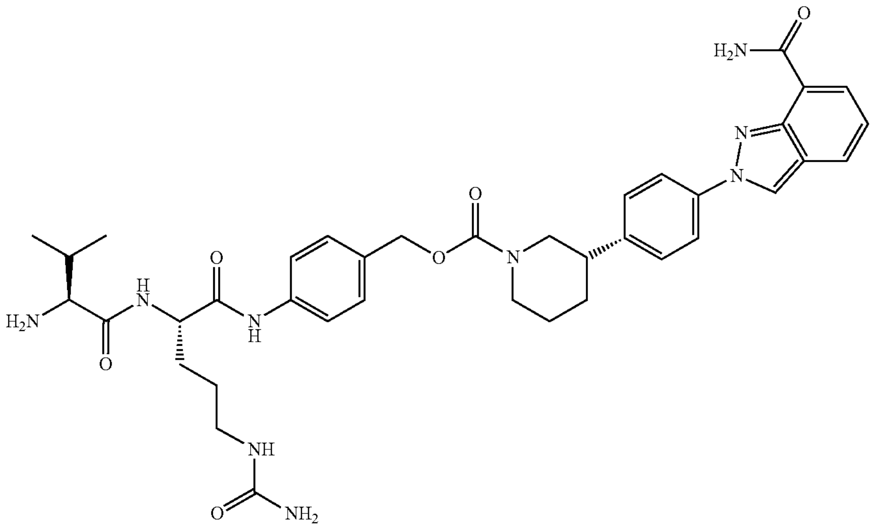

38

200 mg Fmoc-Val-Cit-PAB-PNP 36 (0.260 mmol) and 91.5 mg niraparib (37) (1.1 eq) added to 2 mL of DMF. Then 136 μL of DIEA (3 eq). and the reaction mixture 24 h at ambient temperature. At this point, HPLC and MS analysis confirmed that Fmoc group cleaved and then the reaction mixture was precipitated by adding 25 ml cold diethyl ether and centrifuged to get yellowish solid and the crude product was purified with flash chromatography [$SiO_2$:DCM/MeOH (9:1)] to afford 38 as a white solid (Yield: 150 mg, 80%). MS (ESI) 726.8 (M+H) 748.7 (M+Na).

A procedure for generating Structure 39 is as follows:

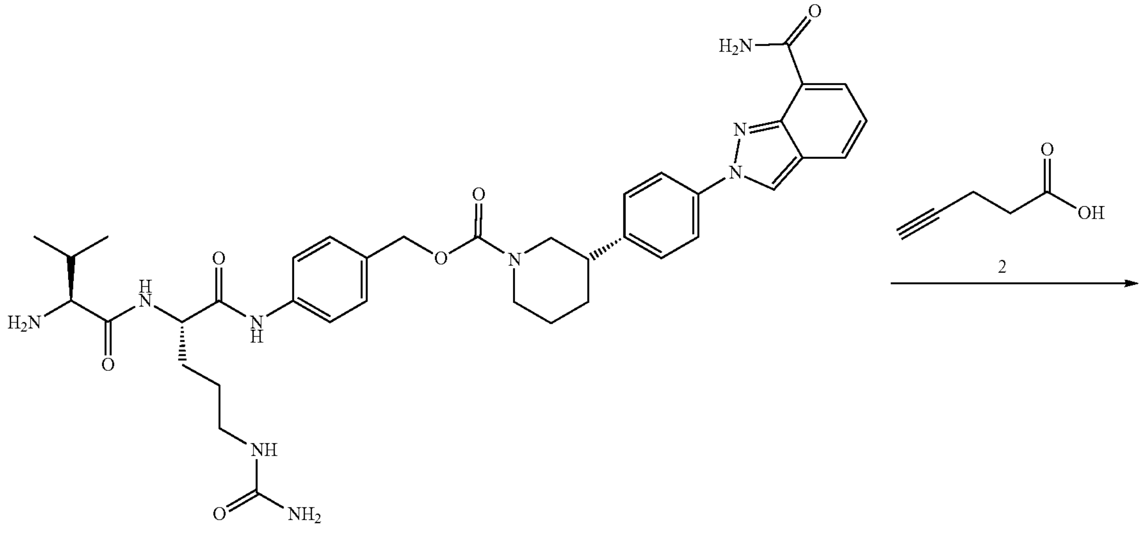

38

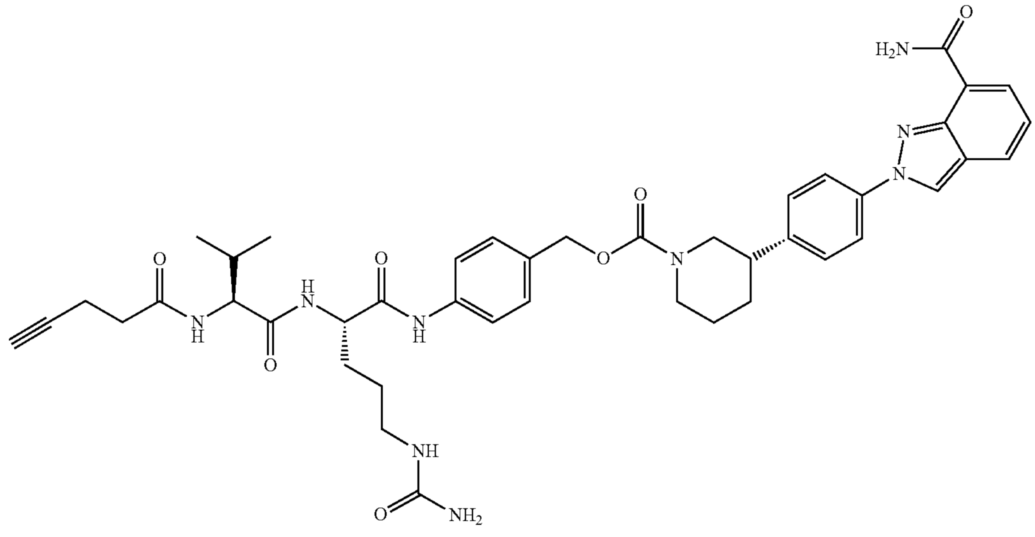

39

100 mg 69 (0.138 mmol), 14.86 mg 4-pentynoic acid 2 (0.152 mmol, 1.1 eq.), 42.76 mg EDC-HCl (0.276 mmol, 2 eq.), and 27.74 mg HOBt (0.206 mmol, 1.5 eq), 3.3 mg DMAP (0.0274 mmol, 0.2 eq.), and 71.5 μl DIPEA (0.411 mmol, 3 eq) were mixed in 2 ml DMF in a vial and the reaction mixture stirred 18 h at room temperature. Then, the reaction mixture was precipitated by adding 20 ml diethyl ether and centrifuged to get yellowish powder and the crude product was purified with flash chromatography [$SiO_2$: DCM/MeOH (9:1)] to afford 39 as a white solid (Yield: 89 mg, 80%). MS (ESI) 806.8 (M+H) 827.7 (M+Na)].

A procedure for generating Structure 40 is as follows:

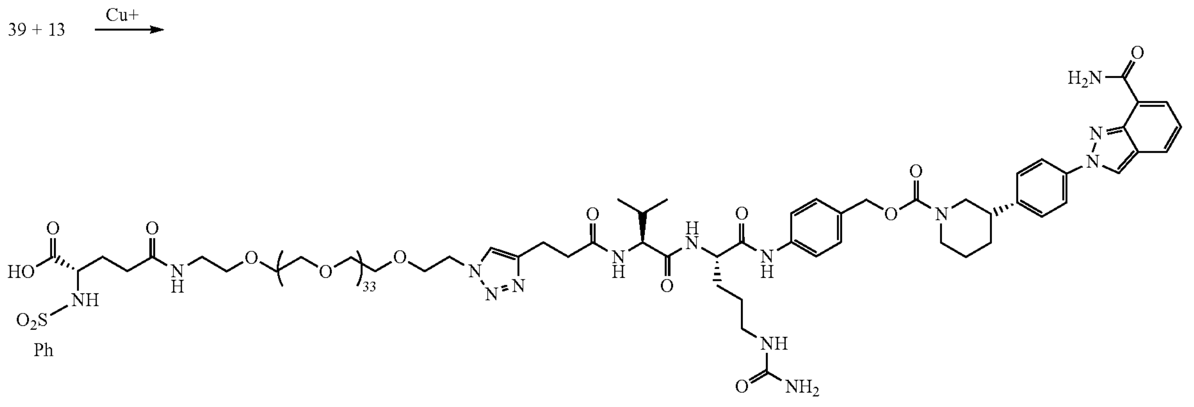

40

9.2 mg 39 (0.0114 mmol) and 21.6 mg 13 (1 eq) and 0.2 mg TBTA dissolved in 0.325 mL tBuOH. 1 mg CuSO4 and 10 mg sodium ascorbate dissolved in 3.75 ml $H_2O$. Both solutions sparged, then 0.5 mL of the aqueous solution added to the tBuOH solution, the reaction was stirred under nitrogen for 6 hours, then the pH was brought to ~3.0 with citric acid and the mixture partitioned between DCM and saturated brine. The aqueous was extracted 4× with DCM, the combined DCM layers were washed 2× with a 1:1 mix of saturated brine and 1M disodium EDTA, the solvent was removed under reduced pressure, and the residue was purified with flash chromatography [$SiO_2$:DCM/MeOH (9:1)] to afford 40 as a white solid (Yield: 26 mg, 85%). MS (ESI) 2702 (M+H) HPLC r.t.=26.872 min.

A procedure for generating Structure 42 is as follows:

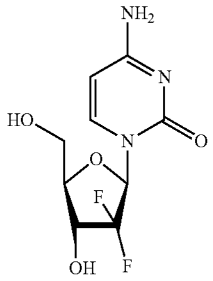

41

-continued

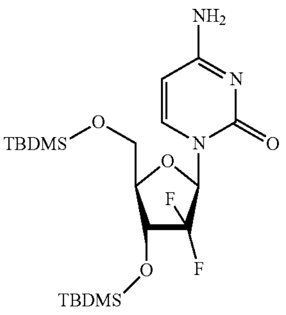

42

200 mg Gemcitabine 41 (0.76 mmol), 400 mg TBDMSCl (4 eq), 180 mg imidazole (4 eq) and triethyl amine (2 eq) were mixed in 5 ml DCM and stirred at room temperature for 18 h. Then the solvent was removed under reduced pressure, and the residue was purified with flash chromatography [$SiO_2$:Hexane/EtOAc (5:5)] to afford 42 as a white solid (Yield: 280 mg, 75%). MS (ESI) 515 (M+H).

A procedure for generating Structure 43 is as follows:

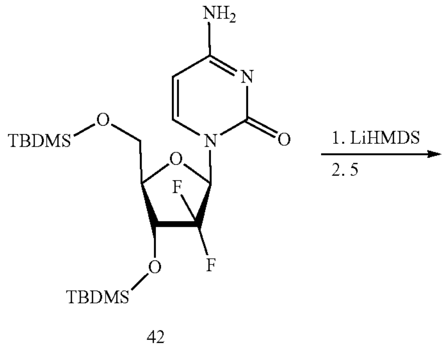

42

-continued

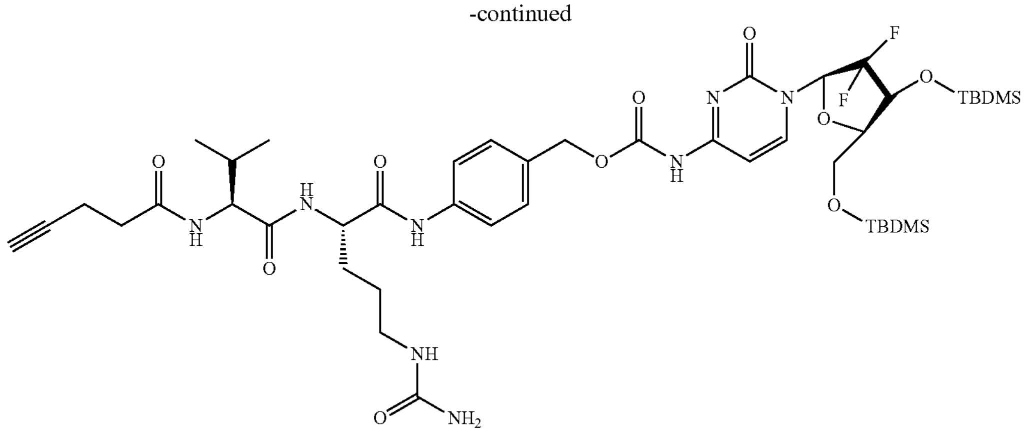

43

20 mg 42 (0.039 mmol) in anhydrous THF (5 mL) was added to flask under nitrogen atmosphere and cooled to −78° C. using a dry ice/acetone bath. While stirring at this temperature, LiHMDS (60 1, 0.059 mmol, 1.50 eq) was added dropwise as a 1 M solution in THF, and the mixture was gradually allowed to warm to room temperature then stirred for 30 min. At this point, 5 (24.3 mg, 1 eq) was added as a solution in 1.5 ml anhydrous THF-DMF (1:0.5), and the reaction mixture was stirred at room temperature for 18 h. Then, the reaction mixture was concentrated under vacuum to get white powder and precipitated with diethyl ether then purified by flash chromatography. [$SiO_2$:DCM/MeOH (9:1)] to afford 43 as a white solid (Yield: 27 mg, 70%). MS (ESI) 977.4 (M+H).

A procedure for generating Structure 44 is as follows:

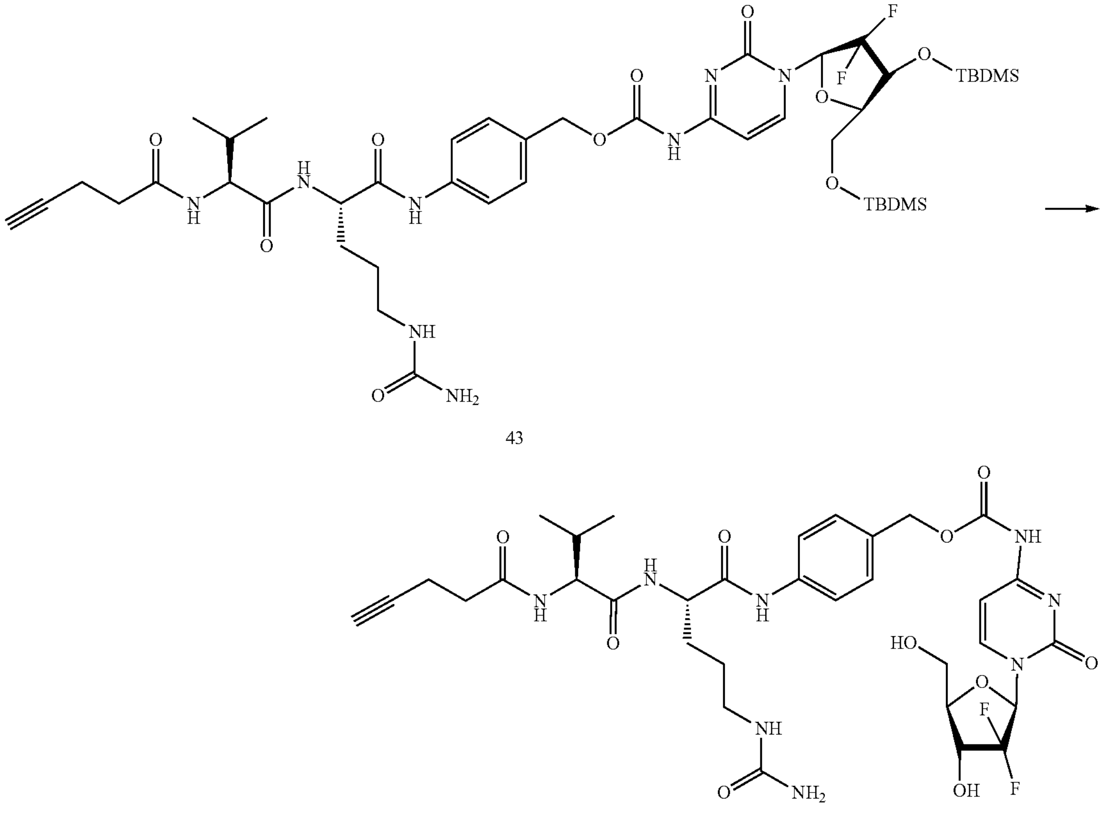

43

44

20 mg 43 (0.020 mmol) and anhydrous THF (13.5 mL) mixed in small vial. While stirring at room temperature, 60 μl TBAF (3 eq) was added dropwise and the mixture was stirred for an additional 30 min. The reaction mixture was concentrated under vacuum to afford 44 as yellowish residue (Yield: 13 mg, 85%). MS (ESI) 749.3 (M+H).

A procedure for generating Structure 45 is as follows:

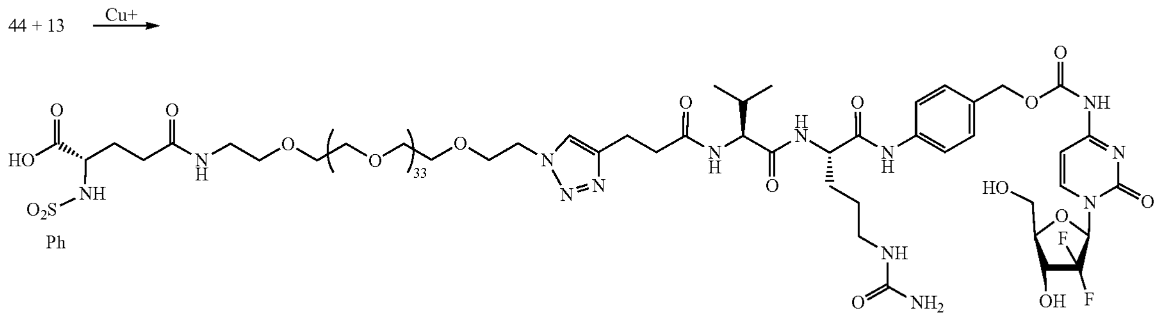

45

9.4 mg 44 (0.013 mmol) and 23.8 mg 13 (1 eq) and 0.2 mg TBTA dissolved in 0.325 mL tBuOH. 1 mg CuSO4 and 10 mg sodium ascorbate dissolved in 3.75 ml $H_2O$. Both solutions sparged, then 0.5 mL of the aqueous solution added to the tBuOH solution, the reaction was stirred under nitrogen for 6 hours, then the pH was brought to ~3.0 with citric acid and the mixture partitioned between DCM and saturated brine. The aqueous was extracted 4× with DCM, the combined DCM layers were washed 2× with a 1:1 mix of saturated brine and 1M disodium EDTA, the solvent was removed under reduced pressure, and the residue was purified with flash chromatography [$SiO_2$:DCM/MeOH (9:1)] to afford 45 as a white solid (Yield: 28 mg, 85%). MS (ESI) 2645 (M+H) HPLC r.t.=14.650 min.

A procedure for generating Structure 47 is as follows:

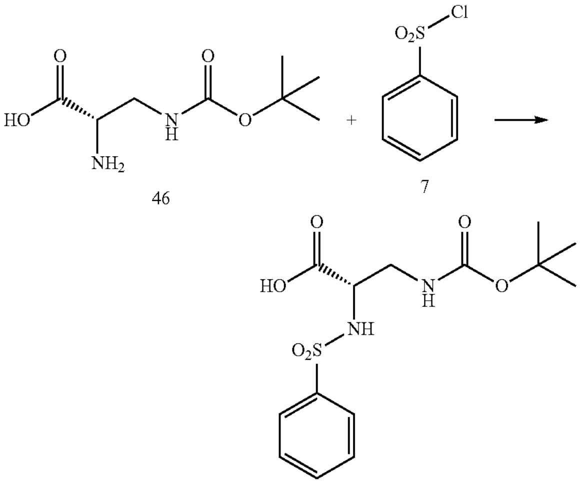

46 7 47

204 mg (1 mmol) BOC-DAP 46 in 7.6 ml acetone was combined with 560 mg of sodium bicarbonate in 9.2 mL of water. The stirred mixture was cooled in an ice bath, and 256 mg on benzenesulfonyl chloride 7 in 7.6 ml of acetone was added dropwise. The mixture was stirred overnight at room temperature, the acetone was removed via rotovap, the remaining aqueous solution was washed 2×5 mL with ethyl acetate, and the remaining aqueous layer was carefully acidified to pH 3 with dilute HCL. The mixture was extracted 3×10 mL with ethyl acetate, the solvent removed via rotvap, and the residue chromatographed on silica gel with hexane/EtOAc to yield 261 mg (76%) of the desired product 47. MS (m/z): 367.2 (M+Na). HPLC ret. Time=9.370 min.

A procedure for generating Structure 48 is as follows:

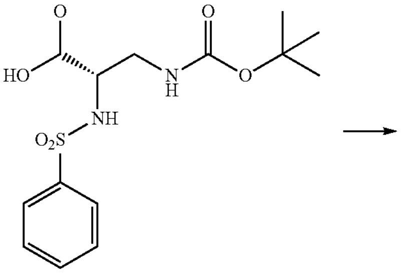

47

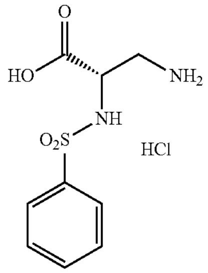

48

200 mg of the BOC protected DAP derivative 47 were dissolved in 2 mL of DCM, and 2 mL of 4M HCl in dioxane was added. The solution was stirred for 6 h, then the solvent was removed via rotovap and triturated 3× with diethyl ether. The HCl salt of the product 48 was used as is, it was very hydroscopic and needs to be kept dry. HPLC ret. Time=2.329 min.

A procedure for generating Structures 51 and 52 is as follows:

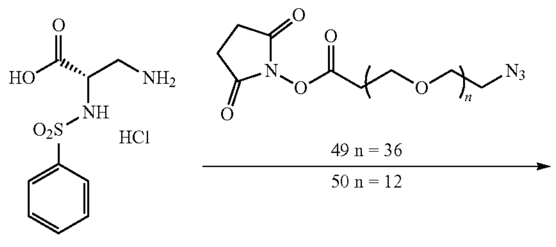

48

50 mg of N3-PEG36-NHS Ester 49 (n=36), 10 mg of the DAP derivative 48 (1.2 eq), and 20 μL of DIPEA were dissolved in 2 mL of anhydrous CH3CN. The mixture was stirred overnight, then the acetonitrile was removed under reduced pressure and the remaining solid was chromatographed on silica gel with a 0-10% MeOH in DCM to yield 43 mg (80%) of the desired product 51. (m/z): 1949.7 (M+Na); 986.8 M+2Na)/2; 665.5 (M+3Na)/3. HPLC ret. Time=16.411 min. The same conditions were used to make the PEG12 derivative 52 (n=12) substituting an equimolar amount of the PEG12 NHS ester 50 for the PEG36 NHS ester, (m/z): 892.6 (M+Na); 457.9 (M+2Na)/2. HPLC ret. Time=9.698 min.

A procedure for generating Structure 54 is as follows:

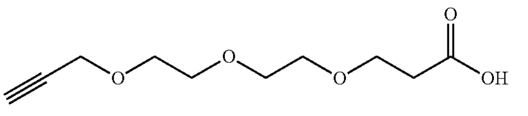

+

53

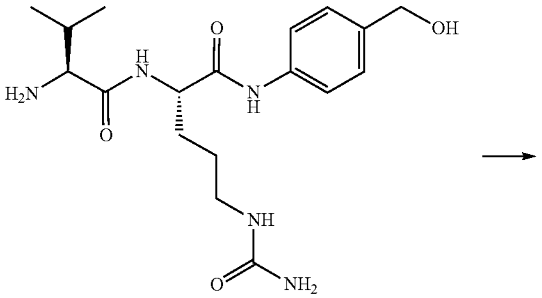

1

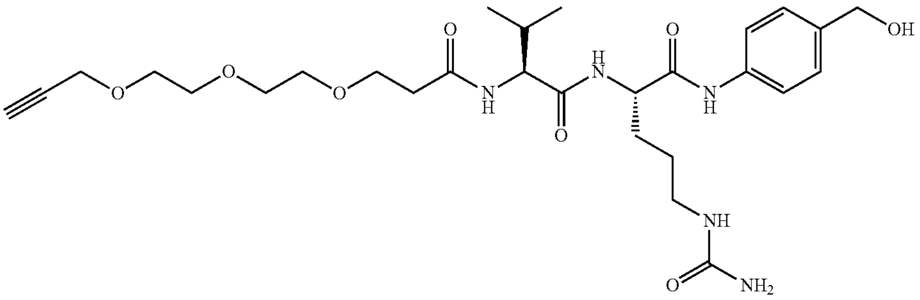

54

-continued

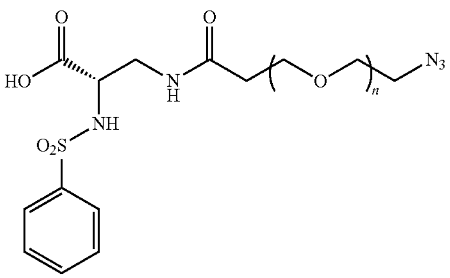

51 n = 36
52 n = 12

100 mg (0.463 mmol) propargyl PEG3 carboxylic acid 53, 175 mg (0.463 mmol) val-cit-PAB 1, 3 mg DMAP, 3 mg HOBt, and 242 uL (3 eq) DIPEA were dissolved in 4 mL of anhydrous DMF. 200 mg of EDC was added, and the mixture was stirred overnight. The product was precipitated by adding 30 mL of diethyl ether, centrifuged, the liquid was decanted off, and the remaining solid was dissolved in 10% MeOH in DCM, and chromatographed on silica gel using 10-15% MeOH in DCM as eluent, yielding 219 mg (82%) of the desired product 54. (m/z): 600.5 (M+Na).

A procedure for generating Structure 55 is as follows:

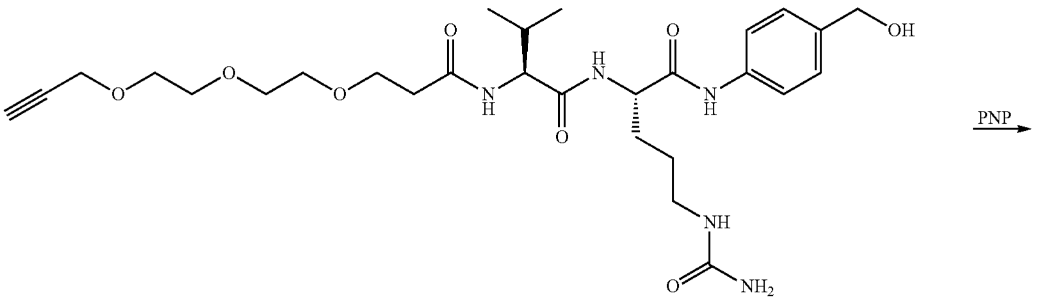

54

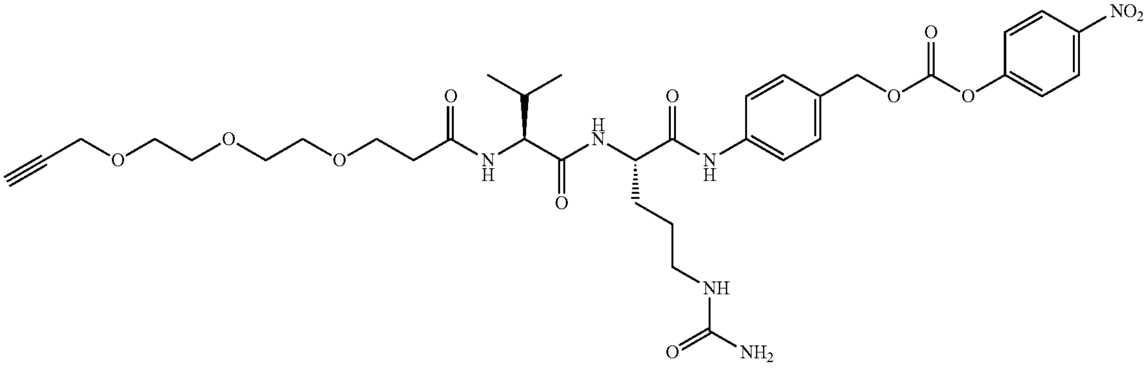

55

180 mg of propargyl-PEG3-VCP 54 (0.312 mmol) was dissolved in 3 mL of ice cold DMF with stirring. Then 283 mg (3 eq) Bis-PNP anhydride was added, followed quickly by 111 μL of DIPEA. The solution was allowed to warm to room temperature and stirred for 3 h, then the product was precipitated with 30 mL of diethyl ether, dissolved in 5% MeOH in DCM, and chromatographed on silica with 5-10% MeOH in DCM eluent, yielding 183 mg (79%) of the desired product 55. (m/z): 765.5 (M+Na).

A procedure for generating Structure 56 is as follows:

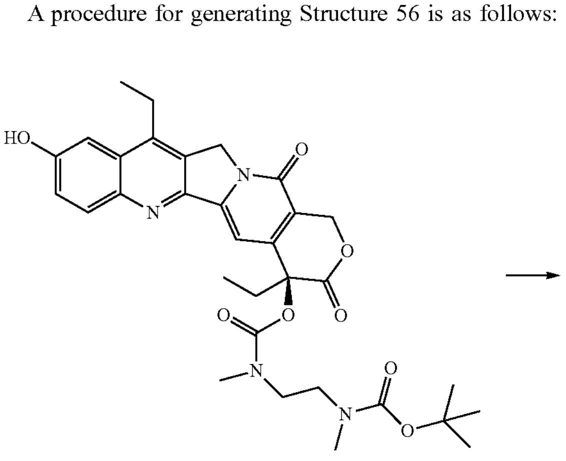

20

-continued

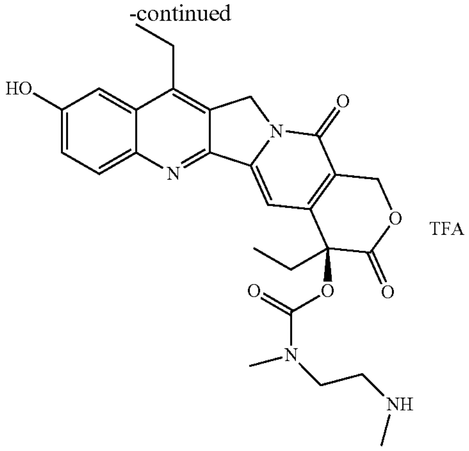

56

100 mg of BOC protected 20 was dissolved in 2 ml of ice cold DCM, and 0.5 mL of TFA was added. The mixture was stirred for 1 hour and then the product was precipitated with 30 mL of diethyl ether, yielding the TFA salt of 56 in quantitative yield. (m/z): 507.3 (M+Na), 1035.5 (2M+Na).

A procedure for generating Structure 57 is as follows:

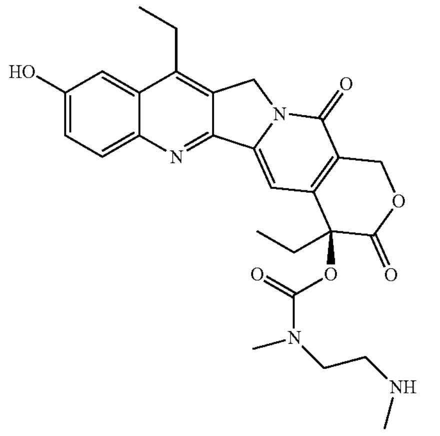

56

+

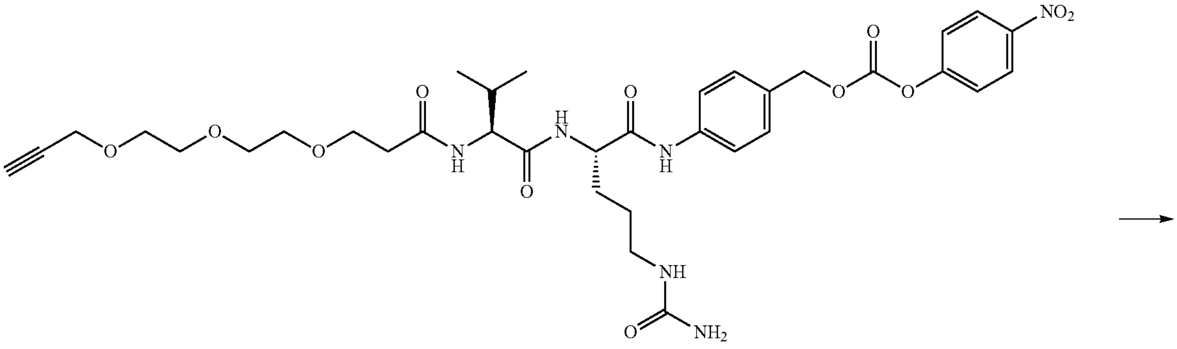

55

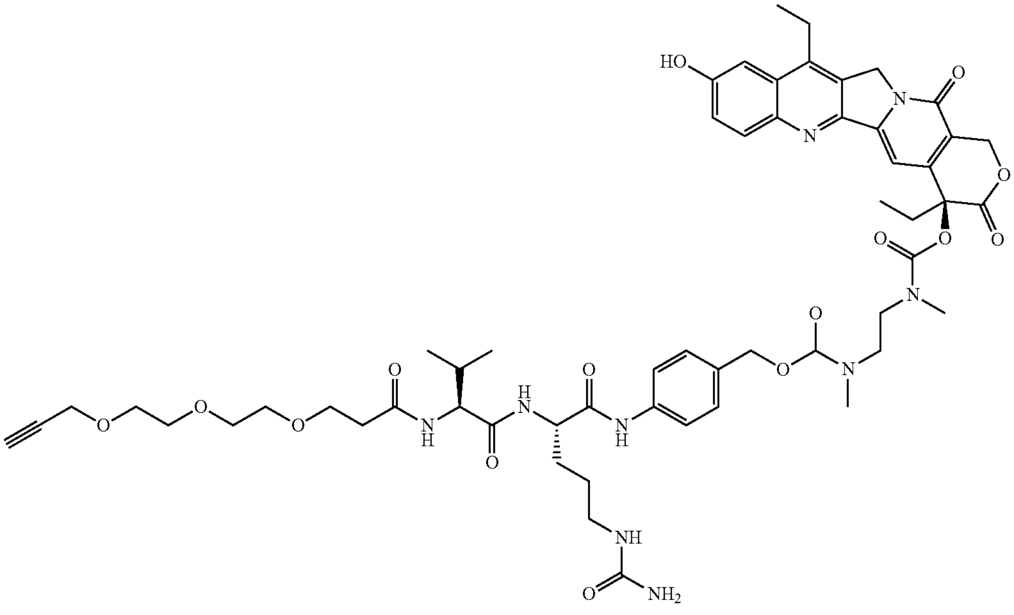

57

62 mg Dimethyldiaminoethylenediamine-SN38 56 (0.123 mmol), 86.8 mg propargylPEG3-VCP-PNP 55 (0.125 mmol), 74 uL DIEA, and 3 mg HOBt were dissolved in 2 mL of anhydrous DMF and 40 μL of anhydrous pyridine. The mixture was stirred for 16 hours, then the product was precipitated with diethyl ether, and the solid chromatographed on silica gel with DCM/MeOH as eluent, yielding 95 mg (69%) of the desired product 57. MS (ESI+) 1133.0 (M+Na), 578.2 (M+2Na)/2. HPLC ret. Time=17.829 min.

A procedure for generating Structure 58 is as follows:

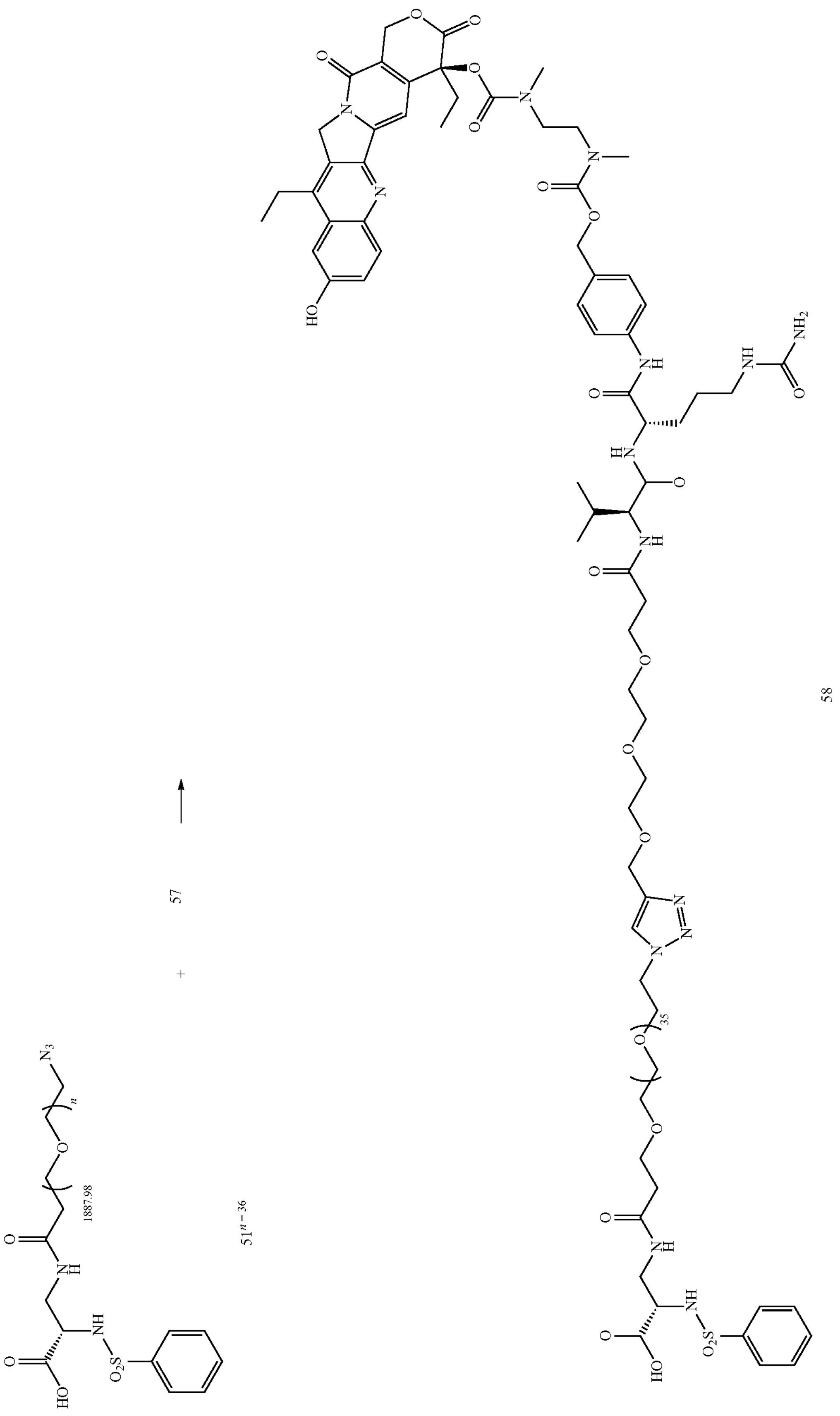
51 n = 36
57
58

54 mg PhSO2-DAP-PEG36-N3 51 (0.028 mmol), 31 mg propargyl-PEG3-VCP-Dimethylethylenediamine-SN38 57 (0.028 mmol) and 0.7 mg TBTA were suspended in 1.8 mL of tBuOH, and the mixture was sparged with N2 for 1 min before capping. In a separate vessel 0.7 mg of CuSO4 hydrate and 15 mg of sodium ascorbate dissolved in 2.8 mL of water, and this was added to the tBuOH mixture. The mix was sparged with N2 again, then capped and stirred for 2 h, at which time HPLC indicated that the reaction was complete. 10 mL of saturated brine was added, the mixture was extracted 5×10 mL with DCM, and the combined organic layers were washed 2× with 10 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 51 mg (60%) of the desired product 58. MS (ESI+) 1540.9 (M+2Na)/2, 1035.4 (M+3Na/3), 782.5 (M+4Na)/4. HPLC retention time 21.970 min.

A procedure for generating Structure 59 is as follows:

56 mg PhSO2-DAP-PEG36-N3 51 (0.028 mmol), 20 mg propargyl-PEG3-VCP 54 (0.035 mmol) and 1 mg TBTA were suspended in 2.5 mL of tBuOH, and the mixture was sparged with N2 for 1 min before capping. In a separate vessel 1 mg of CuSO4 hydrate and 15 mg of sodium ascorbate dissolved in 3.75 mL of water, and this was added to the tBuOH mixture. The mix was sparged with N2 again, then capped and stirred for 3 h, at which time HPLC indicated that the reaction was complete. 10 mL of saturated brine was added, the mixture was extracted 5×10 mL with DCM, and the combined organic layers were washed 2× with 10 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 51 mg (60%) of the desired product 59. MS (ESI+) 857.9 (M+3Na/3), 649.4 (M+4Na)/4. HPLC retention time 14.052 min.

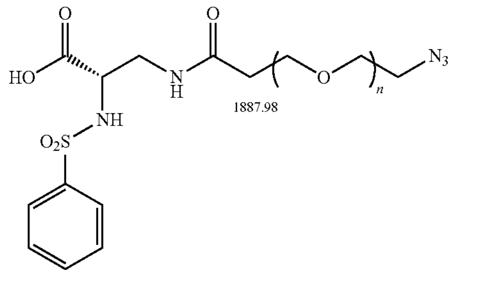

51$^{n = 36}$

+

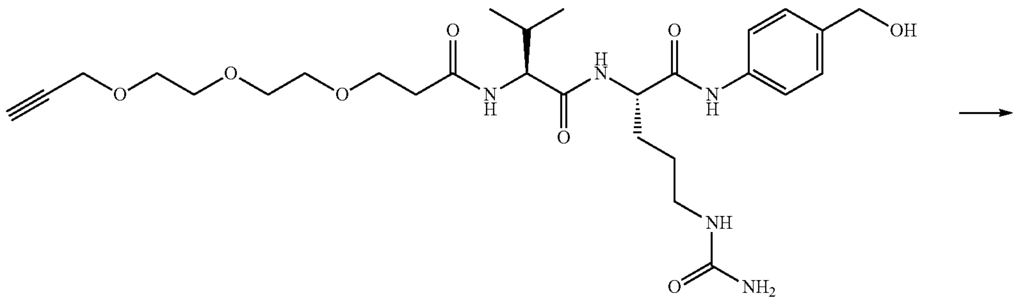

54

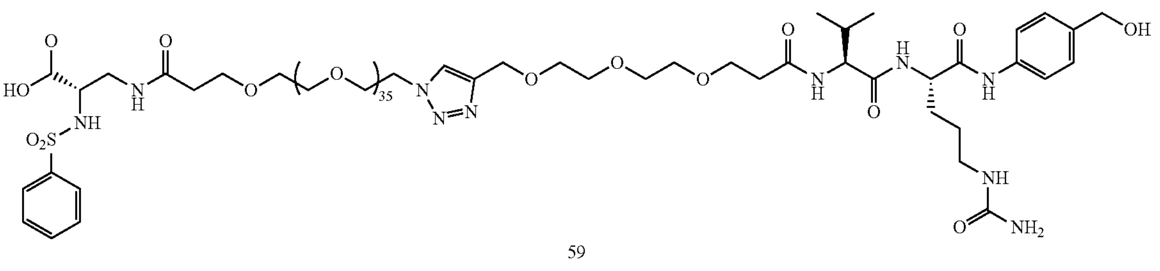

59

A procedure for generating Structure 60 is as follows:

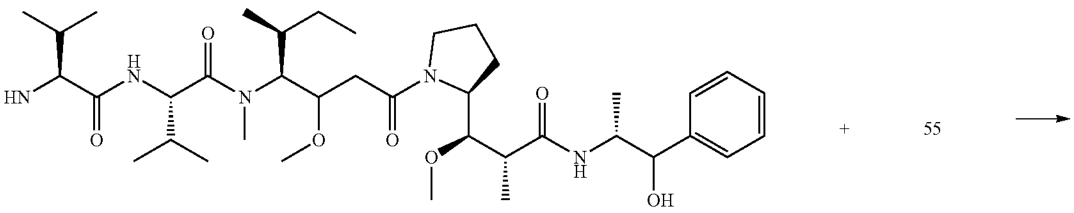

24

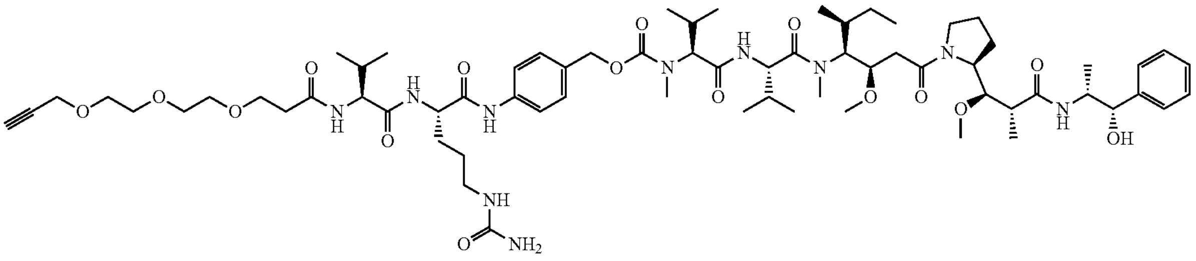

60

50 mg MMAE 24 (0.069 mmol), 49 mg propargylPEG3-VCP-PNP 55 (0.071 mmol), 43 uL DIEA, and 2 mg HOBt were dissolved in 2 mL of anhydrous DMF and 40 μL of anhydrous pyridine. The mixture was stirred for 16 hours, then the product was precipitated with diethyl ether, and the solid chromatographed on silica gel with DCM/MeOH as eluent, yielding 72 mg (78%) of the desired product 60. MS (ESI+) 1343.2 (M+Na), 683.7 (M+2Na)/2. HPLC ret. Time=27.296 min.

A procedure for generating Structure 61 is as follows:

61

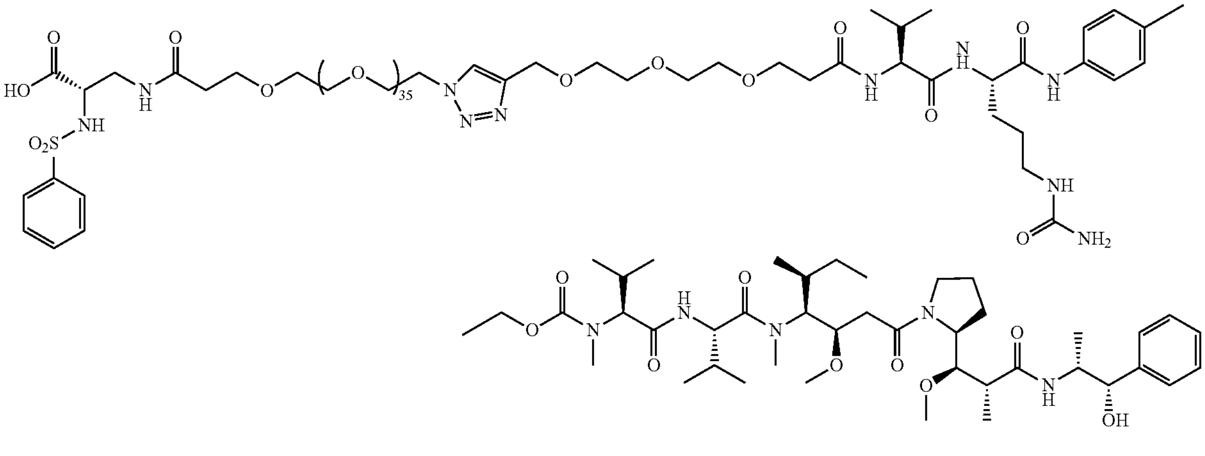

12.8 mg PhSO2-DAP-PEG36-N3 51 (0.00681 mmol), 10 mg propargyl-PEG3-VCP-MMAE 60 (0.00757 mmol) and 0.2 mg TBTA were suspended in 0.5 mL of tBuOH, and the mixture was sparged with N2 for 1 min before capping. In a separate vessel 0.2 mg of CuSO4 hydrate and 5 mg of sodium ascorbate dissolved in 0.75 mL of water, and this was added to the tBuOH mixture. The mix was sparged with N2 again, then capped and stirred for 3 h, at which time HPLC indicated that the reaction was complete. 10 mL of saturated brine was added, the mixture was extracted 5×10 mL with DCM, and the combined organic layers were washed 2× with 10 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 11 mg (50%) of the desired product 61. MS (ESI+) 1645.4.0 (M+2Na)/2, 1105.7 (M+3Na/3). HPLC retention time 28.562 min.

A procedure for generating Structure 62 is as follows:

62

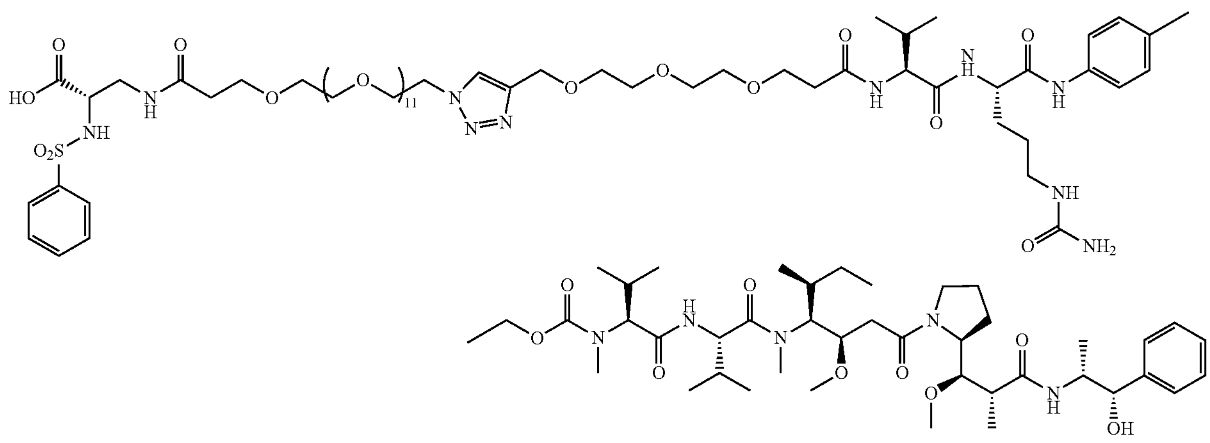

9 mg PhSO2-DAP-PEG12-N3 52 (0.0103 mmol), 15 mg propargyl-PEG3-VCP-MMAE 60 (0.0114 mmol) and 0.3 mg TBTA were suspended in 0.75 mL of tBuOH, and the mixture was sparged with N2 for 1 min before capping. In a separate vessel 0.3 mg of CuSO4 hydrate and 5 mg of sodium ascorbate dissolved in 1.125 mL of water, and this was added to the tBuOH mixture. The mix was sparged with N2 again, then capped and stirred for 3 h, at which time HPLC indicated that the reaction was complete. 10 mL of saturated brine was added, the mixture was extracted 5×10 mL with DCM, and the combined organic layers were washed 2× with 10 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 12 mg (53%) of the desired product 62. MS (ESI+) 1119.0 (M+2Na)/2, 754.0 (M+3Na/3). HPLC retention time 27.626 min.

A procedure for generating Structure 64 is as follows:

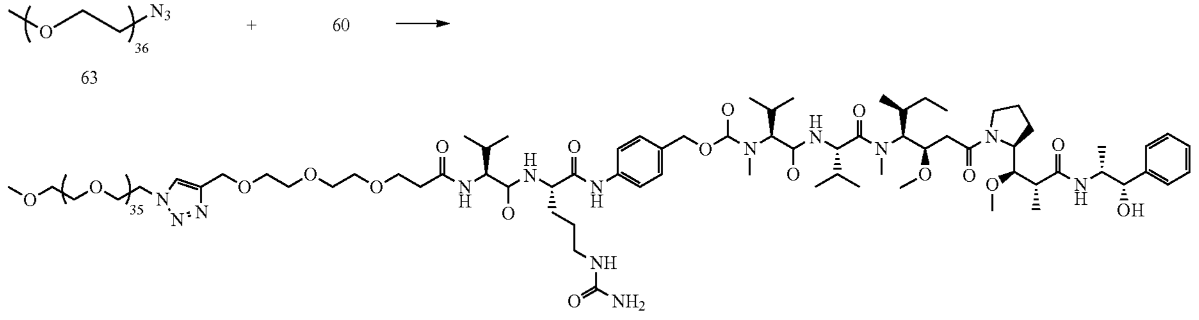

63 + 60

64

17 mg methoxyPEG36N3 63 (0.0114 mmol), 15 mg propargyl-PEG3-VCP-MMAE 60 (0.0114 mmol) and 0.3 mg TBTA were suspended in 0.75 mL of tBuOH, and the mixture was sparged with N2 for 1 min before capping. In a separate vessel 0.3 mg of CuSO4 hydrate and 5 mg of sodium ascorbate dissolved in 1.125 mL of water, and this was added to the tBuOH mixture. The mix was sparged with N2 again, then capped and stirred for 3 h, at which time HPLC indicated that the reaction was complete. 10 mL of saturated brine was added, the mixture was extracted 5×10 mL with DCM, and the combined organic layers were washed 2× with 10 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 27 mg (80%) of the desired product 64. MS (ESI+) 1504.4 (M+2Na)/2, 1011.3 (M+3Na/3), 764.6 (M+4Na)/4. HPLC retention time 27.747 min.

A procedure for generating Structure 66 is as follows:

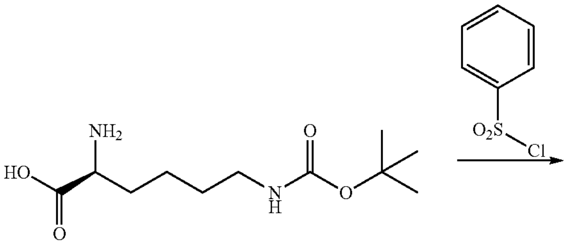

65

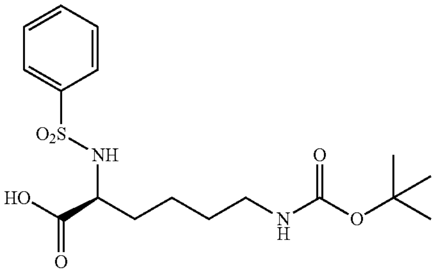

66

246.3 mg (1 mmol) BOC-LYS 65 in 7.6 ml acetone was combined with 560 mg of sodium bicarbonate in 9.2 mL of water. The stirred mixture was cooled in an ice bath, and 256 mg of benzenesulfonyl chloride in 7.6 ml of acetone was added dropwise. The mixture was stirred overnight at room temperature, the acetone was removed via rotovap, the remaining aqueous solution was washed 2×5 mL with ethyl acetate, and the remaining aqueous layer was carefully acidified to pH 3 with dilute HCL. The mixture was extracted 3×10 mL with ethyl acetate, the solvent removed via rotovap, and the residue chromatographed on silica gel with hexane/EtOAc to yield 309 mg (80%) of the desired product 66. MS (m/z): 409.4 (M+Na).

A procedure for generating Structure 67 is as follows:

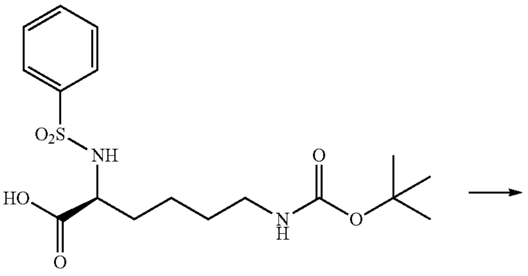

66

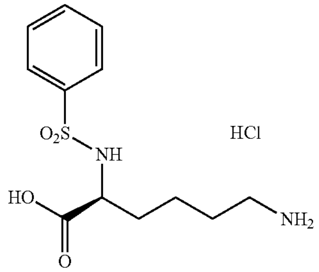

67

300 mg of the BOC protected LYS derivative 66 was dissolved in 2 mL of DCM, and 2 mL of 4M HCl in dioxane were added. The solution was stirred for 6 h, then the solvent was removed via rotovap and triturated 3× with diethyl ether. The product 67 was used as is, it was very hydroscopic and needs to be kept dry. MS (m/z): 287.1 (M+H).

A procedure for generating Structure 68 is as follows:

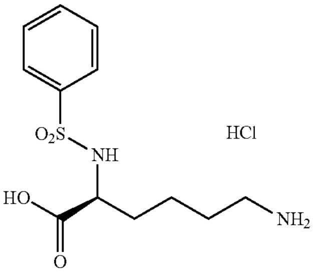

67

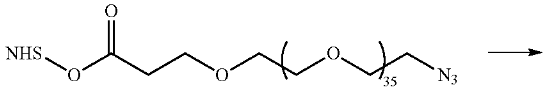

49

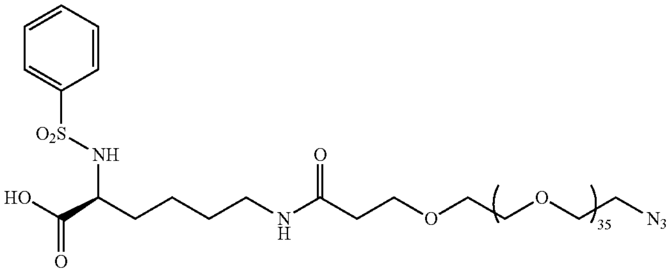

68

50 mg of N3-PEG36-NHS Ester 49, 11 mg of the LYS derivative 67 (1.2 eq), and 20 μL of DIPEA were dissolved in 2 mL of anhydrous CH3CN. The mixture was stirred overnight, then the acetonitrile was removed under reduced pressure and the remaining solid was chromatographed on silica gel with a 0-10% MeOH in DCM to yield 47 mg (85%) of the desired product 68. (m/z): 1991.1 (M+Na); 1008.4 M+2Na)/2; 679.5 (M+3Na)/3. HPLC ret. Time=17.295 min.

A procedure for generating Structure 69 is as follows:

69

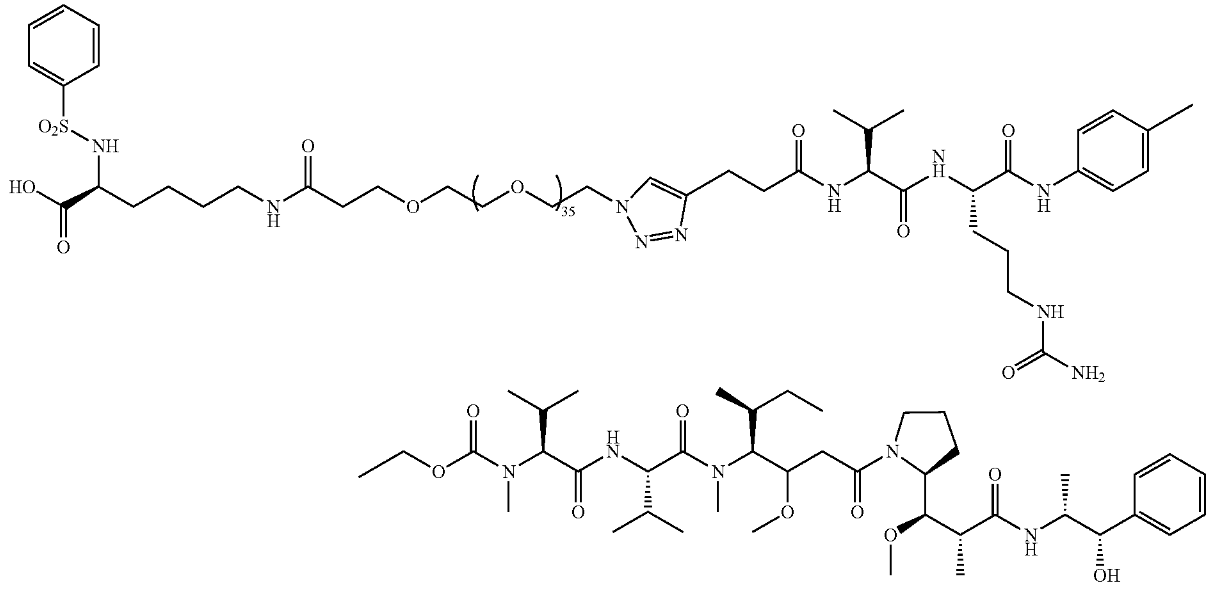

10 mg PhSO2-Lys-PEG36-N3 68 (0.0026 mmol), 31 mg propargyl-VCP-MMAE 25 (0.0026 mmol) and 0.1 mg TBTA were suspended in 0.4 mL of tBuOH, and the mixture was sparged with N2 for 1 min before capping. In a separate vessel 0.1 mg of CuSO4 hydrate and 6 mg of sodium ascorbate were dissolved in 0.6 mL of water, and this was added to the tBuOH mixture. The mix was sparged with N2 again, then capped and stirred for 2 h, at which time HPLC indicated that the reaction was complete. 1 mL of saturated brine was added, the mixture was extracted 5×3 mL with DCM, and the combined organic layers were washed 2× with 3 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 6 mg (60%) of the desired product 69. MS (ESI+) 1609.4 (M+2Na)/2, 1080.4 (M+3Na/3), 816.2 (M+4Na)/4. HPLC retention time 28.751 min.

A procedure s for generating Structure 71 is as follows:

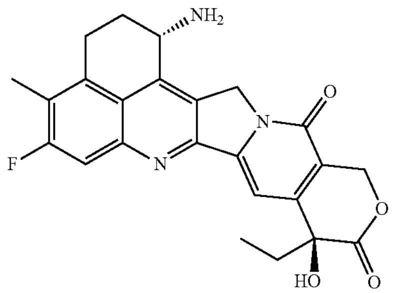

70

+

-continued

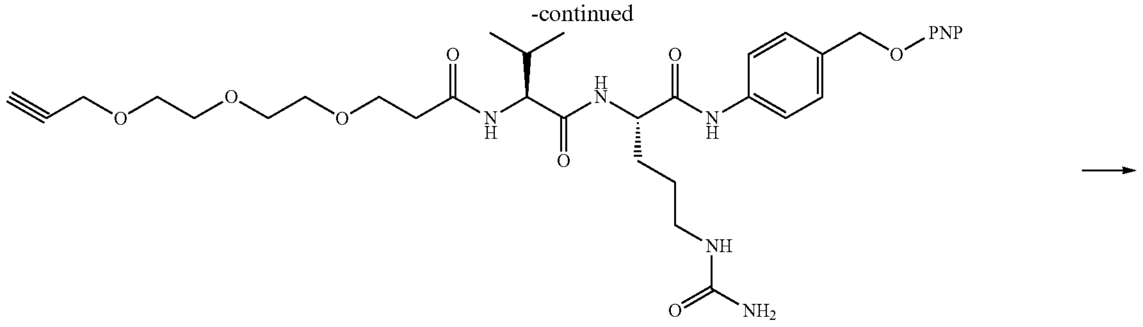

55

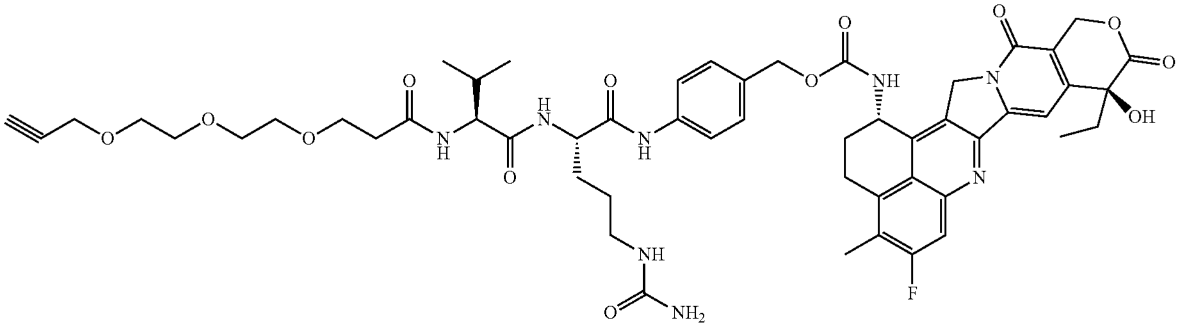

71

4.9 mg exatecan mesylate 70 (0.0092 mmol), 6.8 mg propargylPEG3-VCP-PNP 55 (0.0092 mmol), 8 uL DIEA, and 0.1 mg HOBt were dissolved in 1 mL of anhydrous DMF and 40 μL of anhydrous pyridine. The mixture was stirred for 16 hours, then the product was precipitated with diethyl ether, and the solid chromatographed on silica gel with DCM/MeOH as eluent, yielding 6.5 mg (68%) of the desired product 71. MS (ESI+) 1061.7 (M+Na). HPLC ret. Time=20.098 min.

A procedure for generating Structure 72 is as follows:

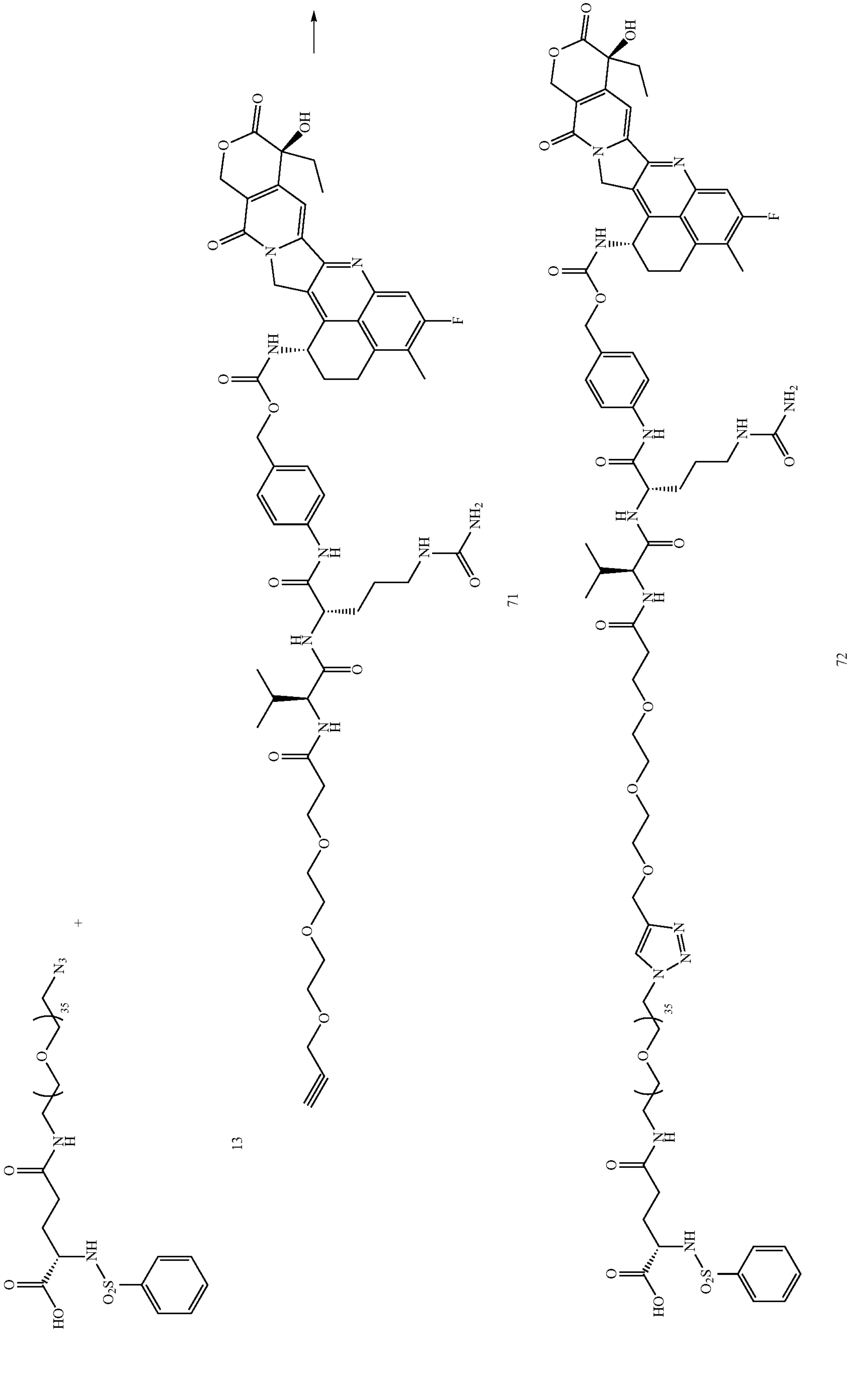
13
71
72

10 mg PhSO2-Glu-PEG36-N3 13 (0.0055 mmol), 6.5 mg propargyl-PEG3-VCP-exatecan 71 (0.0061 mmol) and 0.1 mg TBTA were suspended in 0.5 mL of tBuOH, and the mixture was sparged with N2 for 1 min before capping. In a separate vessel 0.2 mg of CuSO4 hydrate and 6 mg of sodium ascorbate were dissolved in 0.75 mL of water, and this was added to the tBuOH mixture. The mix was sparged with N2 again, then capped and stirred for 2 h, at which time HPLC indicated that the reaction was complete. 1 mL of saturated brine was added, the mixture was extracted 5×3 mL with DCM, and the combined organic layers were washed 2× with 3 mL of a 1:1 mixture of saturated brine and saturated disodium EDTA. The solution was dried over anhydrous sodium sulfate, the solvent was removed under reduced pressure, and the residue chromatographed on silica gel with 0-20% MeOH in DCM with 2% formic acid to yield 8 mg (49%) of the desired product 72. MS (ESI+) 1492.0 (M+2Na)/2, 1002.6 (M+3Na/3), 757.3 (M+4Na)/4. HPLC retention time 23.832 min.

A procedure for generating Structure 73 is as follows:

73

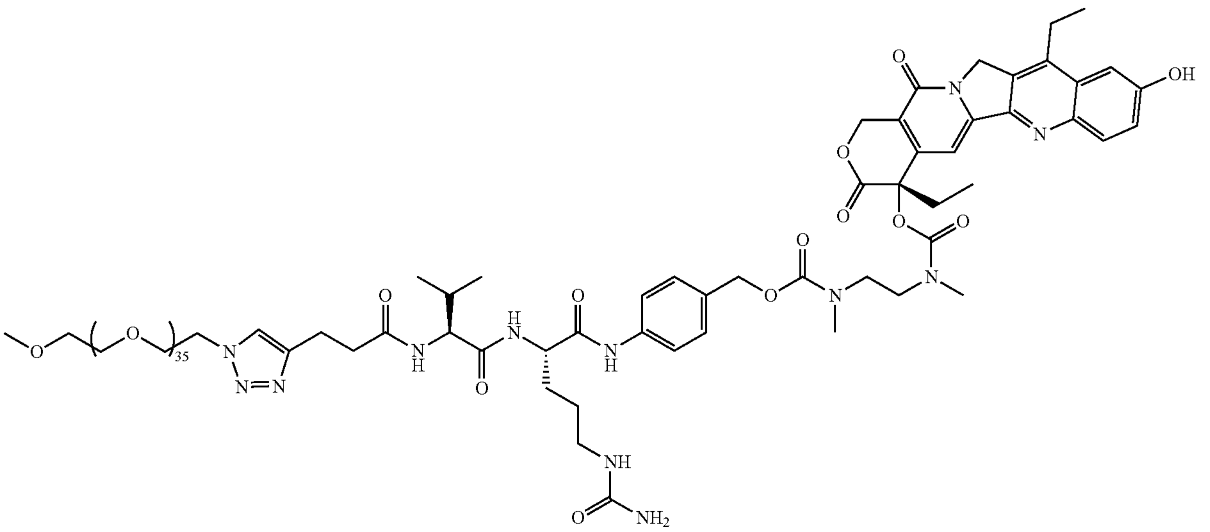

Dissolve 32 mg of 21 (0.0323 mmol), 47.6 mg of 63 (0.9 eq), and 0.7 mg TBTA in 2.275 ml of tBuOH. Dissolve 1 mg CuSO4 and 10 mg of sodium ascorbate in 3 mL of water. Sparge both solutions with nitrogen, combine, and stir under N2 for 3 hr. Bring pH to ~3.0 with citric acid, add an equal volume of saturated brine, and extract 5×2 mL with DCM. Wash the combine extracts 2×2 mL with a 1:1 mix of saturated brine and 1M disodium EDTA, 1× w/2 mL of brine, and dry with anhydrous sodium sulfate. Strip solvents, and chromatograph on silica with 0-20% MeOH in 0.5% formic acid in DCM. 40 mg 52% of 73. MS (ESI+)=1338.3 (M+Na)/2. HPLC=20.574 min.

A procedure for generating Structure 74 is as follows:

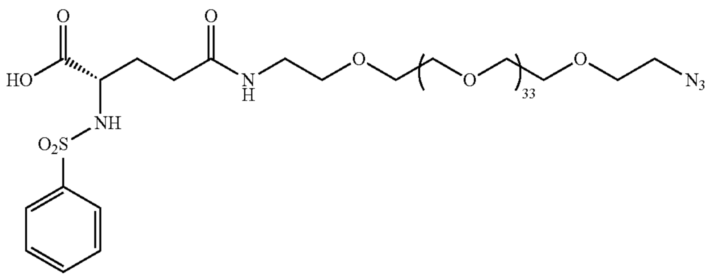

+

13

-continued

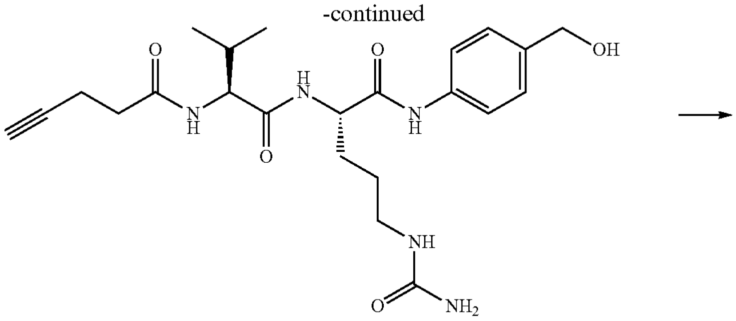

3

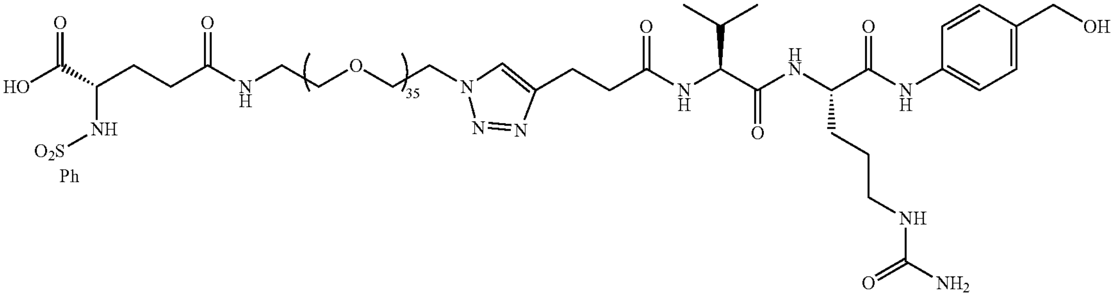

74

19.8 mg 3 (0.0432 mmol), 74 mg 13 (0.9 eq), 1 mg TBTA, dissolved in 2.5 mL tBuOH. 1 mg CuSO4 and 15 mg sodium ascorbate dissolved in 3.75 mL H2O. Both solution sparged with nitrogen, combined, and stirred under N2 for 3 h. Solution acidified to ~pH 3.0 with 2 drops of dilute HCl, and most of the tBuOH removed under reduced pressure. Partition between DCM and saturated brine, extract 4×3 mL with DCM, combine organic layers and wash 2× with a 1:1 mix of saturated brine and 1 M disodium EDTA, dry over sodium sulfate, and strip the solvents under vacuum. Add methanol, strip, then toluene, strip. Chromatograph on silica 0-20% MeOH in 0.5% formic acid in DCM. 45.7 mg compound 74 (50%). MS (ESI+)=1179.4 (M+2H). HPLC r.t.=13.44 min.

A procedure for generating Structure 76 is as follows:

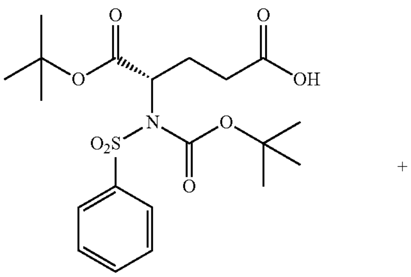

10

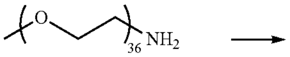

-continued

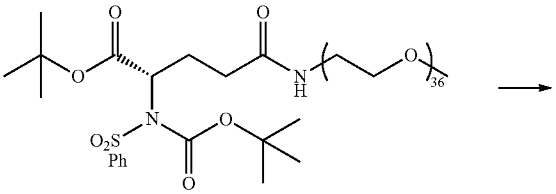

75

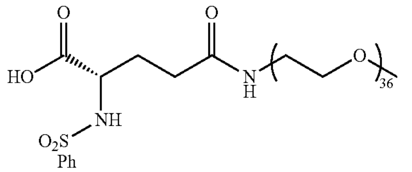

76

100 mg of Methoxy PEG36 amine (0.0619 mmol), 30 mg 10 (1.1 eq), 50 uL DIEA, and catalytic HOBt and DMAP (1 mg of each) was dissolved in 2 mL of DCM, and 35 mg (3 eq) EDC was added. The reaction was stirred overnight and was chromatographed directly on silica gel in 0-15% MeOH in DCM, yielding 105 mg (83%) of 75. MS (ESI+)=1044.2 (M+2Na)/2. 100 mg of 75 (0.0489 mmol) was dissolved in 5 mL of DCM and cooled in an ice bath. 5 mL of 4M HCl in dioxane was added, the reaction was stirred for 4 h at room temperature, then the solvents were removed under reduced pressure. The product was triturated with diethyl ether and dried overnight under vacuum to yield 85 mg (92%) of product 76 MS (ESI+)=966.1 (M+2Na)/2.

A procedure for generating Structure 79 is as follows:

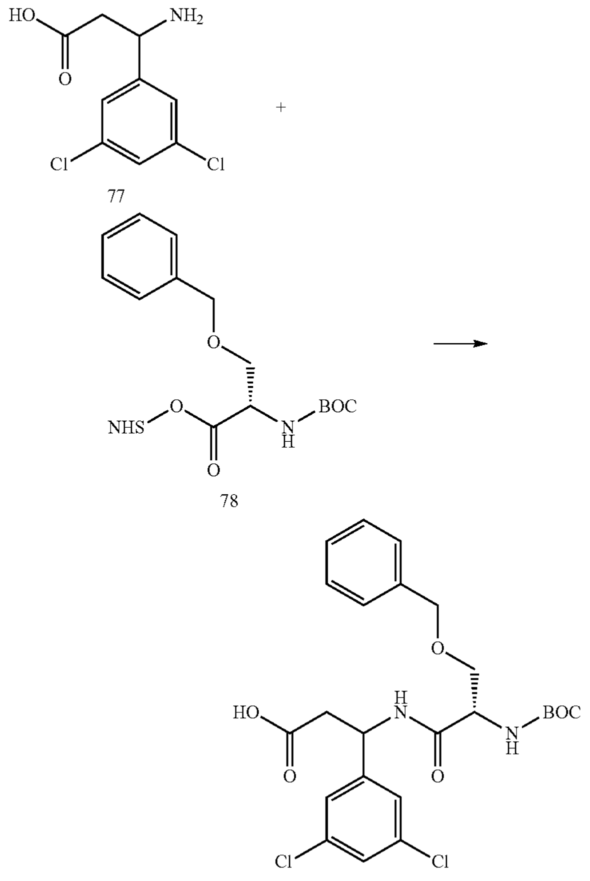

77

78

79

100 mg of 77, 1 eq of 78, 43 uL TEA, and catalytic HOBt and DMAP (1 mg of each) are dissolved in 2 mL of DCM, and 23 mg (2 eq) EDC is added. The reaction is stirred overnight, and is chromatographed directly on silica gel in 0-15% MeOH in DCM, yielding 79.

A procedure for generating Structure 80 is as follows:

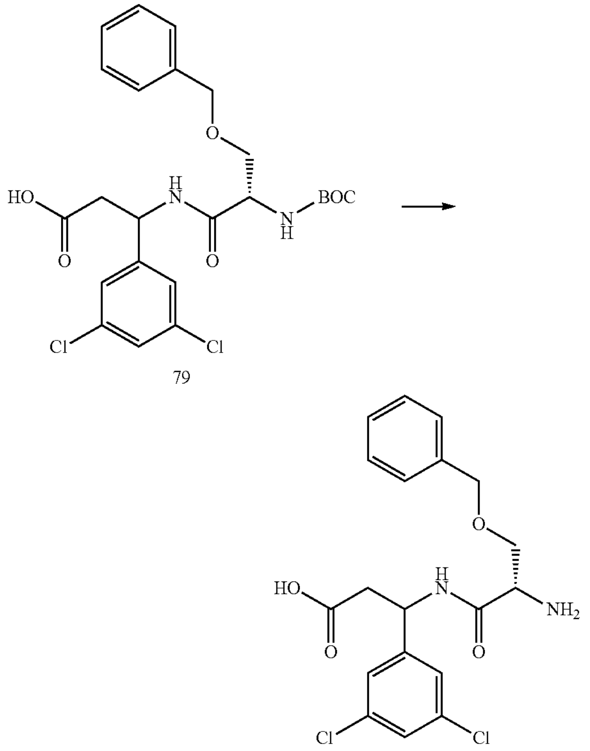

79

80

65 mg of 79 is dissolved in 6.5 mL of DCM and 6.5 mL of 4M HCl in dioxane is added, and the reaction is stirred for 4 h at room temperature, then the solvents are removed under reduced pressure. The product is triturated with diethyl ether, and dried overnight under vacuum to yield product 80.

A procedure for generating Structure 81 is as follows:

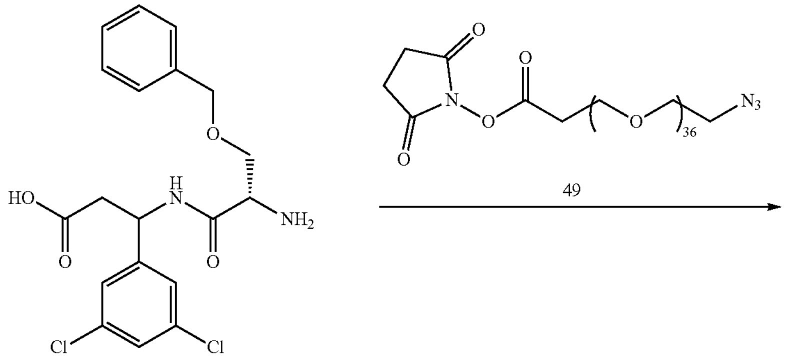

49

80

-continued

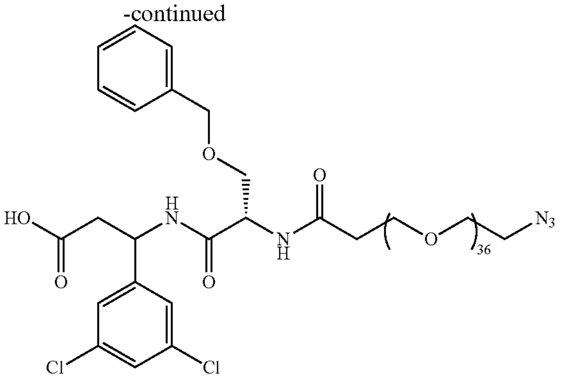

81

50 mg of N3-PEG36-NHS Ester 49, 1.2 equivalents of 80, and 20 μL of DIPEA are dissolved in 2 mL of anhydrous CH3CN. The mixture is stirred overnight, then the acetonitrile is removed under reduced pressure and the remaining solid chromatographed on silica gel with a 0-10% MeOH in DCM to yield the desired product 81.

A procedure for generating Structure 82 is as follows:

82

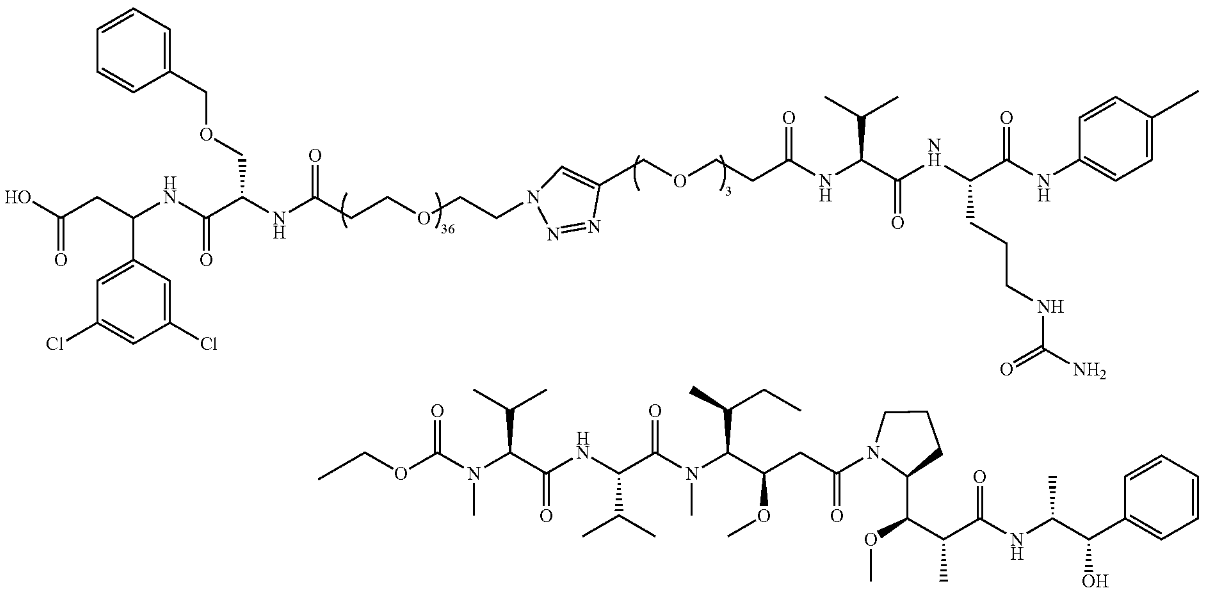

10 mg of 81, 1 eq of 60, and 0.1 mg TBTA are suspended in 0.4 mL of tBuOH, and the mixture is sparged with N2 for 1 min before capping. In a separate vessel 0.1 mg of CuSO4 hydrate and 6 mg of sodium ascorbate are dissolved in 0.6 mL of water, and this is added to the tBuOH mixture. The mix is sparged with N2 again, then capped and stirred for 2 h. 1 mL of saturated brine is added, the mixture is extracted 5×3 mL with DCM, and the combined organic layers are washed 2× with 3 mL of a 1:1 mixture of saturated brine and saturated disodium EDTA. The solution is dried over anhydrous sodium sulfate, the solvent was removed under reduced pressure, and the residue chromatographed on silica gel with 0-20% MeOH in DCM with 2% formic acid to yield the desired product 82.

A procedure for generating Structure 84 is as follows:

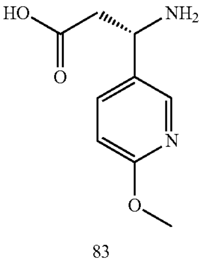

83

+

-continued

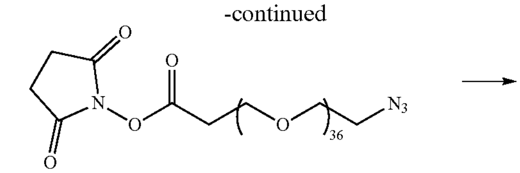

49

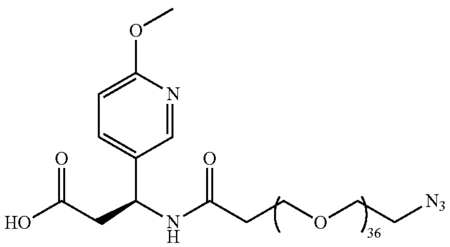

84

50 mg of N3-PEG36-NHS Ester 49, 1.2 equivalents of 83, and 20 μL of DIPEA are dissolved in 2 mL of anhydrous CH3CN. The mixture is stirred overnight, then the acetonitrile is removed under reduced pressure and the remaining solid chromatographed on silica gel with a 0-10% MeOH in DCM to yield the desired product 84.

A procedure for generating Structure 108 is as follows:

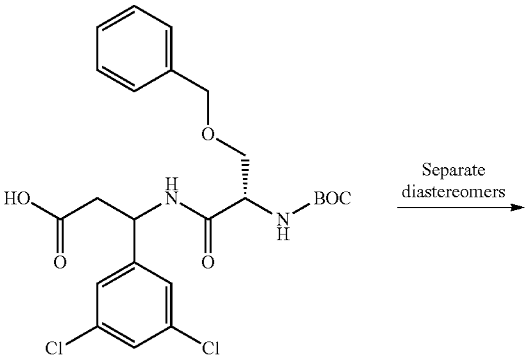

79

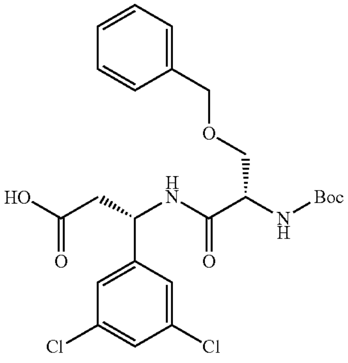

105

50 mg of the diastereomeric mixture 79 is separated into the two diastereomers via chromatography on silica gel with 0-20% methanol in DCM with 0.5% formic acid, yielding pure 105.

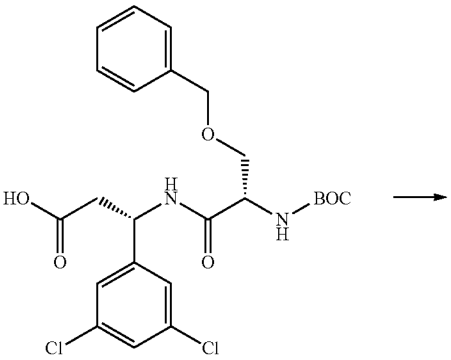

105

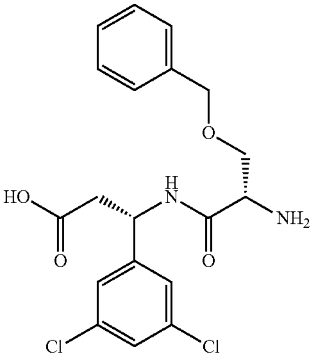

106

105 is dissolved in 1 mL of DCM and 1 mL of 4M HCl in dioxane is added, and the reaction is stirred for 4 h at room temperature. Then the solvents are removed under reduced pressure. The product is triturated with diethyl ether, and dried overnight under vacuum to yield product 106.

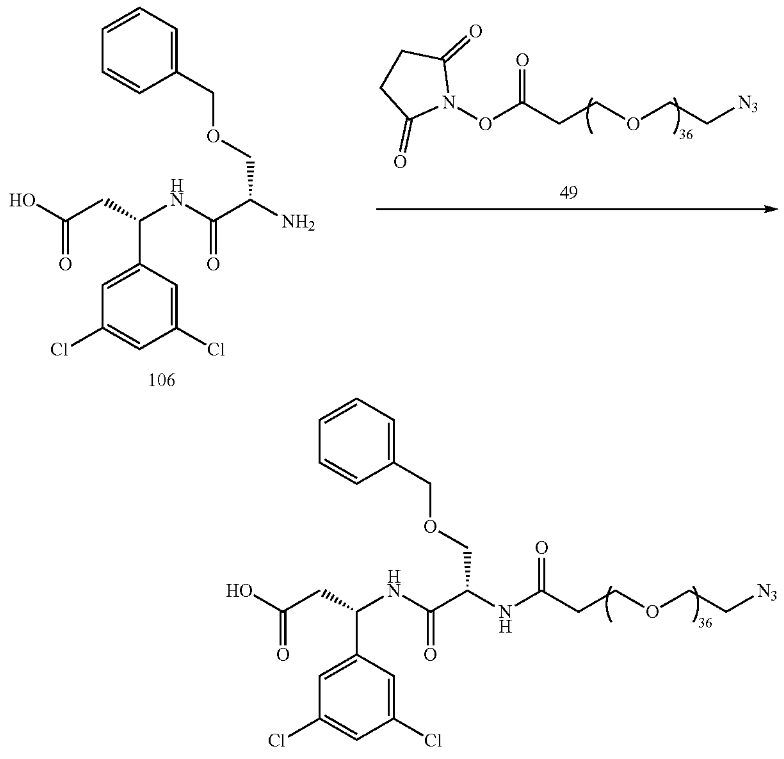
106
49
107
50 mg of N3-PEG36-NHS Ester 49, 1.2 equivalents of 106, and 20 μL of DIPEA are dissolved in 2 mL of anhydrous CH3CN. The mixture is stirred overnight. Then the acetonitrile is removed under reduced pressure and the remaining solid chromatographed on silica gel with a 0-10% MeOH in DCM to yield the desired product 107.
108
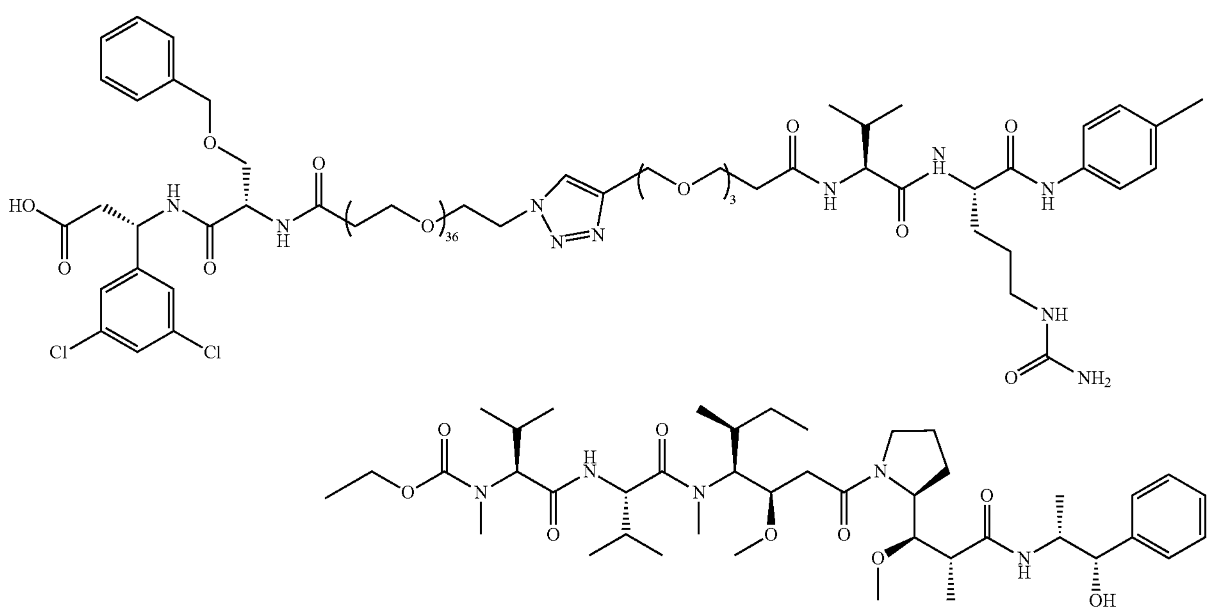

10 mg of 107, 1 eq of 60, and 0.1 mg TBTA are suspended in 0.4 mL of tBuOH, and the mixture is sparged with N2 for 1 min before capping. In a separate vessel, 0.1 mg of CuSO4 hydrate and 6 mg of sodium ascorbate are dissolved in 0.6 mL of water, which is added to the tBuOH mixture. The mixture is sparged with N2 again, then capped and stirred for 2 h. 1 mL of saturated brine is added, the mixture is extracted 5x3 mL with DCM, and the combined organic layers are washed 2x with 3 mL of a 1:1 mixture of saturated brine and saturated disodium EDTA. The solution is dried over anhydrous sodium sulfate, and the solvent is removed under reduced pressure, and the residue is chromatographed on silica gel with 0-20% MeOH in DCM with 2% formic acid to yield the desired product 108.

A procedure for generating Structure 85 is as follows:

A procedure for generating Structure 87 is as follows:

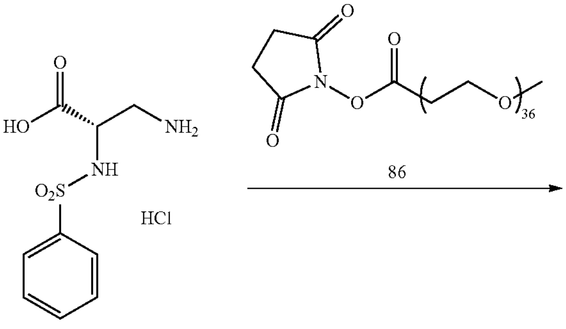

48

86

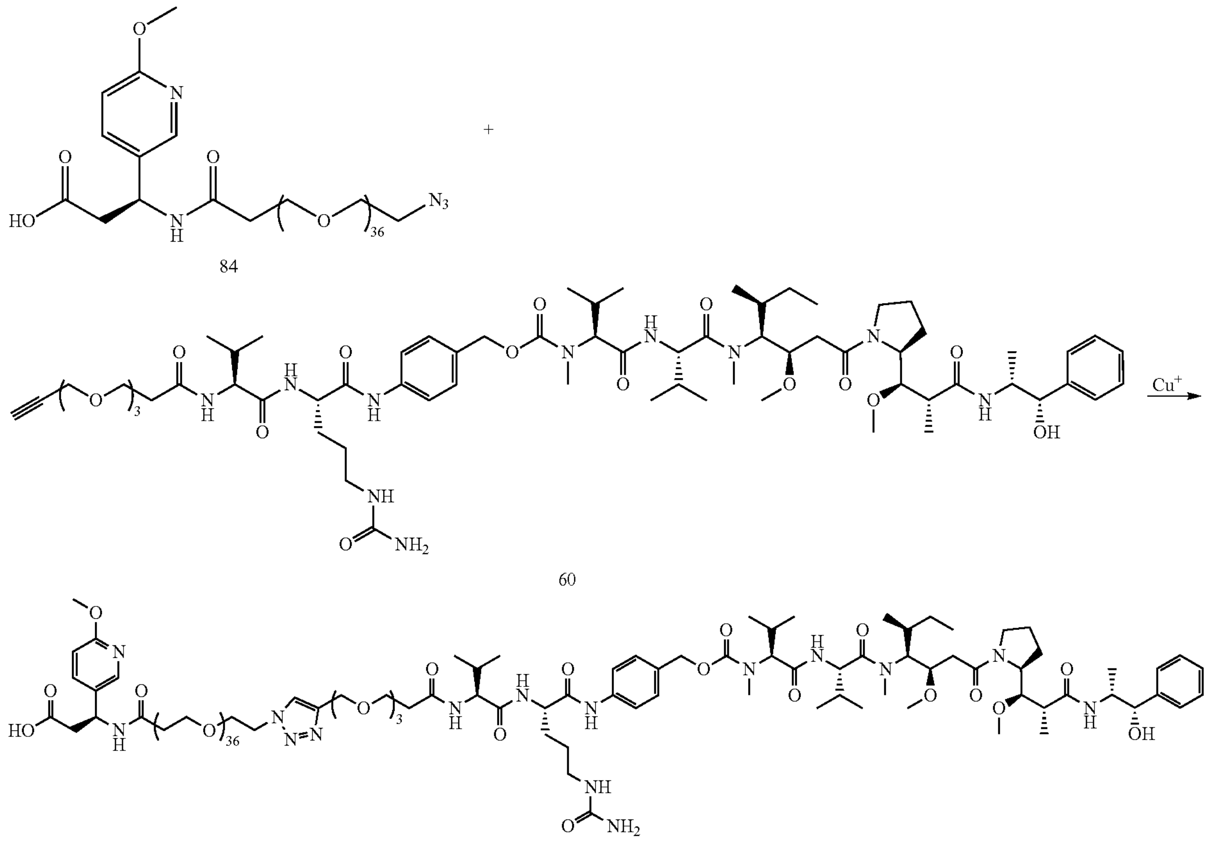

84

60

85

10 mg of 84, 1 eq of 60, and 0.1 mg TBTA are suspended in 0.4 mL of tBuOH, and the mixture is sparged with N2 for 1 min before capping. In a separate vessel 0.1 mg of CuSO4 hydrate and 6 mg of sodium ascorbate are dissolved in 0.6 mL of water, and this is added to the tBuOH mixture. The mix is sparged with N2 again, then capped and stirred for 2 h. 1 mL of saturated brine is added, the mixture is extracted 5x3 mL with DCM, and the combined organic layers are washed 2x with 3 mL of a 1:1 mixture of saturated brine and saturated disodium EDTA. The solution is dried over anhydrous sodium sulfate, the solvent was removed under reduced pressure, and the residue chromatographed on silica gel with 0-20% MeOH in DCM with 2% formic acid to yield the desired product 85.

-continued

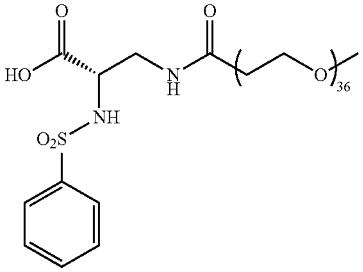

87

50 mg of MeO-PEG36-NHS Ester 86, 1.2 equivalents of 48, and 20 μL of DIPEA are dissolved in 2 mL of anhydrous CH3CN. The mixture is stirred overnight, then the acetonitrile is removed under reduced pressure and the remaining solid chromatographed on silica gel with a 0-10% MeOH in DCM to yield the desired product 87.

A procedure for generating Structure 92 is as follows:

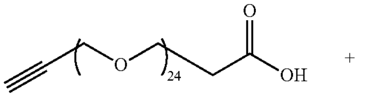

88

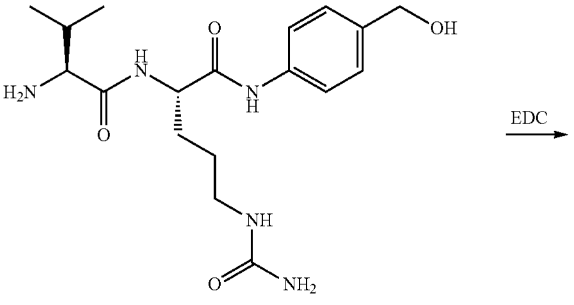

1

-continued

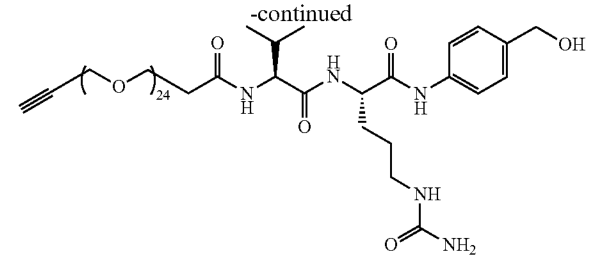

89

60.7 mg (0.060 mmol) propargyl PEG24 carboxylic acid 88, 175 mg (0.060 mmol) val-cit-PAB 1, 1 mg DMAP, 1 mg HOBt, and 30 uL (3 eq) DIPEA are dissolved in 1 mL of anhydrous DMF. 50 mg of EDC is added, and the mixture is stirred overnight. The product is precipitated by adding 5 mL of diethyl ether, centrifuged, the liquid is decanted off, and the remaining solid is dissolved in 10% MeOH in DCM, and chromatographed on silica gel using 10-15% MeOH in DCM as eluent, yielding desired product 89.

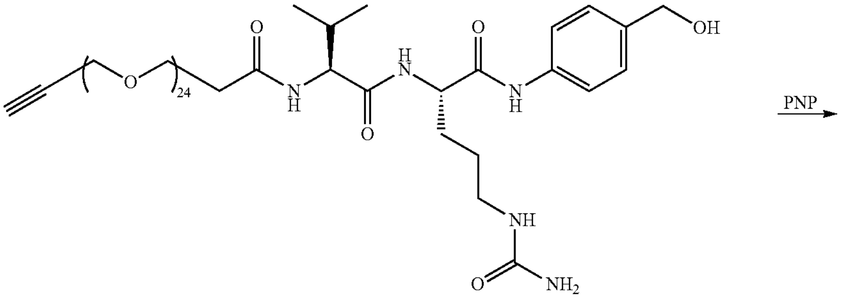

89

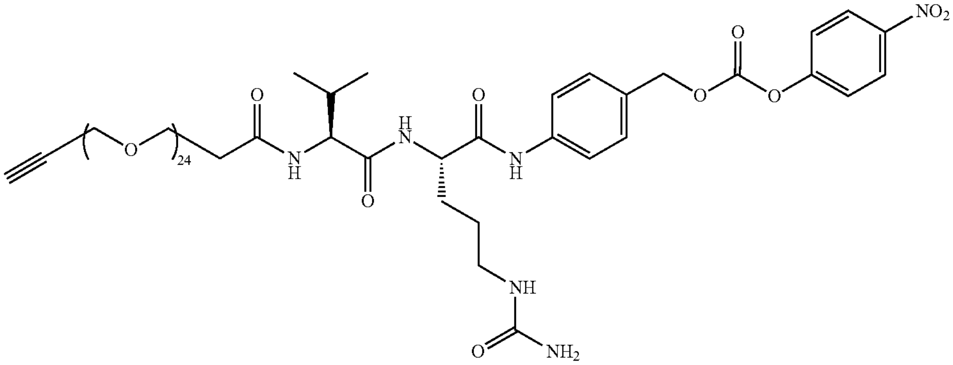

90

75 mg of propargyl-PEG24-VCP 89 (0.05 mmol) is dissolved in 1 mL of ice cold DMF with stirring, then 45 mg (3 eq) Bis-PNP anhydride is added followed quickly by 18 μL of DIPEA. The solution is allowed to warm to room temperature and stirred for 3 h, then the product is precipitated with 5 mL of diethyl ether, dissolved in 5% MeOH in DCM, and chromatographed on silica with 5-10% MeOH in DCM eluent, yielding the desired product 90.

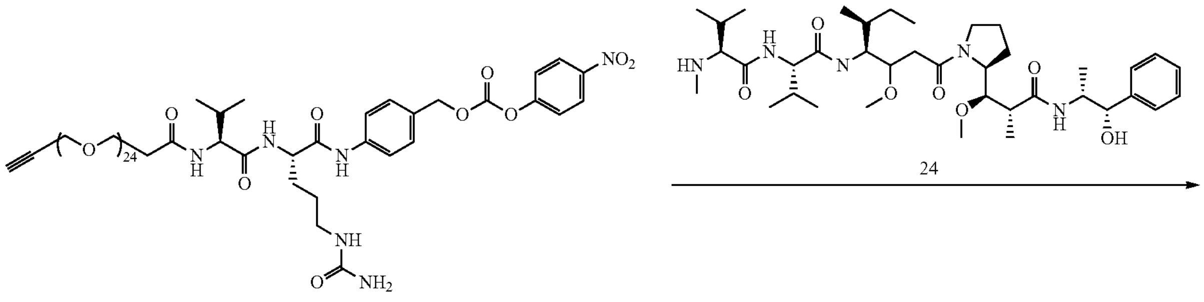

90

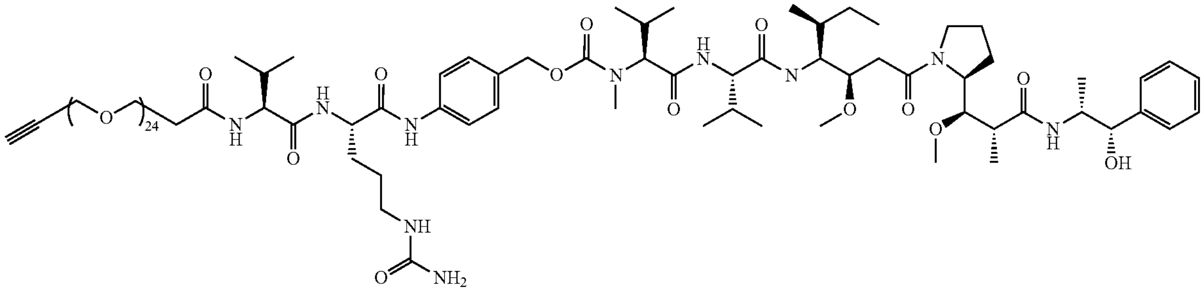

91

35 mg MMAE 24 (0.049 mmol), 84 mg propargyl PEG24-VCP-PNP 90 (1.02 eq), 30 uL DIEA, and 1.4 mg HOBt were dissolved in 2 mL of anhydrous DMF and 40 μL of anhydrous pyridine. The mixture was stirred for 16 hours, then the product was precipitated with diethyl ether, and the solid chromatographed on silica gel with DCM/MeOH as eluent, yielding the desired product 91.

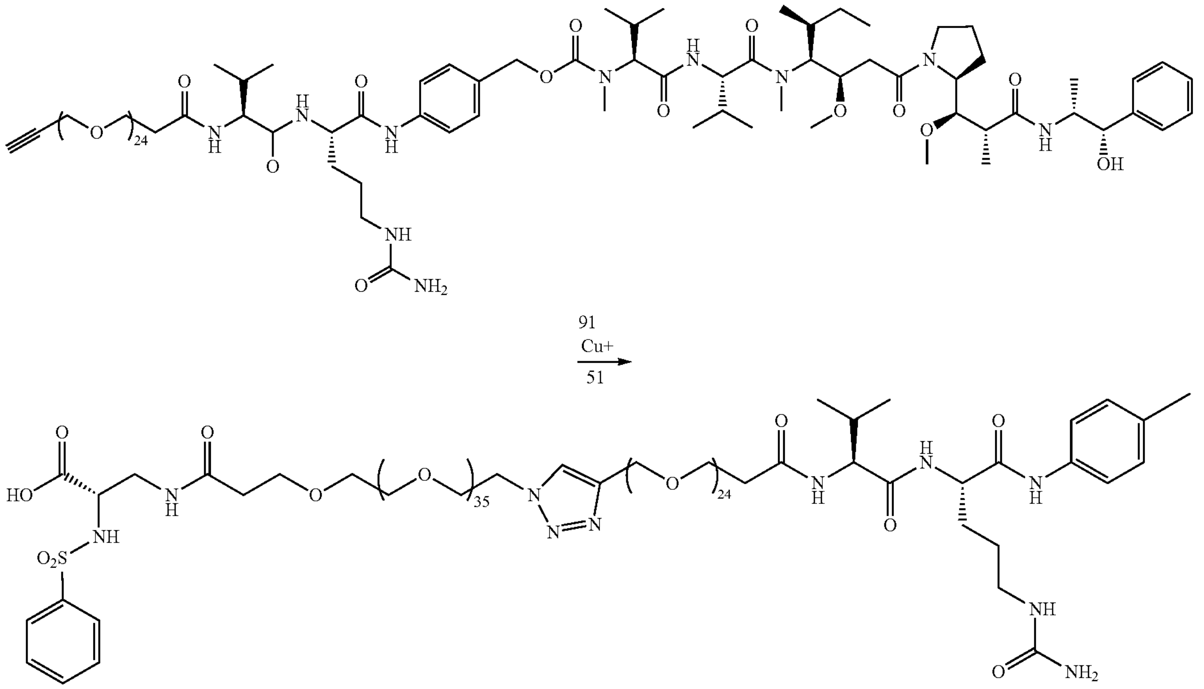

-continued

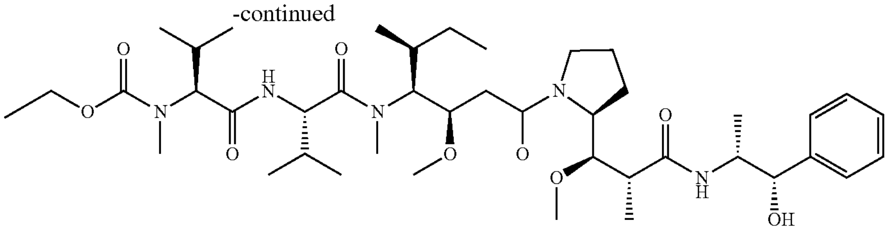

92

14.2 mg PhSO2-DAP-PEG36-N3 51 (0.00757 mmol), 14 mg propargyl-PEG24-VCP-MMAE 91 (0.00757 mmol) and 0.2 mg TBTA are suspended in 0.5 mL of tBuOH, and the mixture is sparged with N2 for 1 min before capping. In a separate vessel 0.2 mg of CuSO4 hydrate and 5 mg of sodium ascorbate are dissolved in 0.75 mL of water, and this is added to the tBuOH mixture. The mix is sparged with N2 again, then capped and stirred for 3 h, at which time HPLC indicated that the reaction is complete. 10 mL of saturated brine is added, the mixture is extracted 5×10 mL with DCM, and the combined organic layers are washed 2× with 10 mL of a 1:1 mixture of saturated brine and saturated disodium EDTA. The solution was dried over anhydrous sodium sulfate, the solvent is removed under reduced pressure, and the residue is chromatographed on silica gel with 0-20% MeOH in DCM with 2% formic acid to yield 11 mg (50%) of the desired product 92.

A procedure for generating Structure 97 is as follows:

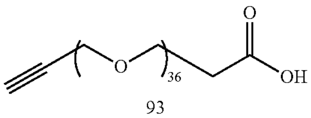

93

+

-continued

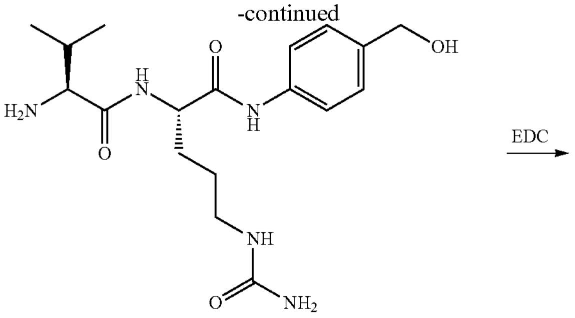

1

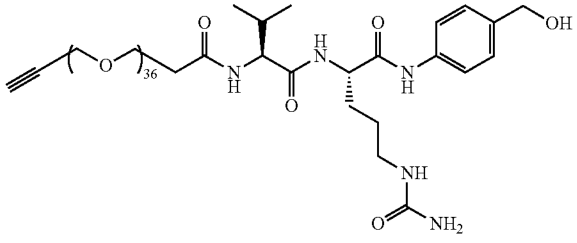

94

100 mg (0.060 mmol) propargyl PEG36 carboxylic acid 93, 175 mg (0.060 mmol) val-cit-PAB 1, 1 mg DMAP, 1 mg HOBt, and 30 uL (3 eq) DIPEA are dissolved in 1 mL of anhydrous DMF. 50 mg of EDC is added, and the mixture is stirred overnight. The product is precipitated by adding 5 mL of diethyl ether, centrifuged, the liquid is decanted off, and the remaining solid is dissolved in 10% MeOH in DCM, and chromatographed on silica gel using 10-15% MeOH in DCM as eluent, yielding desired product 94.

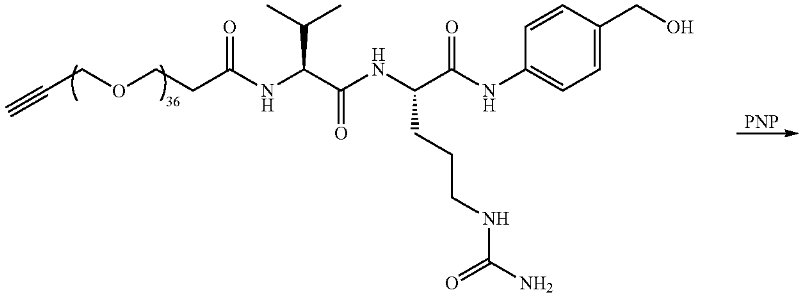

94

-continued

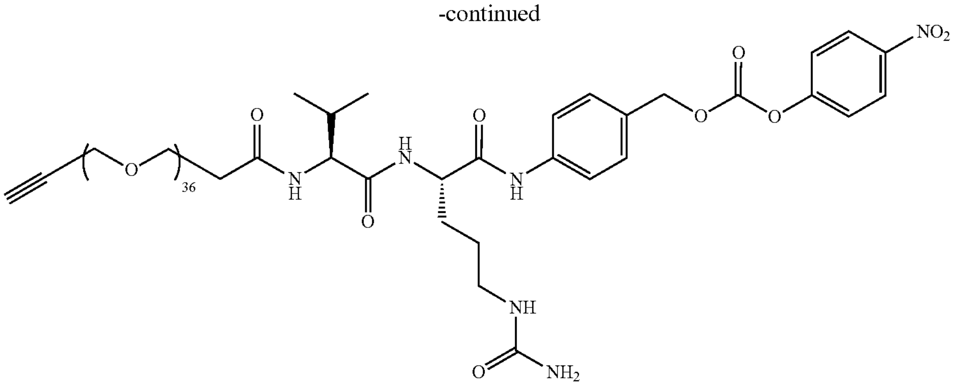

95

101 mg of propargyl-PEG36-VCP 94 (0.05 mmol) is dissolved in 1 mL of ice cold DMF with stirring, then 45 mg (3 eq) Bis-PNP anhydride is added followed quickly by 18 μL of DIPEA. The solution is allowed to warm to room temperature and stirred for 3 h, then the product is precipitated with 5 mL of diethyl ether, dissolved in 5% MeOH in DCM, and chromatographed on silica with 5-10% MeOH in DCM eluent, yielding the desired product 95.

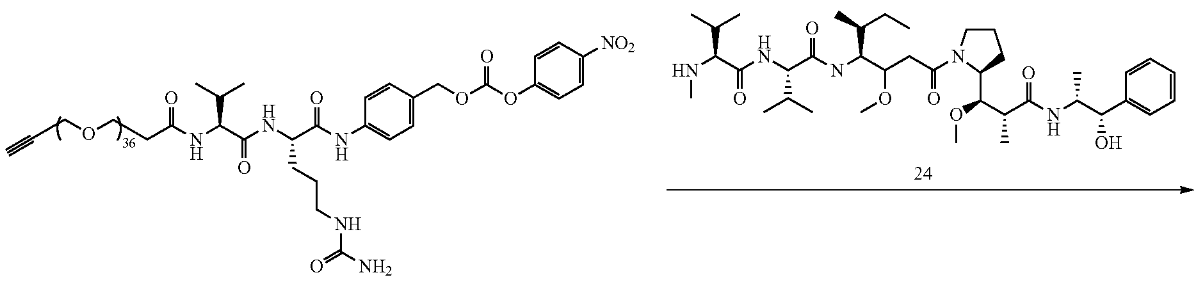

95

24

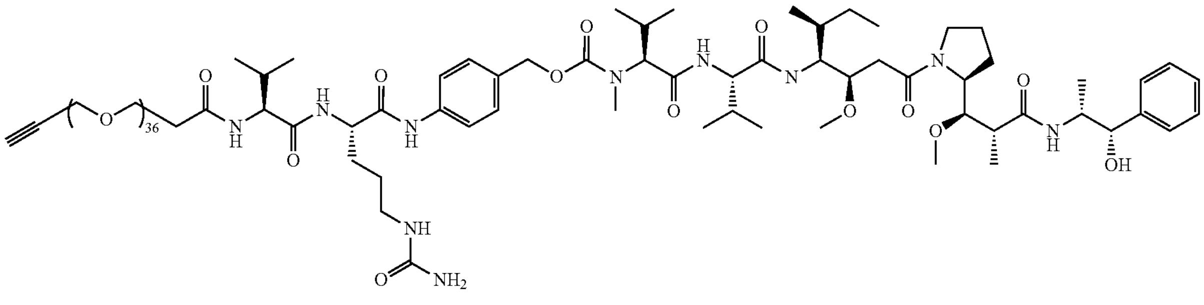

96

35 mg MMAE 24 (0.049 mmol), 110 mg propargylPEG36-VCP-PNP 95 (1.02 eq), 30 uL DIEA, and 1.4 mg HOBt were dissolved in 2 mL of anhydrous DMF and 40 μL of anhydrous pyridine. The mixture was stirred for 16 hours, then the product was precipitated with diethyl ether, and the solid chromatographed on silica gel with DCM/MeOH as eluent, yielding the desired product 96.

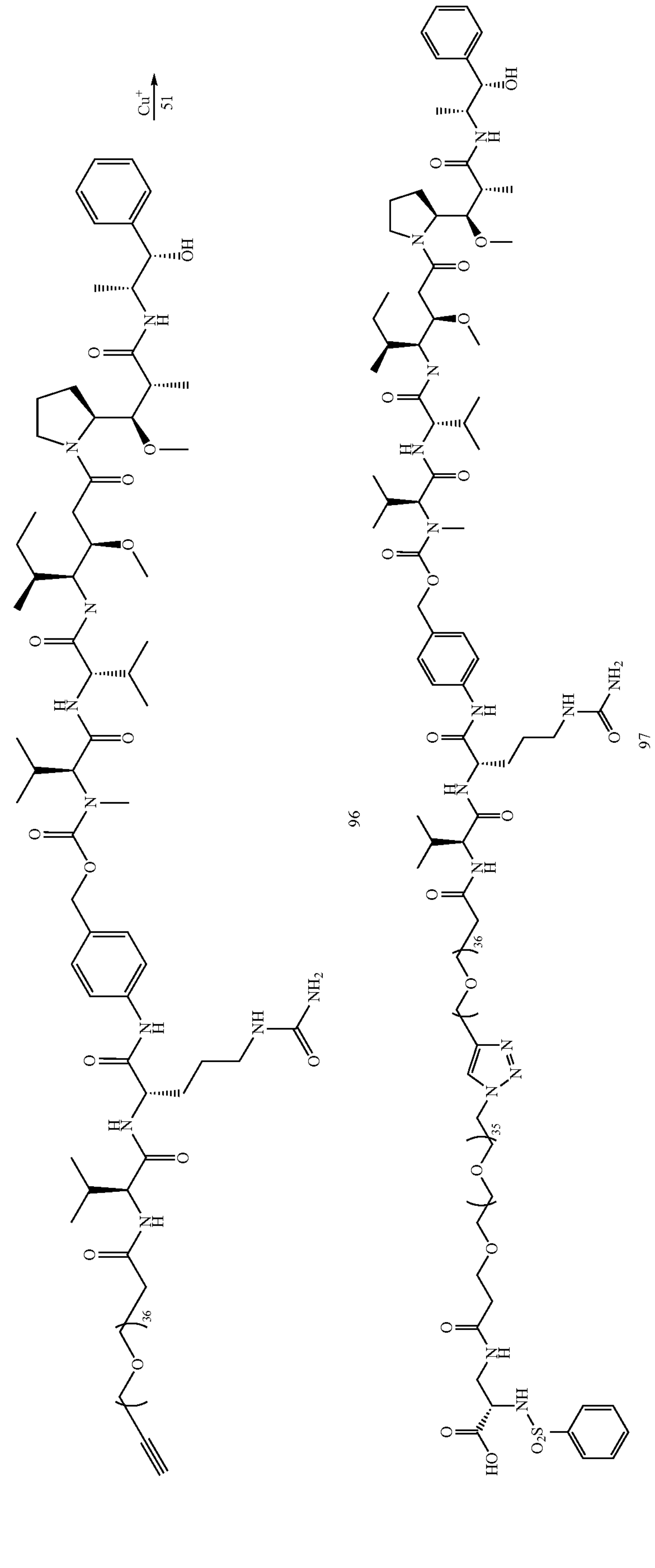
96
97

14.2 mg PhSO2-DAP-PEG36-N3 51 (0.00757 mmol), 17 mg propargyl-PEG36-VCP-MMAE 96 (0.00757 mmol) and 0.2 mg TBTA are suspended in 0.5 mL of tBuOH, and the mixture is sparged with N2 for 1 min before capping. In a separate vessel 0.2 mg of CuSO4 hydrate and 5 mg of sodium ascorbate are dissolved in 0.75 mL of water, and this is added to the tBuOH mixture. The mix is sparged with N2 again, then capped and stirred for 3 h, at which time HPLC indicated that the reaction is complete. 10 mL of saturated brine is added, the mixture is extracted 5×10 mL with DCM, and the combined organic layers are washed 2× with 10 mL of a 1:1 mixture of saturated brine and saturated disodium EDTA. The solution was dried over anhydrous sodium sulfate, the solvent is removed under reduced pressure, and the residue is chromatographed on silica gel with 0-20% MeOH in DCM with 2% formic acid to yield 11 mg (50%) of the desired product 97.

5. Testing Effectiveness of Conjugates

This section describes the following testing of effectiveness of conjugates of the present invention that has been performed in categories of: in vitro integrin αvβ3 binding assay, in vitro cell adhesion assay, in vitro cell viability assay, in vivo efficacy.

$IC_{50}$ is used as a measure of effectiveness of the conjugates in the assays. Generally, an $IC_{50}$ value indicates how much of a particular inhibitory substance (e.g., a conjugate) is needed to inhibit, in vitro, a given biological process or biological component by 50%. The biological component could be an enzyme, cell, cell receptor or microorganism. An $IC_{50}$ numerical value may be expressed as a molar concentration, such in units of nanoMolars (nM), micromolars (M), etc. The meaning of the $IC_{50}$ value specific to each of the assays will be described.

In the testing, human glioblastoma U87-luc cells were purchased from ATCC (Manassas, VA, USA). CWR-R1ca cells was purchased from MilliporeSigma, Brilington, MA. Dulbecco's Modified Eagle Medium (DMEM), penicillin/streptomycin, and trypsin/EDTA, fetal bovine serum (FBS), Bovine serum albumin (BSA) were purchased from Sigma-Aldrich (St. Louis, MO, USA). Integrin αvβ3 was obtained from ACRO Biosystems, Newark, DE, USA. Purified integrin αvβ3 and anti-integrin αvβ3 conjugated with biotin were obtained from Bioss Inc (Woburn, MA), streptavidin HRP conjugate were from ThermoFisher Scientific (Grand Island, NY), fibrinogen was from Millipore Sigma (Burlington, MA), 3,3',5,5'-tetramethylbbenzidine (TMB), and TMB-stop solution were from Abcam Inc (Cambridge, MA).

5.1 In Vitro Integrin αvβ3 Binding Biological Assay

The in vitro integrin αvβ3 binding assay measures the binding affinity for different compounds (i.e., different conjugates or structures) with immobilized integrin αvβ3 receptor. The $IC_{50}$ value is the compound concentration at which the compound displaces 50% of a labelled integrin αvβ3 ligand from the integrin αvβ3 receptor, which inhibits 50% of the labelled integrin αvβ3 ligand from binding to the integrin αvβ3 receptor.

Ninety-six polystyrene microtiter plate was coated with fibrinogen and incubated at 4° C. overnight. The wells were blocked with 3% BSA for 2 hours at room temperature and were washed with buffer A (50 mM Tris/HCl, 100 mM NaCl, 1 mM CaCl2), 1 mM MgCl2, 1% BSA) three times. Integrins αvβ3 and increasing concentrations of the compound of interest were added and incubated for 2 hours at room temperature, and then wells were washed three times with buffer A and incubated with a streptavidin HRP conjugate (1:1000 in buffer A) for 1 hour at room temperature. Finally, wells were washed three times with buffer A and 100 L peroxidase substrate TMB was added, and the reaction was terminated after 30 minutes with 50 L of 450 nm stop solution for TMB. Absorbance was determined at 450 nm with a Microplate Reader (Bio-Rad, Hercules, CA, USA). The best-fit 50% inhibitory concentration ($IC_{50}$ value) for the compounds were calculated by fitting the data with nonlinear regression using GraphPad Prism (GraphPad, San Diego, CA).

The following in vitro integrin αvβ3 binding results are for conjugate 26 (targeted integrin αvβ3 with MMAE chemo), conjugate 40 (targeted integrin αvβ3 with Niraparib chemo), and conjugate 45 (targeted integrin αvβ3 with Gemcitabine chemo).

For conjugate 26, $IC_{50}$=0.12±0.20 nM.

For conjugate 40, $IC_{50}$=3.36±0.22 nM.

For conjugate 45, $IC_{50}$=0.84±0.16 nM.

For the in vitro integrin αvβ3 binding assay, conjugates with low nanomolar $IC_{50}$ values are considered to be very potent. Thus, the preceding $IC_{50}$ values demonstrate that conjugates 26, 40 and 45, have excellent binding affinity to integrin αvβ3.

5.2 In Vitro Cell Adhesion Biological Assay

The cell adhesion assay is a cell-based assay that measures how well different compounds (i.e., different conjugates or structures) block the adhesion of integrin αvβ3 expressing U87 cells to fibrinogen, a macromolecule that binds to the integrin αvβ3 receptor. The $IC_{50}$ value is the compound concentration at which the compound displaces 50% of the cell adhesion to fibrinogen, which inhibits 50% of the cells from adhering to fibrinogen.

The cell adhesion assay is a functional cell assay, so the conjugates cannot be used with chemotherapy attached, because the conjugates will release the chemo over the course of the testing, killing the cells so that no readout can be obtained. Thus, the full conjugate molecule (targeting moiety, PEG, cleavable linker) is used without the chemo for this assay. Two compounds (conjugate 74 and conjugate 59) used are slightly different integrin αvβ3 targeting pieces with a large PEG (PEG 35 and PEG39, respectively), and the VCP cleavable linker attached. The chemo in the full conjugates is on the opposite end of the molecule from the binding portion, with a very large PEG spacer between the binding portion and the chemo. Thus, no significant difference in binding is expected with and without the added chemo.

96-well microtiter plates were coated with up to 1 g fibrinogen per well in 100 L phosphate-buffered saline (PBS) and incubated at 4° C. overnight. After washing with PBS, wells were blocked with PBS containing 1% bovine serum albumin (BSA) for 90 minutes at 22° C. Calcein AM labeled U87 cells were washed twice with PBS and resuspended in DMEM containing 0.1% BSA at a concentration of 1×106 cells per mL. Then, 100-μL aliquots of cell suspension with increasing concentrations of compound of interest were added to wells in triplicate. The plate was incubated in a humidified 37° C. incubator for 2 h. After washing with PBS, the fluorescence intensity of adherent cells was measured at an emission wavelength of 530 nm using an excitation wavelength of 485 nm by using a Microplate Reader.

The following cell adhesion results are for conjugate 74 and conjugate 59.

For conjugate 74, $IC_{50}$=54±2.2 nM.

For conjugate 59, $IC_{50}$=103±1.7 nM.

For the cell adhesion assay, $IC_{50}$ values in the 10-100 nM range are considered to be very potent.

Thus, the preceding IC50 values demonstrate that conjugates 74 and 59 have good potency in the cell adhesion assay. This implies that the comparable chemotherapy containing conjugates 26 and 61, which can't be tested in this assay because the chemotherapy will kill the cells used for the assay, should also be potent integrin avb3 binders.

5.3 In Vitro Cell Viability Biological Assay

The cell viability assay measures how effectively different compounds (i.e., different conjugates or structures) kill cancer cells in vitro. The $IC_{50}$ value is the compound concentration at which the conjugate kills 50% of the cells, which inhibits 50% of the cells from remaining alive.

For the cell viability assay, the actual potency $IC_{50}$ values depend on a number of factors, including the length of incubation time. Thus, the cell viability assay is particularly effective for determining the relative toxicity of different compounds.

Human glioblastoma cells (U87-luc) were seeded in 96-well plates (0.5 million cells per well) and were treated with the compounds of interest at concentrations 1, 3, 10, 30, and 100 M. At the end of the experiments, the cell cultures were supplemented with MTT reagent (3-(4,5-dimethylthiazol-2-yl)-2,5-diphenyltetrazolium bromide) and incubated for an additional 4 hours. Then, dimethyl sulfoxide (0.1% DMSO) was added to the cell culture to dissolve the formazan crystals and incubated for 10 minutes at room temperature. The absorbance rate of the cell cultures was read at 570 nm by using a Microplate Reader. All the reactions were performed in triplicate. Measured data of cellular proliferation were calculated using viability values of untreated control cells (100%).

Figure 1B:
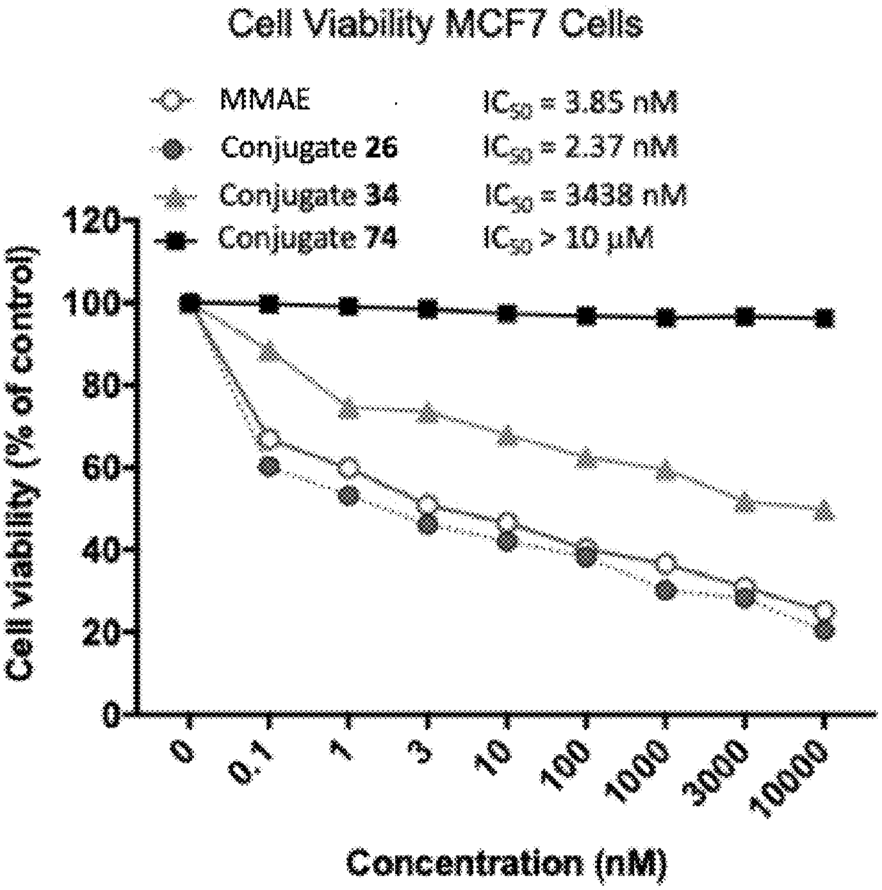

FIGS. 1A and 1B are graphs of cell viability versus compound concentration of conjugates 26, 34 and 74 (PEG35, no chemo, integrin αvβ3 targeting) for human glioblastoma U87 cells and human breast cancer MCF7 cells, respectively, in accordance with embodiments of the present invention.

Conjugate 26 is characterized by: PEG35, MMAE chemo, integrin αvβ3 targeting.

Conjugate 34 is characterized by: PEG10, MMAE chemo, integrin αvβ3 targeting.

Conjugate 74 is characterized by: PEG35, no chemo, integrin αvβ3 targeting.

The following cell adhesion results are for MMAE, conjugate 26, conjugate 34 and conjugate 74 using U87 cells.

FIG. 1A shows the following cell viability results, using U87 cells, for MMAE chemotherapy alone, and conjugates 26, 34 and 59.

For MMAE, $IC_{50}$=2.51 nM.

For conjugate 26, $IC_{50}$=1.12 nM.

For conjugate 34, $IC_{50}$=1028 nM.

For conjugate 74, $IC_{50}$>10 μM.

FIG. 1B shows the following cell viability results, using MCF7 cells, for MMAE chemotherapy alone, and conjugates 26, 34 and 59.

For MMAE, $IC_{50}$=3.85 nM.

For conjugate 26, $IC_{50}$=2.37 nM.

For conjugate 34, $IC_{50}$=3438 nM.

For conjugate 74, $IC_{50}$>10 μM.

Conjugate 26 has a large PEG (PEG35, 35 PEG monomer units) and looks almost identical to, and if anything a little better than, the chemotherapy alone (MMAE) (i.e., lower $IC_{50}$ value) for both U87 cells and MCF7 cells, indicating that the chemo is being released inside the cells with conjugate 26, as expected.

Conjugate 34 is the same as conjugate 26 except that conjugate 34 has a smaller PEG10 linker than the larger PEG35 linker of conjugate 26 and is 3 orders of magnitude less potent than conjugate 26 (deduced from ratios 1028 nM to 1.12 nM and 3438 nM to 2.37 nM of $IC_{50}$ values for U87 cells and MCF7 cells, respectively), which demonstrates the importance of the larger PEG to effectively release the chemo inside the cell.

Conjugate 74, which is a PEG36 conjugate without chemotherapy, does not cause cell death.

Figure 2A:
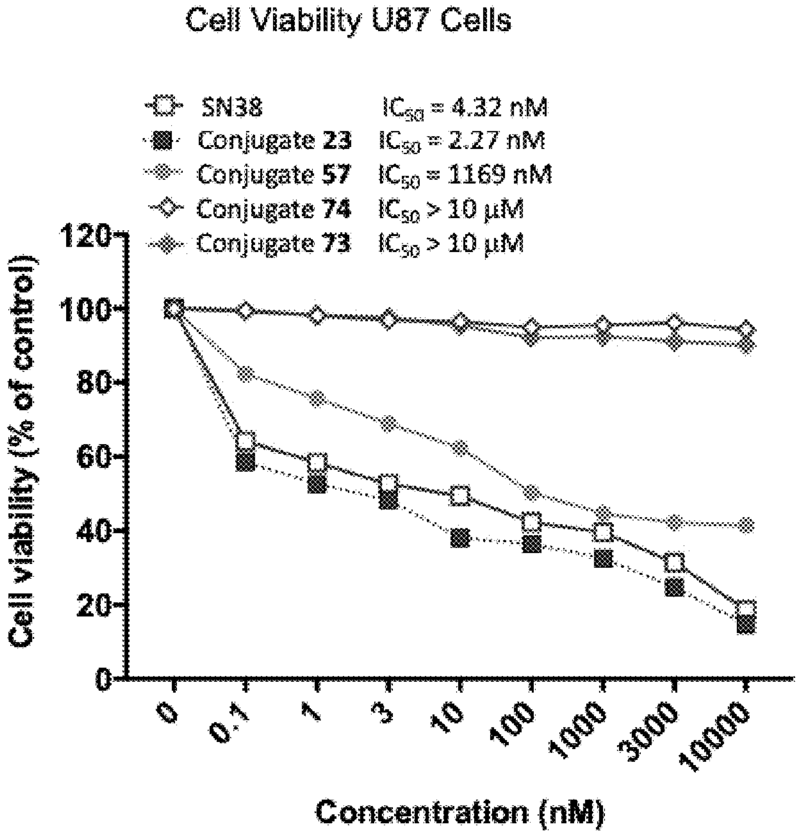
FIGS. 2A and 2B are graphs of cell viability versus compound concentration of conjugates 23, 57, 73 and 74 for the human glioblastoma U87 cells and the human breast cancer MCF7 cells, respectively, in accordance with embodiments of the present invention.
Figure 2B:
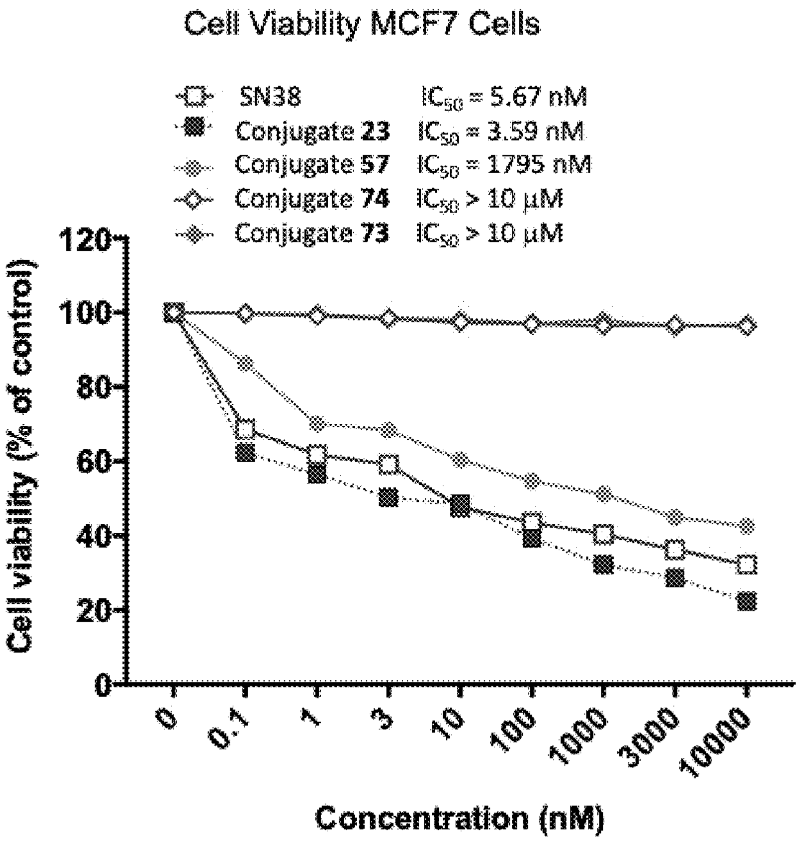

FIGS. 2A and 2B are graphs of cell viability versus compound concentration of conjugates 23, 57, 73 and 74 for the human glioblastoma U87 cells and the human breast cancer MCF7 cells, respectively, in accordance with embodiments of the present invention.

Conjugate 23 is characterized by: PEG35, SN38 chemo, integrin αvβ3 targeting.

Conjugate 57 is characterized by: PEG3, SN38 chemo, no targeting.

Conjugate 73 is characterized by: PEG36, SN38 chemo, no targeting.

Conjugate 74 is characterized by: PEG35, no chemo, integrin αvβ3 targeting.

FIG. 2A shows the following cell viability results, using U87 cells, for SN38 chemotherapy alone, and conjugates 23, 57, 73 and 74.

For SN38, $IC_{50}$=4.32 nM.

For conjugate 23, $IC_{50}$=2.27 nM.

For conjugate 57, $IC_{50}$=1169 nM.

For conjugate 73, $IC_{50}$>10 μM.

For conjugate 74, $IC_{50}$>10 μM.

FIG. 2B shows the following cell viability results, using MCF7 cells, for SN38 chemotherapy alone, and conjugates 23, 57, 73 and 74.

For SN38, $IC_{50}$=5.67 nM.

For conjugate 23, $IC_{50}$=3.59 nM.

For conjugate 57, $IC_{50}$=1795 nM.

For conjugate 73, $IC_{50}$>10 μM.

For conjugate 74, $IC_{50}$>10 μM.

The preceding $IC_{50}$ values demonstrate that conjugate 23, which is a PEG35 integrin αvβ3 targeted SN38 chemotherapy, has equivalent or slightly better than potency compared to SN38 alone for both U87 cells and MCF7 cells (i.e., lower $IC_{50}$ value of 2.27 nM for conjugate 23 than the $IC_{50}$ value of 4.32 nM for SN38 chemo alone for U87 cells; and lower $IC_{50}$ value of 3.59 nM for conjugate 23 than the $IC_{50}$ value of 5.67 nM for SN38 chemo alone for MCF7 cells.

Conjugates 74 is the targeted PEG35 conjugate with no chemotherapy.

Conjugate 73 is a PEG36 conjugate of SN38 and is similar to conjugate 23 which has the integrin αvβ3 targeting piece, except conjugate 73 does not have the integrin αvβ3 targeting piece and thus has no activity, assumedly because of lack of targeting and the large PEG36 keeps the conjugate 73 from entering cells, which is consistent with the relatively high values of IC50 of >10 μM for both U87 cells and MCF7 cells.

Conjugate 57, which is a small PEG (PEG3) attached to the Val-Cit-PAB-SN38 piece, does not have any integrin αvβ3 targeting, but still affects cell viability, although conjugate 57 is of the order of 1000 times less potent than both SN38 alone and conjugate 23 which is a lead SN38 conjugate having integrin αvβ3 targeting (deduced from $IC_{50}$ ratios of 1169 nM (conjugate 57) to 4.32 nM (SN38 alone) and 1169 nM (conjugate 57) to 2.27 nM (conjugate 23) for U87 cells. Similar $IC_{50}$ ratio comparisons from FIGS. 2A and 2B pertain to MCF7 cells. Because conjugate 57 does not have an integrin αvβ3 ligand, conjugate 57 must enter the cell via a non-integrin αvβ3 mediated mechanism, and a small amount of conjugate 57 gets to the late endosome or lysosome, where the SN38 is cleaved and released.

Conjugate 57 (having a small PEG3) has a similar potency to conjugate 34 (having a small PEG10) as deduced from $IC_{50}$ ratios of 1169 nM to 1028 nM and 1795 nM to 3438 nM for U87 cells and MCF7 cells, respectively, (see FIGS. 1A and 1B for $IC_{50}$ values for conjugate 34) which indicates that activity from the small PEG conjugates, whether having an integrin αvβ3 targeting piece or not, enter cells through a non-integrin αvβ3 mediated process. In other words, even if the small PEG conjugates have an integrin αvβ3 targeting piece, the small PEG conjugates should release chemotherapy equally well in tumor cells and non-tumor cells.

Note also that neither conjugate 57 nor conjugate 73 has integrin αvβ3 targeting, but conjugate 57 has some activity where conjugate 73 does not have activity, assumedly because the large PEG36 keeps conjugate 73 out of the cells, but some of the small PEG3 conjugate 57 gets into cells.

Figure 3A:
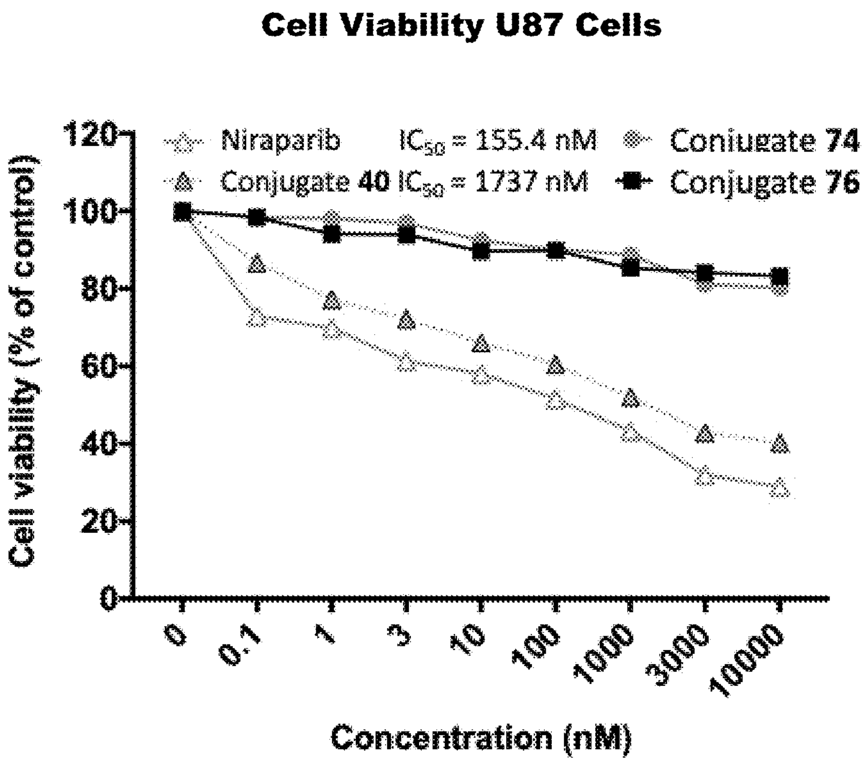
FIG. 3A is a graph of cell viability versus compound concentration of conjugates 40, 74, and 76 for the human glioblastoma U87 cells, in accordance with embodiments of the present invention.

FIG. 3A is a graph of cell viability versus compound concentration of conjugates 40, 74, 76 and Niraparib for the human glioblastoma U87 cells, in accordance with embodiments of the present invention.

Figure 3B:
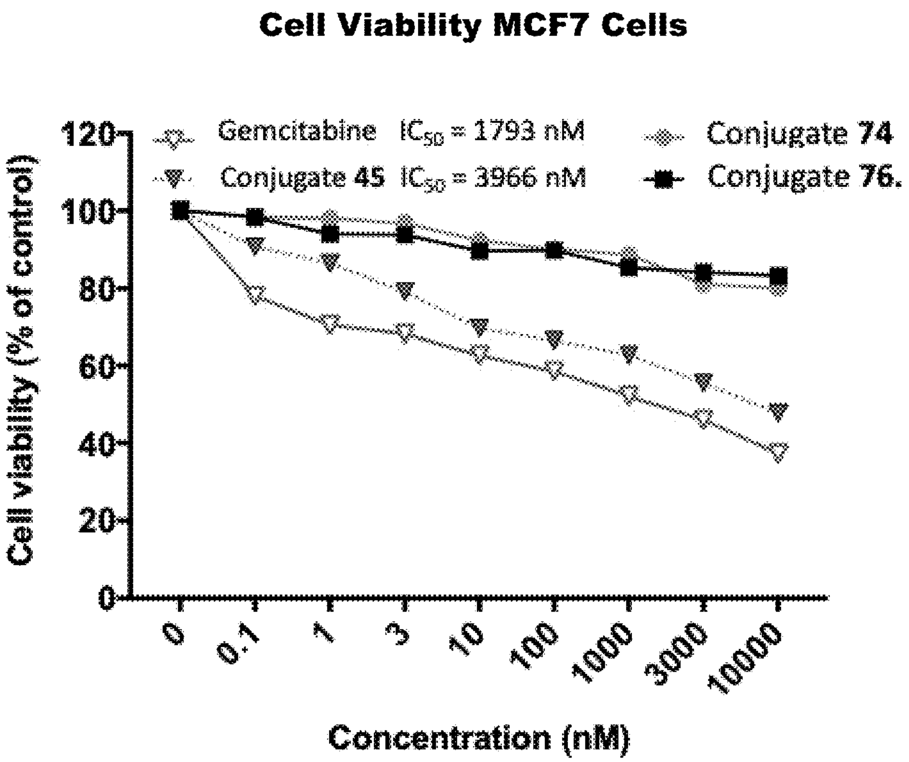
FIG. 3B is a graph of cell viability versus compound concentration of conjugates 45, 74, and 76 for the human breast cancer MCF7 cells, in accordance with embodiments of the present invention.

FIG. 3B is a graph of cell viability versus compound concentration of conjugates 45, 74, 76 and Gencitabine for MCF7 cells, in accordance with embodiments of the present invention.

Conjugate 40 is characterized by: PEG35, Niraparib chemo, integrin αvβ3 targeting.

Conjugate 45 is characterized by: PEG35, Gemcitabine chemo, integrin αvβ3 targeting.

Conjugate 74 is characterized by: PEG35, no chemo, integrin αvβ3 targeting.

Conjugate 76 is characterized by: PEG36, no chemo, integrin αvβ3 targeting.

FIG. 3A shows the following cell viability results using U87 cells for Niraparib chemotherapy alone and conjugate 40 which includes Niraparib chemotherapy.

For Niraparib, $IC_{50}$=155.4 nM.

For conjugate 40, $IC_{50}$=1737 nM.

FIG. 3B shows the following cell viability results using the human breast cancer MCF7 cells for Gemcitabine chemotherapy alone and conjugate 45 which includes Gemcitabine chemotherapy.

For Gemcitabine, $IC_{50}$=1793 nM.

For conjugate 45, $IC_{50}$=3966 nM.

The results in FIGS. 3A and 3B are similar to the results in FIGS. 1A, 1B, 2A and 2B, except that the Niraprib conjugate 40 and the Gemcitabine conjugate 45 are tested for cell viability in FIGS. 3A and 3B. These chemotherapies of Niraparib and Gemcitabine are less potent than MMAE and SN38 in FIGS. 1A, 1B and FIGS. 2A, 2B, respectively, based on the higher $IC_{50}$ values for Niraparib and Gemcitabine in comparison with the lower $IC_{50}$ values for MMAE and SN38, but the in vitro data in FIGS. 3A and 3B demonstrate that integrin αvβ3 selective targeting using the chemotherapies of Niraparib and Gemcitabine can be implemented.

5.4 In Vivo Biological Efficacy

The animal model and treatment used a total of 50 Athymic Nude-Foxn1$^{nu}$ male mice which were purchased from Envigo, Indianapolis, IN, USA. The mice were housed in a clean room under strict conditions. Under the approval of the Institutional Animal Care and Use Committee, all animal protocols were carried out in line with the National Institute of Health Guide for the Care and Use of Laboratory Animals. Once cells reached 70-80% confluency, the cells were collected and counted. About $2\times10^6$ CWR-R1ca-Luc cells were mixed in 1:1 Matrigel® Matrix (Life Sciences, Tewksbury, MA) and injected subcutaneously into the flank of each mouse. Measurement of tumor volume of prostate cancer tumors of mice and mice weights were taken biweekly. When a palpable tumor developed, size 300-500 $mm^3$, mice were randomized into 10 groups with 5 mice in each group. The corresponding treatment was injected subcutaneously every day per each group up to 3 weeks. Before starting the treatment, the mice were injected with luciferin 150 mg/kg intraperitoneally. After 20 minutes, the mice were anesthetized in an induction chamber using 2% isoflurane, and bioluminescence images were taken using IVIS® Lumina III In Vivo Imaging System (PerkinElmer, Boston, MA) as a base line. Before the end of the experiment, the imaging process was repeated for all mice groups.

All compounds were dosed at 0.5 mole of compound/kg mouse each day. Thus, a 20 g mouse was dosed at 10 mole of compound per day, and larger mice were dosed at correspondingly higher doses in proportionality to mouse body weight. The compounds were formulated in phosphate-buffered saline (PBS), except Conjugate 62 was formulated in 5% dimethyl sulfoxide (DMSO) in PBS, and MMAE was formulated in 1% DMSO in PBS, as these compounds were less soluble in straight PBS. The concentration of each formulation was adjusted so that each dose would be 10 μL solution/g mouse.

A person of ordinary skill in the art could apply principles of elementary chemistry to easily convert the dose of 0.5 mole of compound/kg mouse each day to units of mg of compound/kg mouse each day. Such conversion is a function of the molecular weight of the compound. Therefore, the converted dose is different for different conjugates having different respective molecular weights. For example, the converted dose for conjugate 61 is 0.8 mg/kg mouse/day.

FIGS. 4A, 4B, 5, 6 and 7 all pertain to the same experiment conducted with mice having prostate cancer over a study period of three weeks.

Figure 4A:
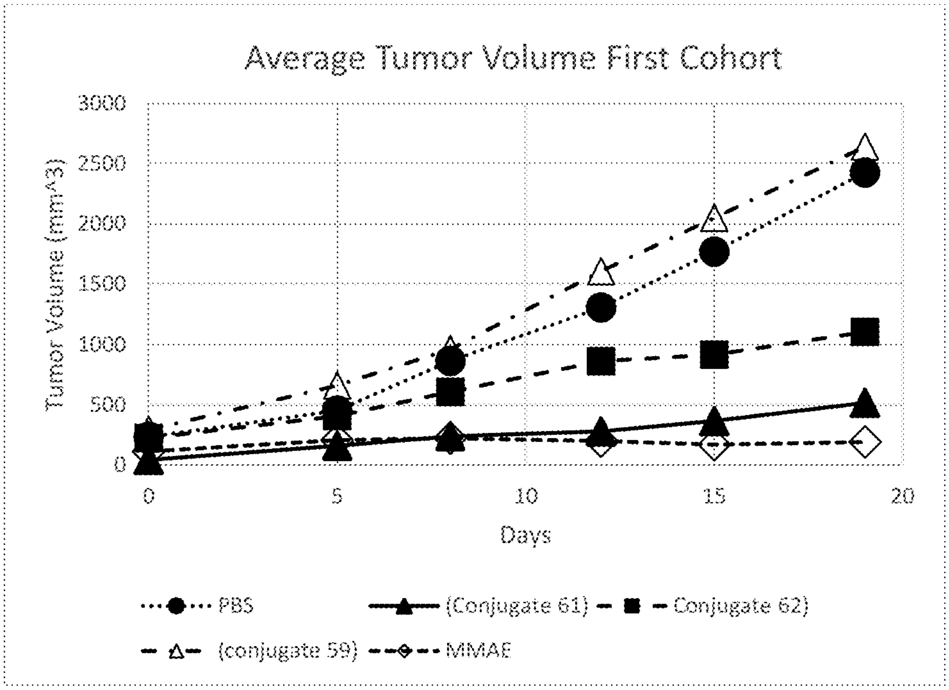
FIG. 4A and FIG. 4B are graphs of average prostate cancer tumor volume of mice versus time over a study period of three weeks in two separate experiments of in vivo efficacy for the mice, denoted as a first cohort and a second cohort, respectively, in accordance with embodiments of the present invention.
Figure 4B:
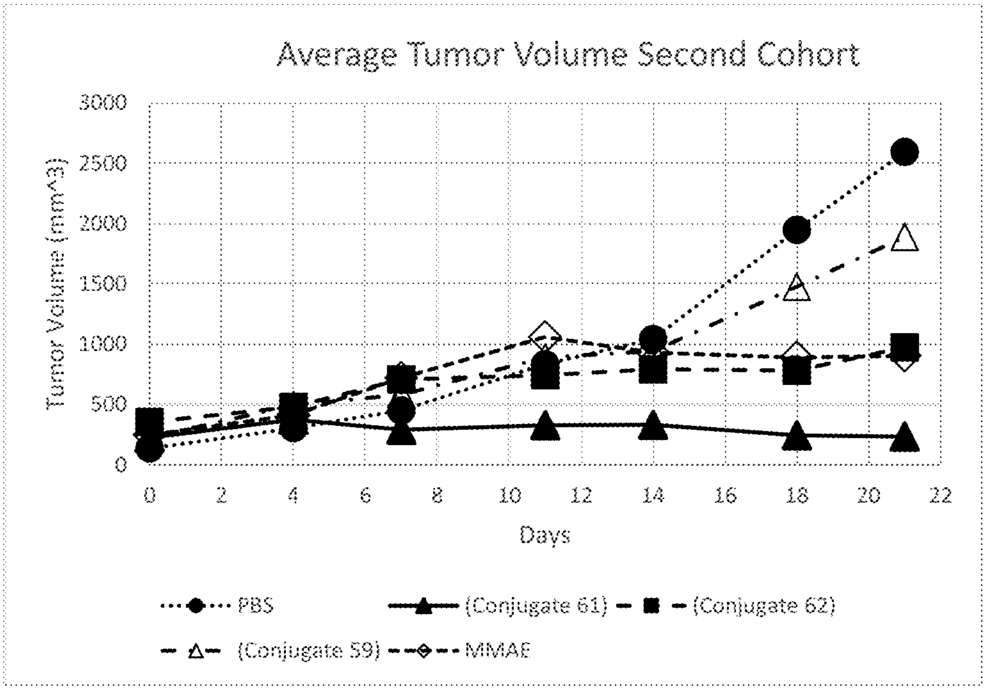

FIG. 4A and FIG. 4B are graphs of average prostate cancer tumor volume of mice versus time over a study period of three weeks in two separate experiments of in vivo efficacy for the mice, denoted as a first cohort and a second cohort, respectively, in accordance with embodiments of the present invention. Time is measured from initial exposure of the tumor to MMAE chemotherapy. Each cohort displays an average tumor volume over the period of 3 weeks with daily injection of different conjugates, namely conjugates 61, 62 and 59, and PBS is the control.

Conjugate 61 is a lead integrin αvβ3 conjugate with MMAE chemotherapy and a PEG39 linker.

Conjugate 62 is a lead integrin αvβ3 conjugate with MMAE chemotherapy and a PEG15 linker.

Conjugate 59 is the integrin αvβ3 targeting piece, PEG39, and cleavable linker with no MMAE, which essentially is conjugate 61 without the chemo.

MMAE is chemotherapy monomethylauristatin E. The 3 MMAE containing treatments (MMAE alone, conjugate 61, conjugate 62) show smaller tumor volumes than the non-MMAE conjugate 59, but the PEG39 MMAE conjugate 61 inhibits tumor growth more than the PEG15 conjugate 62 in the experiments of both FIGS. 4A and 4B. Thus, MMAE chemo is being effectively delivered with conjugates 61 and 62, but the larger PEG39 conjugate 61 is more effective in inhibiting tumor growth than the smaller PEG15 conjugate 62. Thus, although both conjugate 61 and conjugate 62 are therapeutically effective for inhibiting the mice tumor growth, conjugate 61 is more therapeutically effective than is conjugate 62.

Figure 5:
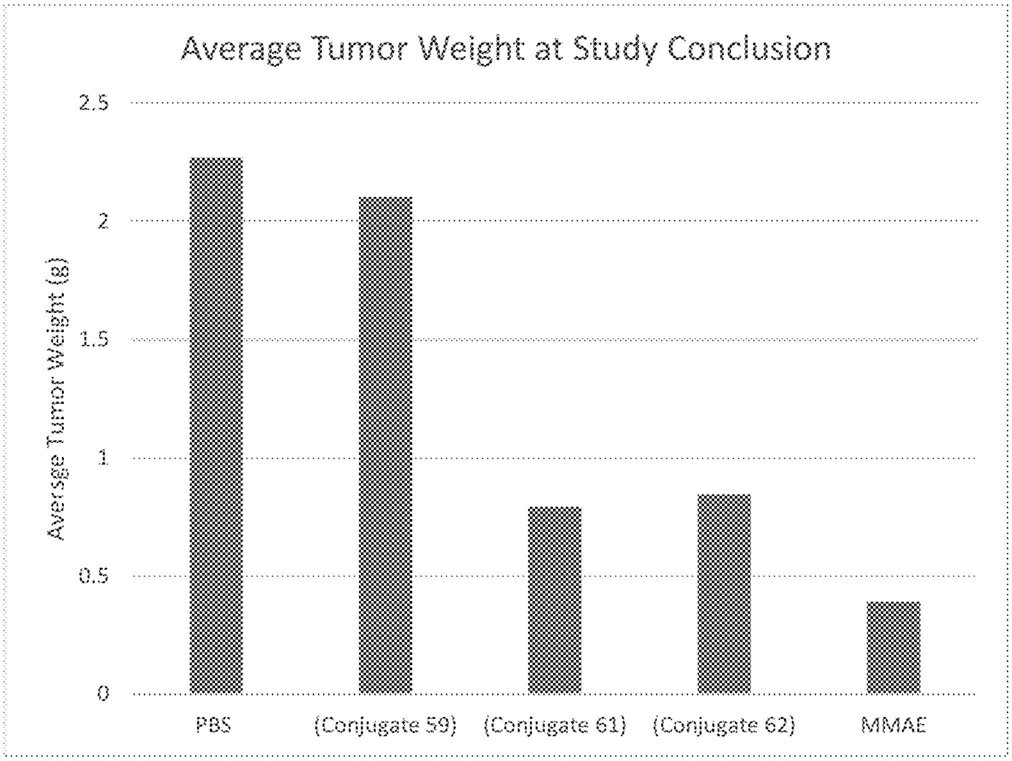
FIG. 5 is a bar graph of average prostate cancer tumor weight of the mice for conjugate 59, conjugate 61, conjugate 62, MMAE chemo, and PBS (control) at the conclusion of a study period of three weeks, in accordance with embodiments of the present invention.

FIG. 5 is a bar graph of average prostate cancer tumor weight of the mice for conjugate 59, conjugate 61, conjugate 62, MMAE chemo, and PBS (control) at the conclusion of the study period of three weeks, in accordance with embodiments of the present invention.

The 3 MMAE containing treatments (i.e., MMAE, conjugate 61, conjugate 62) show smaller tumor weights than the non-MMAE conjugate 59. The tumor weight for the larger PEG39 MMAE conjugate 61 is comparable to the smaller PEG15 MMAE conjugate 62, which does not disclose anything about the tumor viability with the different treatment groups, because it is possible to have 2 tumors of equal weight where 1 tumor has mostly viable tissue, and the other tumor has mostly dead, necrotic tissue.

Figure 6:
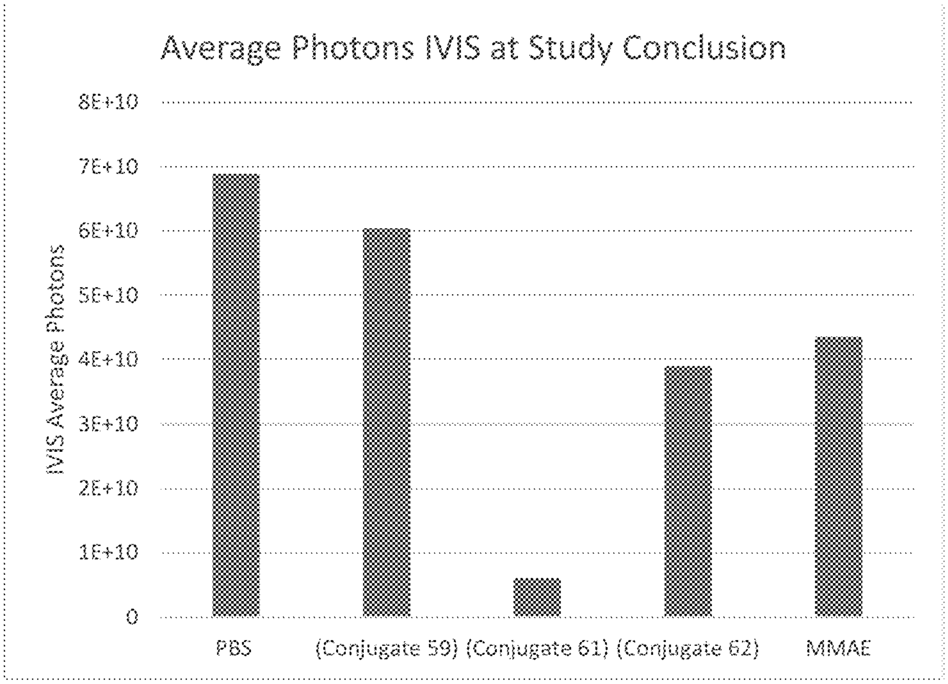
FIG. 6 is a bar graph of average photons, using In Vivo Imaging System (IVIS®) to scan the mice, at the conclusion of the study period of three weeks for conjugate 59, conjugate 61, conjugate 62, MMAE chemo, and PBS (control), in accordance with embodiments of the present invention.

FIG. 6 is a bar graph of average photons, using In Vivo Imaging System (IVIS®) to scan the mice, at the conclusion of the study period of three weeks for conjugate 59, conjugate 61, conjugate 62, MMAE chemo, and PBS (control), in accordance with embodiments of the present invention. The IVIS® average photons are a proportional measure of the amount of viable tumor tissue of the mice for each treatment group.

The 3 MMAE containing treatments (i.e., MMAE, conjugate 61, conjugate 62) show smaller IVIS® numbers than the non-MMAE conjugate 59. The IVIS® numbers for the larger PEG39 MMAE conjugate 61 are much smaller than the smaller PEG15 conjugate 62 and MMAE alone, which implies that the larger PEG39 conjugate 61 treated mice have very little viable tumor tissue compared to the small PEG15 conjugate and MMAE treated mice. Thus, conjugate 61 is more therapeutically effective than is conjugate 62 for destroying viable tumor tissue in the mice.

Figure 7:
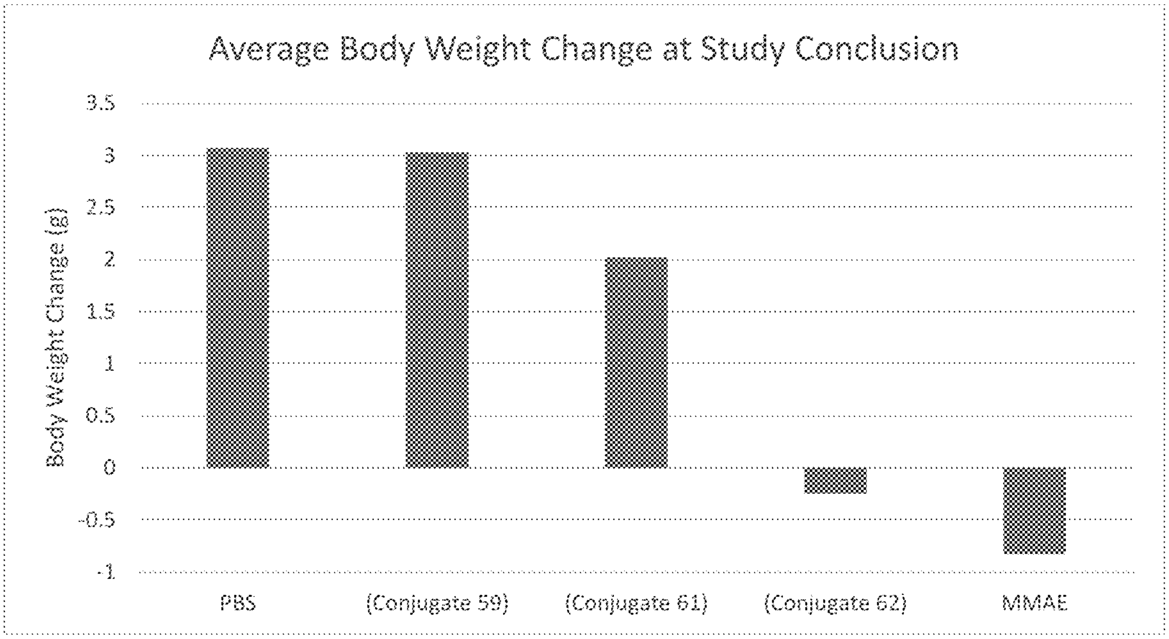
FIG. 7 is a bar graph of average body weight of the mice at the conclusion of the study period of three weeks for conjugate 59, conjugate 61, conjugate 62, MMAE chemo, and PBS (control), in accordance with embodiments of the present invention.

FIG. 7 is a bar graph of average body weight of the mice at the conclusion of the study period of three weeks for conjugate 59, conjugate 61, conjugate 62, MMAE chemo, and PBS (control), in accordance with embodiments of the present invention. Average body weight changes over the course of the study relative to control, particularly due to loss of body weight, which can relate to toxicity of the treatment group.

The 3 MMAE containing treatments (i.e., MMAE, conjugate 61, conjugate 62) show less body weight gain than the non-MMAE conjugate 59 treated animals, but the larger PEG39 MMAE conjugate 61 shows only a small difference compared to the PBS control, and the smaller PEG15 MMAE conjugate 62 and MMAE alone actually show a loss of body weight over the course of the experiment, which indicates high toxicity for PEG 15 conjugate 62 and MMAE alone, and mild toxicity for the larger PEG39 conjugate 61. Thus, conjugate 61 is more therapeutically effective than is conjugate 62 for maintaining relatively low toxicity introduced by the treatments.

Note that the cathepsin B cleavable linker Val-Cit-PAB is used, which can result in small amounts of release of the chemotherapy MMAE in the serum due to small amounts of a specific esterase found in mouse plasma, but not the plasma of other mammals, that can cleave small amounts of the val-cit-PAB linker, releasing small amounts of MMAE, while the conjugate is in the bloodstream, which would not be a problem in humans and most other mammals that do not have this specific esterase.

5.5 Application of Test Results to Treatment of Cancer

αv integrins, including integrin αvβ3, are highly overexpressed and highly upregulated in most cancer cells. The disclosed conjugates of the present invention bind tightly with these αv integrins and are internalized via these αv integrins, which results in release of a high level of chemotherapy in the tumor cells relative to chemotherapy released systemically in normal cells, with an end result of effective chemotherapy mediated death of cancer cells with minimal off-target toxicity in normal cells.

Conjugates of the present invention are effective for treating those types of cancer in which these αv integrins are overexpressed, which encompasses most type of cancers. Research evaluating integrin αvβ3 expression and overexpression in numerous different cancer types, and the down-regulation of the integrin αvβ3 expression in such cancer types by different αvβ3 antagonists, is presented in Godugu et al., *Cancer Treatment and Research Communications* 28 (2021) 100395 which is incorporated by reference in its entirety.

The preceding test results demonstrate successful treatment of prostate cancer (in vivo mouse studies), glioblastoma (in vitro cell viability studies with U87 cells), and breast cancer (in vitro cell viability studies with MCF7 cells). Integrin αvβ3 is highly overexpressed in the prostate cancer cells, glioblastoma cells, and breast cancer cells used in the preceding testing.

In general, conjugates of the present invention are configured to be effective for treating cancer types having solid tumors and/or liquid tumors in mammals (e.g., humans, mice, etc.), as long as there is overexpression of αv integrins in tumors comprising cancer cells of the cancer type, which encompasses most type of cancers. As a matter of definition, αv integrins are overexpressed in tumors comprising cancer cells if there is more of the av integrin receptor protein in the cancer cells in the active state than in normal cells which are quiescent or not active.

Cancers having solid tumors in which αv integrins are overexpressed, and are thus amenable to treatment by conjugates of the present invention, include, inter alia, glioblastoma, pancreatic, ovarian, breast, prostate, bladder, lung and liver cancer. Cancers having liquid tumors in which αv integrins are overexpressed, and are thus amenable to treatment by conjugates of the present invention, include, inter alia, acute myeloid leukemia, multiple myeloma, Lymphoma and chronic lymphocytic leukemia. See U.S. Pat. No. 11,186,551 issued Nov. 30, 2021 to Mousa, S. A et al.

A therapeutically effective dose of a compound or conjugate of the present invention for treating a mouse for cancer can be converted into a human equivalent dose (HED) for treating a human being for the cancer using a scale factor determined by methods known in the art, such as methods described in Nair et al., *A simple practice guide for dose conversion between animals and human*, Journal of Basic and Clinical Pharmacy (2016) 27-31 (hereinafter, "Nair"). As explained in Nair, the scale factor depends on a ratio $(K_m)_{mouse}/(K_m)_{human}$ where $K_m$ is average body weight of species (i.e., mouse, human) divided by body surface area of the species. Illustratively, applying a scale factor of 0.081 appearing in Table 2 in Nair for mice based on an average human body weight of 60 kg and an average mouse body weight of 0.02 kg, to the previously mentioned dose of 0.8 mg/kg mouse/day for conjugate 61, HED for conjugate 61 is 0.0648 mg/kg human/day. For a first human dose, Nair suggests reducing the calculated HED by a factor of 10 to increase the safely of the first dose.

An individualized method of determining HED for a human whose weight differs from the average human body weight of 60 kg utilizes $K_m$ for the actual weight of the human. An example of such an individualized method may be found in the reference of: *Converting mouse dosages to human equivalent dosages (HED)* retrieved on 04/02/2023 from the Internet: <URL: https://www.reddit.com/r/NicotinamideRiboside/comments/4jf3gz/converting_mouse_dosages_t o_human_equivalent>, which determines $K_m$ for a human as a function of the human's weight and height. The preceding reference notes that $K_m$ for a human average weight of 60 kg is 37, in contrast with a $K_m$ of 45 for an actual human weight of 100 kg. It is noted that 45 is about 22% higher than 37.

In summary, a variety of alternative methods for determining HED are known and accessible to a person of ordinary skill in the art.

In one embodiment, a therapeutically effective dose for humans for the compounds and conjugates of the present invention is in a range of 0.01-10 mg/kg human, administered (e.g., subcutaneously) periodically (e.g., daily, weekly, etc.).

The test results, obtained using novel and unobvious conjugates having the larger PEGs and not including the standard multivalent nitrogen moieties, demonstrate surprising and unexpected good av integrin activity with improved in vivo potency and in vivo safety, as shown supra.

Examples and embodiments of the present invention described herein have been presented for illustrative purposes and should not be construed to be exhaustive. While embodiments of the present invention have been described herein for purposes of illustration, many modifications and changes will become apparent to those skilled in the art. The description of the present invention herein explains the principles underlying these examples and embodiments, in order to illustrate practical applications and technical improvements of the present invention over known technologies, computer systems, and/or products.

What is claimed is:

1. A chemical compound comprising the following Markush structure:

$A-L_1-PEG_1-L_2-PEG_2-CL-X$ wherein $A-L_1-PEG_1$ is a targeting structure configured for targeting αv integrins in cancer cells and does not include a standard multivalent nitrogen moiety;

wherein A is a structure that includes a standard carboxylic acid moiety;

wherein $L_1$ is a first linking structure selected from the group consisting of

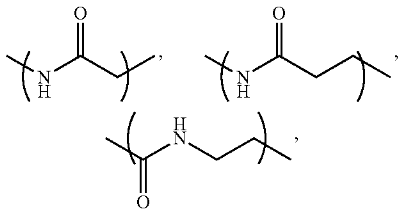

and NULL;

wherein $PEG_1$ is the following polyethylene glycol structure, wherein $n_2$ is in a range of 5-72:

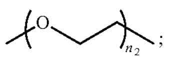

wherein $L_2$ is the following second linker structure, wherein $n_3$ is in a range of 0-4:

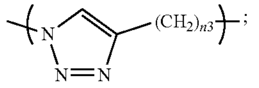

wherein $PEG_2$ is the following polyethylene glycol repeating structure, wherein $n_4$ is in a range of 0-67 and $n_2+n_4$ is in a range of 20-72:

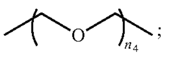

wherein CL is a cleavable linker; and wherein X is either Chemo1 or $L_3$-Chemo2, wherein Chemo1 denotes a first chemotherapy, wherein Chemo2 denotes a second chemotherapy, and wherein $L_3$ is the following linker that links Chemo2 to CL:

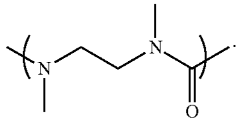

wherein

A =

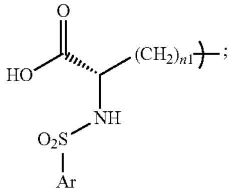

wherein $n_1$ is in a range of 1-6;

wherein Ar is selected from the group consisting of

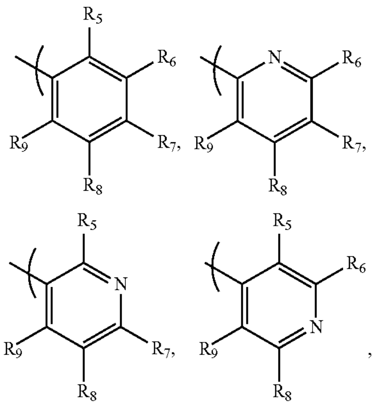

-continued

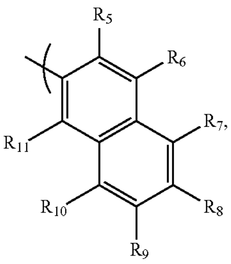

and

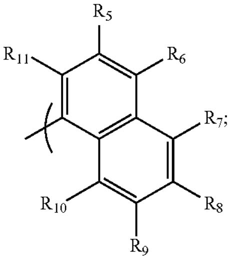

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2$Me, —O-Alkyl, and -3,5-dimethyl-1-pyrazolyl;

wherein Alkyl is selected from the group consisting of: Me, Et, iPr, nPr, nBu, iBu, secBu, tBu, $C_5$-$C_{12}$ n-alkyl, cyclopentyl, and cyclohexyl; and wherein Me denotes Methyl, Et denotes Ethyl, Pr denotes Propyl, and Bu denotes Butyl.

2. The chemical compound of claim 1, wherein $n_4$ is in a range of 0-43 and $n_2$+$n_4$ is in a range of 20-48.

3. The chemical compound of claim 1, wherein $n_4$=0.

4. The chemical compound of claim 1, wherein X is Chemo1.

5. The chemical compound of claim 1, wherein X is $L_3$-Chemo2.

6. The chemical compound of claim 1, wherein $L_1$ is NULL.

7. The chemical compound of claim 1, wherein $L_1$ is selected from the group consisting of

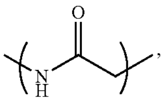

,

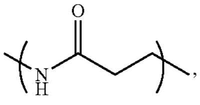

, and

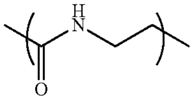

.

8. The chemical compound of claim 1, wherein the chemical compound is

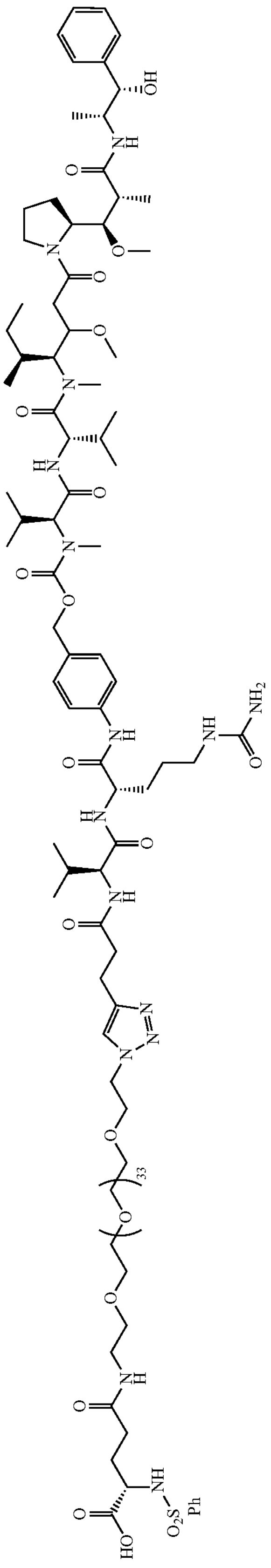
or
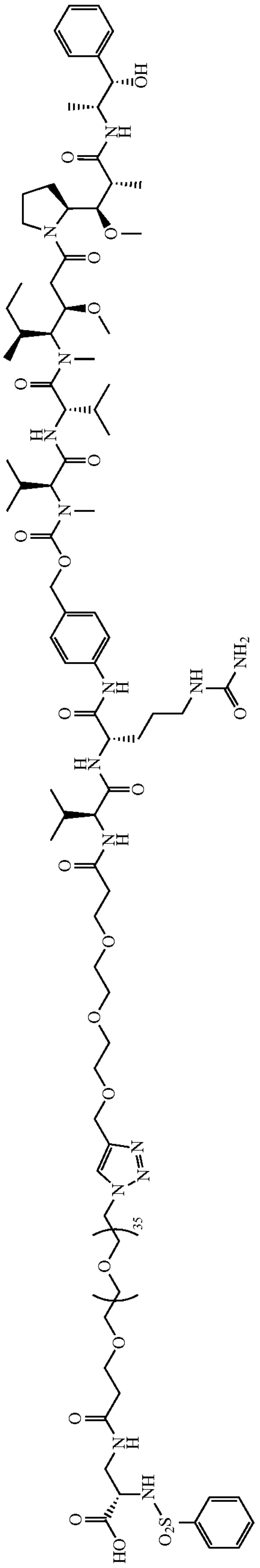

9. A chemical compound, comprising the following Markush structure:

A-$L_1$-$PEG_1$-$L_2$-PEG2-CL-X wherein A-$L_1$-$PEG_1$ is a targeting structure configured for targeting αv integrins in cancer cells and does not include a standard multivalent nitrogen moiety;

wherein A is a structure that includes a standard carboxylic acid moiety;

wherein $L_1$ is a first linking structure selected from the group consisting of

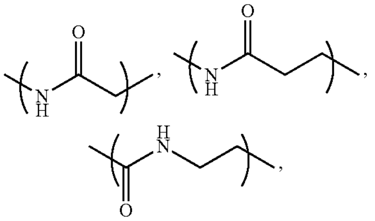

and NULL;

wherein $PEG_1$ is the following polyethylene glycol structure, wherein $n_2$ is in a range of 5-72:

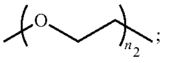

wherein $L_2$ is the following second linker structure, wherein $n_3$ is in a range of 0-4:

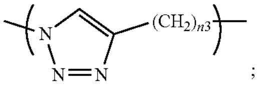

wherein $PEG_2$ is the following polyethylene glycol repeating structure, wherein $n_4$ is in a range of 0-67 and $n_2$+$n_4$ is in a range of 20-72:

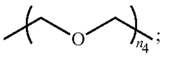

wherein CL is a cleavable linker; and wherein X is either Chemo1 or $L_3$-Chemo2, wherein Chemo1 denotes a first chemotherapy, wherein Chemo2 denotes a second chemotherapy, and wherein $L_3$ is the following linker that links Chemo2 to CL:

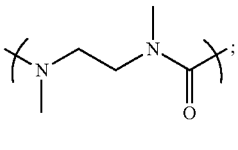

wherein

A =

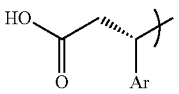

and $L_1$ =

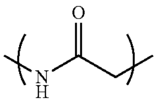

or

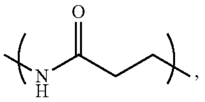

wherein Ar is selected from the group consisting of

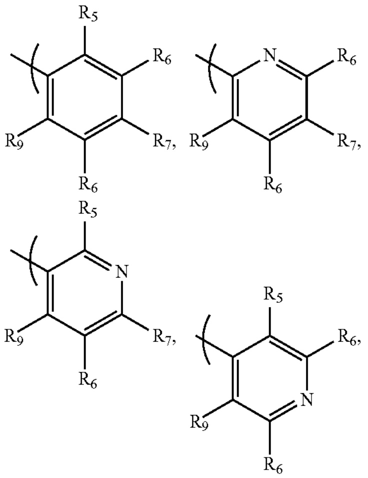

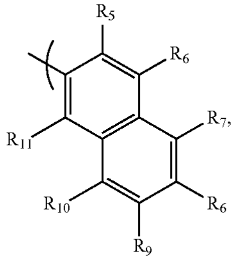

and

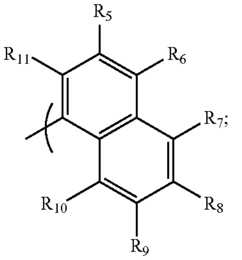

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2$Me, —O-Alkyl, and -3,5-dimethyl-1-pyrazolyl;

wherein Alkyl is selected from the group consisting of: Me, Et, iPr, nPr, nBu, iBu, secBu, tBu, $C_5$-$C_{12}$ n-alkyl, cyclopentyl, and cyclohexyl; and wherein Me denotes Methyl, Et denotes Ethyl, Pr denotes Propyl, and Bu denotes Butyl.

10. The chemical compound of claim 9, wherein the chemical compound is

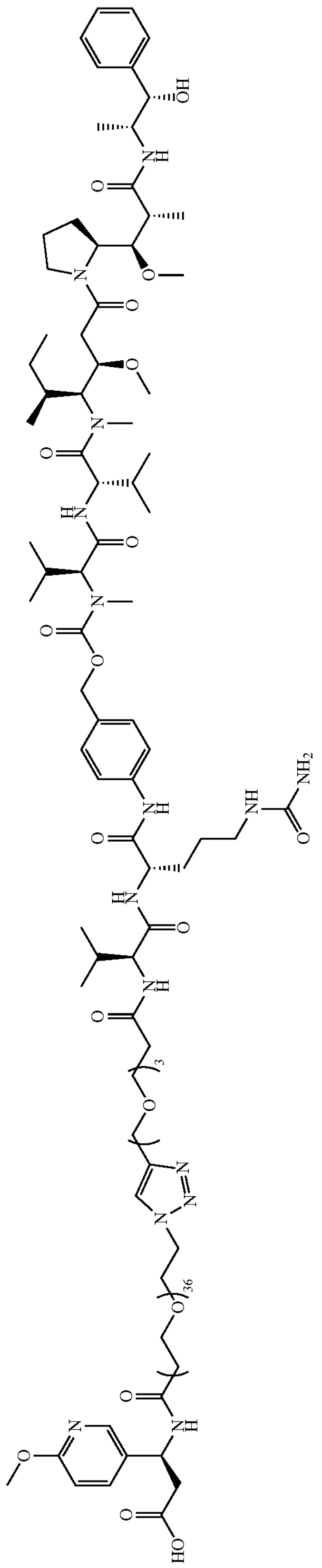

11. A chemical compound, comprising the following Markush structure:

$A\text{-}L_1\text{-}PEG_1\text{-}L_2\text{-}PEG_2\text{-}CL\text{-}X$ wherein $A\text{-}L_1\text{-}PEG_1$ is a targeting structure configured for targeting αv integrins in cancer cells and does not include a standard multivalent nitrogen moiety;

wherein A is a structure that includes a standard carboxylic acid moiety;

wherein $L_1$ is a first linking structure selected from the group consisting of

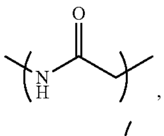
,
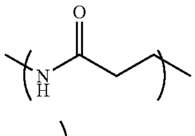
,
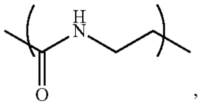
, and NULL;

wherein $PEG_1$ is the following polyethylene glycol structure, wherein $n_2$ is in a range of 5-72:

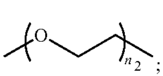
;

wherein $L_2$ is the following second linker structure, wherein $n_3$ is in a range of 0-4:

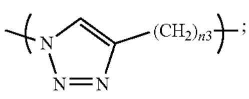

wherein $PEG_2$ is the following polyethylene glycol repeating structure, wherein 114 is in a range of 0-67 and $n_2+n_4$ is in a range of 20-72:

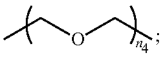

wherein CL is a cleavable linker; and wherein X is either Chemo1 or $L_3$-Chemo2, wherein Chemo1 denotes a first chemotherapy, wherein Chemo2 denotes a second chemotherapy, and wherein $L_3$ is the following linker that links Chemo2 to CL:

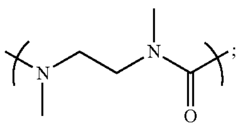

wherein

A =
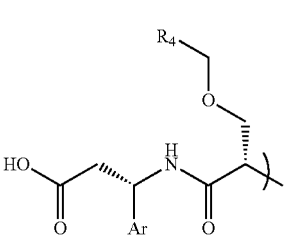

and $L_1$ =
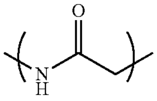
or
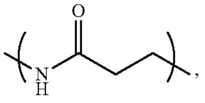
, wherein R4 is selected from the group consisting of hydrogen, Alkyl, and Ar;

wherein Alkyl is selected from the group consisting of Me, Et, iPr, nPr, nBu, iBu, secBu, tBu, $C_5$-$C_{12}$ n-alkyl, cyclopentyl, and cyclohexyl;

wherein Ar is selected from the group consisting of

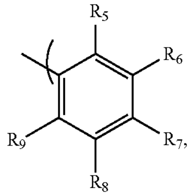
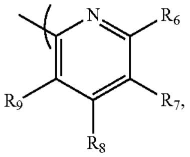
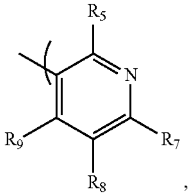
,
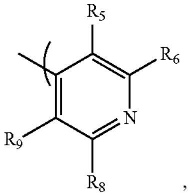
,
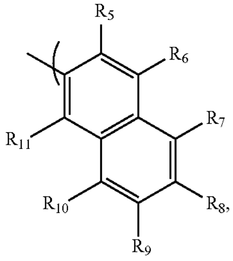
and
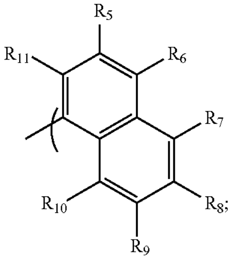

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2Me$, —O-Alkyl, and -3,5-dimethyl-1-pyrazolyl;

wherein Alkyl is selected from the group consisting of: Me, Et, iPr, nPr, nBu, iBu, secBu, tBu, $C_5$-$C_{12}$ n-alkyl, cyclopentyl, and cyclohexyl; and wherein Me denotes Methyl, Et denotes Ethyl, Pr denotes Propyl, and Bu denotes Butyl.

12. The chemical compound of claim 11, wherein the chemical compound is

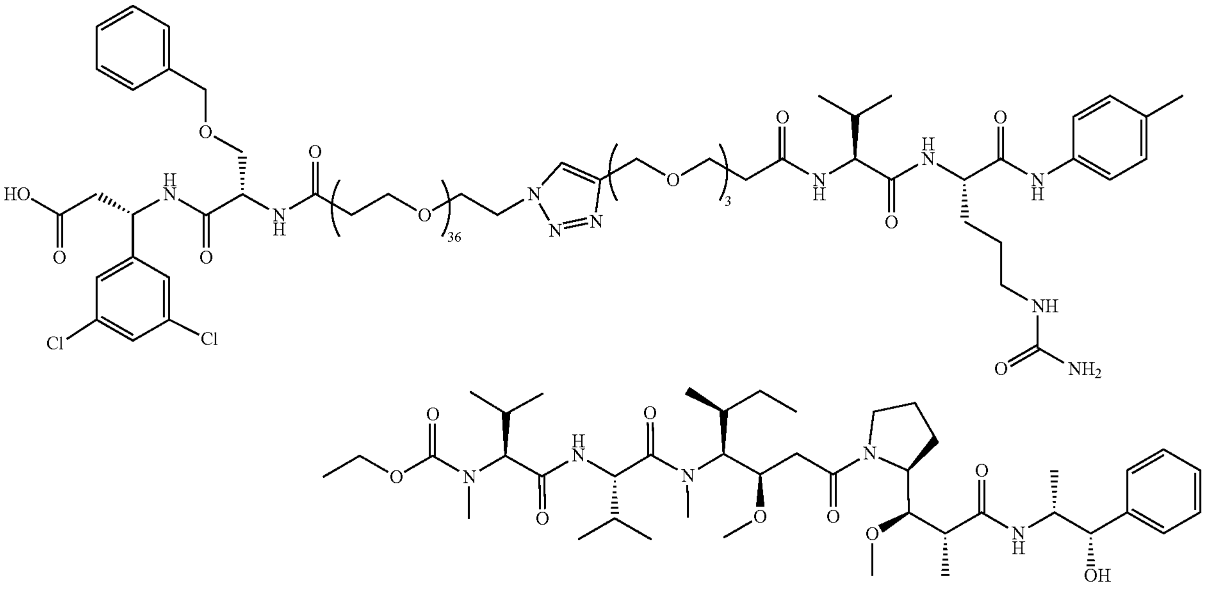

13. A chemical compound, comprising the following Markush structure:

A-$L_1$-$PEG_1$-$N_3$ wherein A-$L_1$-$PEG_1$ is a targeting structure configured for targeting αv integrins in cancer cells and does not include a standard multivalent nitrogen moiety;

wherein A is a structure that includes a standard carboxylic acid moiety;

wherein $L_1$ is a first linking structure selected from the group consisting of;

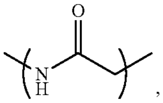 , 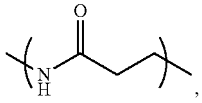 , and 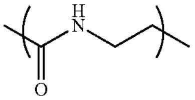 ;

and wherein $PEG_1$ is the following polyethylene glycol structure, wherein $n_2$ is in a range of 5-72:

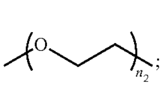 ;

wherein

A = 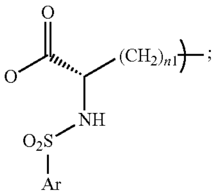 ;

wherein $n_1$ is in a range of 1-6;

wherein Ar is selected from the group consisting of:

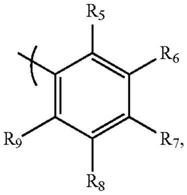 , 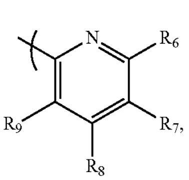 ,

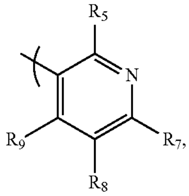 , 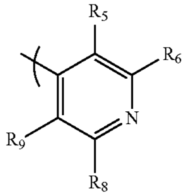 ,

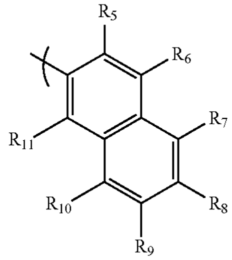 and 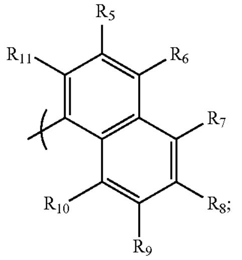 ;

wherein $R_5$-$R_{11}$ are each independently selected from the group consisting of: H, Me, Et, iPr, nPr, nBu, iBu, secBu, tBu, $C_5$-$C_{12}$ n-alkyl, cyclopentyl, phenyl, F, Cl, Br, —CN, —$CF_3$, —$OCF_3$, —$CHF_2$, —$OCHF_2$, —$SO_2Me$, —O-Alkyl, and -3,5-dimethyl-1-pyrazolyl, wherein Alkyl is selected from the group consisting of: Me, Et, iPr, nPr, nBu, iBu, secBu, tBu, $C_5$-$C_{12}$ n-alkyl, cyclopentyl, and cyclohexyl;

and wherein Me denotes Methyl, Et denotes Ethyl, Pr denotes Propyl, and Bu denotes Butyl.

14. The chemical compound of claim 13, wherein the chemical compound is

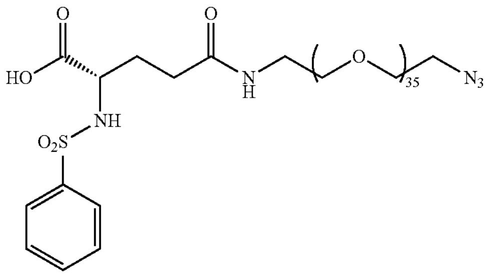

or

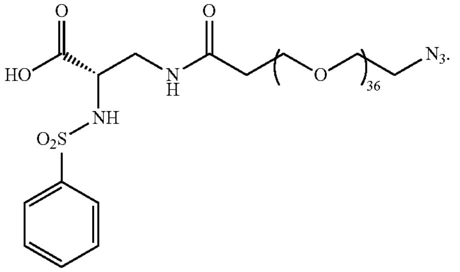

15. A chemical compound, comprising the following Markush structure:

A-$L_1$-$PEG_1$-OMethyl wherein A-$L_1$-$PEG_1$ is a targeting structure configured for targeting αv integrins in cancer cells and does not include a standard multivalent nitrogen moiety;

wherein A is a structure that includes a standard carboxylic acid moiety;

wherein $L_1$ is a first linking structure selected from the group consisting of

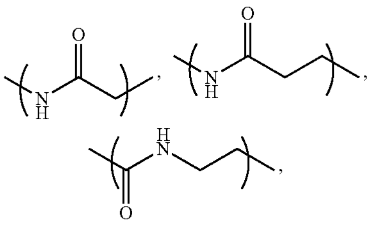

and NULL;

wherein $PEG_1$ is the following polyethylene glycol structure, wherein $n_2$ is in a range of 5-72:

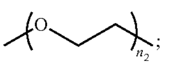

wherein

A = 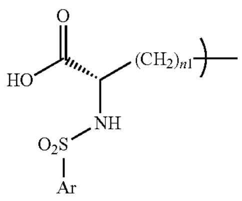

wherein $n_1$ is in a range of 1-6:

wherein Ar is selected from the group consisting of

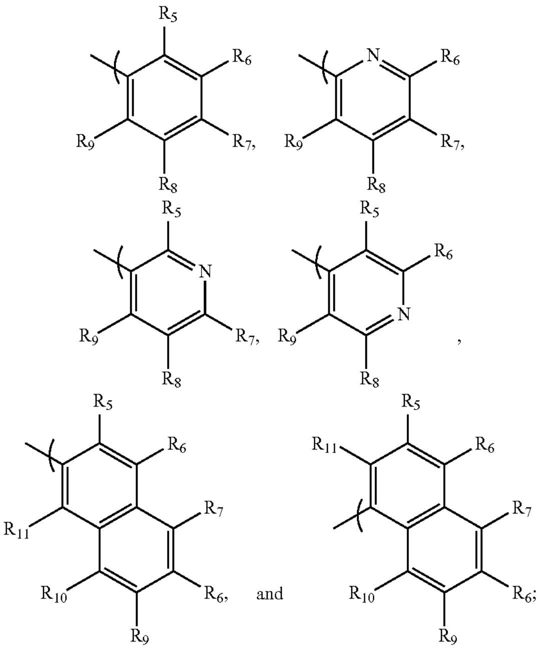

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2$Me, —O-Alkyl, and -3,5-dimethyl-1-pyrazolyl; and wherein Alkyl is selected from the group consisting of: Me, Et, iPr, nPr, nBu, iBu, secBu, tBu, $C_5$-$C_{12}$ n-alkyl, cyclopentyl, and cyclohexyl;

wherein Me denotes Methyl, Et denotes Ethyl, Pr denotes Propyl, and Bu denotes Butyl.

16. The chemical compound of claim 15, wherein $n_2$ is in a range of 20-48.

17. The chemical compound of claim 15, wherein $L_1$ is NULL.

18. The chemical compound of claim 15, wherein $L_1$ is selected from the group consisting of

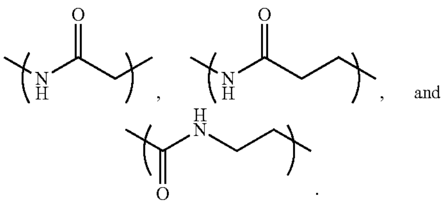

19. The chemical compound of claim 15, wherein the chemical compound is

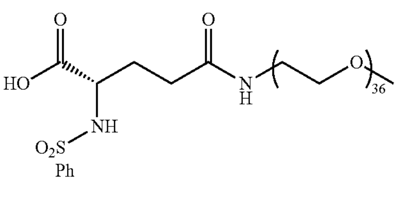

or

-continued

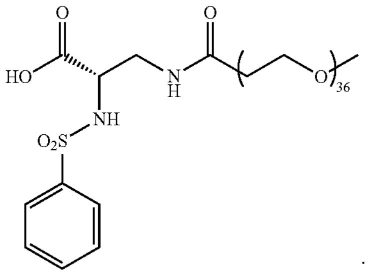

20. A method for treating cancer in a mammal, said method comprising:

administering a therapeutically effective amount of a chemical compound to the mammal;

wherein αv integrins are overexpressed in tumors comprising cancer cells of the cancer in the mammal;

said chemical compound comprising the following Markush structure:

$A-L_1-PEG_1-L_2-PEG_2-CL-X$ wherein $A-L_1-PEG_1$ is a targeting structure configured for targeting the αv integrins in cancer cells and does not include a standard multivalent nitrogen moiety;

wherein A is a structure that includes a standard carboxylic acid moiety;

wherein

A = 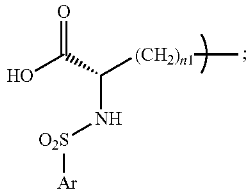

wherein $n_1$ is in a range of 1-6;

wherein Ar is selected from the group consisting of

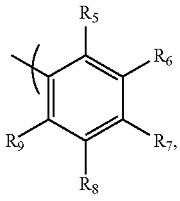, 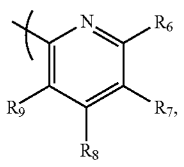, 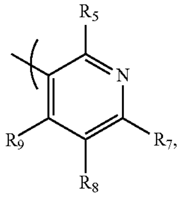, 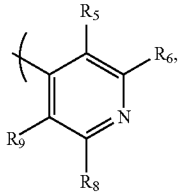,

-continued

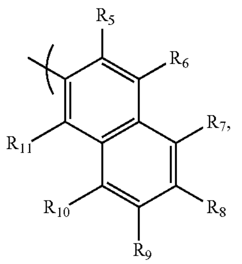, and 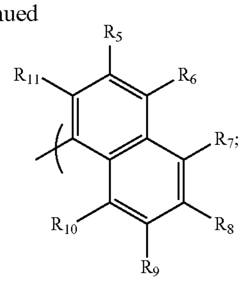;

wherein $R_5$-$R_{11}$ are each independently selected from the group consisting of: H, Me, Et, iPr, nPr, nBu, iBu, secBu, tBu, C5-C12n-alkyl, cyclopentyl, phenyl, F, Cl, Br, —CN, —$CF_3$, —$OCF_3$, —$CHF_2$, —$OCHF_2$, —$SO_2Me$, —O-Alkyl, and -3,5-dimethyl-1-pyrazolyl;

wherein Alkyl is selected from the group consisting of: Me, Et, iPr, nPr, nBu, iBu, secBu, tBu, $C_5$-$C_{12}$ n-alkyl, cyclopentyl, and cyclohexyl;

wherein Me denotes Methyl, Et denotes Ethyl, Pr denotes Propyl, and Bu denotes Butyl;

wherein $L_1$ is a first linking structure selected from the group consisting of

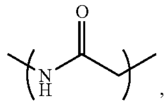, 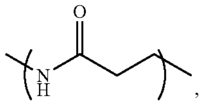, and 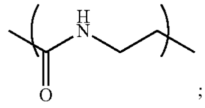;

wherein $PEG_1$ is the following polyethylene glycol structure, wherein $n_2$ is in a range of 5-72:

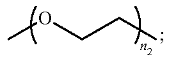

wherein $L_2$ is the following second linker structure, wherein $n_3$ is in a range of 0-4:

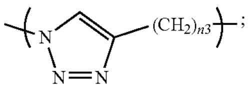

wherein $PEG_2$ is the following polyethylene glycol repeating structure, wherein $n_4$ is in a range of 0-67 and $n_2$+$n_4$ is in a range of 20-72:

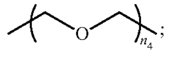

Wherein CL is a cleavable linker; and wherein X is either Chemo1 or $L_3$-Chemo2, wherein Chemo1 denotes a first chemotherapy, wherein Chemo2 denotes a second chemotherapy, and wherein $L_3$ is the following linker that links Chemo2 to CL:

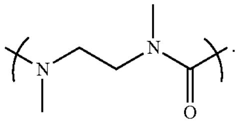

21. The method of claim 20, wherein the mammal is a human being.

22. The method of claim 21, wherein the cancer is selected from the group consisting of glioblastoma, pancreatic cancer, ovarian cancer, breast cancer, prostate cancer, bladder cancer, lung cancer, liver cancer, acute myeloid leukemia, multiple myeloma, Lymphoma, and chronic lymphocytic leukemia.

23. The method of claim 20, wherein the mammal is a non-human mammal.

24. The chemical compound of claim 1, wherein CL is the following cleavable linker:

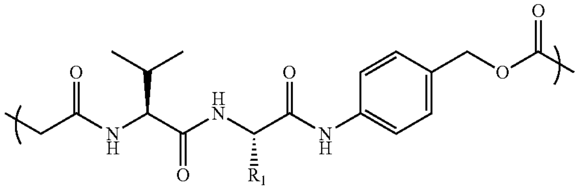

wherein $R_1$ is selected from the group consisting of methyl,

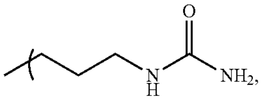
and
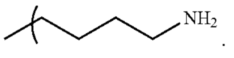

25. The method of claim 20, wherein CL is the following cleavable linker:

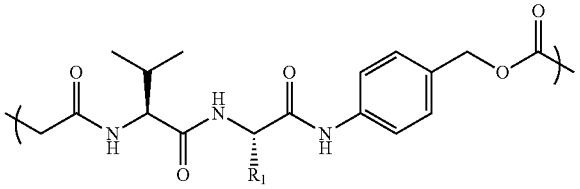

wherein $R_1$ is selected from the group consisting of methyl,

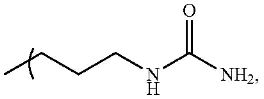
and
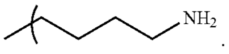

26. The chemical compound of claim 9, wherein CL is the following cleavable linker:

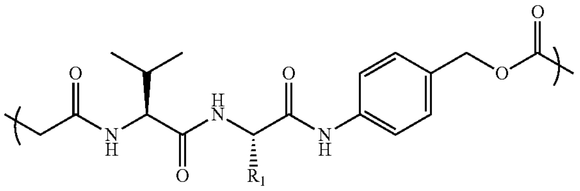

wherein $R_1$ is selected from the group consisting of methyl,

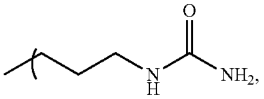
and
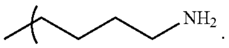

27. The chemical compound of claim 11, wherein CL is the following cleavable linker:

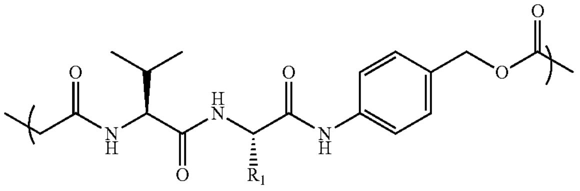

wherein $R_1$ is selected from the group consisting of methyl,

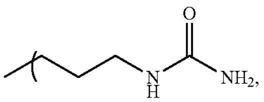
and
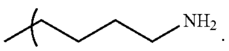

* * * * *